(12) United States Patent
Naka et al.

(10) Patent No.: US 10,077,316 B2
(45) Date of Patent: Sep. 18, 2018

(54) ESOPHAGEAL CANCER MARKER AND USE THEREOF

(71) Applicant: National University Corporation Kochi University, Kochi-shi, Kochi (JP)

(72) Inventors: Tetsuji Naka, Osaka (JP); Satoshi Serada, Osaka (JP); Minoru Fujimoto, Osaka (JP); Masayoshi Toyoura, Kyoto (JP); Yuji Shoya, Kyoto (JP)

(73) Assignee: National University Corporation, Kochi University, Kochi (JP)

( * ) Notice: Subject to any disclaimer, the term of this patent is extended or adjusted under 35 U.S.C. 154(b) by 0 days.

(21) Appl. No.: 15/108,251

(22) PCT Filed: Dec. 25, 2014

(86) PCT No.: PCT/JP2014/006455
§ 371 (c)(1),
(2) Date: Jun. 24, 2016

(87) PCT Pub. No.: WO2015/098112
PCT Pub. Date: Jul. 2, 2015

(65) Prior Publication Data
US 2017/0066836 A1  Mar. 9, 2017

(30) Foreign Application Priority Data

Dec. 27, 2013  (JP) ................. 2013-272085

(51) Int. Cl.
| | |
|---|---|
| *C07K 16/30* | (2006.01) |
| *A61K 31/713* | (2006.01) |
| *G01N 33/574* | (2006.01) |
| *C12Q 1/6886* | (2018.01) |
| *C07K 16/28* | (2006.01) |
| *C12N 15/113* | (2010.01) |
| *A61K 39/00* | (2006.01) |

(52) U.S. Cl.
CPC ............ *C07K 16/30* (2013.01); *A61K 31/713* (2013.01); *C07K 16/28* (2013.01); *C12N 15/1138* (2013.01); *C12Q 1/6886* (2013.01); *G01N 33/57407* (2013.01); *A61K 2039/505* (2013.01); *C07K 2317/23* (2013.01); *C07K 2317/33* (2013.01); *C07K 2317/565* (2013.01); *C07K 2317/622* (2013.01); *C07K 2317/73* (2013.01); *C07K 2317/76* (2013.01); *C07K 2317/92* (2013.01); *C12N 2310/14* (2013.01); *C12Q 2600/158* (2013.01); *G01N 2333/705* (2013.01); *G01N 2400/40* (2013.01)

(58) Field of Classification Search
None
See application file for complete search history.

(56) References Cited

U.S. PATENT DOCUMENTS

2003/0103980 A1* 6/2003 Kore ................. C07K 16/3015
424/155.1

FOREIGN PATENT DOCUMENTS

| JP | 2010-107306 A | 5/2010 |
|---|---|---|
| JP | 2010-526766 A | 8/2010 |
| WO | 2008/092894 A1 | 8/2008 |

OTHER PUBLICATIONS

Gengrinovitch et al., "Glypican-1 Is a VEGF$_{165}$ Binding Proteoglycan That Acts as an Extracellular Chaperone for VEGF$_{165}$," *The Journal of Biological Chemistry* 274(16): 10816-10822, 1999.
Bret et al., "SULFS in human neoplasia: implication as progression and prognosis factors," *Journal of Translational Medicine* 9:72, 2011, 9 pages.
Filmus, "Glypicans in growth control and cancer," *Glycobiology* 11(3):19R-23R, 2001.
Kleeff et al., "The cell-surface heparin sulfate proteoglycan glypican-1 regulates growth factor action in pancreatic carcinoma cells and is overexpressed in human pancreatic cancer," *J. Clin Invest.* 102(9):1662-1673, 1998.

* cited by examiner

*Primary Examiner* — Lei Yao

(74) *Attorney, Agent, or Firm* — Seed IP Law Group LLP

(57) ABSTRACT

The present invention relates to an esophageal cancer marker and application thereof. The present invention relates to: a marker that includes Glypican-1 or an expression product thereof, or a fragment or derivative thereof, and serves to identify esophageal cancer; a detection agent that includes a substance that binds to Glypican-1 or an expression product thereof; and a composition that includes a Glypican-1 inhibitor and serves to prevent or treat esophageal cancer. Herein, Glypican-1 can be SEQ ID NO: 1 (nucleic acid sequence) or SEQ ID NO: 2 (amino acid sequence), or an equivalent thereof.

18 Claims, 40 Drawing Sheets

Specification includes a Sequence Listing.

Fig. 2

| Normal esophageal epithelial cell | Esophageal cancer cell strain | | | | | |
|---|---|---|---|---|---|---|
| Het-1A/ HEEpiC | TE1/ HEEpiC | TE6/ HEEpiC | TE8/ HEEpiC | TE9/ HEEpiC | TE10/ HEEpiC | TE14/ HEEpiC |
| 1.216 | 1.704 | 2.851 | 1.634 | 2.245 | 2.931 | 4.787 |

Cell strains used for iTRAQ

| iTRAQ label | Cell strain name | Primary tissue |
|---|---|---|
| 113 | HEEpiC | Normal esophagus |
| 114 | Het1A | Normal esophagus |
| 115 | TE1 | Human esophageal cancer-derived cell strain squamous cell carcinoma |
| 116 | TE6 | High-differentiated squamous cell carcinoma |
| 117 | TE8 | Medium-differentiated squamous cell carcinoma |
| 118 | TE9 | Human esophageal squamous cell carcinoma-derived cell strain (undifferentiated) |
| 119 | TE10 | High-differentiated squamous cell carcinoma |
| 121 | TE14 | Medium-differentiated squamous cell carcinoma |

Fig. 4B
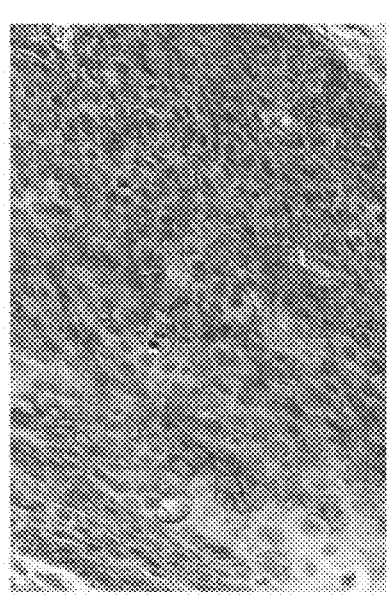
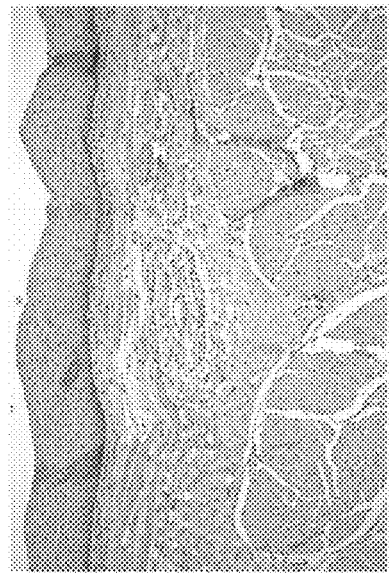
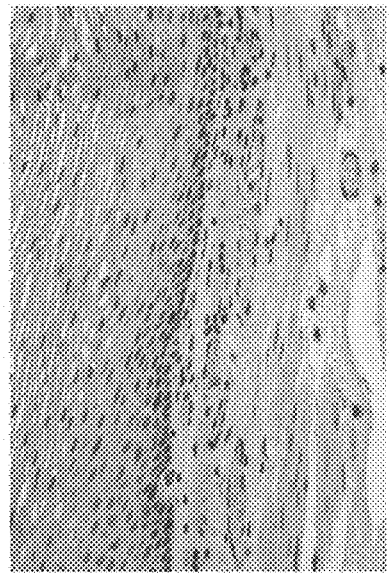

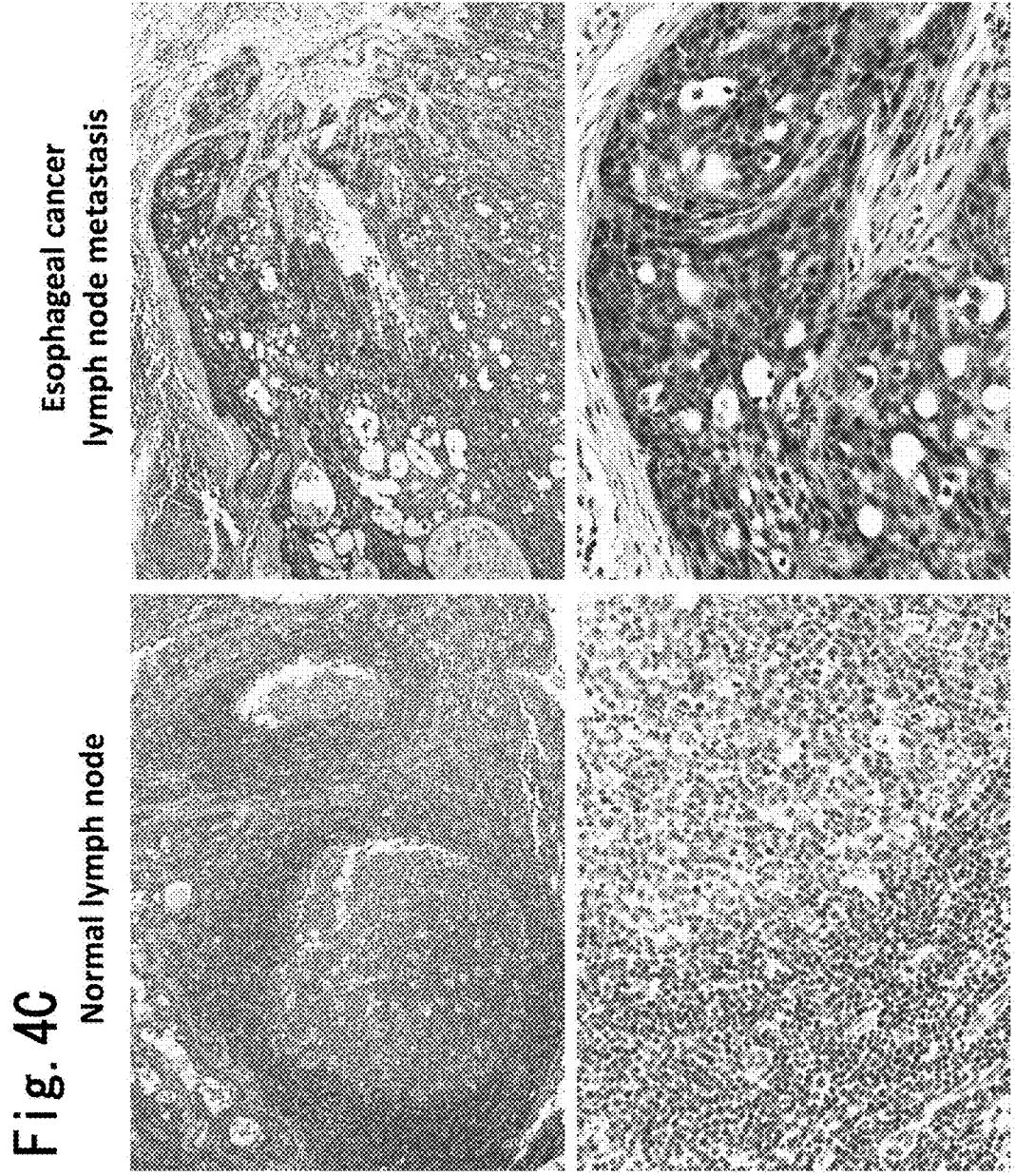

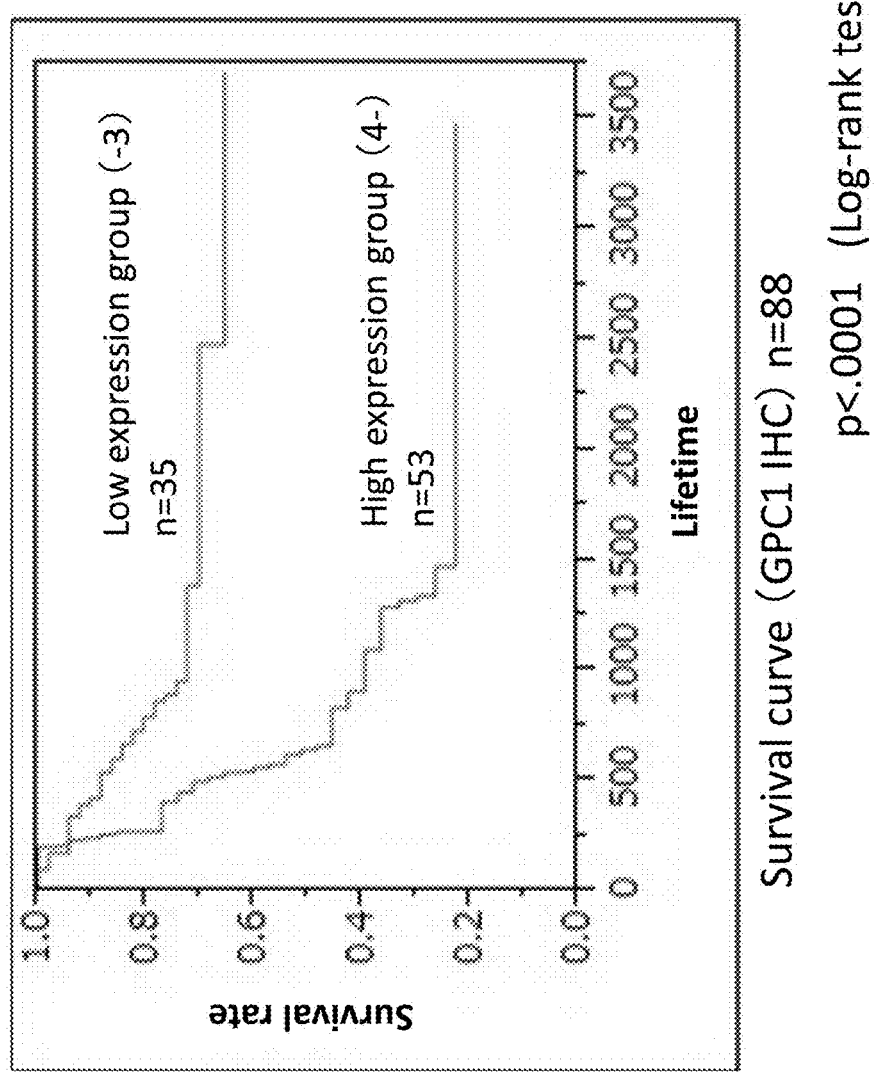

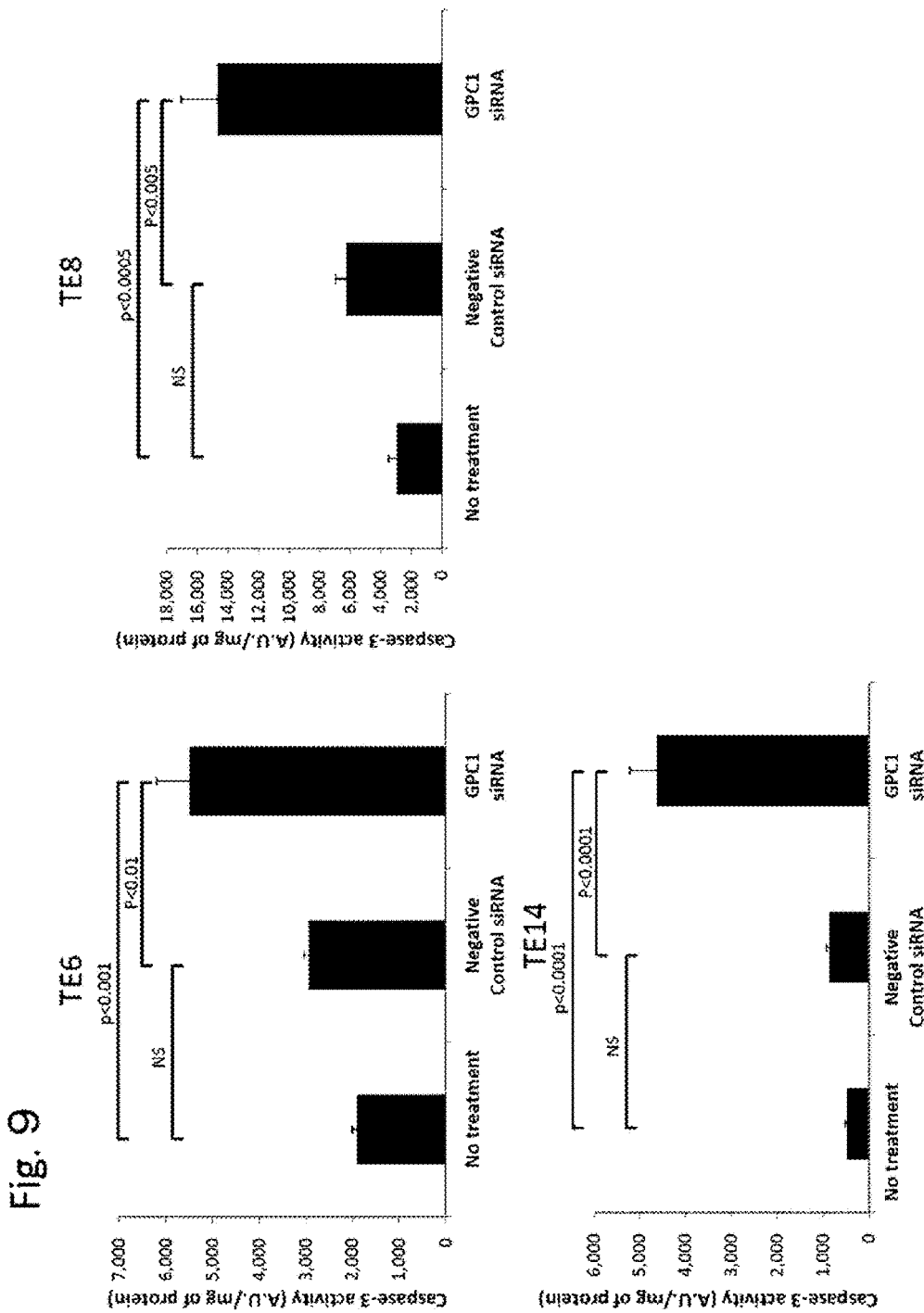

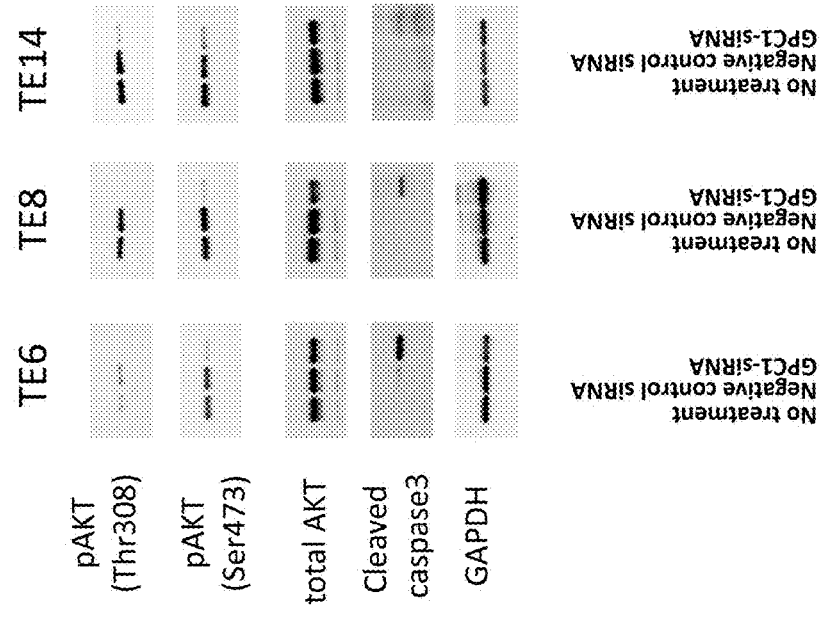

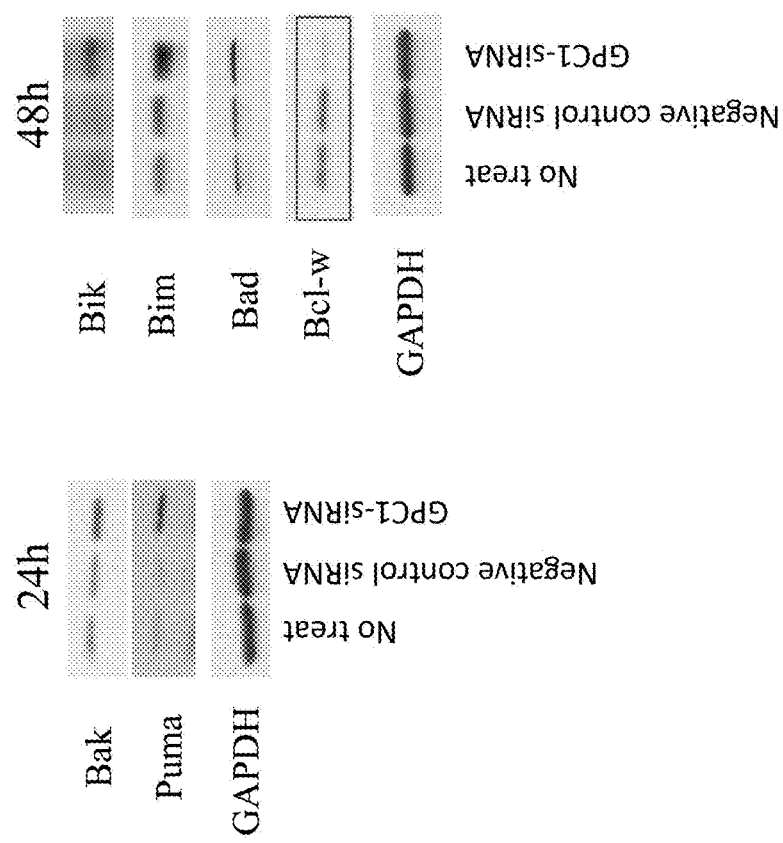

Fig. 12

| | Ka (1/Ms) | Kd (1/s) | K$_D$ |
|---|---|---|---|
| #2 | 4.55x10$^4$ | 9.51x10$^{-4}$ | 20.9 nM |
| #4 | 1.87x10$^5$ | 4.88x10$^{-4}$ | 2.61 nM |
| #7 | 1.64x10$^5$ | 2.13x10$^{-3}$ | 13.0 nM |
| #10 | 1.21x10$^4$ | 2.13x10$^{-3}$ | 176 nM |
| #17 | 6.91x10$^4$ | 1.05x10$^{-3}$ | 15.25 nM |
| #18 | 1.37x10$^5$ | 8.48x10$^{-4}$ | 6.19 nM |
| #19 | 1.23x10$^5$ | 8.45x10$^{-4}$ | 6.88 nM |

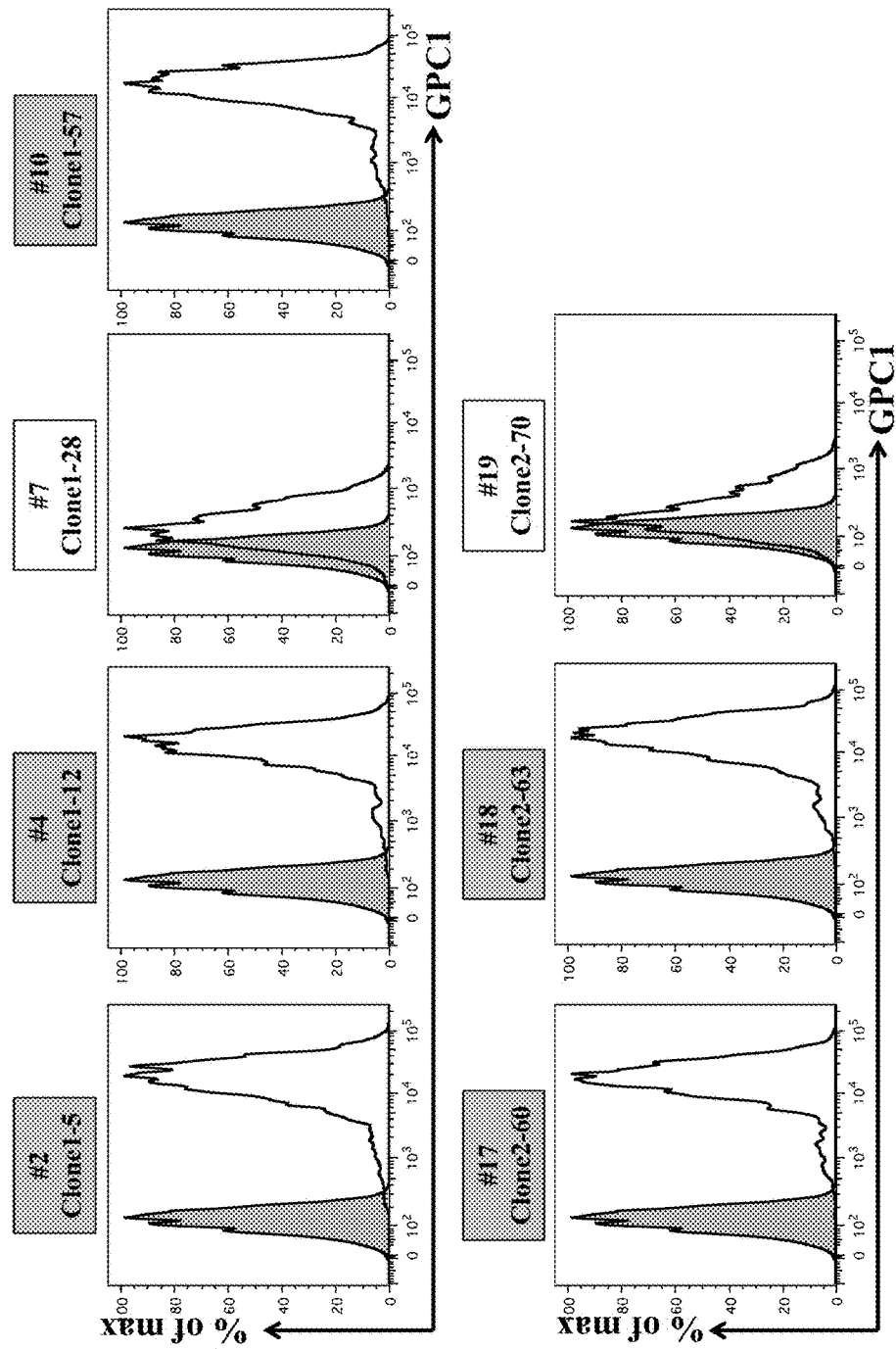

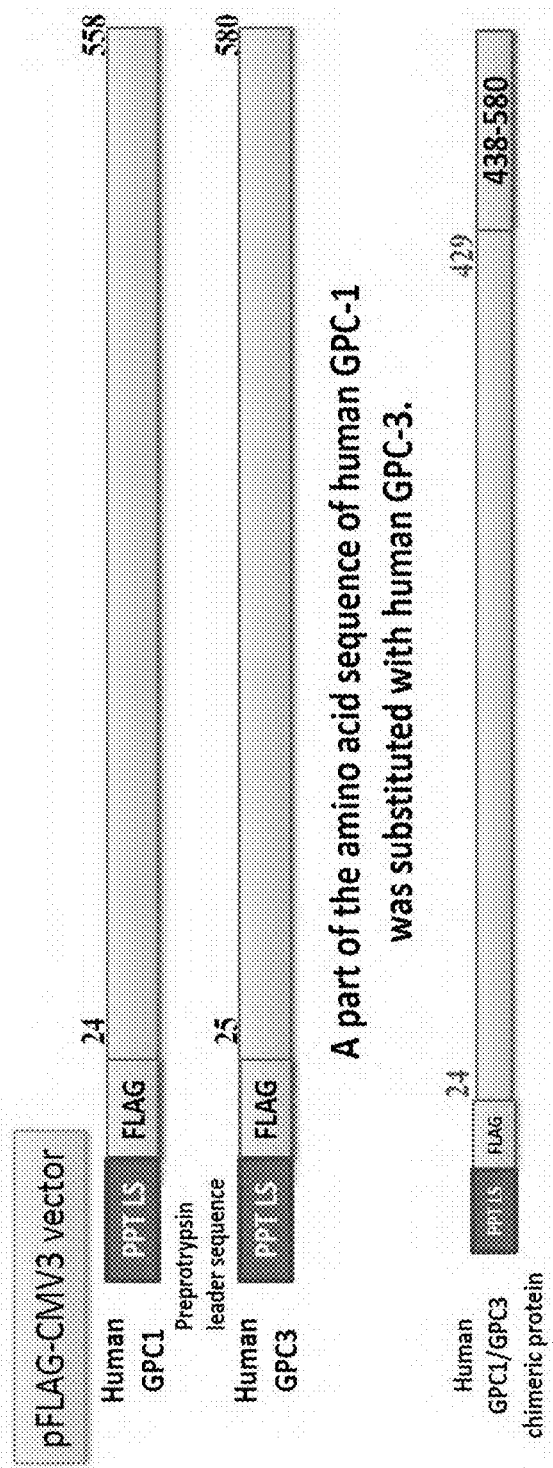

Fig. 16B

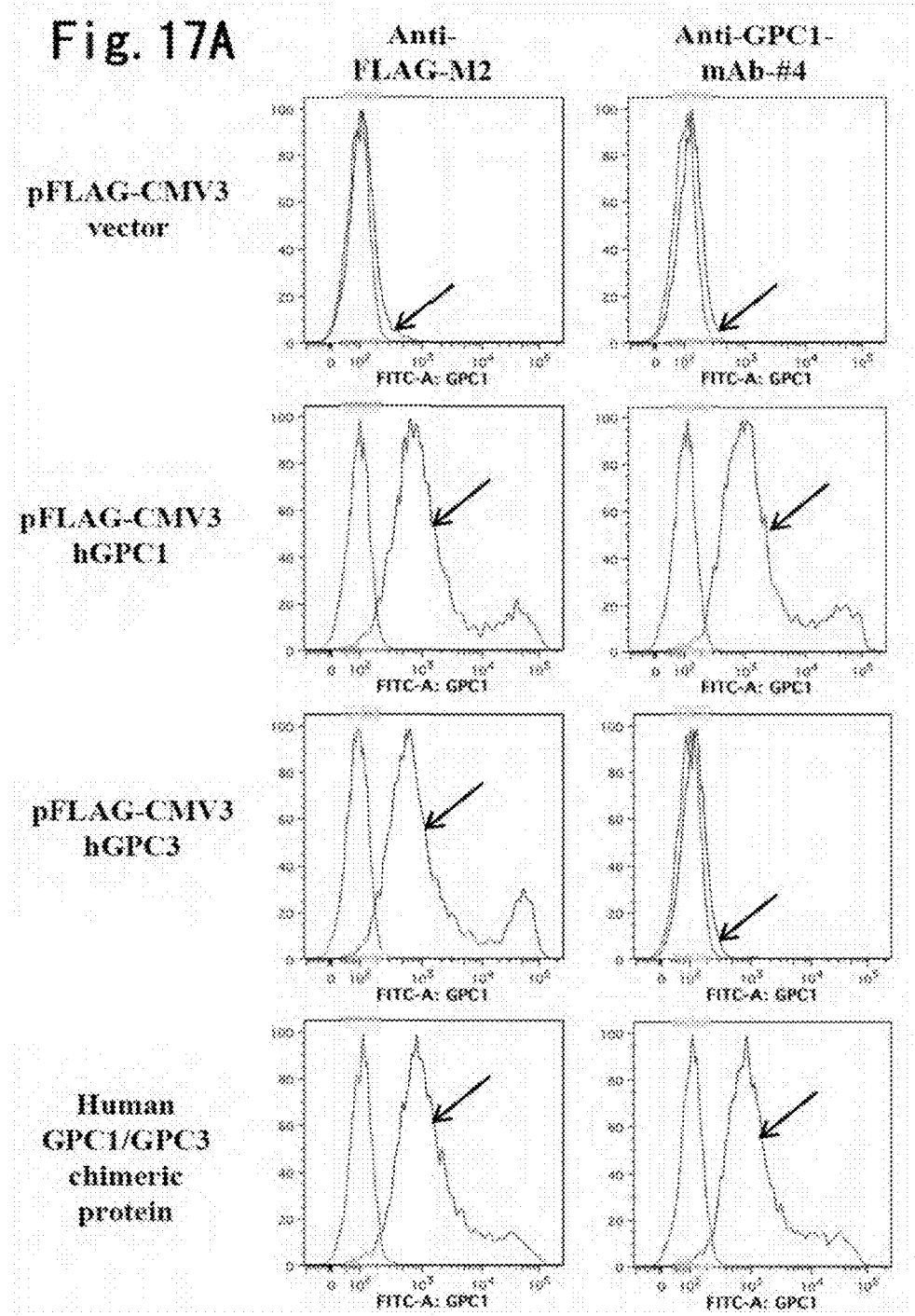

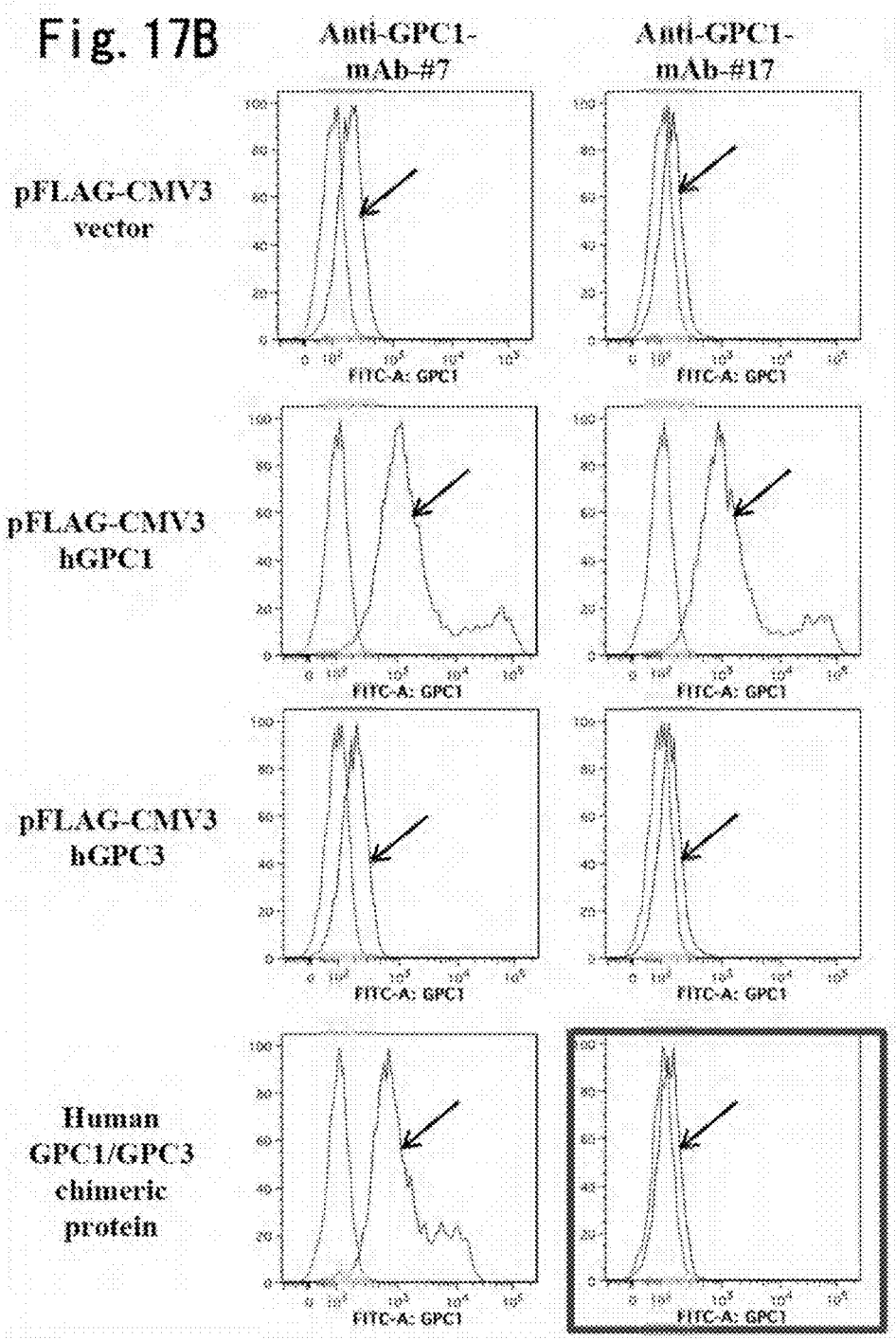

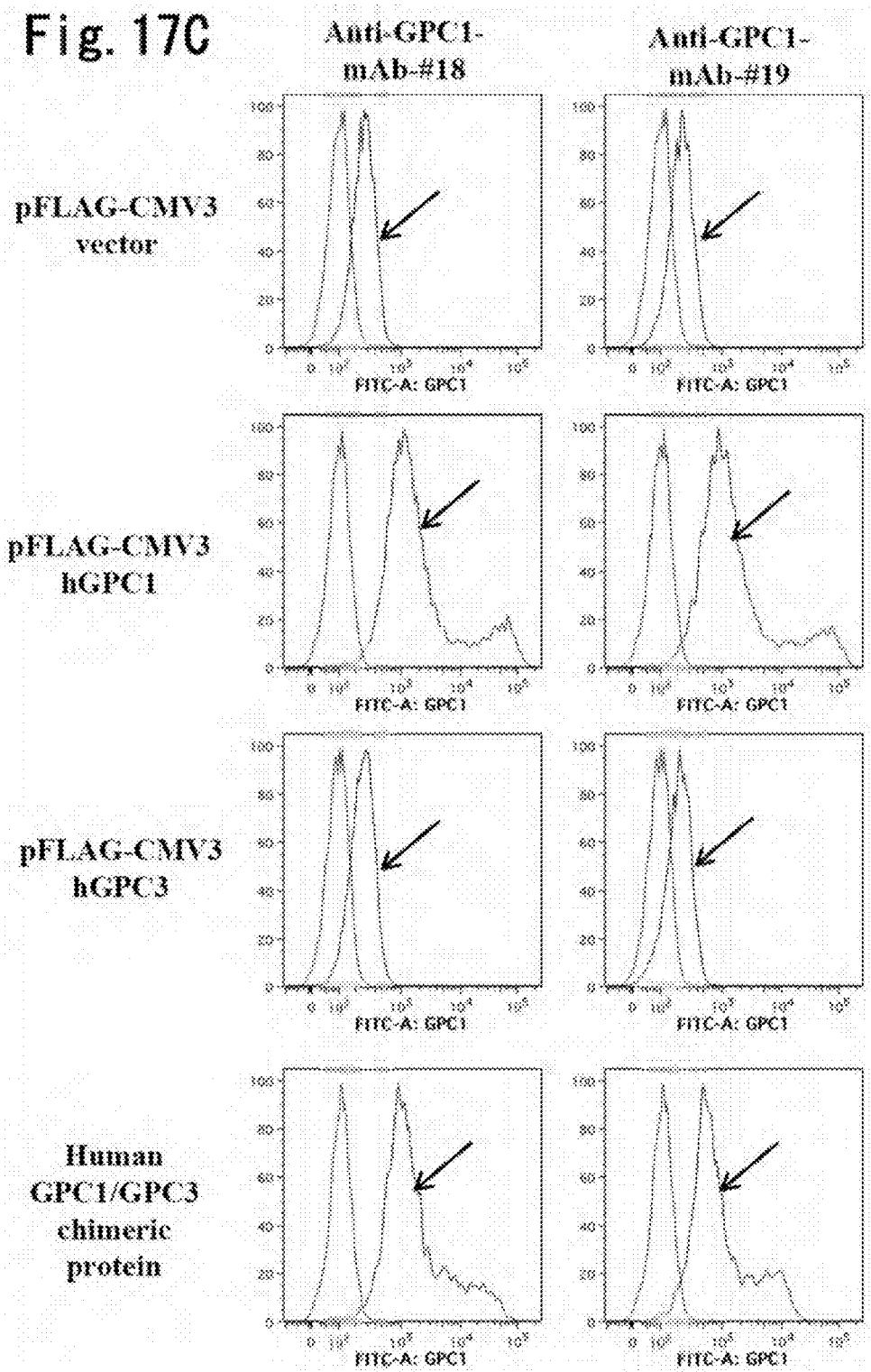

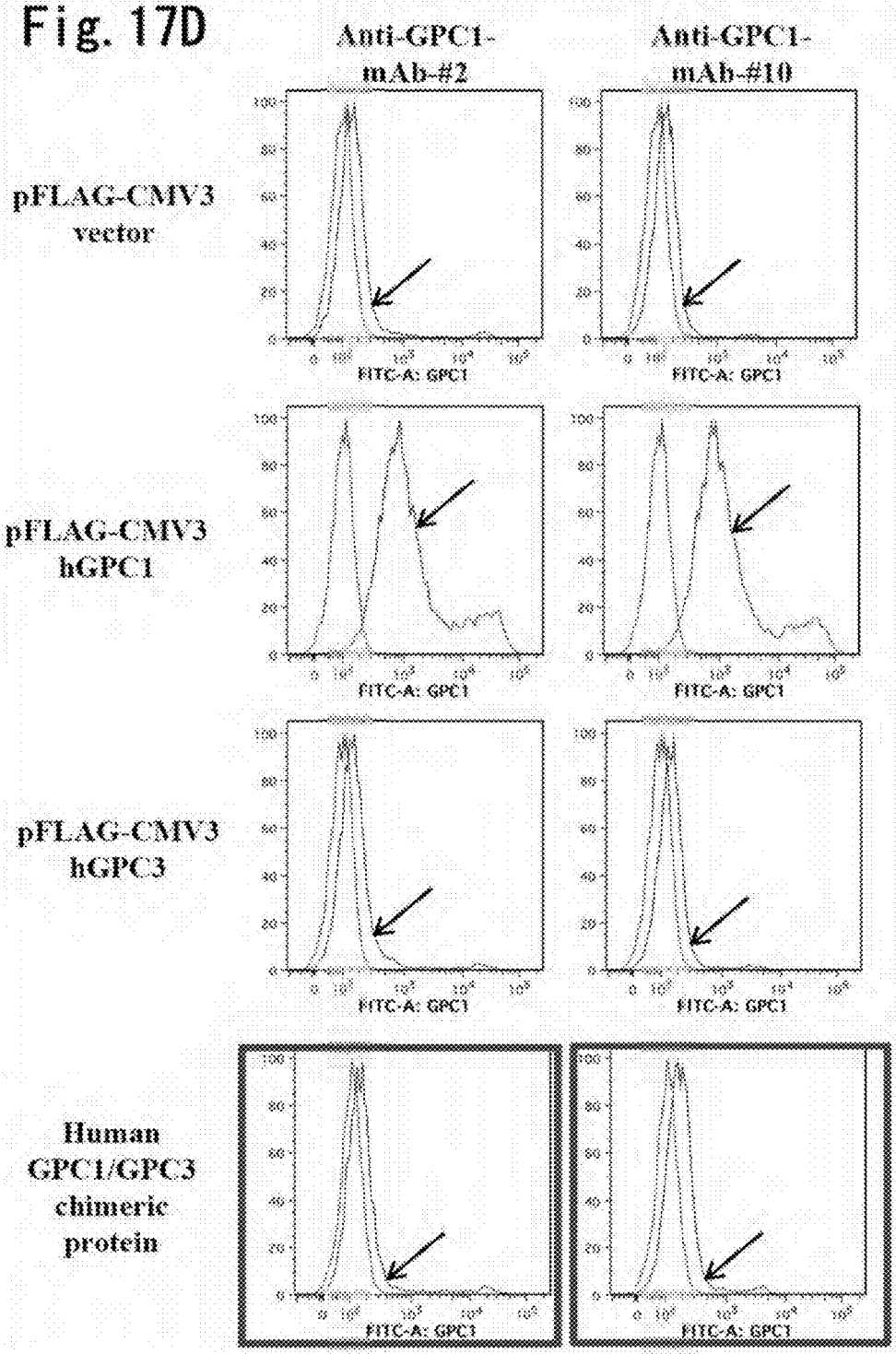

Fig. 26

- To C57BL/6J(8w)), 1mg/body of
  ① Mouse IgG2a (Sigma M7769)
  ② Anti-GPC1 antibody #4
  was intraperitoneally administered, and the following items were assessed on Day7

|   | Cont IgG | GPC |
|---|---|---|
| ♂ | 4 | 3 |
| ♀ | 3 | 3 |

○ Blood collection item:
WBC, RBC, Hb, Plt
T-Bil, ALT, ALP, Amy, BUN, Cr, Ca, P, TP,
Alb, Na, K, Glob, Glu Automated blood cell counter: VetScan HMII
Veterinary biochemical blood analyzer :
VetScanVS2

Fig. 27

| | Control IgG (n=3) | Anti-GPC1 Ab (n=3) | normal | p value |
|---|---|---|---|---|
| WBC(10⁹/l) | 2.60 (1.32-3.27) | 2.24 (1.13-3.27) | 2.3±1.16 | 0.709 |
| Ly(%) | 91.8 (91.1-92.8) | 87.0 (82.4-91.4) | 87.5±3.35 | 0.140 |
| Mo(%) | 2.2 (1.9-2.6) | 2.0 (0.6-2.9) | 2.6±1.19 | 0.800 |
| Gr(%) | 6.0 (5.3-6.8) | 11.1 (5.8-17.0) | 9.2±2.68 | 0.195 |
| RBC(10¹²/l) | 9.21 (8.66-9.56) | 9.40 (9.12-9.70) | 9.86±0.327 | 0.597 |
| Hb | 14.6 (12.5-15.0) | 14.3 (14.1-14.5) | 15.0±0.48 | 0.387 |
| Hct | 44.74 (42.60-46.80) | 43.96 (43.11-44.53) | 44.1±1.58 | 0.578 |
| Plt(10⁹/l) | 487 (475-511) | 352 (269-501) | 1158±104 | 0.148 |

Student's t-test

Fig. 28

| | Control IgG (n=3) | Anti-GPC1 Ab (n=3) | normal | p value |
|---|---|---|---|---|
| WBC(10⁹/l) | 2.61 (1.73-3.16) | 2.97 (2.48-3.77) | 1.5±0.7 | 0.573 |
| Ly(%) | 92.8 (91.8-94.5) | 90.5 (87.7-93.2) | 86.4±3.44 | 0.273 |
| Mo(%) | 3.3 (2.0-4.4) | 3.1 (1.6-5.4) | 2.5±0.79 | 0.873 |
| Gr(%) | 4.0 (3.6-4.7) | 6.5 (4.1-10.1) | 11.1±4.49 | 0.247 |
| RBC(10¹²/l) | 9.53 (9.37-9.62) | 9.98 (9.69-10.29) | 9.53±0.24 | 0.080 |
| Hb | 15.1 (15.0-15.1) | 14.97 (14.8-15.1) | 14.8±0.5 | 0.349 |
| Hct | 45.58 (44.50-46.24) | 45.17 (44.28-45.83) | 42.7±1.24 | 0.593 |
| Plt(10⁹/l) | 375 (247-482) | 339 (301-408) | 942±85.9 | 0.667 |

Student's t-test

Fig. 29

| | Control IgG (n=3) | Anti-GPC1 Ab (n=3) | P value |
|---|---|---|---|
| Alb (g/dl) | 3.4 (3.0-4.1) | 3.1 (3.1-3.2) | 0.427 |
| ALP (U/l) | 149 (142-155) | 141 (126-150) | 0.374 |
| ALT (U/l) | 29 (26-33) | 35 (26-44) | 0.303 |
| Amy (U/l) | 995 (879-1098) | 1058 (913-1314) | 0.683 |
| T-Bil (mg/dl) | 0.3 (0.3-0.4) | 0.4 (0.3-0.4) | 0.519 |
| BUN (mg/dl) | 20 (19-22) | 17 (15-19) | 0.163 |
| Ca (mg/dl) | 10.4 (9.8-11.4) | 8.8 (7.6-9.8) | 0.114 |
| P (mg/dl) | 9.2 (8-11.1) | 9.6 (8.7-10.5) | 0.715 |
| Cr (mg/dl) | (<0.2-0.8) | (<0.2) | |
| Glu (mg/dl) | 197 (190-207) | 186 (166-204) | 0.417 |
| Na (mmol/l) | 158 (153-169) | 149 (144-157) | 0.227 |
| K (mmol/l) | 5.5 (5.2-6.0) | 5.9 (5.1-6.4) | 0.448 |
| TP (g/dl) | 5.4 (5.0-6.1) | 4.7 (4.6-4.7) | 0.087 |
| Glob (g/dl) | 2.0 (1.9-2.0) | 1.6 (1.5-1.8) | 0.024 |

Fig. 30

| | Control IgG (n=3) | Anti-GPC4 Ab (n=3) | p value |
|---|---|---|---|
| Alb (g/dl) | 4.0 (3.8-4.2) | 3.9 (3.8-4.1) | 0.670 |
| ALP (U/l) | 168 (158-178) | 155 (141-173) | 0.326 |
| ALT (U/l) | 23 (15-28) | 27 (25-32) | 0.406 |
| Amy (U/l) | 922 (865-1000) | 824 (753-867) | 0.145 |
| T-Bil (mg/dl) | 0.3 (0.3-0.4) | 0.4 (0.3-0.4) | 0.519 |
| BUN (mg/dl) | 21 (18-25) | 20 (19-22) | 0.587 |
| Ca (mg/dl) | 9.6 (9.2-9.9) | 9.3 (8.9-9.8) | 0.423 |
| P (mg/dl) | 9.3 (8.7-10.1) | 8.7 (8.4-9.4) | 0.380 |
| Cr (mg/dl) | (<0.2-0.3) | (<0.2-0.2) | |
| Glu (mg/dl) | 158 (142-172) | 179 (153-202) | 0.264 |
| Na (mmol/l) | 150 (149-151) | 147 (146-149) | 0.060 |
| K (mmol/l) | 5.0 (4.5-5.6) | 5.5 (5.0-6.0) | 0.342 |
| TP (g/dl) | 5.4 (5.2-5.5) | 5.3 (5.1-5.5) | 0.539 |
| Glob (g/dl) | 1.4 (1.4-1.5) | 1.3 (1.3-1.4) | 0.101 |

ESOPHAGEAL CANCER MARKER AND USE THEREOF

TECHNICAL FIELD

The present invention is related to markers for cancer, in particularly esophageal cancer, and relevant technologies, methods, agents, and the like.

BACKGROUND ART

Statement Regarding Sequence Listing

The Sequence Listing associated with this application is provided in text format in lieu of a paper copy, and is hereby incorporated by reference into the specification. The name of the text file containing the Sequence Listing is 690188_403USPC_SEQUENCE_LISTING.txt. The text file is 54.2 KB, was created on Jun. 23, 2016, and is being submitted electronically via EFS-Web.

Esophageal cancer is cancer occurring in the esophagus and subjective symptoms often do not appear in the early stage thereof, while esophageal cancer found with no symptoms is in the early stage and thus the probability of curing is high. On the other hand, as tumor markers for esophageal cancer, SCC (squamous cell carcinoma related antigen), CEA (carcinoembryonic antigen), CA19-9, p53, and the like are utilized. However, as of present, the tumor markers are used to understand the dynamics of progressing malignant tumor is understood, but a definitive tumor marker for esophageal cancer is not available. Further, it is presumed that even when the cancer is present, some of the tumor markers do not exhibit an abnormal value.

CITATION LIST

Non Patent Literature

[NPL1] Groblewska M et al., Clinica Chimica Acta 413 (2012) 1583-1590

SUMMARY OF INVENTION

Solution to Problem

The present invention provides novel markers for esophageal cancer and applied technologies thereof. In the complete invention, the inverters have found that a Glypican-1 molecule is significantly more strongly expressed in esophageal cancer cells than normal cells, that it may be used as a tumor marker, and also that esophageal cancer may be treated by suppressing Glypican-1.

Since previous studies have not reported those useful as diagnostic markers for esophageal cancer, the present invention is of great utility which is not present in the prior art.

In one aspect, the present invention provides a detection agent to identify esophageal cancer, wherein the detection agent comprises a substance that binds to Glypican-1 or an expression product thereof.

In another aspect, the present invention provides a method of identifying esophageal cancer using a substance that binds to Glypican-1 or an expression product thereof. In this method, the detection agent of the present invention may be used to identify it.

In one embodiment, the detection agent of the present invention is an antibody or a fragment or a functional equivalent thereof, or nucleic acid.

In another embodiment, the detection agent of the present invention is labeled.

In one embodiment, the above-mentioned Glypican-1 is SEQ ID NO: 1 (nucleic acid sequence) or SEQ ID NO: 2 (amino acid sequence), or an equivalent thereof.

In another embodiment, the detection agent of the present invention is nucleic acid, and the nucleic acid is a probe or a primer.

In yet another embodiment, a probe or primer used as a detection agent of the present invention may be the nucleic acid sequence set forth in SEQ ID NO: 1 or a complementary strand thereof, or a fragment of a mutant thereof.

In another embodiment, a probe or primer used as a detection agent of the present invention may be characterized by having SEQ ID NO: 25 and/or SEQ ID NO: 26.

In one embodiment, the above-mentioned esophageal cancer which the detection agent of the present invention targets includes those in lymph node metastasis sites, squamous cell carcinoma, and/or adenocarcinoma.

In one embodiment, with respect to the detection agent and method of the present invention, when the expression of Glypican-1 in a target specimen is increased in comparison with that in a normal specimen, the target specimen may be characterized by being diagnosed as having esophageal cancer.

In another aspect, the present invention provides a marker to identify esophageal cancer, wherein the marker comprises Glypican-1 or an expression product thereof, or a fragment or derivative thereof.

In one embodiment, regarding a target of the marker of the present invention, the above-mentioned esophageal cancer includes those in lymph node metastasis sites, squamous cell carcinoma, and/or adenocarcinoma.

In one embodiment, regarding a target of the marker of the present invention, the above-mentioned esophageal cancer includes squamous cell carcinoma and/or adenocarcinoma.

In a further embodiment, regarding a target of the marker of the present invention, the above-mentioned esophageal cancer includes squamous cell carcinoma.

In yet another embodiment, regarding a target of the marker of the present invention, the above-mentioned esophageal cancer may be of human.

In another embodiment, the above-mentioned Glypican-1 used in the present invention is SEQ ID NO: 1 (nucleic acid sequence) or a complementary strand thereof, or SEQ ID NO: 2 (amino acid sequence), or an equivalent thereof.

In another aspect, the present invention provides a method of using Glypican-1 or an expression product thereof as indicators for identifying esophageal cancer.

In one embodiment, in the method of the present invention, when the expression of Glypican-1 in a target specimen is increased in comparison with that in a normal specimen, the target specimen may be characterized by being diagnosed as having esophageal cancer.

In one embodiment, in the method of the present invention, the above-mentioned identification may be carried out using the detection agent of the present invention.

In one embodiment, the above-mentioned esophageal cancer that the method of the present invention targets includes those in lymph node metastasis sites, squamous cell carcinoma, and/or adenocarcinoma.

In one aspect, the present invention provides a prophylactic or therapeutic drug for esophageal cancer, wherein the drug comprises a Glypican-1 suppressant.

In one embodiment, the above-mentioned esophageal cancer is Glypican-1 positive.

In one embodiment, the above-mentioned esophageal cancer that the prophylactic or therapeutic drug of the present invention targets includes those in lymph node metastasis sites, squamous cell carcinoma, and/or adenocarcinoma.

In another embodiment, the above-mentioned esophageal cancer may include squamous cell carcinoma.

In yet another embodiment, the present invention may be a prophylactic or therapeutic drug to be administered to a patient determined as developing Glypican-1-positive esophageal cancer.

In one embodiment, the Glypican-1 suppressant of the present invention may be an antibody or a fragment or a functional equivalent thereof, or nucleic acid.

In yet another embodiment, the Glypican-1 suppressant of the present invention is nucleic acid and the nucleic acid may be siRNA.

In yet another embodiment, the above-mentioned siRNA comprises SEQ ID NO: 25 and/or SEQ ID NO: 26.

In yet another embodiment, the above-mentioned antibody is an antibody selected from monoclonal antibody, polyclonal antibody, chimeric antibody, humanized antibody, human antibody, multifunctional antibody, bispecific or oligospecific antibody, single chain antibody, scFV, diabody, sc(Fv)$_2$ (single chain (Fv)$_2$), and scFv-Fc.

In one aspect, the present invention provides a method for prevention or treatment of esophageal cancer in a subject, comprising administering an effective amount of a Glypican-1 suppressant to the subject in need thereof.

In another aspect, the present invention provides a method for prevention or treatment of esophageal cancer in the above-mentioned subject, comprising a step of inspecting that a sample of the subject is Glypican-1 positive.

In some embodiments, it is understood that in the method for prevention or treatment of the present invention, any embodiments employed in the prophylactic or therapeutic drug of the present invention can be employed in a similar manner by combining one or plural features.

In yet another aspect, the present invention provides a prophylactic or therapeutic drug for esophageal cancer, wherein the drug comprises a Glypican-1 binding agent.

In one embodiment, the prophylactic or therapeutic drug of the present invention further comprises a cell-killing agent.

In another embodiment, the above-mentioned Glypican-1 binding agent in the present invention may be an antibody or a fragment or a functional equivalent thereof, or nucleic acid.

In another embodiment, the above-mentioned Glypican-1 binding agent used in the present invention is an antibody or a fragment or a functional equivalent thereof and a cell-killing agent may further be linked to the agent.

In another embodiment, the above-mentioned esophageal cancer in the present invention is Glypican-1 positive.

In a further embodiment, the above-mentioned esophageal cancer that a prophylactic or therapeutic drug using the binding agent of the present invention targets includes those in lymph node metastasis sites, squamous cell carcinoma, and/or adenocarcinoma.

In yet another embodiment, the above-mentioned esophageal cancer in the present invention may include squamous cell carcinoma.

In the invention using a detection agent, a binding agent, or a suppressant of the present invention, in a further embodiment, the above-mentioned detection agent, binding agent, or suppressant in the present invention may be characterized by being an antibody or a fragment or a functional equivalent thereof, the antibody having one or more antibodies selected from the group consisting of (a) an antibody of which heavy chain CDRs 1, 2, and 3 and light chain CDRs 1, 2, and 3 comprise the amino acid sequences set forth in positions 31 to 35, positions 50 to 65, positions 98 to 114, positions 163 to 170, positions 187 to 193, and positions 226 to 235 of SEQ ID NO: 3, respectively; (b) an antibody of which heavy chain CDRs 1, 2, and 3 and light chain CDRs 1, 2, and 3 comprise the amino acid sequences set forth in positions 31 to 35, positions 50 to 66, positions 99 to 110, positions 159 to 166, positions 183 to 187, and positions 222 to 231 of SEQ ID NO: 4, respectively; (c) an antibody of which heavy chain CDRs 1, 2, and 3 and light chain CDRs 1, 2, and 3 comprise the amino acid sequences set forth in positions 31 to 35, positions 50 to 66, positions 99 to 113, positions 162 to 170, positions 187 to 193, and positions 226 to 237 of SEQ ID NO: 5, respectively; (d) an antibody of which heavy chain CDRs 1, 2, and 3 and light chain CDRs 1, 2, and 3 comprise the amino acid sequences set forth in positions 31 to 35, positions 51 to 66, positions 99 to 112, positions 160 to 170, positions 187 to 193, and positions 226 to 236 of SEQ ID NO: 6, respectively; (e) an antibody of which heavy chain CDRs 1, 2, and 3 and light chain CDRs 1, 2, and 3 comprise the amino acid sequences set forth in positions 31 to 35, positions 50 to 66, positions 99 to 120, positions 169 to 176, positions 193 to 199, and positions 232 to 242 of SEQ ID NO: 7, respectively; (f) an antibody of which heavy chain CDRs 1, 2, and 3 and light chain CDRs 1, 2, and 3 comprise the amino acid sequences set forth in positions 31 to 35, positions 50 to 65, positions 98 to 114, positions 163 to 170, positions 187 to 193, and positions 226 to 235 of SEQ ID NO: 8, respectively; (g) an antibody of which heavy chain CDRs 1, 2, and 3 and light chain CDRs 1, 2, and 3 comprise the amino acid sequences set forth in positions 31 to 35, positions 50 to 66, positions 99 to 120, positions 169 to 176, positions 193 to 199, and positions 232 to 241 of SEQ ID NO: 9, respectively; (h) an antibody of which heavy chain CDRs 1, 2, and 3 and light chain CDRs 1, 2, and 3 comprise the amino acid sequences set forth in positions 31 to 35, positions 50 to 65, positions 98 to 113, positions 162 to 171, positions 188 to 194, and positions 227 to 237 of SEQ ID NO: 10, respectively; (i) an antibody of which heavy chain CDRs 1, 2, and 3 and light chain CDRs 1, 2, and 3 comprise the amino acid sequences set forth in positions 31 to 35, positions 50 to 65, positions 98 to 114, positions 163 to 170, positions 187 to 193, and positions 226 to 235 of SEQ ID NO: 11, respectively; (j) an antibody of which heavy chain CDRs 1, 2, and 3 and light chain CDRs 1, 2, and 3 comprise the amino acid sequences set forth in positions 31 to 35, positions 50 to 66, positions 99 to 113, positions 162 to 169, positions 186 to 192, and positions 225 to 234 of SEQ ID NO: 12, respectively; (k) an antibody of which heavy chain CDRs 1, 2, and 3 and light chain CDRs 1, 2, and 3 comprise the amino acid sequences set forth in positions 31 to 35, positions 50 to 66, positions 99 to 116, positions 165 to 174, positions 191 to 197, and positions 230 to 240 of SEQ ID NO: 13, respectively; (1) an antibody of which heavy chain CDRs 1, 2, and 3 and light chain CDRs 1, 2, and 3 comprise the amino acid sequences set forth in positions 31 to 35, positions 50 to 66, positions 99 to 113, positions 162 to 169, positions 186 to 192, and positions 225 to 235 of SEQ ID NO: 14, respectively; (m) an antibody of which heavy chain CDRs 1, 2, and 3 and light chain CDRs 1, 2, and 3 comprise the amino acid sequences set forth in positions 31 to 35, positions 50 to 66, positions 99 to 113, positions 162 to 170, positions 187 to 193, and positions 226 to 236 of SEQ ID NO: 15, respectively; (n) an antibody of which heavy chain CDRs 1, 2, and 3 and light chain CDRs 1, 2, and 3 comprise the amino acid sequences set forth in positions 31 to 35, positions 50 to 66, positions 99 to 110, positions 159 to 166, positions 183 to 189, and positions 222 to 237 of SEQ ID NO: 16, respectively; (o) an antibody of which heavy chain CDRs 1, 2, and 3 and light chain CDRs 1, 2, and 3 comprise the amino acid sequences set forth in positions 31 to 35, positions 50 to 65, positions 98 to 113, positions 162 to 171, positions 188 to 194, and positions 227 to 237 of SEQ ID NO: 17, respectively; (p) an antibody of which heavy chain CDRs 1, 2, and 3 and light chain CDRs 1, 2, and 3 comprise the amino acid sequences set forth in positions 31 to 35, positions 50 to 66, positions 99 to 116, positions 165 to 174, positions 191 to 197, and positions 230 to 240 of SEQ ID NO: 18, respectively; (q) an antibody of which heavy chain CDRs 1, 2, and 3 and light chain CDRs 1, 2, and 3 comprise the amino acid sequences set forth in positions 31 to 35, positions 50 to 66, positions 99 to 115, positions 164 to 175, positions 193 to 199, and positions 232 to 241 of SEQ ID NO: 19, respectively; (r) an antibody of which heavy chain CDRs 1, 2, and 3 and light chain CDRs 1, 2, and 3 comprise the amino acid sequences set forth in positions 31 to 35, positions 50 to 66, positions 99 to 117, positions 166 to 177, positions 194 to 200, and positions 233 to 242 of SEQ ID NO: 20, respectively; (s) an antibody of which heavy chain CDRs 1, 2, and 3 and light chain CDRs 1, 2, and 3 comprise the amino acid sequences set forth in positions 32 to 36, positions 51 to 67, positions 100 to 114, positions 163 to 171, positions 188 to 194, and positions 227 to 236 of SEQ ID NO: 21, respectively; and (t) an antibody of which heavy chain CDRs 1, 2, and 3 and light chain CDRs 1, 2, and 3 comprise the amino acid sequences set forth in positions 31 to 35, positions 50 to 65, positions 98 to 114, positions 163 to 170, positions 187 to 193, and positions 226 to 235 of SEQ ID NO: 22, respectively; or a mutant of said antibodies wherein the mutant comprises one or several substitutions, additions, or deletions in a framework of said antibodies, but is free of a mutation in the CDRs. Alternatively, the above-mentioned detection agent, binding agent, or suppressant in the present invention is an antibody or a fragment or a functional equivalent thereof and the antibody may be an antibody having positions 33 to 61 of SEQ ID NO: 2; positions 339 to 358 and/or positions 388 to 421 of SEQ ID NO: 2; or positions 430 to 530 of SEQ ID NO: 2 as an epitope. These antibodies may be an antibody selected from monoclonal antibody, polyclonal antibody, chimeric antibody, humanized antibody, human antibody, multifunctional antibody, bispecific or oligospecific antibody, single chain antibody, scFV, diabody, sc(Fv)$_2$ (single chain (Fv)$_2$), and scFv-Fc.

In yet another aspect, the present invention provides an antibody or a fragment or a functional equivalent thereof, wherein the antibody is selected from the group consisting of the following antibodies: (a) an antibody of which heavy chain CDRs 1, 2, and 3 and light chain CDRs 1, 2, and 3 comprise the amino acid sequences set forth in positions 31 to 35, positions 50 to 65, positions 98 to 114, positions 163 to 170, positions 187 to 193, and positions 226 to 235 of SEQ ID NO: 3, respectively; (b) an antibody of which heavy chain CDRs 1, 2, and 3 and light chain CDRs 1, 2, and 3 comprise the amino acid sequences set forth in positions 31 to 35, positions 50 to 66, positions 99 to 110, positions 159 to 166, positions 183 to 187, and positions 222 to 231 of SEQ ID NO: 4, respectively; (c) an antibody of which heavy chain CDRs 1, 2, and 3 and light chain CDRs 1, 2, and 3 comprise the amino acid sequences set forth in positions 31 to 35, positions 50 to 66, positions 99 to 113, positions 162 to 170, positions 187 to 193, and positions 226 to 237 of SEQ ID NO: 5, respectively; (d) an antibody of which heavy chain CDRs 1, 2, and 3 and light chain CDRs 1, 2, and 3 comprise the amino acid sequences set forth in positions 31 to 35, positions 51 to 66, positions 99 to 112, positions 160 to 170, positions 187 to 193, and positions 226 to 236 of SEQ ID NO: 6, respectively; (e) an antibody of which heavy chain CDRs 1, 2, and 3 and light chain CDRs 1, 2, and 3 comprise the amino acid sequences set forth in positions 31 to 35, positions 50 to 66, positions 99 to 120, positions 169 to 176, positions 193 to 199, and positions 232 to 242 of SEQ ID NO: 7, respectively; (f) an antibody of which heavy chain CDRs 1, 2, and 3 and light chain CDRs 1, 2, and 3 comprise the amino acid sequences set forth in positions 31 to 35, positions 50 to 65, positions 98 to 114, positions 163 to 170, positions 187 to 193, and positions 226 to 235 of SEQ ID NO: 8, respectively; (g) an antibody of which heavy chain CDRs 1, 2, and 3 and light chain CDRs 1, 2, and 3 comprise the amino acid sequences set forth in positions 31 to 35, positions 50 to 66, positions 99 to 120, positions 169 to 176, positions 193 to 199, and positions 232 to 241 of SEQ ID NO: 9, respectively; (h) an antibody of which heavy chain CDRs 1, 2, and 3 and light chain CDRs 1, 2, and 3 comprise the amino acid sequences set forth in positions 31 to 35, positions 50 to 65, positions 98 to 113, positions 162 to 171, positions 188 to 194, and positions 227 to 237 of SEQ ID NO: 10, respectively; (i) an antibody of which heavy chain CDRs 1, 2, and 3 and light chain CDRs 1, 2, and 3 comprise the amino acid sequences set forth in positions 31 to 35, positions 50 to 65, positions 98 to 114, positions 163 to 170, positions 187 to 193, and positions 226 to 235 of SEQ ID NO: 11, respectively; (j) an antibody of which heavy chain CDRs 1, 2, and 3 and light chain CDRs 1, 2, and 3 comprise the amino acid sequences set forth in positions 31 to 35, positions 50 to 66, positions 99 to 113, positions 162 to 169, positions 186 to 192, and positions 225 to 234 of SEQ ID NO: 12, respectively; (k) an antibody of which heavy chain CDRs 1, 2, and 3 and light chain CDRs 1, 2, and 3 comprise the amino acid sequences set forth in positions 31 to 35, positions 50 to 66, positions 99 to 116, positions 165 to 174, positions 191 to 197, and positions 230 to 240 of SEQ ID NO: 13, respectively; (l) an antibody of which heavy chain CDRs 1, 2, and 3 and light chain CDRs 1, 2, and 3 comprise the amino acid sequences set forth in positions 31 to 35, positions 50 to 66, positions 99 to 113, positions 162 to 169, positions 186 to 192, and positions 225 to 235 of SEQ ID NO: 14, respectively; (m) an antibody of which heavy chain CDRs 1, 2, and 3 and light chain CDRs 1, 2, and 3 comprise the amino acid sequences set forth in positions 31 to 35, positions 50 to 66, positions 99 to 113, positions 162 to 170, positions 187 to 193, and positions 226 to 236 of SEQ ID NO: 15, respectively; (n) an antibody of which heavy chain CDRs 1, 2, and 3 and light chain CDRs 1, 2, and 3 comprise the amino acid sequences set forth in positions 31 to 35, positions 50 to 66, positions 99 to 110, positions 159 to 166, positions 183 to 189, and positions 222 to 237 of SEQ ID NO: 16, respectively; (o) an antibody of which heavy chain CDRs 1, 2, and 3 and light chain CDRs 1, 2, and 3 comprise the amino acid sequences set forth in positions 31 to 35, positions 50 to 65, positions 98 to 113, positions 162 to 171, positions 188 to 194, and positions 227 to 237 of SEQ ID NO: 17, respectively; (p) an antibody of which heavy chain CDRs 1, 2, and 3 and light chain CDRs 1, 2, and 3 comprise the amino acid sequences set forth in positions 31 to 35, positions 50 to 66, positions 99 to 116, positions 165 to 174, positions 191 to 197, and positions 230 to 240 of SEQ ID NO: 18, respectively; (q) an antibody of which heavy chain CDRs 1, 2, and 3 and light chain CDRs 1, 2, and 3 comprise the amino acid sequences set forth in positions 31 to 35, positions 50 to 66, positions 99 to 115, positions 164 to 175, positions 193 to 199, and positions 232 to 241 of SEQ ID NO: 19, respectively; (r) an antibody of which heavy chain CDRs 1, 2, and 3 and light chain CDRs 1, 2, and 3 comprise the amino acid sequences set forth in positions 31 to 35, positions 50 to 66, positions 99 to 117, positions 166 to 177, positions 194 to 200, and positions 233 to 242 of SEQ ID NO: 20, respectively; (s) an antibody of which heavy chain CDRs 1, 2, and 3 and light chain CDRs 1, 2, and 3 comprise the amino acid sequences set forth in positions 32 to 36, positions 51 to 67, positions 100 to 114, positions 163 to 171, positions 188 to 194, and positions 227 to 236 of SEQ ID NO: 21, respectively; (t) an antibody of which heavy chain CDRs 1, 2, and 3 and light chain CDRs 1, 2, and 3 comprise the amino acid sequences set forth in positions 31 to 35, positions 50 to 65, positions 98 to 114, positions 163 to 170, positions 187 to 193, and positions 226 to 235 of SEQ ID NO: 22, respectively; and (u) any antibody of the (a) to (t) wherein the any antibody comprises one or several substitutions, additions, or deletions in a framework of the any antibody, but is free of a mutation in the CDRs. These antibodies may have positions 33 to 61 of SEQ ID NO: 2; positions 339 to 358 and/or 388 to 421 positions of SEQ ID NO: 2; or positions 430 to 530 of SEQ ID NO: 2 as an epitope. These antibodies may be an antibody selected from monoclonal antibody, polyclonal antibody, chimeric antibody, humanized antibody, human antibody, multifunctional antibody, bispecific or oligospecific antibody, single chain antibody, scFV, diabody, sc(Fv)$_2$ (single chain (Fv)$_2$), and scFv-Fc.

In yet another aspect, the present invention provides an antibody or a fragment or a functional equivalent thereof, the antibody having positions 33 to 61 of SEQ ID NO: 2; positions 339 to 358 and/or positions 388 to 421 of SEQ ID NO: 2; or positions 430 to 530 of SEQ ID NO: 2 as an epitope. These antibodies may be an antibody selected from monoclonal antibody, polyclonal antibody, chimeric antibody, humanized antibody, human antibody, multifunctional antibody, bispecific or oligospecific antibody, single chain antibody, scFV, diabody, sc(Fv)$_2$ (single chain (Fv)$_2$), and scFv-Fc.

In still another aspect, the present invention provides a treatment method, prevention method, use, and the like using a pharmaceutical composition, therapeutic agent or prophylactic agent of the present invention.

It is understood that one or more of the aforementioned features can be further combined for use.

Those skilled in the art who have read and understood the following Detailed Description as needed would recognize further embodiments and advantages of the present invention.

Advantageous Effects of Invention

According to the present invention, an effective marker for esophageal cancer is provided, and further it was found that the marker can be utilized in the treatment or prevention of esophageal cancer. Therefore, it is possible to carry out diagnosis, treatment, or prevention of esophageal cancer in an early stage, which was previously impossible or difficult.

BRIEF DESCRIPTION OF DRAWINGS

FIG. 2 The upper row in FIG. 2 is a result showing the relative expression level of Glypican-1 (Accession No. P35052) using iTRAQ. The lower row is an explanation of cells used for iTRAQ used in the present examples.

FIG. 4B is a photograph showing the expression of Glypican-1 in normal esophageal epithelium (left) and in esophageal squamous cell carcinoma (right). An antibody used is HPA030571 from Atlas Antibodies. The upper one shows 100 times magnification and the lower one shows 400 times magnification. It was shown that Glypican-1 was highly expressed in esophageal squamous cell carcinoma.

FIG. 4C is a photograph showing that Glypican-1 also exhibits high expression in lymph node metastasis sites of esophageal cancer. The left shows a normal lymph node, the right shows esophageal cancer lymph node metastasis sites. The upper shows 100 times and the lower one shows 400 times.

FIG. 4D shows that in esophageal squamous cell carcinoma patients, the survival rate of Glypican-1 high expression group is higher than that of low expression group. The horizontal axis indicates a lifetime and the vertical axis indicates a survival rate. The low expression group represents those having a level of 3 or less wherein n=35 and the high expression group represents those having a level of 4 or more wherein n=53. The level was calculated by rating the stain intensity by three grades from 0 to 2 and the area by four grades from 0 to 3 as the scores of an immunohistochemical staining method, and obtaining the product of them as a stain score. In the Log-rank test, the case of p<0.001 referred to statistically significant.

FIG. 9 is a figure showing apoptosis by expression suppression using siRNA against Glypican-1. Targeted cell strains are TE6 and TE8 shown from the left in the upper row, and TE14 shown in the lower row. The vertical axis of the graphs shows the activity of caspase-3 as indication of apoptosis in A.U. per mg of protein. In each experiment, three types of experiments were carried out: an experiment without siRNA (No treatment), an experiment using negative control siRNA (Negative Control siRNA), and an experiment using siRNA against Glypican-1 (GPC-1 siRNA). In the graphs, NS denotes no significant difference and the numerical value following p indicates statistical significance with a critical rate in the case of a numerical value shown. In the esophageal cancer cell strain, the expression suppression using siRNA against GPC-1 induced apoptosis. It should be noted that in normal cells (HEEpic), as Glypican-1 negative cells, there is no targeted sequence even if siRNA against Glypican-1 is transfected, and accordingly it is presumed that any change in the cells is not found.

FIG. 10A is a Western blot study that observes fluctuations in the activation of serine-threonine kinase AKT (another name of Protein Kinase B) from expression suppression using siRNA against GPC-1 in an esophageal cancer cell strain. As targeted esophageal cancer cells, TE6, TE8, and TE14 were used. From the top, there are experimental results carried out using a specific antibody against pAKT (Thr308) (the phosphorylation site is Thr308), a specific antibody against pAKT (Ser473) (the phosphorylation site is Ser473), an antibody against total Akt, an antibody against cleaved caspase3, an antibody against GAPDH (negative control). For each cell, three types of experiments were carried out: from the left, an experiment without siRNA (No treatment); an experiment using negative control siRNA (Negative Control siRNA); and an experiment using siRNA against Glypican-1 (GPC-1 siRNA). Expression suppression using siRNA against GPC-1 in an esophageal cancer cell strain suppressed the activation of AKT. It should be noted that in normal cells (HEEpic), as Glypican-1 negative cells, there is no targeted sequence even if siRNA against Glypican-1 is transfected, and accordingly it is presumed that any change in the cells is not found.

FIG. 10B shows that in an esophageal cancer cell strain, an increase in the expression of pre-apoptotic protein and a decrease in the expression of anti-apoptotic protein are seen from expression suppression of GPC1. The left panel of Western blots (24 hours) shows the appearance of Bak, Puma, and GAPDH from the top, and shows No treatment, Negative control siRNA, and GPC-1 siRNA from the left column. The right panel shows after 48 hours, and shows bands of Bik, Bim, Bad, Bcl-w, and GAPDH from the top. It shows No treatment, negative control siRNA, and GPC-1 siRNA from the left column.

FIG. 12 shows a calculation result of a dissociation constant by Biacore analysis. The leftmost column shows the antibody number, the second left column shows Ka (1/Ms), the second right column shows Kd (1/s), and the rightmost column shows $K_D$.

FIG. 15 is a figure showing that in the anti-GPC-1 mABs (#7 and #9), an epitope region is present in the 33rd to the 61st amino acids. The upper section shows, from the left, clones 1-5, 1-12, 1-28, and 1-57 (#2, #4, #7, and #10, respectively) and the lower section shows, from the left, clones 2-60, 2-63, and 2-70 (#17, #18, and #19, respectively). The gray-painted peaks indicate histograms where the 293 cell was stained by respective clones, the white peaks indicate histograms where the 293 cell expressing human GPC1 in which the 33rd to the 61st amino acids had been deleted was stained with respective clones.

FIG. 16A shows the epitope analysis of an anti-GPC-1 antibody using human GPC-1/GPC-3 chimeric proteins. The upper row shows the structure of a pFLAG=CMV3 vector, and human GPC-1 and human GPC-3 are shown in order from the top. A part of the amino acid sequence of human GPC-1 was substituted with human GPC-3. The chimeric protein is shown in the bottom.

FIG. 16B shows an epitope analysis result of an antibody of the present invention. The left panel is a figure where amino acid positions of epitopes in GPC-1 (SEQ ID NO: 2) are surrounded with squares. The right column shows the amino acid positions of an epitope for each antibody. As shown, an epitope for an antibody of the present invention is present in positions 33 to 61 (#7 and #19); positions 339 to 358 and/or positions 388 to 404 and/or positions 405 to 421 (#4, since positions 388 to 404 and positions 405 to 421 are continuous, it is shown as positions 388 to 421); or positions 430 to 530 (#2, #10, and #17).

FIG. 17 (A to D) shows an epitope analysis result of an anti-GPC antibody using a human GPC-1/GPC-3 chimeric protein. In FIG. 17A, the left column shows a result of using an anti-FLAG-M2 and the right column shows a result of using anti-GPC-1 mAb #4. From the top, results of using a pFLAG-CMV3 vector, pFLAG-CMV3 hGPC1, pFLAG-CMV3 hGPC3, a human GPC1/GPC3 chimeric protein are shown. Since the original figure is drawn by red and blue colors, the blue color is indicated by an arrow. The arrows indicate histograms where various vectors were gene-transferred into the 293 cell and then the cell expressing a protein was reacted with an anti-FLAG-M2 antibody or clone 1-12 (#4).

FIG. 17 (A to D) shows an epitope analysis result of an anti-GPC antibody using a human GPC-1/GPC-3 chimeric protein. In FIG. 17B, the left column is a result of using an anti-GPC-1 mAb #7 and the right column shows a result of using an anti-GPC-1 mAb #17. From the top, results of using a pFLAG-CMV3 vector, pFLAG-CMV3 hGPC1, pFLAG-CMV3 hGPC3, and a human GPC1/GPC3 chimeric protein are shown. Since the original figure is drawn by red and blue colors, the blue color is indicated by an arrow. The arrows indicate histograms where various vectors were gene-transferred into the 293 cell and then the cell expressing a protein was reacted with clones 1-28 and 2-60 (#7 and #17, respectively).

FIG. 17 (A to D) shows an epitope analysis result of an anti-GPC antibody using a human GPC-1/GPC-3 chimeric protein. FIG. 17C is a result of using an anti-GPC-1 mAb #18 and the right column shows a result of using an anti-GPC-1 mAb #19. From the top, results of using a pFLAG-CMV3 vector, pFLAG-CMV3 hGPC1, pFLAG-CMV3 hGPC3, and a human GPC1/GPC3 chimeric protein are shown. Since the original figure is drawn by red and blue colors, the blue color is indicated by an arrow. The arrows indicate histograms where various vectors were gene-transferred into the 293 cell and then the cell expressing a protein was reacted with clones 2-63 and 2-70 (#18 and #19, respectively).

FIG. 17 (A to D) shows an epitope analysis result of an anti-GPC antibody using a human GPC-1/GPC-3 chimeric protein. FIG. 17D is a result of using an anti-GPC-1 mAb #2 and the right column shows a result of using an anti-GPC-1 mAb #10. From the top, results of using a pFLAG-CMV3 vector, pFLAG-CMV3 hGPC1, pFLAG-CMV3 hGPC3, and a human GPC1/GPC3 chimeric protein are shown. Since the original figure is drawn by red and blue colors, the blue color is indicated by an arrow. The arrows indicate histograms where various vectors were gene-transferred into the 293 cell and then the cell expressing a protein was reacted with clones 1-5 and 1-57 (#2 and #10, respectively).

The vertical axis indicates tumor weight (mg). The statistical significance was confirmed by one way ANOVA and Dunnett's test. Anti-GPC antibody #4 was statistically significant at p<0.01.

Figure 23:
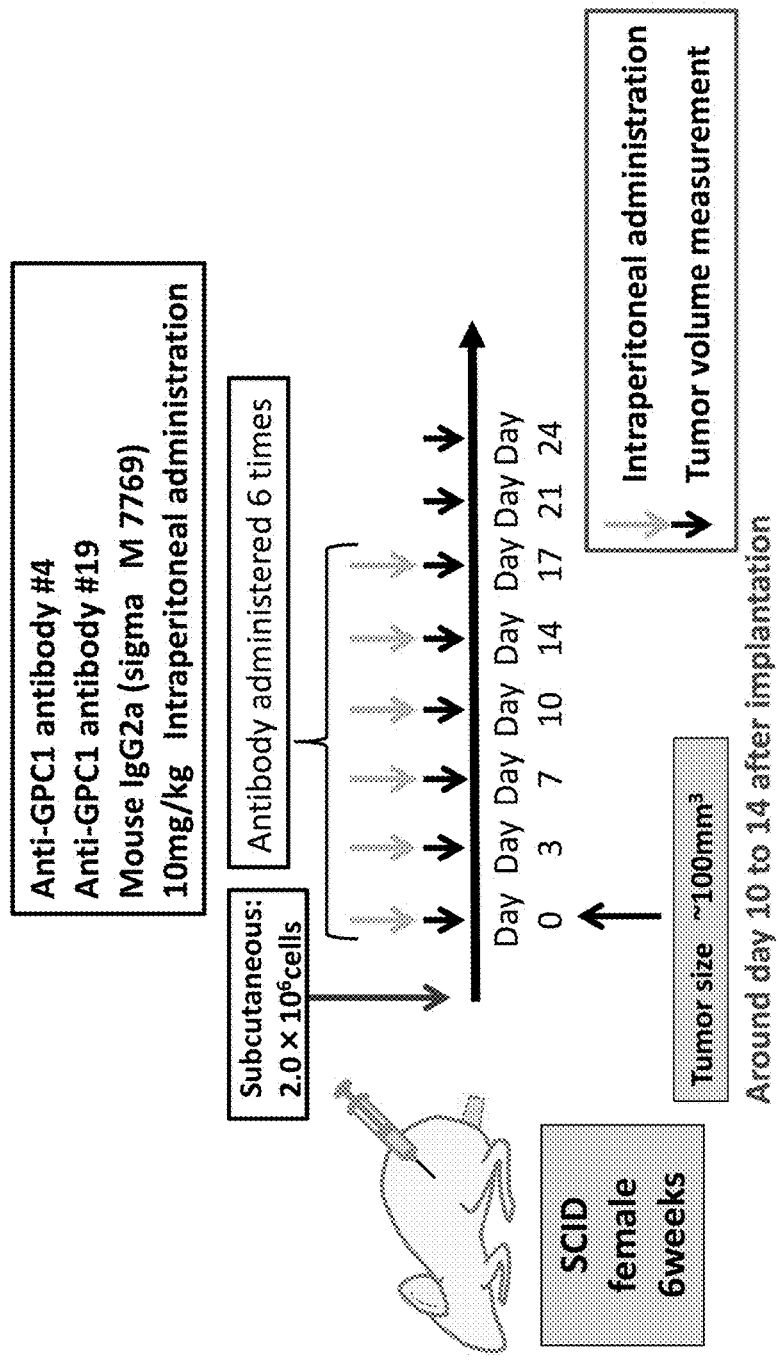

FIG. 23 shows an examination of antitumor effect of an anti-GPC1 antibody on a GPC1 negative cell strain (LK2 xenograft model). As shown, anti-GPC1 antibodies #4 and #19 were used and mouse IgG2a (Sigma M7769) were used. Intraperitoneal administration of 10 mg/kg was carried out. As a model, SCID 6-week-old female mice were used. First, $2 \times 10^6$ cells (LK2) were subcutaneously implanted. The antibody amount was 200 μg per 20 g of body weight. The tumor size reached about 100 mm$^3$ (10 to 14 days after the implantation). Each of the antibodies was administered 6 times. In addition, the tumor volume was measured out two times after the administration (Day 21 and Day 24).

Figure 24:
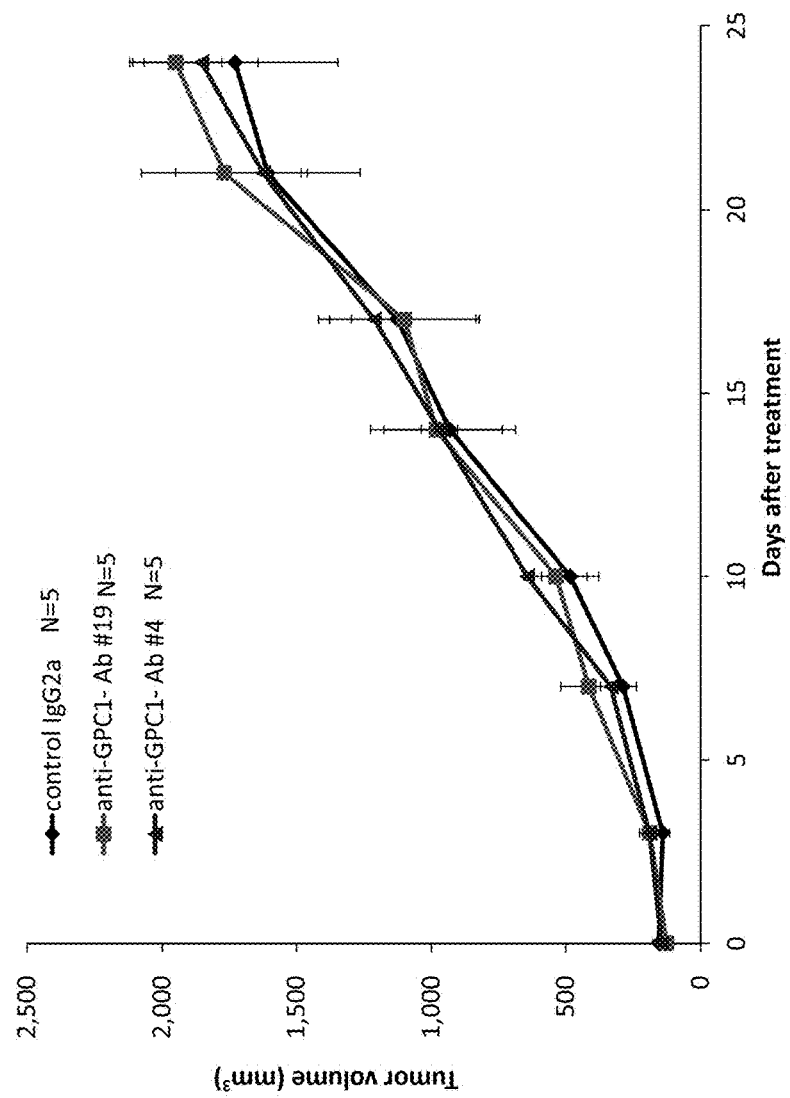

FIG. 24 shows that anti-GPC antibodies do not exhibit an antitumor effect on a GPC1 negative cell strain in vivo (LK2 xenograft model). The vertical axis indicates tumor volume (mm$^3$). The rhombuses indicate control IgG2a (N=5), the squares indicate anti-GPC-1 antibody #19 (N=5), and the triangles indicate anti-GPC-1 antibody #4 (N=5). The statistical significance was confirmed by one way ANOVA and Dunnett's test.

Figure 25:
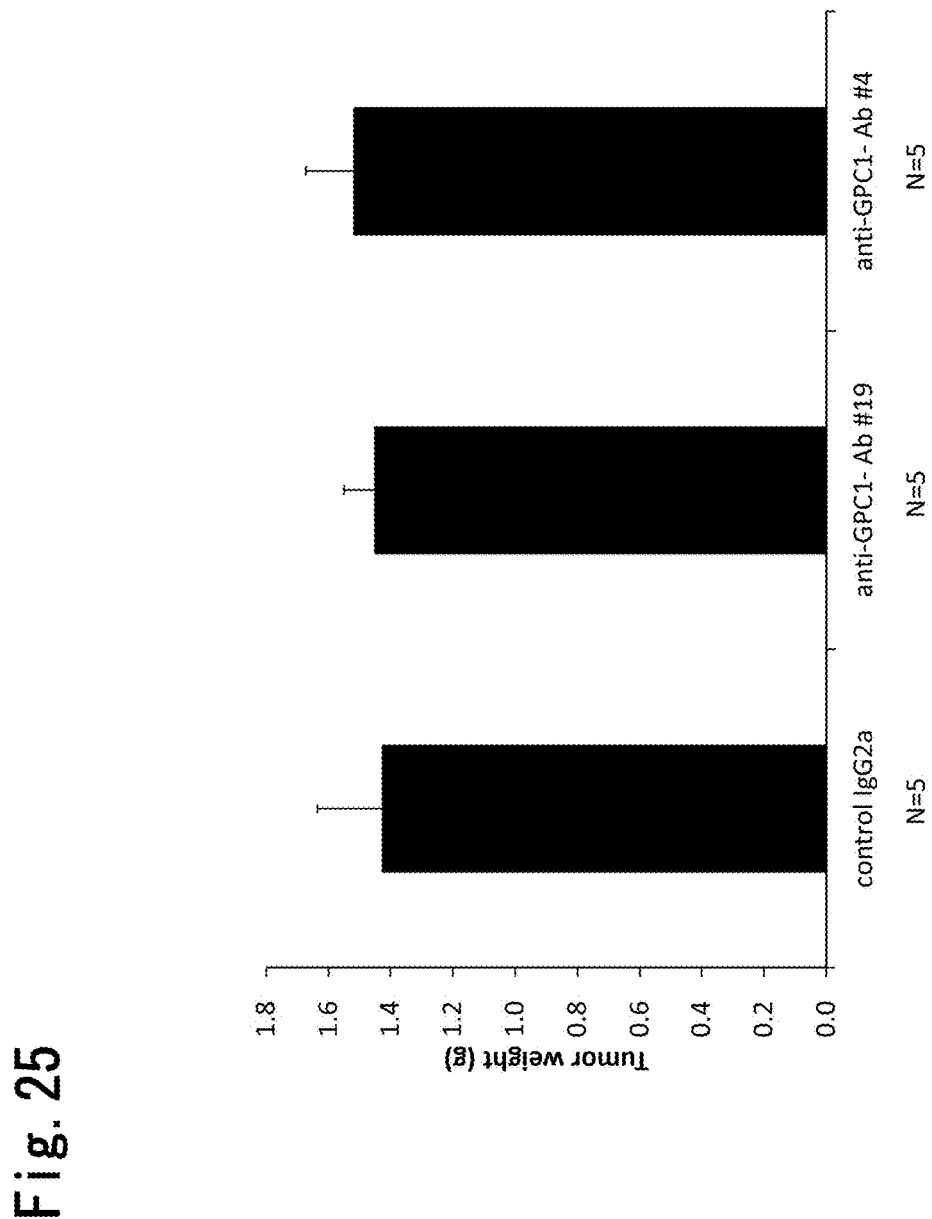

FIG. 25 shows that anti-GPC antibodies do not exhibit an antitumor effect on a GPC1 negative cell strain in vivo (LK2 xenograft model). From the left, control IgG2a, anti-GPC-1 antibody #19, and anti-GPC-1 antibody #4 are shown. All of them are at N=5. The vertical axis indicates tumor weight (g). The statistical significance was confirmed by one way ANOVA and Dunnett's test. All the antibodies were statistically significant at p<0.001.

FIG. 26 shows the protocol for a safety test on an anti-GPC1 antibody using a mouse. 1 mg/body weight of mouse IgG2a (Sigma M7769) and anti-GPC-1 antibody #4 was intraperitoneally administered to C57BL/6J (8 weeks old) to assess the following items on day 7. The brain, heart, kidney, liver, lung and spleen are selected as the extracted organs. The measured items include while blood cell (WBC), red blood cell (RBC), hemoglobin (Hb), platelet (Plt), total bilirubin (T-Bil), alanine aminotransferase (ALT), alkaline phosphatase (ALP), amylase (Amy), blood urea nitrogen (BUN), chrome (Cr), calcium (Ca), phosphorus (P), total protein (TP), albumin (Alb), sodium (Na), potassium (K), globulin (Globn), and glutamine (Glu). VetScan HMII was used as an automated blood cell counter, and VetScan VS2 was used as a veterinary biochemical blood analyzer.

FIG. 27 shows a comparison of control IgG versus anti-GPC1 antibody (female). In the Table, the left column shows the items, the second column from the left shows control IgG (n=3), the third column shows anti-GPC-1 antibodies (n=3), the second column from the right shows normal values, and the right end shows the p value (statistical significance in Student's t-test). In addition to the abbreviations described in FIG. 26, Ly denotes a lymphocyte and Mo denotes a monocyte. Gr denotes a granulocyte and Hct denotes a hematocrit value.

FIG. 28 shows a comparison of control IgG versus anti-GPC1 antibody (female). Each of the values is the same as that in FIGS. 26 to 27.

FIG. 29 shows a comparison of control IgG versus anti-GPC1 antibody (male). In the Table, the left column shows the items, the second column from the left shows control IgG (n=3), the third column shows anti-GPC-1 antibodies (n=3), the second column from the right shows normal values, and the right end shows the p value (statistical significance in Student's t-test). They are the same as the abbreviations described in FIG. 26.

FIG. 30 shows a comparison of control IgG versus anti-GPC1 antibody (female). Each of the values is the same as that in FIGS. 26 to 27 and 29.

DESCRIPTION OF EMBODIMENTS

The embodiments of the present invention are described in detail hereinafter. It should be noted that descriptions are omitted when appropriate for the same content in order to avoid complicating the content by repeating. Throughout the entire specification, a singular expression should be understood as encompassing the concept thereof in the plural form, unless specifically noted otherwise. Thus, singular articles (e.g., "a", "an", "the" and the like in case of English) should also be understood as encompassing the concept thereof in the plural form unless specifically noted otherwise. Further, the terms used herein should be understood as being used in the meaning that is commonly used in the art, unless specifically noted otherwise. Thus, unless defined otherwise, all terminologies and scientific technical terms that are used herein have the same meaning as the terms commonly understood by those skilled in the art to which the present invention pertains. In case of a contradiction, the present specification (including the definitions) takes precedence.

First, explanations are provided for the terms and general techniques used in the present invention.

As used herein, "Glypican-1", "GPC-1", or "GPC1" is a term to be interchangeably used, is a glycosylphosphatidylinositol (GPI) anchored cell surface proteoglycan, and is a substance having heparan sulfate. It is presumed to be related to cell adhesion, migration, lipoprotein metabolism, growth factor activity modulation and blood coagulation inhibition. It is said to be bound to different fibroblast growth factors (FGF), for example, FGF-1, FGF-2, and FGF-7. Glypican-1 is presumed to function as an extracellular chaperon of VEGF165, and to support recovery of receptor binding ability after oxidation. With regard to Glypican, six types, Glypican-1 to Glypican-6, are currently known. However, with respect to cancer, even though they are Glypican-family members, they are not always recognized as cancer markers and the members seem to have no relation to one another. Glypican-1 is registered to have accession number P35052 in UniProt. In addition to this, it is registered in NCBI as NP_002072.2 (precursor amino acid sequence) and NM_002081.2 (mRNA) and in EMBL, GenBank, and DDBJ as X54232.1 (mRNA), BC051279.1 (mRNA), and AC110619.3 (genomic). All these are information available in the present specification and the information is incorporated herein by reference. For Glypican-1, refer to David G et al., J Cell Biol. 1990 December; 111(6 Pt 2):3165-76; Haecker U et al., Nat Rev Mol Cell Biol 2005 July; 6(7):530-41; Aikawa T et al., J Clin Invest. 2008 January; 118(1):89-99; Matsuda K, et al., Cancer Res. 2001 Jul. 15; 61(14):5562-9; and the like. With regard to the nucleic acid sequence (full length) of human Glypican-1, SEQ ID NO: 1 is a representative example, and with the regard to the amino acid sequence, SEQ ID NO: 2 is a representative example. When "Glypican-1", "GPC-1", or "GPC1" is used for an objective of the present specification, it is understood that not only proteins (or nucleic acid encoding the same) having an amino acid sequence set forth in a specific sequence identification number or accession number, but also a functionally active analog or derivative thereof, a functionally active fragment thereof or homolog thereof, or a mutant encoded by a nucleic acid which hybridizes to a nucleic acid encoding said protein under a highly stringent condition or lowly stringent condition can also be used in the present invention, as long as they align with the specific objective of the present invention.

As used herein, "derivative", "analog", or "mutant" preferably includes, but is not intended to be limited to, molecules comprising a region substantially homologous to a target protein (e.g., Glypican-1). Such a molecule, in various embodiments, is at least 30%, 40%, 50%, 60%, 70%, 80%, 90%, 95% or 99% identical throughout the amino acid sequence of the same size or in comparison to a sequence aligned by a homology computer program known in the art. Alternatively, a nucleic acid encoding such a molecule can hybridize to a sequence encoding the constituent protein under a (highly) stringent condition, moderately stringent condition, or non-stringent condition. This refers to a product of altering a naturally-occurring protein by an amino acid substitution, deletion and addition, respectively, a protein whose derivative exhibits the biological function of the naturally-occurring protein, although not necessarily to the same degree. For instance, the biological function of such a protein can be investigated by a suitable and available in vitro assay described herein or known in the art. As used herein, "functionally active" refers to polypeptides, i.e., fragments or derivatives, having a structural function, regulatory function, or biochemical function of a protein such as biological activity in accordance with an embodiment associated with the polypeptides, i.e., fragments or derivatives, of the present invention. Although the present invention mainly discusses human Glypican-1, it is known that many animals other than human, such as chimpanzee (Pantroglodytes) (K7B6W5), rhesus monkey (Macaca mulatta) (F6VPW9), mouse (Mus musculus) (Q9QZF2), rat (Rattus norvegicus) (P35053), chicken (Gallus callus) (F1P150), and the like, express the Glypican-1 protein. Therefore, it is understood that these animals, particularly mammals, fall within the scope of the present invention. Preferably, functional domains of Glypican-1, for example, an extracellular domain (which is about 500 amino acids and contains twelve cysteine residues) and a C-terminal hydrophobic region (GPI-anchor domain), are preferable to be conserved.

A fragment of Glypican-1 in the present invention is a polypeptide comprising any region of the Glypican-1. As long as such a fragment serves the function of interest (e.g., marker or therapeutic target) of the present invention, it is not necessary that the fragment has biological functions of naturally-occurring Glypican-1.

Thus, a representative nucleotide sequence of Glypican-1 may be:
(a) a polynucleotide having a base sequence set forth in SEQ ID NO: 1 or a fragment sequence thereof;
(b) a polynucleotide encoding a polypeptide consisting of the amino acid sequence set forth in SEQ ID NO: 2 or a fragment thereof;
(c) a polypeptide encoding a variant polypeptide having a mutation selected from the group consisting of a substitution, addition, and deletion of one or more amino acids in the amino acid sequence set forth in SEQ ID NO: 2, the variable polypeptide having biological activity, or a fragment thereof;
(d) a polynucleotide, which is a splice mutant or an allelic mutant of the base sequence set forth in SEQ ID NO: 1, or a fragment thereof;
(e) a polynucleotide encoding a species homolog of a polypeptide consisting of the amino acid sequence set forth in SEQ ID NO: 2, or a fragment thereof;
(f) a polynucleotide encoding a polypeptide, which hybridizes with the polynucleotide of any one of (a) to (e) under stringent conditions and has biological activity; or
(g) a polynucleotide encoding a polypeptide consisting of abase sequence, which is at least 70%, at least 80%, at least 90%, at least 95%, at least 96%, at least 97%, at least 98%, or at least 99% identical to the polynucleotide of any one of (a) to (e) or a complementary sequence thereof and has biological activity. Biological activity in this regard typically refers to the property of being distinguishable from other proteins that are present in the same organism as a marker or activity of Glypican-1.

The amino acid of Glypican-1 may be
(a) a polypeptide consisting of the amino acid sequence set forth in SEQ ID NO: 2 or a fragment thereof;
(b) a polypeptide, which has a mutation selected from the group consisting of a substitution, addition, and deletion of one or more amino acids in the amino acid sequence set forth in SEQ ID NO: 2 and has biological activity;
(c) a polypeptide encoded by a splice mutant or an allelic mutant of the base sequence set forth in SEQ ID NO: 1;
(d) a polypeptide, which is a species homolog of the amino acid sequence set forth in SEQ ID NO: 2;
(e) a polypeptide, which has an amino acid sequence that is at least 70%, at least 80%, at least 90%, at least 95%, at least 96%, at least 97%, at least 98% or at least 99% identical to the polypeptide of any one of (a) to (d) and has biological activity.

Biological activity in this regard typically refers to the property of being distinguishable from other proteins that are present in the same organism as a marker or activity of Glypican-1 (for example, when used as an antigen, a property of comprising a region that can function as a specific epitope).

In the context of the present invention, "substance that binds to Glypican-1", "Glypican-1 binding agent", or "Glypican-1 interaction molecule" is a molecule or substance that binds at least transiently to Glypican-1. For detection purposes, it is preferable that such a molecule or substance is advantageously capable of indicating that the molecule or substance is bound (for example, labelled or in a labelable state). For therapeutic purposes, it is more advantageous that such a molecule or substance is bound to a therapeutic agent. Examples of a substance that binds to Glypican-1 include antibodies, antisense oligonucleotides, siRNAs, low molecular weight molecules (LMW), binding peptides, aptamers, ribozymes, peptidomimetics and the like. A substance that binds to Glypican-1 or a Glypican-1 interaction molecule may be a Glypican-1 inhibitor, and encompasses, for instance, binding proteins or binding peptides directed to Glypican-1, especially those directed to an active site of Glypican-1, as well as nucleic acids directed to a gene of Glypican-1. A nucleic acid directed to Glypican-1 refers to, for example, a double stranded or single stranded DNA or RNA inhibiting the expression of a Glypican-1 gene or activity of Glypican-1 or a modified product or derivative thereof, including, but not limited to, antisense nucleic acids, aptamers, siRNAs (small interfering RNA) and ribozymes. As used herein, "binding protein" or "binding peptide", with respect to Glypican-1, refers to any protein or peptide that binds to the Glypican-1, including, but not limited to, antibodies directed to the Glypican-1 (e.g., polyclonal antibodies or monoclonal antibodies), antibody fragments and functional equivalents.

As used herein, "protein", "polypeptide", "oligopeptide" and "peptide" are used herein in the same meaning and refer to an amino acid polymer of any length. The polymer may be straight, branched or cyclic. An amino acid may be a naturally-occurring, non-naturally occurring or altered amino acid. The term may also encompass those assembled into a complex of multiple polypeptide chains. The term also encompasses naturally-occurring or artificially altered amino acid polymers. Examples of such an alteration include disulfide bond formation, glycosylation, lipidation, acetylation, phosphorylation, and any other manipulation or alteration (e.g., conjugation with a labeling component). The definition also encompasses, for example, polypeptides comprising one or more analogs of an amino acid (e.g., including non-naturally occurring amino acids and the like), peptide-like compounds (e.g., peptoids) and other alterations in the art. As used herein, "amino acid" is a general term for organic compounds with an amino group and a carboxyl group. When the antibody according to an embodiment of the present invention comprises a "specific amino acid sequence", any of the amino acids in the amino acid sequence may be chemically modified. Further, any of the amino acids in the amino acid sequence may be forming a salt or a solvate. Further, any of the amino acids in the amino acid sequence may have an L form or a D form. Even for such cases, the protein according to an embodiment of the present invention is considered as comprising the above-described "specific amino acid sequence". Examples of known chemical modifications applied to an amino acid comprised in a protein in a living body include modifications of the N-terminus (e.g., acetylation, myristylation and the like), modifications of the C-terminus (e.g., amidation, addition of glycosylphosphatidylinositol and the like) modifications of a side chain (e.g., phosphorylation, glycosylation and the like) and the like. The amino acid may be naturally-occurring or non-naturally occurring, as long as the objective of the present invention is met.

As used herein, "polynucleotide", "oligonucleotide" and "nucleic acid" are used herein in the same meaning, and refer to a polymer of nucleotides with any length. The terms also encompass "oligonucleotide derivative" and "polynucleotide derivative". "Oligonucleotide derivative" and "polynucleotide derivative" refer to an oligonucleotide or polynucleotide that comprises a nucleotide derivative or has a bond between nucleotides which is different from normal. The terms are used interchangeably. Specific examples of such an oligonucleotide include 2'-O-methyl-ribonucleotide, oligonucleotide derivatives having a phosphodiester bond in an oligonucleotide converted to a phosphorothioate bond, oligonucleotide derivatives having a phosphodiester bond in an oligonucleotide converted to an N3'-P5'' phosphoramidate bond, oligonucleotide derivatives having ribose and phosphodiester bond in an oligonucleotide converted to a peptide nucleic acid bond, oligonucleotide derivatives having uracil in an oligonucleotide replaced with C-5 propynyluracil, oligonucleotide derivatives having uracil in an oligonucleotide replaced with C-5 thiazoleuracil, oligonucleotide derivatives having cytosine in an oligonucleotide replaced with C-5 propynylcytosine, oligonucleotide derivatives having cytosine in an oligonucleotide replaced with phenoxazine-modified cytosine, oligonucleotide derivatives having ribose in DNA replaced with 2'-O-propylribose, oligonucleotide derivatives having ribose in an oligonucleotide replaced with 2'-methoxyethoxyribose and the like. Unless noted otherwise, specific nucleic acid sequences are also intended to encompass conservatively altered variants (e.g., degenerate codon substitute) and complement sequences as well as the expressly shown sequences. Specifically, degenerate codon substitutes can be achieved by preparing a sequence with the third position of one or more selected (or all) codons substituted with a mixed base and/or deoxyinosine residue (Batzer et al., Nucleic Acid Res. 19: 5081 (1991); Ohtsuka et al., J. Biol. Chem. 260: 2605-2608 (1985); Rossolini et al., Mol. Cell. Probes 8: 91-98 (1994)). As used herein, "nucleic acid" is used interchangeably with a gene, cDNA, mRNA, oligonucleotide, and polynucleotide. As used herein, "nucleotide" may be a naturally-occurring or non-naturally occurring.

As used herein, "gene" refers to an agent defining a genetic trait. "Gene" may refer to "polynucleotide", "oligonucleotide" and "nucleic acid".

As used herein, "homology" of genes refers to the level of identity of two or more genetic sequences with one another. In general, having "homology" refers to having a high-level of identity or similarity. Thus, two genes with high homology have higher identity or similarity of sequences. It is possible to investigate whether two types of genes are homologous by direct comparison of sequences or, for nucleic acids, by a hybridization method under a stringent condition. When two genetic sequences are directly compared, the genes are homologous when DNA sequences are representatively at least 50% identical, preferably at least 70% identical, and more preferably at least 80%, 90%, 95%, 96%, 97%, 98%, or 99% identical between the genetic sequences. Thus, as used herein, "homolog" or "homologous gene product" refers to a protein in another species, preferably mammal, exerting the same biological function as a protein constituent of a complex which will be further described herein. Such a homolog is also called "ortholog gene product". It is understood that such a homolog, homologous gene product, ortholog gene product, or the like can also be used, as long as they are in alignment with the objective of the present invention.

Amino acids may be mentioned herein by either their commonly known three letter symbols or their one character symbols recommended by the IUPAC-IUB Biochemical Nomenclature Commission. Similarly, nucleotides may be mentioned by their commonly recognized one character codes. Comparison of similarity, identity and homology of an amino acid sequence and a base sequence is calculated herein by using a default parameter using a sequence analysis tool, BLAST. For example, identity can be searched by using BLAST 2.2.28 (published on Apr. 2, 2013) of the NCBI. Herein, values for identity generally refer to a value obtained by alignment under the default condition using the above-described BLAST. However, when a higher value is obtained by changing a parameter, the highest value is considered the value of identity. When identity is evaluated in a plurality of regions, the highest value thereamong is considered the value of identity. Similarity is a value calculated by taking into consideration a similar amino acid in addition to identity.

In one embodiment of the present invention, "several" may be, for example, 10, 8, 6, 5, 4, 3 or 2, or a value less than any one of the values. It is known that a polypeptide with one or several amino acid residue deletions, additions, insertions, or substitutions by other amino acids maintains its biological activity (Mark et al., Proc Natl Acad Sci USA. 1984 September; 81 (18): 5662-5666. Zoller et al., Nucleic Acids Res. 1982 Oct. 25; 10(20): 6487-6500. Wang et al., Science. 1984 Jun. 29; 224 (4656): 1431-1433.). An antibody with a deletion or the like can be made, for example, by site-directed mutagenesis, random mutagenesis, biopanning using an antibody phage library or the like. For example, KOD-Plus-Mutagenesis Kit (TOYOBO CO., LTD.) can be used for site-directed mutagenesis. An antibody with the same activity as the wild-type can be selected from mutant antibodies introduced with a deletion or the like by performing various characterizations such as FACS analysis and ELISA.

In one embodiment of the present invention, "90% or greater" may be, for example, 90, 95, 96, 97, 98, 99 or 100% or greater or within the range of any two values described above. For the above-described "homology", the percentage of the number of homologous amino acids in two or a plurality of amino acid sequences may be calculated in accordance with a known method in the art. Before calculating the percentage, amino acid sequences in a group of amino acid sequences to be compared are aligned. A space is introduced in a portion of amino acid sequences when necessary to maximize the percentage of the same amino acids. An alignment method, method of calculating the percentage, comparison method, and computer programs associated therewith have been well known in the art (e.g., BLAST, GENETYX and the like). As used herein, "homology" can be represented by a value measured with BLAST of the NCBI, unless specifically noted otherwise. Blastp can be used in the default setting for an algorithm for comparing amino acid sequences with BLAST. Results of measurement are expressed in a numerical form as Positives or Identities.

As used herein, "polynucleotide which hybridizes under a stringent condition" refers to commonly used, well-known conditions in the art. Such a polynucleotide can be obtained by using a method such as colony hybridization, plaque hybridization, or southern blot hybridization while using a polynucleotide selected from among the polynucleotides of the present inventions as a probe. Specifically, the above-described polynucleotide refers to a polynucleotide that can be identified by using a filter with immobilized DNA from a colony or plaque and performing hybridization at 65° C. in the presence of 0.7-1.0 M NaCl and then using an SSC (saline-sodium citrate) solution with 0.1-2 times concentration (composition of an SSC solution with 1 time concentration is 150 mM sodium chloride and 15 mM sodium citrate) to wash the filter under the condition of 65° C. For "stringent condition", the following are examples of conditions that can be used. (1) low ionic strength and a high temperature are used for washing (e.g., 0.015 M sodium chloride/0.0015 M sodium citrate/0.1% sodium dodecyl sulfate at 50° C.), (2) a denaturing agent such as formamide is used in hybridization (e.g., 50% (v/v) formamide, 0.1% bovine serum albumin/0.1% ficoll/0.1% polyvinyl pyrrolidone/50 mM sodium phosphate buffer with a pH of 6.5, 750 mM sodium chloride, and 75 mM sodium citrate at 42° C.), or (3) a solution comprising 20% formamide, 5×SSC, 50 mM sodium phosphate (pH 7.6), 5×Denhardt's solution, 10% dextran sulfate, and 20 mg/ml denatured sheared salmon sperm DNA, is incubated overnight at 37° C. and then a filter is washed with 1×SSC at about 37-50° C. The formamide concentration may be 50% or greater. Washing time may be 5, 15, 30, 60, 120 minutes, or greater. A plurality of elements are considered to affect stringency in a hybridization reaction such as temperature, salt concentration and the like. Ausubel et al., Current Protocols in Molecular Biology, Wiley Interscience Publishers, (1995) can be referred for details. "Highly stringent condition", for example, is 0.0015 M sodium chloride, 0.0015 M sodium citrate, and 65-68° C. or 0.015 M sodium chloride, 0.0015 M sodium citrate, 50% formamide and 42° C. Hybridization can be performed in accordance with the method described in experimental publications such as Molecular Cloning $2^{nd}$ ed., Current Protocols in Molecular Biology, Supplement 1-38, DNA Cloning 1: Core Techniques, A Practical Approach, Second Edition, Oxford University Press (1995).

In this regard, a sequence comprising only an A sequence or only a T sequence is preferably excluded from a sequence that hybridizes under stringent conditions. A moderately stringent condition can be readily determined by those skilled in the art based on, for example, the length of a DNA and is shown in Sambrook et al., Molecular Cloning: A Laboratory Manual, Third Ed., Vol. 1, 42-7.45 Cold Spring Harbor Laboratory Press, 2001, including, for a nitrocellulose filters, use of hybridization conditions of a pre-wash solution of 1.0 mM EDTA (pH 8.0), 5×SSC, 0.5% SDS, and about 50% formamide and 2×SSC–6×SSC at about 40-50° C. (or other similar hybridization solutions such as a Stark's solution in about 50% formamide at about 42° C.) and washing conditions of 0.5×SSC, 0.1% SDS at about 60° C. Thus, the polypeptides used in the present invention encompass polypeptides encoded by a nucleic acid molecule that hybridizes under highly or moderately stringent conditions to a nucleic acid molecule encoding a polypeptide described in the present invention in particular.

As used herein, a "purified" substance or biological agent (e.g., nucleic acid, protein or the like) refers to a substance or a biological agent from which at least a part of an agent naturally accompanying the substance or biological agent has been removed. Thus, the purity of a biological agent in a purified biological agent is generally higher than the purity in the normal state of the biological agent (i.e., concentrated). The term "purified" as used herein refers to the presence of preferably at least 75% by weight, more preferably at least 85% by weight, still more preferably at least 95% by weight, and most preferably at least 98% by weight of a biological agent of the same type. The substance or biological agent used in the present invention is preferably a "purified" substance. An "isolated" substance or biological agent (e.g., nucleic acid, protein, or the like) as used herein refers to a substance or biological agent having agents that naturally accompany the substance or biological agent substantially removed. The term "isolated" as used herein varies depending on the objective. Thus, the term does not necessarily have to be represented by purity. However, when necessary, the term refers to the presence of preferably at least 75% by weight, more preferably at least 85% by weight, still more preferably at least 95% by weight, and most preferably at least 98% by weight of a biological agent of the same type. The substance used in the present invention is preferably an "isolated" substance or biological agent.

As used herein, a "corresponding" amino acid, nucleic acid, or moiety refers to an amino acid or a nucleotide which has or is expected to have, in a certain polypeptide molecule or polynucleotide molecule (e.g., Glypican-1), similar action as a predetermined amino acid, nucleotide or moiety in a benchmark polypeptide or a polynucleotide for comparison, and, particularly in the case of enzyme molecules, refers to an amino acid which is present at a similar position in an active site and makes a similar contribution to catalytic activity and refers to a corresponding moiety in a complex molecule (e.g., heparan sulfate or the like). For example, for an antisense molecule, it can be a similar moiety in an ortholog corresponding to a specified moiety of the antisense molecule. A corresponding amino acid can be a specified amino acid subjected to, for example, cysteination, glutathionylation, S—S bond formation, oxidation (e.g., oxidation of methionine side chain), formylation, acetylation, phosphorylation, glycosylation, myristylation or the like. Alternatively, a corresponding amino acid can be an amino acid responsible for dimerization. Such a "corresponding" amino acid or nucleic acid may be a region or a domain over a certain range. Thus, it is referred herein as a "corresponding" region or domain in such a case. Such a corresponding region or domain is useful for designing a complex molecule in the present invention.

As used herein, a "corresponding" gene (e.g., polynucleotide sequence or molecule) refers to a gene (e.g., polynucleotide sequence or molecule) of a certain species which has or is expected to have similar action as a predetermined gene in a benchmark species for comparison. When there is a plurality of genes having such action, the corresponding gene refers to a gene having the same evolutionary origin. Hence, a gene corresponding to a certain gene may be an ortholog of such a gene. Thus, Glypican-1 corresponding to human Glypican-1 can be found in other animals (especially mammals). Such a corresponding gene can be identified by using a technique that is well known in the art. For example, a corresponding gene in a certain animal (e.g., mouse) can be found by searching a database comprising sequences of the animal from using the sequence of SEQ ID NO: 1, 2 or the like as a query sequence, as a benchmark gene of the corresponding gene (e.g., Glypican-1 or the like).

As used herein, "fragment" refers to a polypeptide or polynucleotide with a sequence length of 1 to n−1 with respect to the full length polypeptide or polynucleotide (with length n). The length of a fragment can be appropriately changed in accordance with the objective. Examples of the lower limit of such a length include 3, 4, 5, 6, 7, 8, 9, 10, 15, 20, 25, 30, 40, 50 and more amino acids for a polypeptide. Lengths represented by an integer that is not specifically listed herein (e.g., 11 and the like) also can be suitable as a lower limit. Further, examples of length include 5, 6, 7, 8, 9, 10, 15, 20, 25, 30, 40, 50, 75, 100, and more nucleotides for a polynucleotide. Lengths represented by an integer that is not specifically listed herein (e.g., 11 and the like) also can be suitable as a lower limit. As used herein, such a fragment is understood to be within the scope of the present invention, for example, when a full length version functions as a marker or a target molecule, as along as the fragment itself also functions as a marker or a target molecule.

The term "activity" according to the present invention refers to a function of a molecule in the broadest sense herein. Activity, although not intended to be limiting, generally includes a biological function, biochemical function, physical function, and chemical function of a molecule. Examples of activity include enzymatic activity, an ability to interact with another molecule, an ability to activate, promote, stabilize, inhibit, suppress, or destabilize a function of another molecule, stability, and an ability to localize at a specific position in a cell. When applicable, the term also relates to a function of a protein complex in the broadest sense.

As used herein, "biological function", when referring to a certain gene or a nucleic acid molecule or a polypeptide related thereto, refers to a specific function that the gene, the nucleic acid molecule or the polypeptide may have in a living body. Examples of such a function include, but are not limited to, production of a specific antibody, enzyme activity, impartation of resistance, and the like. In the present invention, examples thereof can include, but not are limited to, functions by which Glypican-1 is involved in apoptosis of an esophageal cancer cell, cleavage of caspase-3, phosphorylation of AKT, and the like. As used herein, biological function can be exerted by "biological activity". As used herein, "biological activity" refers to the activity a certain agent (e.g., polynucleotide, protein or the like) may have in a living body. Biological activity encompasses an activity of exerting a variety of functions (e.g., transcription promoting activity), and also encompasses, for example, an activity of activating or inactivating another molecule by an interaction with a certain molecule. When two agents interact, biological activity thereof may be a bond between two molecules and a biological change induced thereby. For example, two molecules are considered to be bound together if, when one molecule is precipitated using an antibody, the other molecule co-precipitates. Observation of such co-precipitation is one example of a determination approach. For example, when a certain agent is an enzyme, the biological activity thereof encompasses enzyme activity thereof. In another example, when a certain agent is a ligand, binding to a receptor corresponding to the ligand is encompassed. Such biological activity can be measured by a technique that is well known in the art. Thus, "activity" refers to various measurable indicators, which indicate or reveal a bond (either direct or indirect) or affect a response (i.e., having a measurable effect in response to some exposures of stimuli). Examples thereof includes affinity of a compound that directly binds to the polypeptide or polynucleotide of the present invention, the amount of proteins upstream or downstream after some stimulations or events, or the level of other similar functions.

As used herein, "expression" of a gene, a polynucleotide, a polypeptide or the like refers to the gene or the like being subjected to a certain action in vivo to be converted into another form. Preferably, expression refers a gene, a polynucleotide or the like being transcribed and translated into a form of a polypeptide. However, transcription to make an mRNA is also one embodiment of expression. Thus, "expression product" as used herein encompasses such a polypeptide or protein, or mRNA. More preferably, such a polypeptide form can be a form which has undergone post-translation processing. For example, the Glypican-1 expression level can be determined by any method. Specifically, the Glypican-1 expression level can be found by assessing the amount of mRNA of Glypican-1, the amount of Glypican-1 protein, and the biological activity of the Glypican-1 protein. The amount of mRNA or protein of Glypican-1 can be determined by the method described in detail in other parts of the specification or a method known in the art.

As used herein, "functional equivalent" refers to any entity having the same function of interest but a different structure relative to the original target entity. Thus, it is understood that a functional equivalent of "Glypican-1" or an antibody thereof encompasses mutants or variants (e.g., amino acid sequence variant or the like) of the Glypican-1 or antibody thereof, not the Glypican-1 or antibody thereof itself, which have the biological action of the Glypican-1 or antibody thereof and those that can change, upon action, into the Glypican-1 or the antibody thereof itself or a mutant or variant of the Glypican-1 or the antibody thereof (e.g., including nucleic acid encoding Glypican-1 or an antibody thereof itself or a mutant or variant of the Glypican-1 or antibody thereof, and vector, cell and the like comprising such a nucleic acid). It is understood, even without specific mention, that a functional equivalent of Glypican-1 or an antibody thereof can be used similarly to the Glypican-1 or antibody thereof. A functional equivalent can be found by searching a database or the like. As used herein, "search" refers to utilizing a certain nucleic acid base sequence electronically, biologically, or by another method to find another nucleic acid base sequence having a specific function and/or property. Examples of electronic search include, but are not limited to, BLAST (Altschul et al., J. Mol. Biol. 215: 403-410 (1990)), FASTA (Pearson & Lipman, Proc. Natl. Acad. Sci., USA 85: 2444-2448 (1988)), Smith and Waterman method (Smith and Waterman, J. Mol. Biol. 147: 195-197 (1981)), Needleman and Wunsch method (Needleman and Wunsch, J. Mol. Biol. 48: 443-453 (1970)) and the like. Examples of biological search include, but are not limited to, stringent hybridization, a macroarray with a genomic DNA applied to a nylon membrane or the like or a microarray with a genomic DNA applied to a glass plate (microarray assay), PCR, in situ hybridization and the like. Herein, a gene used in the present invention is intended to include corresponding genes identified by such electronic search or biological search.

As a functional equivalent of the present invention, it is possible to use an amino acid sequence with one or more amino acid insertions, substitutions or deletions, or addition to one or both ends. As used herein, "one or more amino acid insertions, substitutions or deletions, or addition to one or both ends" in an amino acid sequence refers to an alteration with a substitution of a plurality of amino acids or the like to the extent that can occur naturally by a well-known technical method such as site-directed mutagenesis or natural mutation. An altered amino acid sequence can have, for example, 1-30, preferably 1-20, more preferably 1-9, still more preferably 1-5, and especially preferably 1-2 amino acid insertions, substitutions or deletions or additions to one or both ends. Preferably, an altered amino acid sequence may be an amino acid sequence having one or more (preferably 1 or several, or 1, 2, 3 or 4) conservative substitutions in the Glypican-1 amino acid sequence. "Conservative substitution" refers herein to a substitution of one or more amino acid residues with other chemically similar amino acid residue so as not to substantially alter a function of a protein. Examples thereof include cases where a hydrophobic residue is substituted with another hydrophobic residue, cases where a polar residue is substituted with another polar residue having the same charge and the like. Functionally similar amino acids that can be substituted in this manner are known in the art for each amino acid. Specific examples include alanine, valine, isoleucine, leucine, proline, tryptophan, phenylalanine, methionine, and the like for nonpolar (hydrophobic) amino acids, glycine, serine, threonine, tyrosine, glutamine, asparagine, cysteine, and the like for polar (neutral) amino acids. Examples of positively charged (basic) amino acid include arginine, histidine, lysine, and the like. Further, examples of a negatively-charged (acidic) amino acid include aspartic acid, glutamic acid and the like.

As used herein, "suppressant" refers to a substance or agent that inhibits biological action of a receptor or a cell against a target entity (e.g., receptor or cell). A Glypican-1 suppressant of the present invention is an agent that can temporarily or permanently reduce or eliminate a function of target Glypican-1, a cell expressing Glypican-1 or the like. Examples of such a factor include, but are not limited to, antibodies, antigen binding fragments thereof, derivatives, functional equivalents, antisenses, RNAi agents such as siRNAs and other nucleic acid forms.

As used herein, "agonist" refers to a substance that expresses or enhances biological action of a receptor against a target entity (e.g., receptor). Examples thereof include natural agonists (also referred to as ligands), as well as synthesized agonists, altered agonists and the like.

As used herein, "antagonist" refers to a substance that suppresses or inhibits the expression of biological action of a receptor against a target entity (e.g., receptor). Examples thereof include natural antagonists (also referred to as ligands), as well as synthesized antagonists, altered antagonists and the like. Antagonists include those that competitively or non-competitively suppress or inhibit expression against an agonist. An antagonist can also be obtained by altering an agonist. Since physiological phenomena are suppressed or inhibited, an antagonist may be encompassed in the concept of suppressant (inhibitor) or suppressing agent. Thus, antagonists as used herein are substantially used synonymously with "suppressant".

"anti-Glypican-1 antibody" in one embodiment of the present invention encompasses antibodies having binding affinity to Glypican-1. The production method of such an anti-Glypican-1 antibody is not particularly limited. For example, the antibody may be produced by immunizing mammals or birds with Glypican-1.

Further, it is understood that examples of a "functional equivalent" of an "antibody to Glypican-1 (anti-Glypican-1 antibody) or a fragment thereof" includes, for antibodies, antibodies themselves having Glypican-1 binding activity and optionally suppressing activity and fragments thereof themselves, as well as chimeric antibodies, humanized antibodies, human antibodies, multifunctional antibodies, bispecific or oligospecific antibodies, single chain antibodies, scFV, diabodies, sc(Fv)$_2$ (single chain (Fv)$_2$), scFv-Fc and the like.

The anti-Glypican-1 antibody according to one embodiment of the present invention is preferably an anti-Glypican-1 antibody that specifically binds to a specific epitope of Glypican-1 from the viewpoint of malignant tumor growth being particularly highly suppressed.

The anti-Glypican-1 antibody according to one embodiment of the present invention may be a monoclonal antibody. A monoclonal antibody can be made to more efficiently act against Glypican-1 relative to a polyclonal antibody. It is preferred that a chicken is immunized with Glypican-1 from the viewpoint of efficient production of anti-Glypican-1 monoclonal antibodies.

The antibody class of the anti-Glypican-1 antibody according to one embodiment of the present invention is not particularly limited. For example, the class may be IgM, IgD, IgG, IgA, IgE, or IgY.

The anti-Glypican-1 antibody according to one embodiment of the present invention may be an antibody fragment having antigen binding activity (hereinafter, also referred to as "antigen binding fragment"). In such a case, there is an effect of improved stability, antibody production efficiency or the like.

The anti-Glypican-1 antibody according to one embodiment of the present invention may be a fusion protein. The fusion protein may comprise a polypeptide or oligopeptide bound to the N or C-terminus of an anti-Glypican-1 antibody. The oligopeptide in this regard may be a His-tag. The fusion protein may also be fused to a mouse, human, or chicken antibody partial sequence. Such fusion proteins are also encompassed as one form of the anti-Glypican-1 antibody according to the present embodiment.

The anti-Glypican-1 antibody according to one embodiment of the present invention may be, for example, an antibody obtained via the step of immunizing an organism with purified Glypican-1, Glypican-1-expressing cell, or a Glypican-1 containing lipid membrane. It is preferable that a Glypican-1-expressing cell is used for immunization from the viewpoint of enhancing a therapeutic effect against Glypican-1 positive malignant tumor.

The anti-Glypican-1 antibody according to one embodiment of the present invention may be an antibody having a CDR set of an antibody obtained via the step of immunizing an organism with purified Glypican-1, Glypican-1-expressing cell, or a Glypican-1 containing lipid membrane. It is preferable that a Glypican-1-expressing cell is used for immunization from the viewpoint of enhancing a therapeutic effect against Glypican-1 positive malignant tumor. A CDR set is a set of heavy chain CDRs 1, 2, and 3 and light chain CDRs 1, 2, and 3.

"Glypican-1 expressing cell" in one embodiment of the present invention may be obtained, for example, by introducing a polynucleotide encoding Glypican-1 into a cell and having the Glypican-1 expressed. Glypican-1 in this regard encompasses Glypican-1 fragments. Further, "Glypican-1-containing lipid membrane" in one embodiment of the present invention may be obtained, for example, by mixing Glypican-1 and a lipid bilayer. Glypican-1 in this regard encompasses Glypican-1 fragments. Further, the anti-Glypican-1 antibody according to one embodiment of the present invention is preferably an antibody obtained via the step of immunizing a chicken with an antigen or an antibody having a CDR set of such an antibody from the viewpoint of enhancing a therapeutic effect against Glypican-1 positive malignant tumor.

The anti-Glypican-1 antibody according to one embodiment of the present invention may have any binding strength as long as the object can be accomplished. Examples thereof include, but are not limited to, at least $1.0\times10^6$ or greater, $2.0\times10^6$ or greater, $5.0\times10^6$ or greater, and $1.0\times10^7$ or greater. The $K_D$ value (kd/ka) generally may be $1.0\times10^{-7}$ (M) or less and can be $1.0\times10^{-9}$ (M) or $1.0\times10^{-10}$.

The anti-Glypican-1 antibody according to one embodiment of the present invention may have ADCC or CDC activity.

The anti-Glypican-1 antibody according to one embodiment of the present invention may be an antibody that binds to a wild-type or mutant Glypican-1. Mutant Glypican-1 includes mutants due to a difference in the DNA sequences among individuals. The amino acid sequence of a wild-type or mutant Glypican-1 is preferably 80% or more, more preferably 90% or more, more preferably 95% or more, and especially preferably 98% or more homologous to the amino acid sequence set forth in SEQ ID NO: 2.

"Antibody" in the present invention encompasses molecules capable of specifically binding to a specific epitope on an antigen and populations thereof. Further, the antibody may be a polyclonal antibody or monoclonal antibody. The antibody can be present in various forms. For example, the antibody may be in one or more types of forms selected from the group consisting of full-length antibody (antibody having an Fab region and an Fc region), Fv antibody, Fab antibody, F(ab')$_2$ antibody, Fab' antibody, diabody, single chain antibody (e.g., scFv), sc(Fv)$_2$ (single chain (Fv)$_2$) scFv-Fc, dsFv, multi-specific antibody (e.g., oligospecific antibody and bispecific antibody), diabody, peptide or polypeptide having antigen binding affinity, chimeric antibody (e.g., mouse-human chimeric antibody, chicken-human chimeric antibody or the like), mouse antibody, chicken antibody, humanized antibody, human antibody, and similar antibodies (or equivalents). Further, the antibody encompasses modified or non-modified antibodies. Modified antibodies may be formed by an antibody binding to various molecules such as polyethylene glycol. A modified antibody can be obtained by applying a chemical modification to an antibody by using a known approach. Furthermore, such an antibody may be fused by a covalent bond or recombination with an enzyme such as alkaline phosphatase, horseradish peroxidase, or a galactosidase. The anti-Glypican-1 antibody used in the present invention is sufficient if it binds to the Glypican-1 protein, regardless of the origin, type, shape or the like thereof. Specifically, known antibodies such as a non-human animal antibody (e.g., a mouse antibody, a rat antibody, or a camel antibody), a human antibody, a chimeric antibody, or a humanized antibody can be used. In the present invention, a monoclonal or polyclonal antibody can be utilized as the anti-Glypican-1 antibody, but a monoclonal antibody is preferable. It is preferable that an antibody binds specifically to the Glypican-1 protein. Further, the antibody encompasses modified and non-modified antibodies. Modified antibodies may be formed by an antibody binding to various molecules such as polyethylene glycol. A modified antibody can be obtained by applying a chemical modification to an antibody by using a known approach.

"Polyclonal antibody" in one embodiment of the present invention can be produced, for example, by administering an immunogen comprising an antigen of interest to mammals (e.g., rat, mouse, rabbit, cow, monkey or the like), birds or the like in order to induce production of a polyclonal antibody specific to the antigen. An immunogen may be administered by one or more immunizing agents and, when desired, an injection of an adjuvant. An adjuvant may be used to increase immune responses and may comprise a Freund's adjuvant (complete or incomplete), mineral gel (aluminum hydroxide or the like), surfactant (lysolecithin or the like) or the like. Immunization protocols are known in the art and, in some cases, may be implemented by any method that induces an immune response, which matches the selected host organism (Tanpakushitsu Jikken Handobukku [*Protein experiment handbook*], Yodosha (2003): 86-91).

"Monoclonal antibody" in one embodiment of the present invention encompasses individual antibodies constituting a population being antibodies corresponding to substantially a single epitope except for antibodies having a mutation that can occur naturally in small amounts. Further individual antibodies constituting a population may be antibodies that are substantially the same except for antibodies having a mutation that can occur naturally in small amounts. Monoclonal antibodies are highly specific, which are different from common polyclonal antibodies that typically include different antibodies corresponding to different epitopes. In addition to their specificity, monoclonal antibodies are useful in that they can be synthesized from hybridoma culture which is not contaminated with other immunoglobulins. The description "monoclonal" may indicate a characteristic of being obtained from a substantially homogeneous antibody population. However, such a description does not mean that antibodies must be produced by a specific method. For example, monoclonal antibodies may be made by a method similar to a hybridoma method as described in "Kohler G, Milstein C., Nature. 1975 Aug. 7; 256 (5517): 495-497" Alternatively, monoclonal antibodies may be made by a method similar to a recombinant method as described in U.S. Pat. No. 4,816,567. Further, monoclonal antibodies may be isolated from a phage antibody library using a method similar to the technique that is described in, "Clackson et al., Nature. 1991 Aug. 15; 352 (6336): 624-628." or "Marks et al., J Mol Biol. 1991 Dec. 5; 222 (3): 581-597" Further, monoclonal antibodies may be made by the method described in "Tanpakushitsu Jikken Handobukku [*Protein experiment handbook*], Yodosha (2003): 92-96".

Antibodies can be mass-produced by using any approach that is known in the art. Examples of construction of mass production system for a representative antibody and antibody manufacture include the following. Specifically, an H chain antibody expression vector and L chain antibody expression vector are transfected into a CHO cell. The cells are cultured by using a selection reagent 6418 and Zeocin and cloned by limiting dilution. After cloning, clones stably expressing antibodies are selected by ELISA. The culture is expanded with selected CHO cells, and the culture supernatant comprising antibodies are collected. Antibodies can be purified from the collected culture supernatant by Protein A or Protein G purification.

"Fv antibody" in one embodiment of the present invention is an antibody comprising an antigen recognition site. This region comprises a dimer of one heavy chain variable domain non-covalently bound to one light chain variable domain. In this configuration, three CDRs of each variable domain can interact with one another to form an antigen binding site on the surface of a VH-VL dimer.

"Fab antibody" in one embodiment of the present invention is, for example, a fragment obtained by treating an antibody comprising an Fab region and an Fc region with proteinase papain, which is an antibody in which about half of the N-terminus side of the H chain is bound to the entire L chain via some disulfide bonds. Fabs can be obtained, for example, by treating the anti-Glypican-1 antibody according to the embodiments of the present invention comprising a Fab region and an Fc region with proteinase papain.

"F(ab')$_2$ antibody" in one embodiment of the present invention is a fragment obtained by treating an antibody comprising a Fab region and an Fc region with proteinase pepsin, which is an antibody comprising two sites corresponding to Fabs. F(ab)$_2$ can be obtained, for example, by treating the anti-Glypican-1 antibody according to the embodiments of the present invention comprising a Fab region and an Fc region with proteinase pepsin. For example, the following Fab' can be made by thioether bond or a disulfide bond.

"Fab' antibody" in one embodiment of the present invention is an antibody obtained, for example, by cleaving a disulfide bond of a hinge region of F(ab')$_2$. For example, F(ab')$_2$ can be obtained through treatment with a reducing agent dithiothreitol.

"ScFv antibody" in one embodiment of the present invention is an antibody comprising VH and VL linked with a suitable peptide linker. ScFv antibodies can be produced, for example, by obtaining a cDNA encoding VH and VL of the anti-Glypican-1 antibody according to the embodiment of the present invention, constructing a polynucleotide encoding VH-peptide linker-VL, incorporating the polynucleotide into a vector, and using a cell for expression.

"Diabody" in one embodiment of the present invention is an antibody having divalent antigen binding activity. Divalent antigen binding activity can be configured to be identical or configured such that one of them has a different antigen binding activity. A diabody can be produced, for example, by constructing a polynucleotide encoding scFv such that the length of the amino acid sequence of a peptide linker is 8 residues or less, incorporating the resulting polynucleotide into a vector and using a cell for expression.

"dsFv" in one embodiment of the present invention is an antibody in which a polypeptide introduced with cysteine residues in VH and VL is bound via a disulfide bond between the above-described cysteine residues. The position to which cysteine residues are introduced can be selected based on steric structure prediction of an antibody in accordance with the method demonstrated by Reiter et al (Reiter et al., Protein Eng. 1994 May; 7 (5): 697-704).

"Peptide or polypeptide with antigen binding affinity" in one embodiment of the present invention is an antibody comprised of antibody VH, VL or CDR 1, 2 or 3 thereof. A peptide comprising a plurality of CDRs can be bound directly or via a suitable peptide linker.

The production method of the above-described Fv antibody, Fab antibody, F(ab')$_2$ antibody, Fab' antibody, scFv antibody, diabody, dsFv antibody, and peptide or polypeptide having antigen binding affinity (hereinafter, also referred to as "Fv antibodies") is not particularly limited. Fv antibodies can be produced, for example, by incorporating a DNA encoding a region of the Fv antibodies in the anti-Glypican-1 antibody according to the embodiment of the present invention into an expression vector and using an expression cell. Further, Fv antibodies may be produced by a chemical synthesis method such as the Fmoc (fluorenylmethyloxycarbonyl) or tBOC (t-butyloxycarbonyl) method. It should be noted that the antigen binding fragment according to one embodiment of the present invention may be one or more types of the above-described Fv antibodies.

"Chimeric antibody" in one embodiment of the present invention is, for example, a variable region of an antibody linked to a constant region of an antibody between xenogenic organisms and can be constructed by a genetic engineering technique. A mouse-human chimeric antibody can be made by, for example, the method described in "Roguska et al., Proc Natl Acad Sci USA. 1994 Feb. 1; 91 (3): 969-973." For example, the basic method of making a mouse-human chimeric antibody links a mouse leader sequence and a variable region sequence in a cloned cDNA with a sequence encoding a human antibody constant region already present in an expression vector of a mammalian cell. Further, after linking the mouse leader sequence and variable region sequence in a cloned cDNA with the sequence encoding a human antibody constant region, the resultant sequence may be linked with a mammalian cell expression vector. A fragment of a human antibody constant region can be from any human antibody H chain constant region and human antibody L chain constant region. Examples of human H chain fragment include Cγ1, Cγ2, Cγ3, and Cγ4, and examples of L chain fragment include Cλ and Cκ.

"Humanized antibody" in one embodiment of the present invention is, for example, an antibody, which has one or more CDRs from non-human species, a framework region (FR) from a human immunoglobulin, and a constant region from human immunoglobulin and binds to a desired antigen. Antibodies can be humanized by using various approaches known in the art (Almagro et al., Front Biosci. 2008 Jan. 1; 13: 1619-1633). Examples thereof include CDR grafting (Ozaki et al., Blood. 1999 Jun. 1; 93 (11): 3922-3930.), Re-surfacing (Roguska et al., Proc Natl Aced Sci USA. 1994 Feb. 1; 91 (3): 969-973.), FR shuffle (Damschroder et al., Mol Immunol. 2007 April; 44 (11): 3049-3060. Epub 2007 Jan. 22) and the like. An amino acid residue of a human FR region may be substituted with a corresponding residue from a CDR donor antibody in order to alter (preferably in order to improve) the antigen bond. The FR substitution can be implemented by a method well known in the art (Riechmann et al., Nature. 1988 Mar. 24; 332 (6162):323-327.) For example, an FR residue that is important for antigen binding may be identified by modeling an interaction between a CDR and an FR residue. Further, an abnormal FR residue at a specific position may be identified by sequence comparison.

"Human antibody" in one embodiment of the present invention is, for example, an antibody in which a region comprising a variable region and constant region of a heavy chain and variable region and constant region of a light chain constituting the antibody is derived from a gene encoding a human immunoglobulin. Main production methods include a method using a transgenic mouse for making human antibodies, phage display and the like. A method using a transgenic mouse for making human antibodies produces human antibodies with diverse antigen binding capabilities instead of mouse antibodies when a functional human Ig gene is introduced into an endogenous Ig knockout mouse. Furthermore, this mouse can be immunized to obtain human monoclonal antibodies by a conventional hybridoma method. Such antibodies can be made, for example, by the method described in "Lonberg et al., Int Rev Immunol. 1995; 13 (1): 65-93." Phase display is a system that typically expresses an exogenous gene as a fusion protein such that phage infectivity is not lost on the N-terminus side of a coat protein (g3p, g10p, or the like) of fibrous phage such as M13 or T7 which is an *E. coli* virus. Antibodies can be made, for example, by the method described in "Vaughan et al., Nat Biotechnol. 1996 March; 14 (3): 309-314".

Further, antibodies may be prepared by grafting a heavy chain CDR or light chain CDR of the anti-Glypican-1 antibody according to the embodiment of the present invention onto any antibody by CDR-grafting (Ozaki et al., Blood. 1999 Jun. 1; 93 (11): 3922-3930). Further, antibodies can be obtained by linking a DNA encoding a heavy chain CDR or light chain CDR of the anti-Glypican-1 antibody according to the embodiment of the present invention and a DNA encoding a region excluding a heavy chain CDR or light chain CDR of a known antibody derived from a human or a non-human organism to a vector in accordance with a known method in the art and using a known cell for expression. When obtaining antibodies in this manner, a known method in the art (e.g., method of allowing amino acid residues of an antibody to randomly mutate and screening for antibodies with high reactivity, phage display, or the like) may be used to optimize the region excluding a heavy chain CDR or light chain CDR in order to enhance the efficiency of anti-Glypican-1 antibody acting upon a target antigen. Further, an FR region may be optimized by using, for example, FR shuffle (Damschroder et al., Mol Immunol. 2007 April; 44 (11): 3049-3060. Epub 2007 Jan. 22) or a method of replacing a vernier zone amino acid residue or packaging residue (Japanese Laid-Open Publication No. 2006-241026 or Foote et al., J Mol Biol. 1992 Mar. 20; 224 (2): 487-499).

"Heavy chain" in one embodiment of the present invention is typically the main constituent element of a full-length antibody. A heavy chain is generally bound to a light chain by a disulfide bond and non-covalent bond. A region called a variable region (VH) which has an amino acid sequence that is not constant even among antibodies in the same class of the same species, is present in a domain on the N-terminus side of a heavy chain. VH is generally known to greatly contribute to the specificity and affinity to an antigen. For example, "Reiter et al., J Mol Biol. 1999 Jul. 16; 290 (3): 685-98." describes that a molecule with only a VH, when made, bound to an antigen with specificity and high level of affinity. Furthermore, "Wolfson W, Chem Biol 2006 December; 13 (12): 1243-1244." describes that there are antibodies having only a heavy chain without a light chain among camel antibodies.

"CDR (complementarity determining region)" in one embodiment of the present invention is a region that is in actual contact with an antigen to form a binding site in an antibody. CDRs are generally located on an Fv (variable region: including heavy chain variable region (VH) and light chain variable region (VL)) of an antibody. Further, CDRs generally have CDR1, CDR2, and CDR3 consisting of about 5-30 amino acid residues. In addition, CDRs of a heavy chain are particularly known for their contribution to binding of an antibody to an antigen. Among the CDRs, CDR3 is known to contribute the most in binding of an antibody to an antigen. For example, "Willy et al., Biochemical and Biophysical Research Communications Volume 356, Issue 1, 27 Apr. 2007, Pages 124-128" describes that a heavy chain CDR3 was altered to elevate the binding capability of an antibody. An Fv region other than the CDRs is called a framework region (FR), consisting of FR1, FR2, FR3, and FR4, which are conserved relatively well among antibodies (Kabat et al., "Sequence of Proteins of Immunological Interest" US Dept. Health and Human Services, 1983.) Specifically, a factor characterizing the reactivity of an antibody is considered to be in CDRs, especially heavy chain CDRs.

A plurality of methods for defining CDRs and determining the positions thereof have been reported. For example, the Kabat definition (Sequences of Proteins of Immunological Interest, 5th ed., Public Health Service, National Institutes of Health, Bethesda, Md. (1991)) or the Chothia definition (Chothia et al., J. Mol. Biol., 1987; 196: 901-917) may be used. One embodiment of the present invention uses the Kabat definition as an optimal example, but the definition is not necessarily limited thereto. Further, the definitions may be determined in some cases after considering both the Kabat definition and the Chothia definition. For example, an overlapping portion of CDR according to each of the definitions, or a portion comprising both CDRs according to each of the definitions can be deemed the CDR. A specific example of such a method is the method of Martin et al using Oxford Molecular's AbM antibody modeling software, which is a proposal combining the Kabat definition and the Chothia definition (Proc. Natl. Acad. Sci. USA, 1989; 86: 9268-9272). Such CDR information can be used to produce a mutant that can be used in the present invention. Such an antibody mutant comprises one or several (e.g., 2, 3, 4, 5, 6, 7, 8, 9, and 10) substitutions, additions, or deletions in the framework of the original antibody, but can be produced such that it is free of a mutation in the CDRs.

As used herein, "antigen" refers to any substrate that can be specifically bound by an antibody molecule. As used herein, "immunogen" refers to an antigen that can initiate lymphocyte activation which leads to an antigen specific immune response. As used herein, "epitope" or "antigen determinant" refers to a site in an antigen molecule to which an antibody or a lymphocyte receptor binds. A method of determining an epitope is well known in the art. Such an epitope can be determined by those skilled in the art by using a well-known and conventional technique when a primary sequence of an amino acid or a nucleic acid is provided. It is understood that the antibody of the present invention can be similarly used even for antibodies having other sequences, as long as the epitope is the same.

It is understood that antibodies with any specificity may be used as the antibody used herein, as long as false positive reactions are reduced. Thus, the antibodies used in the present invention may be a polyclonal antibody or a monoclonal antibody.

As used herein, "means" refers to anything that can be a tool for accomplishing an objective (e.g., detection, diagnosis, treatment). As used herein, "selective recognizing means" in particular refers to means capable of recognizing a certain subject differently from others.

As used herein, "marker (substance, protein or gene)" refers to a substance that can be an indicator for tracking whether a target is in or at risk of being in a certain condition (e.g., diseased state, disorder state, level of or presence of malignant state or the like). Examples of such a marker include genes, gene products, metabolites, enzymes and the like. In the present invention, detection, diagnosis, preliminary detection, prediction, or prediagnosis of a certain state (e.g., state of a disease such as cancer) can be materialized by using an agent or means specific to a marker associated with such a state, or a composition, kit or system comprising the same or the like. As used herein, "expression product" (also referred to as a gene product) refers to a protein or mRNA encoded by a gene. It is found in the present specification that a gene product (Glypican-1), which does not exhibit association with esophageal cancer can be used as an indicator for esophageal cancer.

As used herein, "esophageal cancer" is used as the general meaning and used in a broad meaning comprising cancer in the esophagus. Esophageal cancer encompasses, but is not limited to, adenocarcinoma, those in lymph node metastasis sites, and the like in addition to squamous cell carcinoma. With regard to Japanese people's esophageal cancer, it is presumed that approximately half occurs from the vicinity of the center of the esophagus in the chest, and in the second place, a quarter occurs at the lower part of the esophagus. It is understood that the present invention targets both. While not wishing to be bound by theory, in the present invention, it is expected that it may be used as an indicator of overall esophageal cancer including adenocarcinoma and those in lymph node metastasis sites in addition to squamous cell carcinoma.

As used herein, "subject" refers to a target subjected to diagnosis, detection, treatment or the like of the present invention (e.g., an organism such as a human or a cell, blood, serum or the like extracted from an organism).

As used herein, "sample" refers to any substance obtained from a subject or the like. For example, serum and the like are encompassed thereby. Those skilled in the art can appropriately select a preferred sample based on the descriptions herein.

As used herein, "agent" is used broadly and may be any substance or other elements (e.g., energy, radiation, heat, electricity and other forms of energy) as long as the intended objective can be achieved. Examples of such a substance include, but are not limited to, protein, polypeptide, oligopeptide, peptide, polynucleotide, oligonucleotide, nucleotide, nucleic acid (including, for example, DNAs such as cDNA and genomic DNA and RNAs such as mRNA), polysaccharide, oligosaccharide, lipid, organic small molecule (e.g., hormone, ligand, information transmitting substance, organic small molecule, molecule synthesized by combinatorial chemistry, small molecule that can be used as a pharmaceutical product (e.g., small molecule ligand and the like)) and a complex molecule thereof. Typical examples of an agent specific to a polynucleotide include, but are not limited to, a polynucleotide having complementarity with a certain sequence homology (e.g., 70% or greater sequence identity) to a sequence of the polynucleotide, polypeptide such as a transcription factor that binds to a promoter region and the like. Typical examples of an agent specific to a polypeptide include, but are not limited to, an antibody directed specifically to the polypeptide or a derivative or analog thereof (e.g., single chain antibody), a specific ligand or receptor when the polypeptide is a receptor or ligand, a substrate when the polypeptide is an enzyme and the like.

As used herein, "diagnosis" refers to identifying various parameters associated with a disease, disorder, condition (e.g., esophageal cancer) or the like in a subject to determine the current or future state of such a disease, disorder, or condition. The condition in the body can be investigated by using the method, apparatus, or system of the present invention. Such information can be used to select and determine various parameters of a formulation or method for the treatment or prevention to be administered, disease, disorder, or condition in a subject or the like. As used herein, "diagnosis" when narrowly defined refers to diagnosis of the current state, but when broadly defined includes "early diagnosis", "predictive diagnosis", "prediagnosis" and the like. Since the diagnostic method of the present invention in principle can utilize what comes out from a body and can be conducted away from a medical practitioner such as a physician, the present invention is industrially useful. In order to clarify that the method can be conducted away from a medical practitioner such as a physician, the term as used herein may be particularly called "assisting" "predictive diagnosis, prediagnosis or diagnosis".

As used herein, "detecting drug (agent)" or "inspection drug (agent)" broadly refers to all agents capable of detecting or inspecting a target of interest.

As used herein, "diagnostic drug (agent)" broadly refers to all agents capable of diagnosing a condition of interest (e.g., disease such as esophageal cancer or the like).

As used herein, "treatment" refers to the prevention of exacerbation, preferably maintaining of the current condition, more preferably alleviation, and still more preferably disappearance of a disease or disorder (e.g., esophageal cancer) in case of such a condition, including being capable of exerting a prophylactic effect or an effect of improving a disease of a patient or one or more symptoms accompanying the disease. Preliminary diagnosis with suitable treatment may be referred to as "companion therapy" and a diagnostic agent therefor may be referred to as "companion diagnostic agent".

As used herein, "therapeutic drug (agent)" broadly refers to all agents capable of treating a condition of interest (e.g., diseases such as esophageal cancer or the like). In one embodiment of the present invention, "therapeutic drug" may be a pharmaceutical composition comprising an effective ingredient and one or more pharmacologically acceptable carriers. A pharmaceutical composition can be manufactured, for example, by mixing an effective ingredient and the above-described carriers by any method known in the technical field of pharmaceuticals. Further, mode of usage of a therapeutic drug is not limited, as long as it is used for treatment. A therapeutic drug may be an effective ingredient alone or a mixture of an effective ingredient and any ingredient. Further, the shape of the above-described carriers is not particularly limited. For example, the carrier may be a solid or liquid (e.g., buffer solution). It should be noted that a therapeutic drug of esophageal cancer includes a drug (prophylactic drug) for preventing esophageal cancer or a growth suppressant for esophageal cancer cells.

As used herein, "prevention" refers to the action of taking a measure against a disease or disorder (e.g., esophageal cancer) from being in such a condition prior to being in such a condition. For example, it is possible to use the agent of the present invention to perform diagnosis, and optionally use the agent of the present invention to prevent or take measures to prevent esophageal cancer or the like.

As used herein, "prophylactic drug (agent)" broadly refers to all agents capable of preventing a condition of interest (e.g., diseases such as esophageal cancer or the like).

As used herein, "interaction" refers, for two substances, to applying a force (e.g., intermolecular force (Van der Weals force), hydrogen bond, hydrophobic interaction, or the like) between one substance and the other substance. Generally, two substances that have interacted are in a conjugated or bound state. The detection, inspection, and diagnosis in the present invention can be materialized by utilizing such interaction.

As used herein, the term "bond" refers to a physical or chemical interaction between two substances or between combinations thereof. A bond includes an ionic bond, non-ionic bond, hydrogen bond, Van der Weals bond, hydrophobic interaction and the like. A physical interaction (bond) may be direct or indirect. Indirect physical interaction (bond) is mediated by or is due to an effect of another protein or compound. A direct bond refers to an interaction, which does not occur through or due to an effect of another protein or compound and does not substantially involve another intermediate.

Thus, an "agent" (or detection agent or the like) that "specifically" interacts (or binds) to a biological agent such as a polynucleotide or a polypeptide as used herein encompasses agents with affinity to the biological agent such as a polynucleotide or polypeptide that is typically similar or higher, preferably significantly (e.g., statistically significantly) higher, than affinity to other unrelated polynucleotides or polypeptides (especially those with less than 30% identity). Such affinity can be measured, for example, by hybridization assay, binding assay or the like.

As used herein, "specific" interaction (or bond) of a first substance or agent with a second substance or agent refers to the first substance or agent interacting with (or binding to) the second substance or agent at a higher level of affinity than to substances or agents other than the second substance or agent (especially other substances or agents in a sample comprising the second substance or agent). Examples of an interaction (or bond) specific to a substance or agent include, but are not limited to, hybridization in a nucleic acid, antigen-antibody reaction in a protein, enzyme-substrate reaction, other nucleic acid protein reactions, protein-lipid interaction, nucleic acid-lipid interaction and the like. Thus, when substances or agents are both nucleic acids, a first substance or agent "specifically interacting" with a second substance or agent encompasses the first substance or agent having at least partial complementarity to the second substance or agent. Further, examples of a first substance or agent "specifically" interacting with (or binding to) a second substance or agent when substances or agents are both proteins include, but are not limited to, interaction by an antigen-antibody reaction, interaction by a receptor-ligand reaction, enzyme-substrate interaction and the like. When two types of substances or agents include a protein and a nucleic acid, a first substance or agent "specifically" interacting with (or binding to) a second substance or factor encompasses an interaction (or a bond) between an antibody and an antigen. Such a specific interactive or binding reaction can be utilized to detect or quantify a target in a sample.

As used herein, "detection" or "quantification" of polynucleotide or polypeptide expression can be accomplished by using a suitable method including, for example, an immunological measuring method and measurement of mRNAs, including a bond or interaction to a detection agent, inspection agent or diagnostic agent. Examples of a molecular biological measuring method include northern blot, dot blot, PCR and the like. Examples of an immunological measurement method include ELISA using a microtiter plate, RIA, fluorescent antibody method, luminescence immunoassay (LIA), immunoprecipitation (IP), single radial immunodiffusion (SRID), turbidimetric immunoassay (TIA), western blot, immunohistochemical staining and the like. Further, examples of a quantification method include ELISA, RIA and the like. Quantification may also be performed by a gene analysis method using an array (e.g., DNA array, protein array). DNA arrays are outlined extensively in (Ed. by Shujunsha, Saibo Kogaku Bessatsu "DNA Mai- kuroarei to Saishin PCR ho" [*Cellular engineering, Extra issue, "DNA Microarrays and Latest PCR Methods"*]. Protein arrays are discussed in detail in Nat Genet. 2002 December; 32 Suppl: 526-532. Examples of a method of analyzing gene expression include, but are not limited to, RT-PCR, RACE, SSCP, immunoprecipitation, two-hybrid system, in vitro translation and the like, in addition to the methods discussed above. Such additional analysis methods are described in, for example, Genomu Kaiseki Jikkenho Nakamura Yusuke Labo Manyuaru [*Genome analysis experimental method Yusuke Nakamura Lab Manual*], Ed. by Yusuke Nakamura, Yodosha (2002) and the like. The entirety of the descriptions therein is incorporated herein by reference.

As used herein, "amount of expression" refers to the amount of polypeptide, mRNA or the like expressed in a cell, tissue or the like of interest. Examples of such an amount of expression include amount of expression of the polypeptide of the present invention at a protein level assessed by any suitable method including an immunological measurement method such as ELISA, RIA, fluorescent antibody method, western blot, and immunohistochemical staining by using the antibody of the present invention, and the amount of expression of the polypeptide used in the present invention at an mRNA level assessed by any suitable method including a molecular biological measuring method such as northern blot, dot blot, and PCR. "change in amount of expression" refers to an increase or decrease in the amount of expression of the polypeptide used in the present invention at a protein level or mRNA level assessed by any suitable method including the above-described immunological measuring method or molecular biological measuring method. A variety of detection or diagnosis based on a marker can be performed by measuring the amount of expression of a certain marker.

As used herein, "decrease" or "suppression" of activity or expression product (e.g., protein, transcript (RNA or the like)) or synonyms thereof refers to: a decrease in the amount, quality or effect of a specific activity, transcript or protein; or activity that decreases the same. Among decrease, "elimination" refers to activity, expression product or the like being less than the detection limit and especially referred to as "elimination". As used herein, "elimination" is encompassed by "decrease" or "suppression".

As used herein, "increase" or "activation" of activity or expression product (e.g., protein, transcript (RNA or the like)) or synonyms thereof refers to: an increase in the amount, quality or effect of a specific activity, transcript or protein; or activity that increases the same.

As used herein, "(nucleic acid) primer" refers to a substance required for initiating a reaction of a polymeric compound to be synthesized in a polymer synthesizing enzyme reaction. A synthetic reaction of a nucleic acid molecule can use a nucleic acid molecule (e.g., DNA, RNA or the like) complementary to a portion of a sequence of a polymeric compound to be synthesized. A primer can be used herein as a marker detecting means.

As used herein, "probe" refers to a substance that can be means for search, which is used in a biological experiment such as in vitro and/or in vivo screening. Examples thereof include, but are not limited to, a nucleic acid molecule comprising a specific base sequence, a peptide comprising a specific amino acid sequence, a specific antibody, a fragment thereof and the like. As used herein, a probe is used as means for marker detection, inspection, or diagnosis.

As used herein, "label" refers to an entity (e.g., substance, energy, electromagnetic wave or the like) for distinguishing a molecule or substance of interest from others. Such a method of labeling includes RI (radioisotope) method, fluorescence method, biotin method, chemiluminescent method and the like. When a plurality of markers of the present invention or agents or means for capturing the same are labeled by a fluorescence method, labeling is performed with fluorescent substances having different fluorescent emission maximum wavelengths. It is preferable that the difference in fluorescent emission maximum wavelengths is 10 nm or greater. When labeling a ligand, any label that does not affect the function can be used. However, Alexa™ Fluor is desirable as a fluorescent substance. Alexa™ Fluor is a water-soluble fluorescent dye obtained by modifying coumarin, rhodamine, fluorescein, cyanine or the like. This is a series compatible with a wide range of fluorescence wavelengths. Relative to other fluorescent dyes for the corresponding wavelength, Alexa™ Fluor is very stable, bright and has a low level of pH sensitivity. Combinations of fluorescent dyes with fluorescence maximum wavelength of 10 nm or greater include a combination of Alexa™555 and Alexa™633, combination of Alexa™488 and Alexa™555 and the like. When a nucleic acid is labeled, any label can be used that can bind to a base portion thereof. However, it is preferable to use a cyanine dye (e.g., Cy3, Cy5 or the like of the CyDye™ series), rhodamine 6G reagent, 2-acetylaminofluorene (AAF), AAIF (iodine derivative of AAF) or the like. Examples of a fluorescent substance with a difference in fluorescent emission maximum wavelengths of 10 nm or greater include a combination of Cy5 and a rhodamine 6G reagent, a combination of Cy3 and fluorescein, a combination of a rhodamine 65 reagent and fluorescein and the like. The present invention can utilize such a label to alter a subject of interest to be detectable by the detecting means to be used. Such alteration is known in the art. Those skilled in the art can appropriately carry out such a method in accordance with the label and subject of interest.

As used herein, "tag" refers to a substance for distinguishing a molecule by a specific recognition mechanism such as receptor-ligand, or more specifically, a substance serving the role of a binding partner for binding a specific substance (e.g., having a relationship such as biotin-avidin or biotin-streptavidin). A tag can be encompassed in the scope of "label". Accordingly, a specific substance to which a tag is bound can distinguish the specific substance by a contact with a substrate, to which a binding partner of a tag sequence is bound. Such a tag or label is well known in the art. Typical tag sequences include, but are not limited to, myc tag, His tag, HA, Avi tag and the like. Such a tag may be bound to the marker of the present invention or a detection agent, inspection agent, or diagnostic agent (may be a primer, probe or the like) of the marker.

As used herein, "in vivo" refers to inside of a living body. In specific context, "in a living body" refers to the position where a substance of interest should be disposed.

As used herein, "in vitro" refers to a state where a portion of a living body is extracted or freed "outside of a living body" (e.g., in a test tube) for various research purposes. This is a term that is an antonym of in vivo.

As used herein, when a procedure is performed outside of the body, but the subject of the procedure is intended to be subsequently returned in the body, the series of operations is referred to as "ex vivo". An embodiment that treats a cell in a living body with an agent of the present invention and returns the cell in a patient is also anticipated in the present invention.

As used herein, "kit" refers to a unit generally providing portions to be provided (e.g., inspection drug, diagnostic drug, therapeutic drug, antibody, label, manual and the like) into two or more separate sections. This form of a kit is preferred when a composition that should not be provided in a mixed state and is preferably mixed immediately before use for safety or the like is intended to be provided. Such a kit advantageously comprises an instruction or manual describing how the provided portions (e.g., inspection drug, diagnostic drug, or therapeutic drug) are used or how a reagent should be handled. When the kit is used herein as a reagent kit, the kit generally comprises an instruction describing how to use an inspection drug, diagnostic drug, therapeutic drug, antibody and the like.

As used herein, "instruction" is a document with an explanation of the method of use of the present invention for a physician or other users. The instruction has a description of the detection method of the present invention, method of use of a diagnostic agent, or administration of a medicament, or the like. Further, an instruction may have a description instructing oral administration or administration to the esophagus (e.g., by injection or the like) as a site of administration. The instruction is prepared in accordance with a format defined by the regulatory agency of the country in which the present invention is practiced (e.g., the Ministry of Health, Labor and Welfare in Japan, Food and Drug Administration (FDA) in the U.S. or the like), with an explicit description showing approval by the regulatory agency. The instruction is a so-called package insert and is typically provided in, but not limited to, paper media. The instructions may also be provided in a form such as electronic media (e.g., web sites provided on the Internet or emails).

PREFERRED EMBODIMENTS

Preferred embodiments of the present invention are described hereinafter. The embodiments are provided hereinafter for better understanding of the present invention. It is understood that the scope of the present invention should not be limited to the following descriptions. Thus, it is apparent that those skilled in the art can readily make modifications within the scope of the present invention while referring to the descriptions herein. It is understood that the following embodiments of the present invention can be used alone or in combine.

(Marker, Detection, Inspection, and Diagnosis of Esophageal Cancer)

In one aspect, the present invention provides a marker for identifying esophageal cancer, comprising Glypican-1 or an expression product thereof, or a fragment or derivative thereof. Glypican-1 is a substance present in vivo, the expression in a healthy individual or a sample derived therefrom is low, and the expression in esophageal cancer is significantly higher. From this, it has been found in the present invention that it can be used as an effective indicative marker for esophageal cancer.

In the present invention, it has been found that the expression of Glypican-1 is an indicator of esophageal cancer. Therefore, according to the present invention, by detecting the expression of Glypican-1 in a subject or a sample derived therefrom (e.g., serum) that is targeted, esophageal cancer can be detected or selected. In addition, it is thus understood that using the modulation ability, such as decrease, suppression, increase, activation, or the like, of the marker of the present invention as an indicator, an agent to carry out esophageal cancer treatment can be detected and screened.

In another aspect, the present invention provides a detection agent, an inspecting agent, or a diagnostic agent for identifying esophageal cancer, comprising a substance that binds to or interacts with Glypican-1. For such detection, inspection, or diagnosis, it is preferable that the binding of the substance is specific.

As such a detection agent, an inspecting agent, or a diagnostic agent, any substance may be utilized as long as it can bind to or interact with Glypican-1. Representative examples thereof can include, but are not limited to, for example, an antibody of these agents or a fragment or a functional equivalent thereof, or nucleic acid encoding these agents, particularly, a nucleic acid primer that may amplify Glypican-1, or a probe that may bind to or interact with Glypican-1.

The detection agent, an inspecting agent, or a diagnostic agent of the present invention can be utilized as a detection kit, an inspection kit, or a diagnostic kit.

In one embodiment, esophageal cancer that the present invention targets comprises, but is not limited to, those in lymph node metastasis sites, squamous cell carcinoma, and/or adenocarcinoma, in particular squamous cell carcinoma. In another embodiment, esophageal cancer that the present invention targets is Glypican-1 positive cancer. In another embodiment, esophageal cancer that the present invention targets is human cancer.

In one embodiment, the detection agent, inspecting agent, or diagnostic agent of the present invention may be a complex or a complex molecule in which another substance (e.g., label and the like) is bound to a moiety (e.g., antibody and the like) enabling detection, inspection, or diagnosis. As used herein, "complex" or "complex molecule" means any construct comprising two or more moieties. For example, when one moiety is a polypeptide, the other moiety may be a polypeptide or may be a different substance (e.g., sugar, lipid, nucleic acid, other hydrocarbon, and the like). Two or more moieties that compose the complex in the present specification may be bound through a covalent bond or alternative bonds (e.g., hydrogen bond, ionic bond, hydrophobic interaction, van der Waals forces, and the like). When two or more moieties are polypeptides, they may be referred to as chimeric polypeptides. Accordingly, "complex" in the present specification comprises a molecule obtained by linking plural types of molecules, such as polypeptides, polynucleotides, lipids, sugars, low molecules, and the like.

The detection agent, inspecting agent, or diagnostic agent of the present invention can take the form of probe and primer. The probe and primer of the present invention can be specifically hybridized with Glypican-1. As described herein, the expression of Glypican-1 is an indicator of esophageal cancer and useful as the indicator. Thus, a probe and a primer according to the present invention can be used to identify esophageal cancer. The probe and primer of the present invention, in one embodiment, may be able to detect the expression of Glypican-1 or refers to a polymer consisting of a plurality of bases or base pairs such as deoxyribonucleic acid (DNA), ribonucleic acid (RNA), or the like. It is known that double-stranded cDNA can also be utilized in tissue in situ hybridization, and the probe and primer of the present invention comprise such double-stranded cDNA. A probe and a primer that are particularly preferable in detection of RNA in tissue can include a RNA probe (riboprobe).

In specific embodiments, the present invention can take the form of primer. A nucleic acid molecule that is generally used as a primer includes those having at least 8 continuous nucleotide length of nucleic acid sequence that is complementary to the nucleic acid sequence of a target gene (e.g., SEQ ID NO: 1). Such a nucleic acid sequence may be preferably at least 9 continuous nucleotide length, more preferably at least 10 continuous nucleotide length, further preferably at least 11 continuous nucleotide length, at least continuous nucleotide length, at least 13 continuous nucleotide length, at least 14 continuous nucleotide length, at least 15 continuous nucleotide length, at least 16 continuous nucleotide length, at least 17 continuous nucleotide length, at least 18 continuous nucleotide length, at least 19 continuous nucleotide length, at least 20 continuous nucleotide length, at least 25 continuous nucleotide length, at least 30 continuous nucleotide length, at least 40 continuous nucleotide length, or at least 50 continuous nucleotide length of nucleic acid sequence. A nucleic acid sequence used as a probe comprises a nucleic acid sequence having at least 70% homology, more preferably at least 80% homology, further preferably at least 90% homology, or at least 95% homology to a sequence mentioned above. A suitable sequence as a primer may vary depending on characteristics of a sequence of which the synthesis (amplification) is intended, however, those skilled in the art can design a primer as appropriate in response to an intended sequence. Design of such a primer is well known in the art and may be carried out manually or using a computer program (e.g., LASERGENE, PrimerSelect, DNAStar).

In specific embodiments, a primer according to the present invention can also be used as a primer set consisting of two or more types of the primer. In specific embodiments, a primer and a primer set according to the present invention can be utilized as a primer and a primer set in accordance with a routine method of detecting a target gene utilizing a nucleic acid amplification method, such as PCR method, RT-PCR method, real-time. PCR method, in situ PCR method, LAMP method, and the like.

In a primer set according to the present invention, the nucleotide sequence of a target protein, such as Glypican-1 and the like, can be selected such that it can be amplified by a nucleic acid amplification method, such as PCR method and the like. Nucleic acid amplification methods are well known and selection of a primer pair in a nucleic acid amplification method is apparent to those skilled in the art. For example, in PCR, it is possible to select a primer such that one of two primers (a primer pair) pairs to the plus strand of the double-stranded DNA of a target protein, such as Glypican-1 and the like, and the other primer pairs to the minus strand of the double-stranded DNA, and the other primer pairs to an extended chain that has been extended by the one primer. Further, in a LAMP method (International Publication No. WO 00/28082), three regions F3c, F2c, and F1c from the 3'-terminal side and three regions B1, B2, and B3 from 5'-terminal side are individually defined for a target gene and these six regions can be used to design four types of primers. The primer of the present invention can be chemically synthesized based on a nucleotide sequence disclosed herein. Preparation of a primer is well known and can be carried out in accordance with, for example, "Molecular Cloning, A Laboratory Manual $2^{nd}$ ed." (Cold Spring Harbor Press (1989)) and "Current Protocols in Molecular Biology" (John Wiley & Sons (1987-1997)).

In specific embodiments, the present invention can take the form of "probe". A nucleic acid molecule that is generally used as a probe includes those having at least 8 continuous nucleotide length of nucleic acid sequence that is homologous or complementary to the nucleic acid sequence of a target gene (e.g., SEQ ID NO: 1). Such a nucleic acid sequence may be preferably at least 9 continuous nucleotide length, more preferably at least 10 continuous nucleotide length, further preferably at least 11 continuous nucleotide length, at least continuous nucleotide length, at least 13 continuous nucleotide length, at least 14 continuous nucleotide length, at least 15 continuous nucleotide length, at least 16 continuous nucleotide length, at least 17 continuous nucleotide length, at least 18 continuous nucleotide length, at least 19 continuous nucleotide length, at least 20 continuous nucleotide length, at least 25 continuous nucleotide length, at least 30 continuous nucleotide length, at least 40 continuous nucleotide length, or at least 50 continuous nucleotide length of at least nucleic acid sequence. A nucleic acid sequence used as a probe comprises a nucleic acid sequence having at least 70% homology, more preferably at least 80% homology, further preferably at least 90% homology, or at least 95% homology to a sequence mentioned above.

In one embodiment, the detection agent of the present invention may be labeled. Alternatively, the detection agent, inspecting agent, or diagnostic agent of the present invention may be a tag-bound one A label or tag used in the present invention can take any form described herein.

In one aspect, the present invention provides a method for using Glypican-1 as an indicator for identifying esophageal cancer, or a method of detecting, inspecting, or diagnosing esophageal cancer.

In one embodiment, in the method of the present invention, in order to use Glypican-1 as an indicator for identifying esophageal cancer, for example, it can be performed by carrying out a step of detecting in vivo an expression product of Glypican-1, for example, a protein or mRNA. For example, at this time, it is possible to use a detection agent, an inspecting agent, or a diagnostic agent comprising a substance that binds to an expression product of Glypican-1, for example, a protein or mRNA. Such a detection agent, an inspecting agent, or a diagnostic agent is described herein and it is understood that based on such description, if necessary, those skilled in the art can carryout the method of the present invention using known techniques in the art.

The method of the present invention contacts the detection agent, inspecting agent, or diagnostic agent with an intended sample, and measures whether an expression product of Glypican-1 being an intended target, for example, a protein or mRNA, is present or not in the sample, or the level or amount thereof.

"Contact" in the present invention is to place a plurality of substances such that the interaction or binding between the plurality of substances occurs. In the present invention, it is achieved by placing a substance capable of functioning as a detection agent, an inspecting agent, or a diagnostic agent (e.g., polypeptide or polynucleotide) either directly or indirectly, physically close to the marker of the present invention or a sample comprising it. A polypeptide or a polynucleotide can be allowed to be present in many buffer solutions, salts, solutions, and the like. Contact includes placing a compound in, for example, a beaker, a microtiter plate, a cell culture flask, microarray (e.g., gene chip), or the like comprising a polypeptide encoding a nucleic acid molecule or a fragment thereof. A specific method of detecting an expression product of Glypican-1, for example, a protein or mRNA, is not particularly limited as long as it is a method that can detect an expression product of Glypican-1 in a sample (e.g., serum and the like), for example, a protein or mRNA, and includes, for example, a hybridization method, a nucleic acid amplification method, an antigen-antibody reaction method. In this regard, a substance used as a sample may be any sample as long as it is believed to comprise the expression product. For example, serum can be used. Serum can be obtained according to a conventional method.

In specific embodiments, detection, inspection, or diagnosis according to the present invention can detect the expression of Glypican-1 in a cell sample by hybridizing a probe according to the present invention with a nucleic acid sample (mRNA, complementary DNA (cDNA) transcribed therefrom, or the like) and directly or indirectly detecting a hybridization complex, i.e. nucleotide double-strand. With regard to a detailed procedure of a hybridization method, "Molecular Cloning, A Laboratory Manual $2^{nd}$ ed." (Cold Spring Harbor Press (1989), in particular Section 9.47-9.58), "Current Protocols in Molecular Biology" (John Wiley & Sons (1987-1997), in particular Section 6.3-6.4), "DNA Cloning 1:Core Techniques, A Practical Approach $2^{nd}$ ed." (Oxford University (1995), for a condition, in particular Section 2.10) may be referred to.

Detection of an expression product of Glypican-1, for example, mRNA, by utilizing a hybridization method can be performed, for example, by (a) a step of contacting a tested-sample-derived polynucleotide with a probe according to the present invention; and (b) a step of detecting a hybridization complex. In the step (a), mRNA prepared from an intended tested sample or complementary DNA (cDNA) transcribed from the mRNA as a tested-cell-sample-derived polynucleotide can be contacted with a probe. In a detection method using a probe, the probe can be labeled and used. A label includes, for example, labels utilizing radioactivity (e.g., $^{32}P$, $^{14}C$, and $^{35}S$), fluorescence (e.g., FITC and europium), enzymatic reaction such as chemical color development (e.g., peroxidase and alkaline phosphatase), and the like. Detection of a hybridization product can be carried out using a well-known method, such as Northern hybridization, Southern hybridization, colony hybridization, and the like. Since a sample in which a hybridization complex has been detected indicates that a tissue of a subject expresses Glypican-1, it can be determined for a subject from which the sample is derived that there is high possibility that the subject have esophageal cancer.

According to another embodiment of detection, inspection, or diagnosis according to the present invention, by amplifying a nucleic acid sample (mRNA or a transcriptional product thereof) with a nucleic acid amplification method using a primer or a primer set according to the present invention and detecting an amplification product, the expression of Glypican-1 in a sample can be detected or inspected or the diagnosis can be carried out using it.

Detection of the expression of Glypican-1 by utilizing a nucleic acid amplification method can be carried out, for example, by (i) a step of carrying out a nucleic acid amplification method using a tested-sample-derived polynucleotide as a template and using a primer or a primer set according to the present invention; and (ii) a step of detecting the formed amplification product.

In the step (i), mRNA prepared from an intended tested sample or complementary DNA (cDNA) transcribed from the mRNA can be used as a template. Detection of an amplification product can be carried out using a nucleic acid amplification method, such as a PCR method, a RT-PCR method, a real-time PCR method, a LAMP method, and the like. Since the fact that an amplification product is detected in this sample indicates that a tissue of a subject expresses Glypican-1, it can be determined for a subject from which the sample is derived that there is high possibility that the subject have esophageal cancer.

According to another embodiment of detection according to the present invention, by contacting an antibody according to the present invention with a sample and detecting an antigen-antibody reaction, the expression of Glypican-1 in a sample can be detected or inspected or the diagnosis can be carried out using it.

Detection of the expression of Glypican-1 utilizing an antigen-antibody reaction can be carried out, for example, by (I) a step of contacting a tested-cell-sample-derived protein with an antibody according to the present invention; and (II) a step of measuring an antigen-antibody complex. Detection methods of an antigen-antibody reaction are well known, and for example, Glypican-1 in serum can be detected according to an immunological method. As an immunological method, an already-known method, such as an immunohistological staining method, enzyme immunoassay, a Western blot method, a coagulation method, a competition method, a sandwich method, and the like, can be applied for a sample obtained by appropriately treating a cell sample, for example, cell separation, extracting operation, and the like, as necessary. An immunohistological staining method can be carried out, for example, according to a direct method using a labeled antibody, an indirect method using a labeled antibody against the antibody, or the like. A known labeled substance, such as a fluorescent substance, a radioactive substance, an enzyme, a metal, a pigment, and the like, can be used as a labeling agent. Since a sample for which an antigen-antibody complex is detected comprises a cell expressing Glypican-1, a subject from which the sample is derived can be determined as being highly probable to have esophageal cancer.

By carrying out each detecting step mentioned above not only once but repeatedly or in combination, the diagnostic accuracy of esophageal cancer can be increased further. Therefore, when such an embodiment is adopted, esophageal cancer can be diagnosed with higher accuracy by carrying out the above-mentioned steps two or more times according to a detection, inspection, or diagnosis method by the present invention.

In addition, by using another marker gene, preferably a growth marker gene other than Glypican-1 (for example, SCC, CEA, or the like, which are already-known markers), or the combination thereof, the diagnostic accuracy of esophageal cancer can be increased further.

Formulation procedures of a diagnostic drug and the like of the present invention as medicaments are known in the art and, for example, are described in the Japanese Pharmacopoeia, the United States Pharmacopeia, Pharmacopeia of other countries, or the like. Thus, if there are descriptions of the present specification, those skilled in the art can decide an embodiment, such as an amount that should be used, and the like, without undue experiments.

In one embodiment, the concentration of a marker can be measured by mass spectrometry. As an ionization method in this case, both of matrix-assisted laser desorption/ionization (MALDI) and electrospray ionization (ESI) can be applied, while MALDI, in which the amount of multivalent ions generated is small, is preferable. In particular, by MALDI-TOF-MS, which is a combination with time-of-flight mass spectrometer (TOF), the concentration of a marker can be measured more accurately. Further, by MS/MS in which two mass spectrometers are used, the concentration of a marker can be measured more accurately.

When the concentration of a marker is measured by electrophoresis, for example, a material to be inspected may be subjected to SDS-polyacrylamide gel electrophoresis (SDS-PAGE) to separate an intended marker, stain the gel with an appropriate dye or fluorescent substance, and measure the density and the fluorescence intensity of a band corresponding to the intended marker. When the separation of the marker by SDS-PAGE only is insufficient, two dimensional electrophoresis, which is a combination with isoelectric focusing (IEF), can also be used. Further, the amount of the marker on a membrane can also be measured by Western blotting, not direct detection from the gel.

When the concentration of a marker is measured by chromatography, for example, a method with high performance liquid chromatography (HPLC) can be used. Specifically, a sample can be subjected to HPLC to separate an intended marker, measure the peak area of the chromatogram, and thereby measure the concentration of the marker in the sample.

In yet another aspect, the present invention provides an antibody or a fragment or a functional equivalent thereof, wherein the antibody is selected from the group consisting of the following antibodies: (a) an antibody of which heavy chain CDRs 1, 2, and 3 and light chain CDRs 1, 2, and 3 comprise the amino acid sequences set forth in positions 31 to 35, positions 50 to 65, positions 98 to 114, positions 163 to 170, positions 187 to 193, and positions 226 to 235 of SEQ ID NO: 3, respectively; (b) an antibody of which heavy chain CDRs 1, 2, and 3 and light chain CDRs 1, 2, and 3 comprise the amino acid sequences set forth in positions 31 to 35, positions 50 to 66, positions 99 to 110, positions 159 to 166, positions 183 to 187, and positions 222 to 231 of SEQ ID NO: 4, respectively; (c) an antibody of which heavy chain CDRs 1, 2, and 3 and light chain CDRs 1, 2, and 3 comprise the amino acid sequences set forth in positions 31 to 35, positions 50 to 66, positions 99 to 113, positions 162 to 170, positions 187 to 193, and positions 226 to 237 of SEQ ID NO: 5, respectively; (d) an antibody of which heavy chain CDRs 1, 2, and 3 and light chain CDRs 1, 2, and 3 comprise the amino acid sequences set forth in positions 31 to 35, positions 51 to 66, positions 99 to 112, positions 160 to 170, positions 187 to 193, and positions 226 to 236 of SEQ ID NO: 6, respectively; (e) an antibody of which heavy chain CDRs 1, 2, and 3 and light chain CDRs 1, 2, and 3 comprise the amino acid sequences set forth in positions 31 to 35, positions 50 to 66, positions 99 to 120, positions 169 to 176, positions 193 to 199, and positions 232 to 242 of SEQ ID NO: 7, respectively; (f) an antibody of which heavy chain CDRs 1, 2, and 3 and light chain CDRs 1, 2, and 3 comprise the amino acid sequences set forth in positions 31 to 35, positions 50 to 65, positions 98 to 114, positions 163 to 170, positions 187 to 193, and positions 226 to 235 of SEQ ID NO: 8, respectively; (g) an antibody of which heavy chain CDRs 1, 2, and 3 and light chain CDRs 1, 2, and 3 comprise the amino acid sequences set forth in positions 31 to 35, positions 50 to 66, positions 99 to 120, positions 169 to 176, positions 193 to 199, and positions 232 to 241 of SEQ ID NO: 9, respectively; (h) an antibody of which heavy chain CDRs 1, 2, and 3 and light chain CDRs 1, 2, and 3 comprise the amino acid sequences set forth in positions 31 to 35, positions 50 to 65, positions 98 to 113, positions 162 to 171, positions 188 to 194, and positions 227 to 237 of SEQ ID NO: 10, respectively; (i) an antibody of which heavy chain CDRs 1, 2, and 3 and light chain CDRs 1, 2, and 3 comprise the amino acid sequences set forth in positions 31 to 35, positions 50 to 65, positions 98 to 114, positions 163 to 170, positions 187 to 193, and positions 226 to 235 of SEQ ID NO: 11, respectively; (j) an antibody of which heavy chain CDRs 1, 2, and 3 and light chain CDRs 1, 2, and 3 comprise the amino acid sequences set forth in positions 31 to 35, positions 50 to 66, positions 99 to 113, positions 162 to 169, positions 186 to 192, and positions 225 to 234 of SEQ ID NO: 12, respectively; (k) an antibody of which heavy chain CDRs 1, 2, and 3 and light chain CDRs 1, 2, and 3 comprise the amino acid sequences set forth in positions 31 to 35, positions 50 to 66, positions 99 to 116, positions 165 to 174, positions 191 to 197, and positions 230 to 240 of SEQ ID NO: 13, respectively; (l) an antibody of which heavy chain CDRs 1, 2, and 3 and light chain CDRs 1, 2, and 3 comprise the amino acid sequences set forth in positions 31 to 35, positions 50 to 66, positions 99 to 113, positions 162 to 169, positions 186 to 192, and positions 225 to 235 of SEQ ID NO: 14, respectively; (m) an antibody of which heavy chain CDRs 1, 2, and 3 and light chain CDRs 1, 2, and 3 comprise the amino acid sequences set forth in positions 31 to 35, positions 50 to 66, positions 99 to 113, positions 162 to 170, positions 187 to 193, and positions 226 to 236 of SEQ ID NO: 15, respectively; (n) an antibody of which heavy chain CDRs 1, 2, and 3 and light chain CDRs 1, 2, and 3 comprise the amino acid sequences set forth in positions 31 to 35, positions 50 to 66, positions 99 to 110, positions 159 to 166, positions 183 to 189, and positions 222 to 237 of SEQ ID NO: 16, respectively; (o) an antibody of which heavy chain CDRs 1, 2, and 3 and light chain CDRs 1, 2, and 3 comprise the amino acid sequences set forth in positions 31 to 35, positions 50 to 65, positions 98 to 113, positions 162 to 171, positions 188 to 194, and positions 227 to 237 of SEQ ID NO: 17, respectively; (p) an antibody of which heavy chain CDRs 1, 2, and 3 and light chain CDRs 1, 2, and 3 comprise the amino acid sequences set forth in positions 31 to 35, positions 50 to 66, positions 99 to 116, positions 165 to 174, positions 191 to 197, and positions 230 to 240 of SEQ ID NO: 18, respectively; (q) an antibody of which heavy chain CDRs 1, 2, and 3 and light chain CDRs 1, 2, and 3 comprise the amino acid sequences set forth in positions 31 to 35, positions 50 to 66, positions 99 to 115, positions 164 to 175, positions 193 to 199, and positions 232 to 241 of SEQ ID NO: 19, respectively; (r) an antibody of which heavy chain CDRs 1, 2, and 3 and light chain CDRs 1, 2, and 3 comprise the amino acid sequences set forth in positions 31 to 35, positions 50 to 66, positions 99 to 117, positions 166 to 177, positions 194 to 200, and positions 233 to 242 of SEQ ID NO: 20, respectively; (s) an antibody of which heavy chain CDRs 1, 2, and 3 and light chain CDRs 1, 2, and 3 comprise the amino acid sequences set forth in positions 32 to 36, positions 51 to 67, positions 100 to 114, positions 163 to 171, positions 188 to 194, and positions 227 to 236 of SEQ ID NO: 21, respectively; (t) an antibody of which heavy chain CDRs 1, 2, and 3 and light chain CDRs 1, 2, and 3 comprise the amino acid sequences set forth in positions 31 to 35, positions 50 to 65, positions 98 to 114, positions 163 to 170, positions 187 to 193, and positions 226 to 235 of SEQ ID NO: 22, respectively; and (u) any antibody of the (a) to (t) wherein the any antibody comprises one or several substitutions, additions, or deletions in a framework of the any antibody, but is free of a mutation in the CDRs. These antibodies may have positions 33 to 61 of SEQ ID NO: 2; positions 339 to 358 and/or positions 388 to 421 of SEQ ID NO: 2; or positions 430 to 530 of SEQ ID NO: 2 as an epitope. These antibodies may be an antibody selected from monoclonal antibody, polyclonal antibody, chimeric antibody, humanized antibody, human antibody, multifunctional antibody, bispecific or oligospecific antibody, single chain antibody, scFV, diabody, sc(Fv)$_2$ (single chain (Fv)$_2$), and scFv-Fc. These antibodies can be used for any purposes described herein.

In yet another aspect, the present invention provides an antibody or a fragment or a functional equivalent thereof, the antibody having positions 33 to 61 of SEQ ID NO: 2; positions 339 to 358 and/or positions 388 to 421 of SEQ ID NO: 2; or positions 430 to 530 of SEQ ID NO: 2 as an epitope. These antibodies may an antibody selected from monoclonal antibody, polyclonal antibody, chimeric antibody, humanized antibody, human antibody, multifunctional antibody, bispecific or oligospecific antibody, single chain antibody, scFV, diabody, sc(Fv)$_2$ (single chain (Fv)$_2$), and scFv-Fc. These antibodies can be used for any purposes described herein.

(Kit)

In one aspect, a kit for detection, inspection, and/or diagnosis for carrying out a method for detection, inspection, and/or diagnosis by the present invention is provided according to the present invention. This kit comprises a detection agent, an inspecting agent, and/or a diagnostic agent of the present invention. As its embodiment, any embodiment described herein can be used alone or in combination.

In one embodiment, the detection kit according to the present invention includes a detection kit for carrying out the detection of an embodiment according to the present invention. Specifically, it includes a kit for detecting the expression of Glypican-1, the kit at least comprising a probe according to the present invention. This probe may be labeled. This kit for detection detects the expression of Glypican-1 by a hybridization method. Therefore, the detection method of the first embodiment, if desired, can further comprise various reagents for carrying out a hybridization method, for example, a substrate compound used in detecting a label, a hybridization buffer solution, instructions, and/or instruments, and the like.

In order to carrying out highly accurate detection, the detection kit of this embodiment according to the present invention may further comprise a probe, a primer, a primer set, or an antibody that can detect the expression of a marker gene for esophageal cancer other than Glypican-1 (e.g., SCC, CEA, and the like). Such a probe, a primer, a primer set, or an antibody may be labeled. This kit for detection further detects the expression of a marker gene for esophageal cancer other than Glypican-1 accordingly to any of a hybridization method, a nucleic acid amplification method, and an antigen-antibody reaction method.

In another embodiment, the kit for detection according to the present invention includes a detection kit for carrying out detection of another embodiment according to the present invention. Specifically, it includes a kit for detecting the expression of Glypican-1, the kit at least comprising a primer according to the present invention or a primer set according to the present invention. This kit for detection detects the expression of Glypican-1 according to a nucleic acid amplification method. Therefore, the detection method of the second embodiment, if desired, can further comprise various reagents for carrying out a nucleic acid amplification method, for example, a buffer solution, an internal standard indicating that PCR can normally progress, instructions, and/or instruments, and the like.

In order to carrying out highly accurate detection, the detection kit of this embodiment according to the present invention may further comprise a probe, a primer, a primer set, or an antibody that can detect the expression of a marker gene for esophageal cancer other than Glypican-1. Such a probe, a primer, a primer set, or an antibody may be labeled. This kit for detection further detects the expression of a marker for esophageal cancer other than Glypican-1 according to any of a hybridization method, a nucleic acid amplification method, and an antigen-antibody reaction method.

In a further embodiment, the detection kit according to the present invention includes a detection kit for carrying out detection of a further embodiment according to the present invention. Specifically, it includes a kit for detecting a protein of Glypican-1, the kit at least comprising an antibody according to the present invention. This antibody may be labeled. This kit for detection detects the expression of Glypican-1 by detecting an antigen-antibody reaction. The detection method of this embodiment, if desired, can further comprise various reagents for carrying out an antigen-antibody reaction, for example, a secondary antibody used in an ELISA method and the like, a coloring reagent, a buffer solution, instructions, and/or instruments, and the like.

It may be understood that as long as a marker of the present invention (e.g., Glypican-1) can be identified, such a kit, a composition, or a system can use a marker in any subject-derived sample, an agent of specifically interacting on the marker, or a means of selectively recognizing the marker. Accordingly, it is understood possible to use not only an agent or a means specifically described herein but also any equivalent agent or means known in the art.

In one embodiment, an agent used in the present invention is selected from the group consisting of nucleic acid molecules, polypeptides, lipids, sugar chains, organic low molecules, and complex molecules thereof. Preferably, the agent is a protein or a complex molecule (e.g., a glycoprotein, a lipoprotein, and the like). Preferably, the agent is an antibody (e.g., polyclonal antibody or monoclonal antibody). It is preferable that such an agent is labeled or can be labeled. The reason is that diagnosing is made easier.

In a preferable embodiment of the present invention, a means to be used is selected from the group consisting of a mass spectrometer, a nuclear magnetic resonance measuring apparatus, an X-ray analyzer, SPR, chromatography (e.g., HPLC, thin layer chromatography, and gas chromatography), an immunological means (e.g., Western blotting, ETA (enzyme immunoassay), RIA (radioimmunoassay), and ELISA (enzyme-linked immunosorbent assay)), a biochemical means (e.g., pI electrophoresis, Southern blotting, two-dimensional electrophoresis), an electrophoresis device, a chemical analyzer, a fluorescence two-dimensional differential electrophoresis method (2DE-DIGE), an isotope labeling method (ICAT), a tandem affinity purification method (TAP method), a physical means, laser microdissection, and combinations thereof.

In a preferable embodiment of the present invention, the system or kit of the present invention further comprises a standard of a marker. It is preferable that such a standard is used to confirm whether a means of detecting a marker (an agent of specifically interacting on the marker, a means of selectively recognizing the marker, or the like) normally functions.

In a preferable embodiment, the present invention can further comprise a means of purifying a targeted sample. Examples of such a purifying means can include Chromatography and the like. Since purification increases the accuracy of diagnosis, it can be used in a preferable embodiment. However, it is not essential.

In one embodiment, the agent or means used in the present invention has an ability to quantify a marker of the present invention. In such quantification, it is preferred to have an agent or means by which a calibration curve can be properly drawn in drawing a standard curve. Preferably, examples thereof can include an antibody, mass spectroscopy, chromatography analysis, and the like. Therefore, in an embodiment, the system of the present invention further comprises a quantifying means to quantify a marker.

In one embodiment, a quantifying means comprises a determining means to determine whether the marker falls within the range of a normal value by comparing a standard curve with a measurement result. Such a determining means can be achieved using a computer.

In one embodiment, the kit or system of the present invention comprises a composition comprising a marker or the above-mentioned specifically interacting agent of the marker.

In one aspect, the present invention provides the use of a marker in a subject-derived sample, a specifically interacting agent of the marker, or a means of selectively recognizing the marker in the manufacture of a medicament for predictive diagnosis, prediagnosis, prediction, detection, or diagnosis of the growth ability level or a differentiated state, or a disease, a disorder, or a condition associated therewith. In this regard, a sample may be obtained in any way. Generally, when a person responsible other than a doctor engages in measurement, it can be a sample obtained by a doctor in some way. Decision from a measurement result on the growth ability level or a differentiated state or on whether there is a disease, a disorder, or a condition associated therewith, or the possibility thereof can be made by determining whether it is abnormal by comparing each marker with a normal value. In the method of the present invention, it is understood that a marker to be used and the like may have any one or plural characteristics described in other portions of the present specification as long as the characteristics are not contradictory. In the detection or diagnosis of the present invention, a method generally used in quantifying a protein as it is can be used as a method of measuring the concentration of a marker as long as it is a method that can specifically measure the concentration of the marker. For example, various immunoassays, mass spectroscopy (MS), chromatography, electrophoresis, and the like can be used.

One of preferable embodiments in the detection or diagnosis of the present invention is to capture a marker on a carrier and measure the concentration of the captured marker. Specifically, a substance having an affinity for a marker is immobilized to a carrier and the marker is captured on the carrier via the substance having the affinity. According to the present embodiment, the influence of a contaminant contained in a sample can be reduced and the concentration of a marker can be measured with higher sensitivity and higher accuracy.

In one embodiment, when immunoassay is used as a measuring method of a marker, it is preferable to use a carrier to which an antibody is immobilized. If do so, an immunoassay system using an antibody immobilized to a carrier as a primary antibody can easily be constructed. For example, a system of sandwich EIA can be constructed by providing two types of marker-specific antibodies of which the epitopes are different, immobilizing one as a primary antibody to a carrier, enzyme-labeling the other as a secondary antibody. Other than that, an immunoassay system by a binding inhibition assay method or a competition method can also be constructed. Further, when a basal plate is used as a carrier, immunoassay with an antibody chip is possible. With an antibody chip, the concentrations of plural markers can be measured at the same time and rapid measurement is possible.

Meanwhile, in one embodiment, when mass spectroscopy is used in a measurement method of a marker, the marker can also be captured to a carrier by ionic bond or hydrophobic interaction other than an antibody. Ionic bond and hydrophobic interaction do not have so much specificity as bioaffinity between an antigen and an antibody or the like, and substances other than a marker are also captured. However, it is no problem since quantification with a mass spectrometer spectrum reflecting a molecular weight is carried out according to mass spectroscopy. Particularly, when a protein chip using a basal plate is used as a carrier and surface-enhanced laser desorption/ionization-time-of-flight mass spectrometry (herein referred to as "SELDI-TOF-MS") is carried out, the concentration of a marker can be more accurately measured. With regard to the type of a basal plate that can be used, a cation exchange basal plate, an anion exchange basal plate, a normal phase basal plate, a reverse phase basal plate, a metal ion basal plate, an antibody basal plate, and the like can be used, while a cation exchange basal plate, particularly a weak cation exchange basal plate, and a metal ion basal plate are preferably used.

When a marker is captured to a carrier by ionic bond, an ion exchanger is immobilized to the carrier. In this case, both of an anion exchanger and a cation exchanger can be used as an ion exchanger. Further, all of a strong anion exchanger, a weak anion exchanger, a strong cation exchanger, and a weak cation exchanger can be used. Examples of the weak anion exchanger include, for example, those having a weak anion exchange group, such as dimethylaminoethyl (DE), diethylaminoethyl (DEAF), and the like. In addition, examples of the strong anion exchanger include those having a strong anion exchange group, such as quaternary ammonium (trimethylaminomethyl) (QA), quaternary aminoethyl (diethyl, mono-2-hydroxybutylaminoethyl) (QAE), quaternary ammonium (trimethylammonium) (QMA), and the like. Furthermore, examples of the weak cation exchanger include those having a weak cation exchange group, such as carboxymethyl (CM) and the like. Further, examples of the strong cation exchanger include those having a strong cation exchange group, such as sulfopropyl (SP) and the like. Meanwhile, when a marker is captured to a carrier by hydrophobic interaction, a substance having a hydrophobic group is immobilized to the carrier. Examples of the hydrophobic group include C4 to C20 alkyl groups, a phenyl group, and the like. Furthermore, a marker can be captured to a carrier to which a metal ion, such as $Cu^{2+}$, $Zn^{2+}$, $Ni^{2+}$, $Ca^{2+}$, $Co^{2+}$, $Mg^{2+}$, and the like, is immobilized.

In one embodiment, known carrier, such as beads, a microtiter plate, a resin, and the like, can be used as an example of a carrier to be used. Particularly, beads and a microtiter plate are conventionally used in immunoassay and easy to construct a measuring system. Meanwhile, a carrier having a flat part, such as a basal plate, can also be used. In this case, it is preferable to immobilize a substance having an affinity to a marker to a portion of the flat part. Examples thereof include a carrier in which a chip is used as the base and a marker-specific antibody is immobilized to plural portions on the surface thereof in spots.

The detection, inspection, or diagnosis method according to the present invention can be applied to screening for substances effective for prevention or treatment of esophageal cancer. Specifically, substances to be tested can be screened for effective binding or interaction with Glypican-1 or a nucleic acid molecule encoding it, wherein the binding or interaction is used as indicator. Substances to be tested that can be used include, but are not limited to, a synthetic low molecule compound, a protein, a synthetic peptide, a purified or partially purified polypeptide, an andtibody, a substance released by bacteria (including a metabolite of bacteria), nucleic acid (antisense, ribozyme, RNAi, and the like), and the like, and are preferably compounds or salts thereof, or solvates thereof (e.g., hydrates). A substance to be tested may be a novel substance or a known substance. A substance identified according to a screening method by the present invention can be used as a substance effective for treatment or prevention of esophageal cancer.

(Treatment and Prevention of Esophageal Cancer)

In one aspect, the present invention provides a composition or a medicament (a therapeutic drug or a prophylactic drug) for prevention or treatment of esophageal cancer, comprising a Glypican-1 suppressant. Esophageal cancer can be treated or prevented by using such a therapeutic or prophylactic drug. Since such a therapeutic or prophylactic drug uses antibodies, it is an excellent drug from the viewpoint of safety.

In one embodiment, esophageal cancer that the present invention targets is Glypican-1 positive. In one embodiment, esophageal cancer that the present invention targets comprises those in lymph node metastasis sites, squamous cell carcinoma, and/or adenocarcinoma. In specific embodiments, esophageal cancer that the present invention targets comprises squamous cell carcinoma.

In one specific embodiment, the composition or medicament (therapeutic drug, prophylactic drug, or the like) of the present invention is formulated in anticipation of implementation in administration to a patient determined to have an episode of Glypican-1 positive esophageal cancer. In one embodiment, the Glypican-1 suppressant used in the present invention is an antibody, a fragment or a functional equivalent thereof, or a nucleic acid.

In a specific embodiment, the Glypican-1 suppressant used in the present invention is a nucleic acid, which is an antisense nucleic acid, siRNA, or the like. Specifically, the siRNA comprise SEQ ID NO: 23 and/or SEQ ID NO: 24 and may comprise SEQ ID NO: 25 and SEQ ID NO: 26.

In another embodiment, the Glypican-1 suppressant is an antibody or a fragment or a functional equivalent thereof and the antibody is characterized by having any of the following SEQ ID NOs: 1 to 22, or a fragment or a functional equivalent thereof. The antibody may be an antibody or antigen binding fragment thereof comprising any sequence comprising CDRs of the full length sequence, or an antibody or antigen binding fragment thereof comprising a variable region of the following sequence, the framework region thereof comprising 1, 2, 3, 4, 5, 6, 7, 8, 9, 10, 12, 15, 17, 20 or more substitutions, additions, or deletions. More particularly, the present invention may be one or more antibodies selected from the group consisting of (a) an antibody of which heavy chain CDRs 1, 2, and 3 and light chain CDRs 1, 2, and 3 comprise the amino acid sequences set forth in positions 31 to 35, positions 50 to 65, positions 98 to 114, positions 163 to 170, positions 187 to 193, and positions 226 to 235 of SEQ ID NO: 3, respectively; (b) an antibody of which heavy chain CDRs 1, 2, and 3 and light chain CDRs 1, 2, and 3 comprise the amino acid sequences set forth in positions 31 to 35, positions 50 to 66, positions 99 to 110, positions 159 to 166, positions 183 to 187, and positions 222 to 231 of SEQ ID NO: 4, respectively; (c) an antibody of which heavy chain CDRs 1, 2, and 3 and light chain CDRs 1, 2, and 3 comprise the amino acid sequences set forth in positions 31 to 35, positions 50 to 66, positions 99 to 113, positions 162 to 170, positions 187 to 193, and positions 226 to 237 of SEQ ID NO: 5, respectively; (d) an antibody of which heavy chain CDRs 1, 2, and 3 and light chain CDRs 1, 2, and 3 comprise the amino acid sequences set forth in positions 31 to 35, positions 51 to 66, positions 99 to 112, positions 160 to 170, positions 187 to 193, and positions 226 to 236 of SEQ ID NO: 6, respectively; (e) an antibody of which heavy chain CDRs 1, 2, and 3 and light chain CDRs 1, 2, and 3 comprise the amino acid sequences set forth in positions 31 to 35, positions 50 to 66, positions 99 to 120, positions 169 to 176, positions 193 to 199, and positions 232 to 242 of SEQ ID NO: 7, respectively; (f) an antibody of which heavy chain CDRs 1, 2, and 3 and light chain CDRs 1, 2, and 3 comprise the amino acid sequences set forth in positions 31 to 35, positions 50 to 65, positions 98 to 114, positions 163 to 170, positions 187 to 193, and positions 226 to 235 of SEQ ID NO: 8, respectively; (g) an antibody of which heavy chain CDRs 1, 2, and 3 and light chain CDRs 1, 2, and 3 comprise the amino acid sequences set forth in positions 31 to 35, positions 50 to 66, positions 99 to 120, positions 169 to 176, positions 193 to 199, and positions 232 to 241 of SEQ ID NO: 9, respectively; (h) an antibody of which heavy chain CDRs 1, 2, and 3 and light chain CDRs 1, 2, and 3 comprise the amino acid sequences set forth in positions 31 to 35, positions 50 to 65, positions 98 to 113, positions 162 to 171, positions 188 to 194, and positions 227 to 237 of SEQ ID NO: 10, respectively; (i) an antibody of which heavy chain CDRs 1, 2, and 3 and light chain CDRs 1, 2, and 3 comprise the amino acid sequences set forth in positions 31 to 35, positions 50 to 65, positions 98 to 114, positions 163 to 170, positions 187 to 193, and positions 226 to 235 of SEQ ID NO: 11, respectively; (j) an antibody of which heavy chain CDRs 1, 2, and 3 and light chain CDRs 1, 2, and 3 comprise the amino acid sequences set forth in positions 31 to 35, positions 50 to 66, positions 99 to 113, positions 162 to 169, positions 186 to 192, and positions 225 to 234 of SEQ ID NO: 12, respectively; (k) an antibody of which heavy chain CDRs 1, 2, and 3 and light chain CDRs 1, 2, and 3 comprise the amino acid sequences set forth in positions 31 to 35, positions 50 to 66, positions 99 to 116, positions 165 to 174, positions 191 to 197, and positions 230 to 240 of SEQ ID NO: 13, respectively; (1) an antibody of which heavy chain CDRs 1, 2, and 3 and light chain CDRs 1, 2, and 3 comprise the amino acid sequences set forth in positions 31 to 35, positions 50 to 66, positions 99 to 113, positions 162 to 169, positions 186 to 192, and positions 225 to 235 of SEQ ID NO: 14, respectively; (m) an antibody of which heavy chain CDRs 1, 2, and 3 and light chain CDRs 1, 2, and 3 comprise the amino acid sequences set forth in positions 31 to 35, positions 50 to 66, positions 99 to 113, positions 162 to 170, positions 187 to 193, and positions 226 to 236 of SEQ ID NO: 15, respectively; (n) an antibody of which heavy chain CDRs 1, 2, and 3 and light chain CDRs 1, 2, and 3 comprise the amino acid sequences set forth in positions 31 to 35, positions 50 to 66, positions 99 to 110, positions 159 to 166, positions 183 to 189, and positions 222 to 237 of SEQ ID NO: 16, respectively; (o) an antibody of which heavy chain CDRs 1, 2, and 3 and light chain CDRs 1, 2, and 3 comprise the amino acid sequences set forth in positions 31 to 35, positions 50 to 65, positions 98 to 113, positions 162 to 171, positions 188 to 194, and positions 227 to 237 of SEQ ID NO: 17, respectively; (p) an antibody of which heavy chain CDRs 1, 2, and 3 and light chain CDRs 1, 2, and 3 comprise the amino acid sequences set forth in positions 31 to 35, positions 50 to 66, positions 99 to 116, positions 165 to 174, positions 191 to 197, and positions 230 to 240 of SEQ ID NO: 18, respectively; (q) an antibody of which heavy chain CDRs 1, 2, and 3 and light chain CDRs 1, 2, and 3 comprise the amino acid sequences set forth in positions 31 to 35, positions 50 to 66, positions 99 to 115, positions 164 to 175, positions 193 to 199, and positions 232 to 241 of SEQ ID NO: 19, respectively; (r) an antibody of which heavy chain CDRs 1, 2, and 3 and light chain CDRs 1, 2, and 3 comprise the amino acid sequences set forth in positions 31 to 35, positions 50 to 66, positions 99 to 117, positions 166 to 177, positions 194 to 200, and positions 233 to 242 of SEQ ID NO: 20, respectively; (s) an antibody of which heavy chain CDRs 1, 2, and 3 and light chain CDRs 1, 2, and 3 comprise the amino acid sequences set forth in positions 32 to 36, positions 51 to 67, positions 100 to 114, positions 163 to 171, positions 188 to 194, and positions 227 to 236 of SEQ ID NO: 21, respectively; and (t) an antibody of which heavy chain CDRs 1, 2, and 3 and light chain CDRs 1, 2, and 3 comprise the amino acid sequences set forth in positions 31 to 35, positions 50 to 65, positions 98 to 114, positions 163 to 170, positions 187 to 193, and positions 226 to 235 of SEQ ID NO: 22, respectively; or a mutant of said antibodies wherein the mutant comprises one or several substitutions, additions, or deletions in a framework of said antibodies, but is free of a mutation in the CDRs. The antibody can be manufactured by using an embodiment described in other parts of the specification and/or an approach known in the art. For treatment or prevention of the present invention, it is preferable that such an antibody or a fragment or a functional equivalent thereof has activity to suppress Glypican-1 or downstream information transmitting pathway thereof. Such activity may be confirmed by observing the amount of expression or activity of Glypican-1, or by directly using esophageal cancer cell strains to observe inhibition of cell growth, cytotoxic activity with antibody-dependent cell-mediated cytotoxicity (ADCC), tumor regression after transplantation into model animals or the like. Such approaches are well known in the art, while the approach used herein may also be used. These antibodies of the present invention, in specific embodiments, can be antibodies selected from monoclonal antibody, polyclonal antibody, chimeric antibody, humanized antibody, human antibody, multifunctional antibody, bispecific or oligospecific antibody, single chain antibody, scFV, diabody, sc(Fv)$_2$ (single chain (Fv)$_2$), and scFv-Fc.

In another aspect, the present invention provides a method of preventing or treating esophageal cancer of a subject, comprising administering an effective amount of Glypican-1 suppressant to the subject in need thereof. It is understood that any form described in other parts of the present specification can be used as the Glypican-1 suppressant used in the prevention or treatment method of the present invention.

In another aspect, the present invention also provides a composition or a medicament (therapeutic drug or prophylactic drug) for preventing or treating esophageal cancer, comprising a Glypican-1 binding agent. In a preferred embodiment, the composition or medicament (therapeutic drug, prophylactic drug, or the like) further comprises a cell-killing agent. Thus, such a composition or medicament (therapeutic drug, prophylactic drug or the like) may include a complex molecule.

In a specific embodiment, the Glypican-1 binding agent is an antibody, a fragment or a functional equivalent thereof, or a nucleic acid. In a preferred embodiment, the Glypican-1 binding agent is an antibody or a fragment or a functional equivalent thereof, further bound to a cell-killing agent.

As used herein, "cell-killing agent" is an agent that may dissolve a cell membrane. When the agent is a peptide, the cell killing agent is called a cytotoxic peptide. Cytotoxic peptide has various nomenclatures in the art. For example, "soluble peptidic component" and "cell-killing sequence" are also called "cytolic peptide (sequence)", "cell dissolving peptide (sequence)" or the like. However, they are used synonymously in the content of the present invention. Representative examples of such a cytotoxic agent include those listed in Gail D. et al., Cancer Res 2008; 68: 9280-9290; Ian Krop and Eric P. Winer, Clin Cancer Res; 20 (1); 1-6. and K Naito et al., Leukemia (2000) 14, 1436-144, as well as, but not limited to, maytansinoid, emtansine, N-acetyl-γ calicheamicin dimethyl hydrazide (NAc-γ calicheamicin, DMH) comprised in CMA-676 and the like. Representative cell killing peptide includes, but is not limited to, cell membrane dissolving peptide, cell membrane potential destabilizing peptide, cell membrane dissolving/nucleic acid binding peptide, and mitochondrial membrane disintegrating peptide.

Such a cell-killing agent may be bound to the binding agent of the present invention such as an antibody with a spacer as needed. As used herein, "spacer" refers to a moiety that forms a chemical bond between molecules of chain-like polymers so as to bridge the molecules. Such a spacer is also called a linker. Representative spacers of a peptide include, but are not limited to, a sequence of 0-5 amino acids consisting of G and P. A spacer is not essential and may not be present.

A combination of the binding agent of the present invention and cell-killing agent can also be considered a complex molecule. An example is provided to explain such a molecule. Such a molecule can be explained as a molecule made by combining a cytotoxic portion corresponding to the explosive charge portion and a portion responsible for specificity to a cancer cell corresponding to the warhead portion (e.g., peptide/sequence that specifically binds to a receptor which is highly expressed in cancer cells, typically an antibody). When a spacer is used, the molecule would be comprised of a cancer cell specific binding agent+spacer+cell-killing agent. Any cancer specific binding agent, any spacer, and any cell-killing agent can be combined herein in any manner. Examples of a manufacturing method and usage method thereof are described. Such a molecule is generally made by a chemical synthesis method, but when such a molecule is comprised of peptides, a method of forced expression and purification by genetic engineering or a method combining such a method can also be used.

For use of the present invention, Glypican-1 expression on the cell surface and sensitivity to damage of cancer cells to cell-killing agent are investigated for cancer cells to be subjected to treatment. Warhead and explosive charge are selected base on the result thereof to design an optimal molecule for the cancer cell. A custom-made peptide toxin obtained from chemical synthesis or the like can be combined as needed with DDS such as atelocollagen and administered locally or systemically for treatment.

Therefore, in preferable embodiments, esophageal cancer that the complex molecule of the present invention targets is Glypican-1 positive. In specific embodiments, this esophageal cancer comprises squamous cell carcinoma.

In one embodiment, a Glypican-1 binding agent is an antibody or a fragment or a functional equivalent thereof. The antibody may have any sequence described above.

It is preferable that an administration pathway of a therapeutic drug that is effective in treatment is used. For example, the administration pathway may be intravenous, subcutaneous, intramuscular, intraperitoneal, oral administration or the like. The mode of administration may be, for example, injection, capsule, tablet, granule or the like. When an antibody or polynucleotide is administered, use thereof as an injection is effective. An aqueous solution for injection may be stored, for example, in a vial or a stainless street container. Further, an aqueous solution for injection may contain, for example, saline, saccharide (e.g., trehalose), NaCl, NaOH or the like. Further, a therapeutic drug may contain a buffer (e.g., phosphate buffer), stabilizer, or the like.

The composition, medicament, therapeutic agent, prophylactic agent and the like of the present invention generally comprise a therapeutically effective amount of therapeutic agent or effective ingredient and a pharmaceutically acceptable carrier or excipient. As used herein, "pharmaceutically acceptable" means that government regulatory agency-approved or pharmacopoeia or other commonly recognized pharmacopoeia-listed for use in animals and more specifically in humans. As used herein "carrier" refers to a diluent, adjuvant, excipient or vehicle administered in conjunction with a therapeutic agent. Such a carrier can be an aseptic liquid such as water or oil, including but not limited to liquids derived from petroleum, animal, plant or synthesis, as well as peanut oil, soybean oil, mineral oil, sesame oil and the like. When a medicament is orally administered, water is a preferred carrier. For intravenous administration of a pharmaceutical composition, saline and aqueous dextrose are preferred carriers. Preferably, aqueous saline solution and aqueous dextrose and glycerol solution are used as a liquid carrier of an injectable solution. Suitable excipients include light anhydrous silicic acid, crystalline cellulose, mannitol, starch, glucose, lactose, sucrose, gelatin, malt, rice, wheat flour, chalk, silica gel, sodium stearate, glyceryl monostearate, talc, sodium chloride, powdered skim milk, glycerol, propylene, glycol, water, ethanol, carmellose calcium, carmellose sodium, hydroxypropyl cellulose, hydroxypropyl methylcellulose, polyvinyl acetal diethylamino acetate, polyvinylpyrrolidone, gelatin, medium-chain fatty acid triglyceride, polyoxyethylene hydrogenated castor oil 60, saccharose, carboxymethylcellulose, corn starch, inorganic salt and the like. When desired, the composition can contain a small amount of wetting agent or emulsifier or pH buffer. These compositions can be in a form of solution, suspension, emulsion, tablet, pill, capsule, powder, sustained release mixture or the like. It is also possible to use traditional binding agents and carriers, such as tryglyceride, to prepare a composition as a suppository. Oral preparation can also comprise a standard carrier such as medicament grade mannitol, lactose, starch, magnesium stearate, sodium saccharin, cellulose, or magnesium carbonate. Examples of a suitable carrier are described in E. W. Martin, Remington's Pharmaceutical Sciences (Mark Publishing Company, Easton, U. S. A). Such a composition contains a therapeutically effective amount of therapy agent and preferably in a purified form, together with a suitable amount of carrier, such that the composition is provided in a form suitable for administration to a patient. A preparation must be suitable for the administration format. In addition, the composition may comprise, for example, a surfactant, excipient, coloring agent, flavoring agent, preservative, stabilizer, buffer, suspension, isotonizing agent, binding agent, disintegrant, lubricant, fluidity improving agent, corrigent, or the like.

When the present invention is administered as a medicament, various delivery systems are known, and such systems can be used to administer a therapeutic agent of the present invention to a suitable site (e.g., esophagus). Such a system, for example, can use a recombinant cell that can express encapsulated therapeutic agent (e.g., polypeptide) in liposomes, microparticles and microcapsules or use of endocytosis mediated by a receptor; construction of a therapy nucleic acid as a part of a retrovirus vector or other vector or the like. The method of introduction includes, but not limited to, intradermal, intramuscular, intraperitoneal, intravenous, subcutaneous, intranasal, epidural and oral pathways. A medicament can be administered by any suitable pathway, such as by injection, bolus injection, or by absorption through epithelial or mucocutaneous lining (e.g., oral cavity, rectum, intestinal mucosa or the like). In addition, an inhaler or mistifier using an aerosolizing agent can be used as needed. Moreover, other biological activating agents can also be administered together. Administration can be systemic or local. When the present invention is used in an esophagus region, a medicament may further be administered through any suitable pathway such as direct injection into an esophagus.

In a specific embodiment where a therapeutic agent is a nucleic acid, the nucleic acid can be constructed as a part of a suitable nucleic acid expression vector and administered in vivo to be present in a cell to promote expression of an encoded protein. This can be implemented, for example, by using a retrovirus vector, direct injection, use of a microparticle gun, coating the nucleic acid with lipid, cell surface receptor or transfection agent, or administering a nucleic acid linked to a tag sequence known to enter the nucleus. Alternatively, a nucleic acid therapeutic agent can be introduced in a cell such that it is incorporated into a host cell DNA by homologous recombination for expression.

In a preferred embodiment, a composition can be prepared as a pharmaceutical composition adapted to administration to humans in accordance with a known method. Such a composition can be administered by an injection. A composition for injection is typically a solution in an aseptic isotonic aqueous buffer. A composition can also comprise a local anesthetic such as lidocaine which alleviates the pain at the site of injection and a solubilizing agent as needed. Generally, ingredients can be supplied separately or by mixing the ingredients together in a unit dosing form and supplied, for example, in a sealed container such as an ampoule or sachet showing the amount of active agent or as a lyophilized powder or water-free concentrate. When a composition is to be administered by injection, the composition can be distributed by using an injection bottle containing aseptic agent-grade water or saline. When a composition is to be administered by injection, an aseptic water or saline ampoule for injection can also be provided such that the ingredients can be mixed prior to administration.

The composition, medicament, therapeutic agent, and prophylactic agent of the present invention can be prepared as a neutral or salt form or other prodrugs (e.g., ester or the like). Pharmaceutically acceptable salts include salts formed with a free carboxyl group, derived from hydrochloric acid, phosphoric acid, acetic acid, oxalic acid, tartaric acid or the like, salts formed with a free amine group, derived from isopropylamine, trimethylamine, 2-ethylaminoethanol, histidine, procaine or the like, and salts derived from sodium, potassium, ammonium, calcium, or ferric hydroxide or the like.

The amount of therapeutic agent of the present invention that is effective in treatment of a specific disorder or condition may vary depending on the properties of the disorder or condition. However, such an amount can be determined by those skilled in the art by a standard clinical technique based on the descriptions herein. Furthermore, an in vitro assay can be used in some cases to assist the identification of the optimal dosing range. The precise dose to be used in a preparation may also vary depending on the administration pathway or the severity of the disease or disorder. Thus, the dose should be determined in accordance with the judgment of the attending physician or the condition of each patient. The dosage is not particularly limited, but may be 0.001, 1, 5, 10, 15, 100 or 1000 mg/kg body weight per dosage or within a range between any two values described above. The dosing interval is not particularly limited, but may be, for example, 1 or 2 administration every 1, 7, 14, 21, or 28 days or 1 or 2 administrations in the range of period between any two values described above. The dosage, dosing interval, and dosing method may be appropriately selected depending on the age, weight, symptom, target organ or the like of the patient. Further, it is preferable that a therapeutic drug contains a therapeutically effective amount, or an amount effective for exerting a desired effect, of effective ingredients. When a malignant tumor marker significantly decreases after administration, the presence of a therapeutic effect may be acknowledged. An effective dose can be estimated from a dose-response curve obtained from an in vitro or animal model test system.

"Patient" in one embodiment of the present invention includes humans and mammals excluding humans (e.g., one or more types of mice, guinea pigs, hamsters, rats, rabbits, pigs, sheep, goats, cows, horses, cats, dogs, marmosets, monkeys and the like). Further, the patient may be a patient determined or diagnosed as having an episode of Glypican-1 positive malignant tumor. It is preferable that determination or diagnosis in this regard is performed by detecting the Glypican-1 protein level.

The pharmaceutical composition, therapeutic agent or prophylactic agent of the present invention can be provided as a kit.

In a specific embodiment, the present invention provides an agent pack or kit comprising one or more containers filled with one or more ingredients of the composition or medicament of the present invention. Optionally, information indicating approval for manufacture, use or sale for administration to a human by a government agency regulating the manufacture, use or sale of medicaments or biological products in a stipulated form can be appended to such a container.

The kit of the present invention can also contain an expression vector encoding a protein to be used as the composition, therapeutic agent, prophylactic agent or medicament of the present invention. Since such a protein, after expression, forms a biologically active complex, the protein may be reconstituted. Such a kit preferably contains a required buffer and a reagent. Optionally, instruction (package insert) for use of the kit and/or information indicating approval for manufacture, use or sale for administration to a human by a government agency regulating the manufacture, use or sale of medicaments or biological products in a stipulated form can be appended to such a container.

In a specific embodiment, the pharmaceutical composition comprising a nucleic acid of the present invention can be administered via liposomes, microparticles, or microcapsules. In various embodiments of the present invention, it may be useful to use such a composition to achieve sustained release of the nucleic acid.

One embodiment of the present invention may be an anti-Glypican-1 antibody, which is one or more antibodies selected from the group consisting of (a) an antibody of which heavy chain CDRs 1, 2, and 3 and light chain CDRs 1, 2, and 3 comprise the amino acid sequences set forth in positions 31 to 35, positions 50 to 65, positions 98 to 114, positions 163 to 170, positions 187 to 193, and positions 226 to 235 of SEQ ID NO: 3, respectively; (b) an antibody of which heavy chain CDRs 1, 2, and 3 and light chain CDRs 1, 2, and 3 comprise the amino acid sequences set forth in positions 31 to 35, positions 50 to 66, positions 99 to 110, positions 159 to 166, positions 183 to 187, and positions 222 to 231 of SEQ ID NO: 4, respectively; (c) an antibody of which heavy chain CDRs 1, 2, and 3 and light chain CDRs 1, 2, and 3 comprise the amino acid sequences set forth in positions 31 to 35, positions 50 to 66, positions 99 to 113, positions 162 to 170, positions 187 to 193, and positions 226 to 237 of SEQ ID NO: 5, respectively; (d) an antibody of which heavy chain CDRs 1, 2, and 3 and light chain CDRs 1, 2, and 3 comprise the amino acid sequences set forth in positions 31 to 35, positions 51 to 66, positions 99 to 112, positions 160 to 170, positions 187 to 193, and positions 226 to 236 of SEQ ID NO: 6, respectively; (e) an antibody of which heavy chain CDRs 1, 2, and 3 and light chain CDRs 1, 2, and 3 comprise the amino acid sequences set forth in positions 31 to 35, positions 50 to 66, positions 99 to 120, positions 169 to 176, positions 193 to 199, and positions 232 to 242 of SEQ ID NO: 7, respectively; (f) an antibody of which heavy chain CDRs 1, 2, and 3 and light chain CDRs 1, 2, and 3 comprise the amino acid sequences set forth in positions 31 to 35, positions 50 to 65, positions 98 to 114, positions 163 to 170, positions 187 to 193, and positions 226 to 235 of SEQ ID NO: 8, respectively; (g) an antibody of which heavy chain CDRs 1, 2, and 3 and light chain CDRs 1, 2, and 3 comprise the amino acid sequences set forth in positions 31 to 35, positions 50 to 66, positions 99 to 120, positions 169 to 176, positions 193 to 199, and positions 232 to 241 of SEQ ID NO: 9, respectively; (h) an antibody of which heavy chain CDRs 1, 2, and 3 and light chain CDRs 1, 2, and 3 comprise the amino acid sequences set forth in positions 31 to 35, positions 50 to 65, positions 98 to 113, positions 162 to 171, positions 188 to 194, and positions 227 to 237 of SEQ ID NO: 10, respectively; (i) an antibody of which heavy chain CDRs 1, 2, and 3 and light chain CDRs 1, 2, and 3 comprise the amino acid sequences set forth in positions 31 to 35, positions 50 to 65, positions 98 to 114, positions 163 to 170, positions 187 to 193, and positions 226 to 235 of SEQ ID NO: 11, respectively; (j) an antibody of which heavy chain CDRs 1, 2, and 3 and light chain CDRs 1, 2, and 3 comprise the amino acid sequences set forth in positions 31 to 35, positions 50 to 66, positions 99 to 113, positions 162 to 169, positions 186 to 192, and positions 225 to 234 of SEQ ID NO: 12, respectively; (k) an antibody of which heavy chain CDRs 1, 2, and 3 and light chain CDRs 1, 2, and 3 comprise the amino acid sequences set forth in positions 31 to 35, positions 50 to 66, positions 99 to 116, positions 165 to 174, positions 191 to 197, and positions 230 to 240 of SEQ ID NO: 13, respectively; (1) an antibody of which heavy chain CDRs 1, 2, and 3 and light chain CDRs 1, 2, and 3 comprise the amino acid sequences set forth in positions 31 to 35, positions 50 to 66, positions 99 to 113, positions 162 to 169, positions 186 to 192, and positions 225 to 235 of SEQ ID NO: 14, respectively; (m) an antibody of which heavy chain CDRs 1, 2, and 3 and light chain CDRs 1, 2, and 3 comprise the amino acid sequences set forth in positions 31 to 35, positions 50 to 66, positions 99 to 113, positions 162 to 170, positions 187 to 193, and positions 226 to 236 of SEQ ID NO: 15, respectively; (n) an antibody of which heavy chain CDRs 1, 2, and 3 and light chain CDRs 1, 2, and 3 comprise the amino acid sequences set forth in positions 31 to 35, positions 50 to 66, positions 99 to 110, positions 159 to 166, positions 183 to 189, and positions 222 to 237 of SEQ ID NO: 16, respectively; (o) an antibody of which heavy chain CDRs 1, 2, and 3 and light chain CDRs 1, 2, and 3 comprise the amino acid sequences set forth in positions 31 to 35, positions 50 to 65, positions 98 to 113, positions 162 to 171, positions 188 to 194, and positions 227 to 237 of SEQ ID NO: 17, respectively; (p) an antibody of which heavy chain CDRs 1, 2, and 3 and light chain CDRs 1, 2, and 3 comprise the amino acid sequences set forth in positions 31 to 35, positions 50 to 66, positions 99 to 116, positions 165 to 174, positions 191 to 197, and positions 230 to 240 of SEQ ID NO: 18, respectively; (q) an antibody of which heavy chain CDRs 1, 2, and 3 and light chain CDRs 1, 2, and 3 comprise the amino acid sequences set forth in positions 31 to 35, positions 50 to 66, positions 99 to 115, positions 164 to 175, positions 193 to 199, and positions 232 to 241 of SEQ ID NO: 19, respectively; (r) an antibody of which heavy chain CDRs 1, 2, and 3 and light chain CDRs 1, 2, and 3 comprise the amino acid sequences set forth in positions 31 to 35, positions 50 to 66, positions 99 to 117, positions 166 to 177, positions 194 to 200, and positions 233 to 242 of SEQ ID NO: 20, respectively; (s) an antibody of which heavy chain CDRs 1, 2, and 3 and light chain CDRs 1, 2, and 3 comprise the amino acid sequences set forth in positions 32 to 36, positions 51 to 67, positions 100 to 114, positions 163 to 171, positions 188 to 194, and positions 227 to 236 of SEQ ID NO: 21, respectively; and (t) an antibody of which heavy chain CDRs 1, 2, and 3 and light chain CDRs 1, 2, and 3 comprise the amino acid sequences set forth in positions 31 to 35, positions 50 to 65, positions 98 to 114, positions 163 to 170, positions 187 to 193, and positions 226 to 235 of SEQ ID NO: 22, respectively; or a mutant of said antibodies wherein the mutant comprises one or several substitutions, additions, or deletions in a framework of said antibodies, but is free of a mutation in the CDRs. Use of such an anti-Glypican-1 antibody can effectively suppress especially the growth of Glypican-1-positive malignant tumor (e.g., esophageal cancer) cells. Further, Glypican-1-positive malignant tumor (e.g., esophageal cancer) can be efficiently diagnosed. Further, another embodiment of the present invention is an anti-Glypican-1 antibody comprising at least one of the sets of amino acid sequences of heavy chain CDRs 1, 2, and 3 listed above. These antibodies may be an antibody selected from monoclonal antibody, polyclonal antibody, chimeric antibody, humanized antibody, human antibody, multifunctional antibody, bispecific or oligospecific antibody, single chain antibody, scFV, diabody, sc(Fv)$_2$ (single chain (Fv)$_2$), and scFv-Fc.

The anti-Glypican-1 antibody according to one embodiment of the present invention may comprise a set of amino acid sequences of heavy chain CDRs 1, 2, and 3 and light chain CDRs 1, 2, and 3, and at least one, preferably, 2, 3, 4, 5, 6, 7 or all frameworks of the heavy chain FRs 1, 2, 3, and 4 and light chain FRs 1, 2, 3, and 4 are identical, substantially identical, or identical except for a conservative substitution with any one of SEQ ID NOs: 1-6. It may be one or more antibodies. Further, another embodiment of the present invention is an anti-Glypican-1 antibody comprising at least one of the amino acid sequence set of heavy chain FRs 1, 2, 3, and 4 listed above.

An anti-Glypican-1 antibody according to one embodiment of the present invention may be in the form of scFv, and in this case, the linker between the heavy chain and the light chain may have an amino acid sequence between the heavy chain and the light chain. For respective antibodies used in the present invention, the VH and the VL is respectively as below: SEQ ID NO: 3: anti-GPC-1 antibody 1-4 sequence (VH=1 to 125, VL=143 to 244); SEQ ID NO: 4: anti-GPC-1 antibody 1-5 sequence (VH=1 to 121, VL=139 to 240); SEQ ID NO: 5: anti-GPC-1 antibody 1-10 sequence (VH=1 to 124, VL=142 to 246); SEQ ID NO: 6: anti-GPC-1 antibody 1-12 sequence (VH=1 to 123, VL=141 to 245); SEQ ID NO: 7: anti-GPC-1 antibody 1-18 sequence (VH=1 to 131, VL=149 to 251); SEQ ID NO: 8: anti-GPC-1 antibody 1-27 sequence (VH=1 to 125, VL=143 to 244); SEQ ID NO: 9: anti-GPC-1 antibody 1-28 sequence (VH=1 to 131, VL=149 to 250); SEQ ID NO: 10: anti-GPC-1 antibody 1-30 sequence (VH=1 to 124, VL=142 to 246); SEQ ID NO: 11: anti-GPC-1 antibody 1-50 sequence (VH=1 to 125, VL=143 to 244); SEQ ID NO: 12: anti-GPC-1 antibody 1-57 sequence (VH=1 to 124, VL=142 to 243); SEQ ID NO: 13: anti-GPC-1 antibody 1-66 sequence (VH=1 to 127, VL=145 to 249); SEQ ID NO: 14: anti-GPC-1 antibody 1-77 sequence (VH=1 to 125, VL=142 to 243); SEQ ID NO: 15: anti-GPC-1 antibody 1-91 sequence (VH=1 to 124, VL=142 to 245); SEQ ID NO: 16: anti-GPC-1 antibody 2-11 sequence (VH=1 to 121, VL=139 to 241); SEQ ID NO: 17: anti-GPC-1 antibody 2-14 sequence (VH=1 to 124, VL=142 to 246); SEQ ID NO: 18: anti-GPC-1 antibody 2-57 sequence (VH=1 to 127, VL=145 to 249); SEQ ID NO: 19: anti-GPC-1 antibody 2-60 sequence (VH=1 to 125, VL=143 to 251); SEQ ID NO: 20: anti-GPC-1 antibody 2-63 sequence (VH=1 to 128, VL=146 to 251); SEQ ID NO: 21: anti-GPC-1 antibody 2-70 sequence (VH=1 to 125, VL=143 to 245); and SEQ ID NO: 22: anti-GPC-1 antibody 2-77 sequence (VH=1 to 125, VL=143 to 244).

The amino acid sequences listed above may be one or more amino acid sequences selected from the group consisting of (i) the above-described amino acid sequence with one or several base sequence deletions, substitutions, insertions or additions, (ii) an amino acid sequence with 90% or greater homology to the above-described amino acid sequence, and (iii) an amino acid sequence encoded by a polynucleotide that hybridizes specifically to a polynucleotide consisting of a base sequence complementary to a base sequence encoding the above-described amino acid under stringent conditions, as long as an anti-Glypican-1 antibody has a desired effect.

A vector or polynucleotide encoding the anti-Glypican-1 antibody according to one embodiment of the present invention can be introduced into a cell to produce a transformant. Such a transformant can be used to make the anti-Glypican-1 antibody according to the embodiment of the present invention. The transformant may be a cell of a human or a mammal excluding humans (e.g., rat, mouse, guinea pig, rabbit, cow, monkey or the like). Examples of a mammalian cell include Chinese hamster ovary cells (CHO cells), monkey cells COS-7 and the like. Further, the tranformant may be *Escherichia* bacteria, yeasts or the like.

For example, an *E. coli* derived plasmid (e.g., pET-Blue), a *Bacillus subtilis* derived plasmid (e.g., pUB110), a yeast derived plasmid (e.g. pSH19), an animal cell expression plasmid (e.g., pA1-11, pcDNA3.1-V5/His-TOPO), bacteriophage such as λ phage, a virus-derived vector or the like can be used as the above-described vector. Such vectors may comprise a constituent element required for protein expression such as a promotor, origin of replication, or antibiotic resistant gene. The vector may be an expression gene.

Examples of method of introducing the above-described polynucleotide or vector into cells that can be used include calcium phosphate method, lipofection, electroporation, method using adenovirus, method using a retrovirus, and microinjection (Revised 4th edition Shin Idenshikogaku Handobukku [*New Genetic Engineering Handbook*], Yodosha (2003) 152-179). Examples of a method of producing an antibody using a cell that can be used include the methods described in "Tanpakushitsu Jikken Handobukku [*Protein experiment handbook*], Yodosha (2003): 128-142". Purification of antibodies can use, for example, ammonium sulfate, ethanol precipitation, protein A, protein G, gel filtration chromatography, anion, cation exchange chromatography, phosphocellulose chromatography, hydrophobic interaction chromatography, affinity chromatography, hydroxyapatite chromatography, lectin chromatography or the like "Tanpakushitsu Jikken Handobukku [*Protein experiment handbook*], Yodosha (2003): 27-52".

To implement the present invention, a nucleic acid can be selected as the suppressant in a nucleic acid form of the present invention by using antisense activity as an indicator. In this regard, "antisense activity" refers to activity that can specifically suppress or decrease expression of a target gene. More specifically, antisense activity refers to activity that can decrease the amount of protein expression, depending on the nucleotide sequence introduced into cells, by specifically reducing the amount of mRNA of a gene having a nucleotide sequence region complementary to such a sequence. The approach thereof is roughly classified into a method of introducing an RNA molecule complementary to mRNA made from a target gene directly into cells, and a method of introducing a construct vector that can express an RNA complementary to a gene of interest into cells.

Antisense activity is achieved by a nucleic acid sequence with a length of at least 8 contiguous nucleotides, which is complementary to a nucleic acid sequence of a gene of interest. Such a nucleic acid sequence may be a nucleic acid sequence preferably with a length of at least 9 contiguous nucleotides, more preferably with a length of 10 contiguous nucleotides, and still more preferably with a length of 11 contiguous nucleotides, a length of 12 contiguous nucleotides, a length of 13 contiguous nucleotides, a length of 14 contiguous nucleotides, a length of 15 contiguous nucleotides, a length of 16 contiguous nucleotides, a length of 17 contiguous nucleotides, a length of 18 contiguous nucleotides, a length of 19 contiguous nucleotides, a length of 20 contiguous nucleotides, a length of 21 contiguous nucleotides, a length of 22 contiguous nucleotides, a length of 23 contiguous nucleotides, a length of 24 contiguous nucleotides, a length of 25 contiguous nucleotides, a length of 30 contiguous nucleotides, a length of 40 contiguous nucleotides, or a length of 50 contiguous nucleotides. Such a nucleic acid sequence includes nucleic acid sequences that are at least 70% homologous, more preferably at least 80% homologous, still more preferably 90% homologous or 95% homologous to the aforementioned sequences. Such antisense activity is preferably complementary to a sequence at the 5' terminus of a nucleic acid sequence of a gene of interest. Such an antisense nucleic acid sequence includes the aforementioned sequences with one or several or one or more nucleotide substitutions, additions, and/or deletions. Thus, antisense activity as used herein includes, but is not limited to, decrease in the amount of gene expression.

Common antisense techniques are described in text books (Murray, J A H eds Antisense RNA and DNA, Wiley-Liss Inc, 1992). Furthermore, the latest research has elucidated a phenomenon called RNA interference (RNAi), leading to development of antisense techniques.

As used herein, "RNAi" is an abbreviation of "RNA interference" and is commonly known in the art. RNA interference is a biological process that inhibits or down-regulates gene expression in cells, mediated by an agent inducing RNAi. For example, RNA interference refers to a phenomenon of specific degradation of homologous mRNA to suppress the synthesis of gene products by introducing into a cell an agent inducing RNAi, such as a double stranded RNA (also called dsRNA), or a technique used therein. As used herein, "RNAi" may in some cases be used synonymously with "agent inducing RNAi", "agent causing RNAi", "RNAi agent" or the like. For RNAi, see, for example, Zamore and Haley, 2005, Science, 309, 1519-1524; Vaughn and Martienssen, 2005, Science, 309, 1525-

1526; Zamore et al., 2000, Cell, 101, 25-33; Bass, 2001, Nature, 411, 428-429; Elbashir at al., 2001, Nature, 411, 494-498; and Kreutzer et al, International Publication No. WO 00/44895; Zernicka-Goetz et al, International Publication No. WO 01/36646; Fire, International Publication No. WO 99/32619; Plaetinck, at al., International Publication No. WO 00/01846; Mello and Fire, International Publication No. WO 01/29058; Deschamps-Depaillette, International Publication No. WO 99/07409 and Li et al., International Publication No. WO 00/44914; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237; Hutvagner and Zamore, 2002, Science, 297, 2056-60; McManus et al., 2002, RNA, 8, 842-850; Reinhart et al., 2002, Gene & Dev., 16, 1616-1626; and Reinhart & Bartel, 2002, Science, 297, 1831. Further, it is understood that the term RNAi as used herein represents a synonym of other terms used to describe sequence specific RNA interference such as post-transcription gene silencing, inhibition of translation, inhibition of transcription, or epigenetics. As used herein, "agent causing RNAi" may be any agent as long as "RNAi" is caused.

Examples of "agent causing RNAi" as used herein include "small interfering nucleic acid" "siNA", "small interfering RNA", "siRNA", "small interfering nucleic acid molecule", "small oligonucleotide molecule", "chemically modified small interfering nucleic acid molecule" and the like. These terms refer to any nucleic acid molecule that can inhibit or downregulate gene expression or virus replication by sequence specifically mediating RNA interference "RNAi" or gene silencing. These terms may represent an individual nucleic acid molecule, multiple such nucleic acid molecules, or a pool of such nucleic acid molecules. The molecules may be a double stranded nucleic acid molecule comprising a self-complementary sense region and an antisense region.

"SiRNA" that is typically used in the present invention is a doubled stranded RNA that is short with a length of generally about 20 bases (e.g., typically about 21-23 bases long) or less. Such an siRNA, when expressed in cells, suppresses gene expression and suppresses expression of a target pathogenic gene of the siRNA. Thus, such an siRNA can be used in treatment, prevention, prognosis or the like of a disease. The siRNA used in the present invention may be in any form, as long as it is capable of inducing RNAi.

In the present invention, an antisense region in an agent causing RNAi such as an siRNA comprises a sense region having a nucleotide sequence which is complementary to a nucleotide sequence in a target nucleic acid molecule or a portion thereof and a nucleotide sequence corresponding to the target nucleic acid sequence or a portion thereof. These molecules can be assembled from two separate oligonucleotides, one being a sense strand and the other being an antisense strand. The antisense strand and sense strand in this regard are self-complementary (i.e., each strand comprises a nucleotide sequence that is complementary to the nucleotide sequence in the other strand, e.g., the antisense strand and the sense strand form a double strand or double stranded structure). A double stranded region in this regard can be, for example, about 15 to about 30 base pairs such as about 15, 16, 17, 18, 19, 20, 21, 22, 23, 24, 25, 26, 27, 28, 29 or 30 base pairs or longer. The antisense strand comprises a nucleotide sequence that is complementary to a nucleotide sequence in a target nucleic acid molecule or a portion thereof, and the sense strand comprises a nucleotide sequence corresponding to the target nucleic acid sequence or a portion thereof (e.g., about 15 to about 25 or more nucleotides of the molecule are complementary to a target nucleic acid or a portion thereof). Alternatively, these molecules are assembled from a single oligonucleotide, and the self-complementary sense region and antisense region of these molecules are linked by a nucleic acid linker or a non-nucleic acid linker. These molecules can be polynucleotides having a double stranded, asymmetrical double stranded, hairpin, or asymmetrical hairpin secondary structure comprising a self-complementary sense region and antisense region. The antisense region in this regard comprises a separate sense region having a nucleotide sequence which is complementary to a nucleotide sequence in a target nucleic acid molecule or a portion thereof and a nucleotide sequence corresponding to the target nucleic acid sequence or a portion thereof. These molecules may be a cyclic single stranded polynucleotide having two or more loop structures and a stem comprising a self-complementary sense region and antisense region. The antisense region in this regard comprises a separate sense region having a nucleotide sequence which is complementary to a nucleotide sequence in a target nucleic acid molecule or a portion thereof and a nucleotide sequence corresponding to the target nucleic acid sequence or a portion thereof. In addition, a cyclic polynucleotide can be processed in vivo or in vitro to generate an active molecule that can mediate RNAi. These agents may also comprise a single stranded polynucleotide having a nucleotide sequence, which is complementary to a nucleotide sequence in a target nucleic acid molecule or a portion thereof (for instance, for these agents, a nucleotide sequence corresponding to the target nucleic acid molecule or a portion thereof does not need to be present in these agents). A single stranded polynucleotide may further comprise a terminal phosphoric acid group such as 5' phosphoric acid (for example, see Martinez et Al., 2002, Cell., 110, 563-574 and Schwarz et al., 2002, Molecular Cell, 10, 537-568) or 5', 3'-diphosphoric acid. In a certain embodiment, the Glypican-1 suppressant of the present invention comprises separate sense and antisense sequences or regions. The sense region and antisense region in this regard are covalently attached by a nucleotide or non-nucleotide linker molecule known in the art, or non-covalently attached to each other by ionic interaction, hydrogen bond, Van der Waal's interaction, hydrophobic interaction and/or stacking interaction. In a certain embodiment, the Glypican-1 suppressant of the present invention comprises a nucleotide sequence that is complementary to a nucleotide sequence of a target gene. In another embodiment, the Glypican-1 suppressant of the present invention interacts with a nucleotide sequence of a target gene such that expression of the target gene is inhibited. The Glypican-1 suppressant is not necessarily limited herein to molecules comprising only an RNA. The Glypican-1 suppressant also encompasses chemically modified nucleotides and non-nucleotides. In a certain embodiment, when the present invention is a small interfering nucleic acid molecule, a 2' hydroxy (2'-OH) containing nucleotide may be lacking. In a certain embodiment, the present invention can be a small interfering nucleic acid, which does not require the presence of a nucleotide having a 2' hydroxyl group for mediating RNAi. Thus, when the present invention is a small interfering nucleic acid molecule, ribonucleotide (e.g., nucleotide having a 2'-OH group) does not need to be included. However, when the presence of a ribonucleotide in a Glypican-1 suppressant is not required for maintaining RNAi, it may have a bound linker, or another bound or conjugated group, moiety or strand comprising one or more nucleotides having a 2'-OH group. Optionally, an agent suppressing Glypican-1 of the present invention may comprise a ribonucleotide in about 5, 10, 20, 30, 40 or 50% of the nucleotide positions. Herein, the Glypican-1 suppressant may be a nucleic acid molecule that can mediate sequence specific RNAi, such as small interfering RNA (siRNA), double stranded RNA (dsRNA) microRNA (miRNA), short hairpin RNA (snRNA), small interfering oligonucleotide, small interfering nucleic acid, small interfering modified oligonucleotide, chemically modified siRNA, or post-transcriptional gene silencing RNA (ptgsRNA).

Examples of agents inducing RNAi herein include, but are not limited to, RNAs comprising a double stranded moiety with a length of at least 10 nucleotides, comprising a sequence having at least about 70% homology or a sequence that hybridizes under stringent conditions to a portion of a nucleic acid sequence of a target gene and variants thereof. The agent in this regard can preferably comprise a 3' overhang, and more preferably the 3' overhang is a DNA with a length of 2 nucleotides or longer (e.g., DNA with a length of 2-4 nucleotides).

Alternatively, examples of RNAi used in the present invention include, but are not limited to, a pair of short complementary sequences in the opposite direction (e.g., 15 bp or longer such as 24 bp or the like).

Although not wishing to be bound by any theory, as one conceivable working mechanism of RNAi, when a molecule inducing RNAi such as dsRNA is introduced into cells for a relatively long (e.g., 40 base pairs or greater) RNA, an RNase III-like nuclease called a dicer having a helicase domain cuts out the molecule into about 20 base pair each from the 3' terminus in the presence of ATP to produce short dsRNA (also called siRNA). As used herein, "siRNA" is an abbreviation for short interfering RNA and refers to a short double stranded RNA with 10 base pairs or more prepared by artificial chemical synthesis or biochemical synthesis, synthesis in the body of an organism, or degradation of a double stranded RNA with about 40 bases or more in vivo. An siRNA generally has a 5'-phosphoric acid or 3'-OH structure, and the 3' terminus overhangs by about 2 bases. A specific protein binds to the siRNA to form an RISC (RNA-induced-silencing-complex). Such a complex recognizes and binds to an mRNA having the same sequence as the siRNA and cleaves the mRNA in the middle portion of the siRNA by RNase III-like enzymatic activity. The relationship of the siRNA sequence and mRNA sequence to be cleaved as a target is preferably a 100% match. However, for a mutation of a base at a position away from the middle of the siRNA, cleaving activity due to RNAi would not be completely lost, but instead partially remains. On the other hand, a mutation of a base in the middle portion of the siRNA has a significant effect, such that mRNA cleaving activity due to RNAi is dramatically reduced. For mRNAs with a mutation, such a property can be utilized to degrade only mRNAs comprising a specific mutation by synthesizing an siRNA with the mutation positioned in the middle and introducing the siRNA into cells. Thus, the present invention can use an siRNA itself as an agent inducing RNAi or an agent that would produce an siRNA (e.g., typically a dsRNA with about 40 or more bases) as such an agent.

Although not wishing to be bound by any theory, it is intended for siRNAs that, aside from the above-described pathway, an antisense strand of the siRNA binds to an mRNA and acts as a primer of an RNA-dependent RNA polymerase (RdRP), such that a dsRNA is synthesized and the dsRNA is used again as a substrate of a dicer to produce a new siRNA and amplify the action. Thus, the siRNA itself and agents producing an siRNA are also useful in the present invention. In fact, for example, 35 dsRNA molecules nearly completely degrade 1000 or more mRNA copies in cells in insects or the like. Thus, it is understood that the siRNA itself and agents producing an siRNA are also useful.

In another embodiment, the agent inducing RNAi of the present invention can be a short hairpin structure (shRNA; short hairpin RNA) having an overhang at the 3' terminus. As used herein, "shRNA" refers to a molecule with about 20 or more base pairs, which comprises a partially palindrome-like base sequence in a single stranded RNA to be in a double stranded structure in a molecule to have a hairpin-like structure. Such an shRNA is artificially made by chemical synthesis. Alternatively, such an shRNA can be produced by synthesizing a hairpin structure DNA comprising DNA sequences of sense and antisense strands linked in opposite directions in vitro into an RNA with a T7RNA polymerase. Although not wishing to be bound by any theory, it should be understood that such an shRNA, after introduction into cells, is degraded into a length of about 20 bases (typically, for example, 21 bases, 22 bases or 23 bases) in the cells and induces RNAi as in an siRNA, resulting in a treatment effect of the present invention. It should be understood that such an effect is exerted in a wide range of organisms such as insects, plants and animals (including mammals). Since an shRNA induces RNAi as in siRNAs in this manner, it can be used as an effective ingredient of the present invention. Further, an shRNA preferably can have a 3' overhang. The length of a double stranded moiety is not particularly limited, but the length can be preferably about 10 nucleotides long or longer and more preferably about 20 nucleotides long or longer. The 3' overhang in this regard can be preferably a DNA, more preferably a DNA with a length of at least two nucleotides or more, and still more preferably a DNA with a length of 2-4 nucleotides. The agent inducing RNAi used in the present invention can be artificially synthesized (e.g., chemically or biochemically) or naturally occurring. There is no fundamental difference in the effect of the present invention therebetween. A chemically synthesized agent is preferably purified by liquid chromatography or the like.

The agent inducing RNAi used in the present invention can also be synthesized in vitro. In such a synthesis system, a T7RNA polymerase and T7 promoter are used to synthesize antisense and sense RNAs from a template DNA. After annealing is performed thereon in vitro, RNAi is induced through the aforementioned mechanism when cells are introduced to achieve the effect of the present invention. In this regard, such an RNA can be introduced into cells, for example, by any suitable method such as the calcium phosphate method. Examples of the agents inducing RNAi of the present invention include agents such as a single strand that can hybridize with an mRNA or all similar nucleic acid analogs thereof. Such agents are also useful in the present invention.

One embodiment of the present invention is a therapeutic drug for Glypican-1 positive esophageal cancer comprising an RNAi molecule against Glypican-1 or a polynucleotide encoding the RNAi molecule. Growth of Glypican-1 positive esophageal cancer cells can be suppressed when such an RNAi molecule or polynucleotide encoding the RNAi molecule is used. "Polynucleotide" in one embodiment of the present invention may be a polymeric compound having 10 or more nucleotides, comprising a nucleotide polymerized in a straight chain.

"RNAi molecule" in one embodiment of the present invention is an RNA strand having RNAi action. Examples thereof include siRNA, shRNA, miRNA, small RNA having RNAi action and the like.

"RNAi" in one embodiment of the present invention includes a phenomenon of suppressing or silencing a function of a target gene, mRNA or the like by one or more of siRNA, shRNA, miRNA, single or double stranded RNA with a short or long chain, modified products thereof and the like.

For example, siDirect 2.0 (Naito et al., BMC Bioinformatics. 2009 Nov. 30; 10: 392) or the like can be used to design an RNAi molecule. Further, designing can be commissioned to a specialist company (e.g., Takara Bio Inc. or the like). RNAi action can be verified by quantification of the amount of RNA strand expression by real-time RT-PCR. RNAi action can also be confirmed by analysis of the amount of RNA strand expression by Northern blot or a method of analyzing the amount of protein and observing the phenotype or the like by Western blot. Further, a plasmid producing siRNAs or shRNAs for a specific gene can be purchased, for example, from a specialist company (e.g., Takara Bio Inc. or the like).

"siRNA" in one embodiment of the present invention comprises an RNA strand capable of inducing RNAi. Two strands of an siRNA can generally be separated into a guide strand and a passenger strand, where the guide strand in incorporated into a RISC. The guide strand incorporated into the RISC is used to recognize a target RNA. Although an artificially created guide strand is mainly used in RNAi research, those endogenous in a living body are also known. The above-described guide chain may be composed of an RNA with 15 bases or more. When there are 15 bases or more, the possibility of being able to precisely bind to a target nucleotide increases. Further, the guide strand may be composed of an RNA with 40 bases or less. With 40 bases or less, the risk of a disadvantageous phenomenon such as interferon response occurring is further reduced.

"shRNA" in one embodiment of the present invention comprises a single strand of RNA strand that can induce RNAi and form a structure folded into a hairpin shape (hairpin-like structure). Typically, an shRNA is cleaved by a dicer in a cell to cut out an siRNA. It is known that a target RNA is cleaved by the siRNA. The above-described shRNA may be composed of 35 or more nucleotides. With 35 or more, the possibility of being able to precisely form a hairpin-like structure unique to shRNAs increases. Further, the above-described shRNA may be composed of an RNA with 100 bases or less. With 100 bases or less, the risk of a disadvantageous phenomenon such as interferon response occurring is reduced. However, many of the pre-miRNAs that generally have a similar structure and function as shRNAs have a length of about 100 nucleotides or more. Thus, it is conceivable that they can function as a shRNA even when the length of the shRNA is not necessarily 100 bases or less.

It is known that "miRNA" in one embodiment of the present invention comprises an RNA strand having a function similar to an siRNA and suppresses translation of, and degrades, a target RNA strand. The difference in miRNAs and siRNAs is generally in the production pathway and the detailed mechanism.

"Small RNA" in one embodiment of the present invention refers to a relatively small RNA strand. Examples thereof include siRNAs, shRNAs, miRNAs, antisense RNAs, small RNAs with one or two strands and the like.

The RNAi molecules may comprise an overhang consisting of 1-5 bases at the 5' terminus or the 3' terminus. It is understood that RNAi efficiency is enhanced in such a case. The number of bases may be, for example, 5, 4, 3, 2, or 1, or within a range of any two values described above. When the above-described RNAi molecule is double stranded, a mismatching RNAs may be present between each RNA strand. The number of mismatching RNAs may be, for example, 1, 2, 3, 4, 5, or 10 or less, or within the range of any two values described above. Further, the above-described RNAi molecule may comprise a hairpin loop. The number of bases of a hairpin loop may be, for example, 10, 8, 6, 5, 4, or 3 or within any two values described above. The base sequence may have one or a plurality of base sequence deletions, substitutions, insertions or additions, as long as the sequence has a desired effect. The left side of each base sequence is denoted as the 5' terminus and the right side as the 3' terminus.

The length of the above-described RNAi molecule may be, for example, 15, 18, 20, 25, 30, 40, 50, 60, 80, 100, 200, or 400 bases or within a range between any two values described above. The number is preferably 15 or more or 100 or less from the viewpoint of improving the therapeutic effect on Glypican-1 positive malignant tumor.

"RNA strand" in one embodiment of the present invention includes those constituted in a form in which a plurality of RNAs or equivalents thereof are bound. "DNA strand" in one embodiment of the present invention includes those constituted in a form in which a plurality of DNAs or equivalents thereof are bound. The RNA strand or DNA strand includes RNA strands or DNA strands in a single stranded or multi-stranded (e.g., double stranded) form. The RNA strand or DNA strand may be bound to a substance promoting incorporation into cells (e.g., PEG or derivative thereof), labeling tag (e.g., fluorescent labeling tag or the like), a linker (e.g., nucleotide linker or the like) or the like. The RNA strand or DNA strand can be synthesized by using a nucleic acid synthesizer or purchased from a specialist company (e.g., Invitrogen or the like). An RNA strand or DNA strand in a living body may form a salt or a solvate. Further, an RNA strand or DNA strand in a living body may be chemically modified. The term RNA strand or DNA strand includes, for example, RNA strands or DNA strands forming a salt or solvate, RNA strands or DNA strands subjected to chemical modification, and the like. Further, an RNA strand or DNA strand may be an analog of the RNA strand or an analog of the DNA strand.

Examples of "salt" in one embodiment of the present invention include anionic salts formed with any acidic (e.g., carboxyl) group and cationic salts formed with any basic (e.g., amino) group. Salts include inorganic salts and organic salts, as well as salts described in, for example, Berge et al., J. Pharm. Sci., 1977, 66, 1-19. Further examples include metal salts, ammonium salts, salts with organic base, salts with inorganic acid, salts with organic acid and the like. "Solvent" in one embodiment of the present invention is a compound formed with a solute or solvent. For example, J. Honig et al., The Van Nostrand Chemist's Dictionary P650 (1953) can be referred for solvates. When a solvent is water, a solvate formed is a hydrate. It is preferable that the solvent does not obstruct the biological activity of the solute. Examples of such a preferred solvent include, but not particularly limited to water and various buffers. Examples of "chemical modification" in one embodiment of the present invention include modification with PEG or a derivative thereof, fluorescein modification, biotin modification and the like.

The above-described RNAi molecule preferably comprises a base sequence that is complementary to a portion of a base sequence of the Glypican-1 mRNA from the viewpoint of stably exerting RNAi action. The above-described "portion" may be, for example, 5, 10, 15, 18, 20, 22, 24, 26, 28, 30, 35, 40 or 50 bases or more or within a range of any two values described above.

The siRNA used in an example described below comprises the base sequence of SEQ ID NO: 25. These base sequences are considered to be base sequences complementary to a portion of the Glypican-1 mRNA and responsible for the function as a guide strand. One embodiment of the present invention comprises an RNAi molecule comprising such the base sequence of SEQ ID NO: 25. The RNAi molecule may further comprise a base sequence complementary to the base sequence set forth in SEQ ID NO: 25 (e.g., SEQ ID NO: 26). "Complementary base sequence" in one embodiment of the present invention is a base sequence having a polynucleotide with high complementarity capable of hybridizing to another polypeptide. The full length sense strand of the siRNA used in an Example described below is the base sequence of SEQ ID NO: 27 (5'-GGGACACGCU-CACGGCCAATT-3'(SEQ ID NO: 25)), and the full length antisense strand is the base sequence of SEQ ID NO: 28 (5'-UUGGCCGUGAGCGUGUCCCTG-3'(SEQ ID NO: 26)).

As long as the Glypican-1 siRNA has a desired effect, the base sequences listed above may be (i) an amino acid sequence with one or several base sequence deletions, substitutions, insertions or additions in the above-described base acid sequence, or (ii) a base sequence encoded by a polynucleotide that specifically hybridizes with a polynucleotide consisting of a base sequence complementary to the above-described base sequence under stringent conditions.

One embodiment of the present invention is a therapeutic drug for Glypican-1 positive malignant tumor, comprising a Glypican-1 antagonist. The Glypican-1 antagonist comprises a substance inhibiting the expression or function of Glypican-1. The growth of Glypican-1 positive malignant tumor cells can be suppressed by using such a Glypican-1 antagonist. The form of antagonist is not particularly limited as long as it has an action of inhibiting the expression or function of Glypican-1. For example, the antagonist may be in a form of an antibody, RNA strand, DNA strand, low molecular weight organic compound, or polypeptide. The above-described RNA strand may be an RNAi molecule against Glypican-1. A DNA strand encoding an RNAi molecule against Glypican-1 can be used as the above-described DNA strand. For example, the DNA strand may be in a form of a vector.

Examples of "inhibit the expression of a protein" in one embodiment of the present invention include inhibiting the transcription mechanism from a gene to an mRNA or inhibiting the translation mechanism from an mRNA to a protein. Examples further include inducing degradation of a gene, mRNA or protein to ultimately decrease the amount of protein. "Inhibit a function of protein" in one embodiment of the present invention includes causing a structural change in a protein to reduce the activity of the protein. Examples thereof further include inhibiting the expression of a gene, resulting in reduction in the amount of mRNA or protein production.

"State where expression is inhibited" in one embodiment of the present invention includes a state of significantly decreased amount of expression relative to normal levels. The amount of mRNA or protein may be used as an indicator for the amount of expression. "Significantly" in one embodiment of the present invention may be, for example, a state where there is a statistically significant difference, when assessed by Student's t-test (one or two tailed), at $p<0.05$. Further, a state where a substantial difference has occurred is also included. "State where a function is inhibited" in one embodiment of the present invention includes a state with significantly decreased activity relative to normal levels.

One embodiment of the present invention is a novel method of treatment for esophageal cancer. Such a treatment method comprises, for example, a step of administering an anti-Glypican-1 antibody to a patient. Glypican-1 positive esophageal cancer can be treated by using such a treatment method. Further, such a treatment method is excellent from the viewpoint of safety as demonstrated in the Examples, since the method uses antibodies. Targeted esophageal cancer includes those in lymph node metastasis sites, squamous cell carcinoma, and/or adenocarcinoma, and particularly includes squamous cell carcinoma. In particular, the present specification describes a significant effect in the case of Glypican-1 positive squamous cell carcinoma, and it is understood that a remarkable effect on Glypican-1 positive esophageal cancer is exhibited.

In specific embodiments, an antibody used in the treatment method of the present invention may be an anti-Glypican-1 antibody that is one or more antibodies selected from the group consisting of (a) an antibody of which heavy chain CDRs 1, 2, and 3 and light chain CDRs 1, 2, and 3 comprise the amino acid sequences set forth in positions 31 to 35, positions 50 to 65, positions 98 to 114, positions 163 to 170, positions 187 to 193, and positions 226 to 235 of SEQ ID NO: 3, respectively; (b) an antibody of which heavy chain CDRs 1, 2, and 3 and light chain CDRs 1, 2, and 3 comprise the amino acid sequences set forth in positions 31 to 35, positions 50 to 66, positions 99 to 110, positions 159 to 166, positions 183 to 187, and positions 222 to 231 of SEQ ID NO: 4, respectively; (c) an antibody of which heavy chain CDRs 1, 2, and 3 and light chain CDRs 1, 2, and 3 comprise the amino acid sequences set forth in positions 31 to 35, positions 50 to 66, positions 99 to 113, positions 162 to 170, positions 187 to 193, and positions 226 to 237 of SEQ ID NO: 5, respectively; (d) an antibody of which heavy chain CDRs 1, 2, and 3 and light chain CDRs 1, 2, and 3 comprise the amino acid sequences set forth in positions 31 to 35, positions 51 to 66, positions 99 to 112, positions 160 to 170, positions 187 to 193, and positions 226 to 236 of SEQ ID NO: 6, respectively; (e) an antibody of which heavy chain CDRs 1, 2, and 3 and light chain CDRs 1, 2, and 3 comprise the amino acid sequences set forth in positions 31 to 35, positions 50 to 66, positions 99 to 120, positions 169 to 176, positions 193 to 199, and positions 232 to 242 of SEQ ID NO: 7, respectively; (f) an antibody of which heavy chain CDRs 1, 2, and 3 and light chain CDRs 1, 2, and 3 comprise the amino acid sequences set forth in positions 31 to 35, positions 50 to 65, positions 98 to 114, positions 163 to 170, positions 187 to 193, and positions 226 to 235 of SEQ ID NO: 8, respectively; (g) an antibody of which heavy chain CDRs 1, 2, and 3 and light chain CDRs 1, 2, and 3 comprise the amino acid sequences set forth in positions 31 to 35, positions 50 to 66, positions 99 to 120, positions 169 to 176, positions 193 to 199, and positions 232 to 241 of SEQ ID NO: 9, respectively; (h) an antibody of which heavy chain CDRs 1, 2, and 3 and light chain CDRs 1, 2, and 3 comprise the amino acid sequences set forth in positions 31 to 35, positions 50 to 65, positions 98 to 113, positions 162 to 171, positions 188 to 194, and positions 227 to 237 of SEQ ID NO: 10, respectively; (i) an antibody of which heavy chain CDRs 1, 2, and 3 and light chain CDRs 1, 2, and 3 comprise the amino acid sequences set forth in positions 31 to 35, positions 50 to 65, positions 98 to 114, positions 163 to 170, positions 187 to 193, and positions 226 to 235 of SEQ ID NO: 11, respectively; (j) an antibody of which heavy chain CDRs 1, 2, and 3 and light chain CDRs 1, 2, and 3 comprise the amino acid sequences set forth in positions 31 to 35, positions 50 to 66, positions 99 to 113, positions 162 to 169, positions 186 to 192, and positions 225 to 234 of SEQ ID NO: 12, respectively; (k) an antibody of which heavy chain CDRs 1, 2, and 3 and light chain CDRs 1, 2, and 3 comprise the amino acid sequences set forth in positions 31 to 35, positions 50 to 66, positions 99 to 116, positions 165 to 174, positions 191 to 197, and positions 230 to 240 of SEQ ID NO: 13, respectively; (1) an antibody of which heavy chain CDRs 1, 2, and 3 and light chain CDRs 1, 2, and 3 comprise the amino acid sequences set forth in positions 31 to 35, positions 50 to 66, positions 99 to 113, positions 162 to 169, positions 186 to 192, and positions 225 to 235 of SEQ ID NO: 14, respectively; (m) an antibody of which heavy chain CDRs 1, 2, and 3 and light chain CDRs 1, 2, and 3 comprise the amino acid sequences set forth in positions 31 to 35, positions 50 to 66, positions 99 to 113, positions 162 to 170, positions 187 to 193, and positions 226 to 236 of SEQ ID NO: 15, respectively; (n) an antibody of which heavy chain CDRs 1, 2, and 3 and light chain CDRs 1, 2, and 3 comprise the amino acid sequences set forth in positions 31 to 35, positions 50 to 66, positions 99 to 110, positions 159 to 166, positions 183 to 189, and positions 222 to 237 of SEQ ID NO: 16, respectively; (o) an antibody of which heavy chain CDRs 1, 2, and 3 and light chain CDRs 1, 2, and 3 comprise the amino acid sequences set forth in positions 31 to 35, positions 50 to 65, positions 98 to 113, positions 162 to 171, positions 188 to 194, and positions 227 to 237 of SEQ ID NO: 17, respectively; (p) an antibody of which heavy chain CDRs 1, 2, and 3 and light chain CDRs 1, 2, and 3 comprise the amino acid sequences set forth in positions 31 to 35, positions 50 to 66, positions 99 to 116, positions 165 to 174, positions 191 to 197, and positions 230 to 240 of SEQ ID NO: 18, respectively; (q) an antibody of which heavy chain CDRs 1, 2, and 3 and light chain CDRs 1, 2, and 3 comprise the amino acid sequences set forth in positions 31 to 35, positions 50 to 66, positions 99 to 115, positions 164 to 175, positions 193 to 199, and positions 232 to 241 of SEQ ID NO: 19, respectively; (r) an antibody of which heavy chain CDRs 1, 2, and 3 and light chain CDRs 1, 2, and 3 comprise the amino acid sequences set forth in positions 31 to 35, positions 50 to 66, positions 99 to 117, positions 166 to 177, positions 194 to 200, and positions 233 to 242 of SEQ ID NO: 20, respectively; (s) an antibody of which heavy chain CDRs 1, 2, and 3 and light chain CDRs 1, 2, and 3 comprise the amino acid sequences set forth in positions 32 to 36, positions 51 to 67, positions 100 to 114, positions 163 to 171, positions 188 to 194, and positions 227 to 236 of SEQ ID NO: 21, respectively; and (t) an antibody of which heavy chain CDRs 1, 2, and 3 and light chain CDRs 1, 2, and 3 comprise the amino acid sequences set forth in positions 31 to 35, positions 50 to 65, positions 98 to 114, positions 163 to 170, positions 187 to 193, and positions 226 to 235 of SEQ ID NO: 22, respectively; or a mutant of said antibodies wherein the mutant comprises one or several substitutions, additions, or deletions in a framework of said antibodies, but is free of a mutation in the CDRs. By using this anti-Glypican-1 antibody, it is possible to particularly effectively suppress the growth of Glypican-1 positive malignant tumor (for example, esophageal cancer) cells. In addition, Glypican-1 positive malignant tumor (for example, esophageal cancer) can efficiently be diagnosed. In addition, another embodiment of the present invention is an anti-Glypican-1 antibody comprising at least one of amino acid sequence sets of heavy chain CDRs 1, 2, and 3 listed above. These antibodies, in specific embodiments, can be antibodies selected from monoclonal antibody, polyclonal antibody, chimeric antibody, humanized antibody, human antibody, multifunctional antibody, bispecific or oligospecific antibody, single chain antibody, scFV, diabody, sc(Fv)$_2$ (single chain (Fv)$_2$), and scFv-Fc.

There are Glypican-1 positive and Glypican-1 non-positive patients among esophageal cancer patients. For this reason, the above-described treatment method is preferably administered to an esophageal cancer patient determined to have esophageal cancer that is Glypican-1 positive esophageal cancer. In this manner, diagnosis for the presence or absence of a Glypican-1 positive condition in advance enables a more optimal dosing.

Thus, the above-described treatment method for esophageal cancer preferably comprises a step of diagnosing whether a patient has an episode of Glypican-1 positive esophageal cancer from the viewpoint of administering a more optimal dosing. Further, the treatment method may comprise a step of investigating whether esophageal cancer cells derived from a patient express Glypican-1. An episode of Glypican-1 positive esophageal cancer may be diagnosed, for example, by diagnosing mRNA expression or protein expression. The diagnosis is preferably conducted by diagnosis of protein expression from the viewpoint of accurately diagnosing Glypican-1 positive to realize a more optimal dosing. Protein expression may be diagnosed by using, for example, an anti-Glypican-1 antibody. In diagnosis of an episode, an episode of Glypican-1 positive esophageal cancer may be determined to be present when a protein obtained from esophageal cancer cells to be tested derived from a patient is subjected to Western blot and a band corresponding to Glypican-1 can be confirmed by visual inspection. Further, an episode of Glypican-1 positive esophageal cancer may be determined to be present when the amount of Glypican-1 expression of esophageal cancer cells derived from a patient is significantly larger relative to normal cells or Glypican-1 negative esophageal cancer cells. Further, an episode of Glypican-1 positive esophageal cancer may be determined to be present when total protein obtained from esophageal cancer cells derived from a patient and total protein obtained from normal cells or Glypican-1 negative esophageal cancer cells are subjected to Western blot and the esophageal cancer cells derived from the patient have a significantly stronger band intensity corresponding to Glypican-1 relative to the normal cells or Glypican-1 negative esophageal cancer cells. RT-PCR may be used instead of Western blot in such diagnosis for an episode of Glypican-1 positive esophageal cancer. Further, an episode of Glypican-1 positive malignant tumor may be determined to be present when serum or plasma obtained from malignant tumor patients and serum or plasma obtained from healthy individuals or Glypican-1 negative malignant tumor patients are subjected to ELISA using anti-Glypican-1 antibodies and the amount of Glypican-1 expression is significantly more for the serum or plasma derived from malignant tumor patients relative to healthy individuals or Glypican-1 negative malignant tumor patients. The serum or plasma sample itself may be quantified, or exosomes may be isolated from the serum or plasma to subject Glypican-1 in the exosomes to ELISA for analysis.

The treatment method of esophageal cancer according to one embodiment of the present invention may comprise a step of administering a Glypican-1 antagonist to a patient. Further, the method may comprise a step of administering an RNAi molecule against Glypican-1 or a polynucleotide encoding the RNAi molecule to the patient.

One embodiment of the present invention is a novel diagnostic drug for esophageal cancer, comprising an anti-Glypican-1 antibody. The diagnostic drug may be, for example, a companion diagnostic drug for esophageal cancer treatment targeting Glypican-1, comprising an anti-Glypican-1 antibody. Since there are Glypican-1 positive and Glypican-1 non-positive patients among esophageal cancer patients, therapeutic efficacy of the esophageal cancer treatment targeting Glypican-1 can be diagnosed if the companion diagnostic drug is used to inspect in advance whether esophageal cancer is Glypican-1 positive. In such diagnosis, when the result is Glypican-1 positive, esophageal cancer treatment targeting Glypican-1 can be determined to be effective. "Companion diagnosis" in one embodiment of the present invention comprises diagnosis implemented in order to assist in the optimal dosing by predicting individual differences in the effect of agent or side effects for patients by inspection.

A diagnostic drug for esophageal cancer according to one embodiment of the present invention may be a diagnostic drug comprising an anti-Glypican-1 antibody for diagnosis of therapeutic efficacy of the anti-Glypican-1 antibody or Glypican-1 antagonist on esophageal cancer. Since there are Glypican-1 positive and Glypican-1 non-positive patients among esophageal cancer patients, it is possible to diagnose the therapeutic efficacy of an anti-Glypican-1 antibody or Glypican-1 antagonist to patients if the diagnostic agent is used in advance to inspect whether esophageal cancer is Glypican-1 positive.

One embodiment of the present invention is a companion diagnostic method for esophageal cancer treatment targeting Glypican-1, comprising inspecting whether an esophageal cancer sample of an esophageal cancer patient is Glypican-1 positive. Since there are Glypican-1 positive and Glypican-1 non-positive patients among esophageal cancer patients, it is possible to diagnose the therapeutic efficacy of esophageal cancer treatment targeting Glypican-1 if the companion diagnosis method is used to inspect in advance whether esophageal cancer is Glypican-1 positive. Such a diagnostic method may further comprise a step of isolating or extracting an esophageal cancer sample of an esophageal cancer patient. "Esophageal cancer sample" in one embodiment of the present invention may be esophageal cancer tissue or cells obtained from an esophageal cancer patient.

One embodiment of the present invention is a method of inspecting therapeutic efficacy of an anti-Glypican-1 antibody or Glypican-1 antagonist on esophageal cancer. The inspection method comprises, for example, inspecting whether an esophageal cancer sample of an esophageal cancer patient is Glypican-1 positive. The inspection method, which may comprise a step of detecting the presence of Glypican-1 in an esophageal cancer sample, may comprise a step of detecting that the amount of Glypican-1 in the esophageal cancer sample is significantly larger relative to normal cells or Glypican-1 negative esophageal cancer cells. For example, RT-PCR, Western blot, or immunohistochemical staining method may be used in detecting Glypican-1. The standard of assessing the presence or absence of Glypican-1 may be the same as that in the aforementioned diagnosis of episode of Glypican-1 positive esophageal cancer. A method of inspecting therapeutic efficacy includes a method of inspecting whether the method is effective for treatment.

One embodiment of the present invention is a suppressant for growth of esophageal cancer cells, comprising anti-Glypican-1 antibodies. Further, it is a method of suppressing growth of esophageal cancer cells, comprising contacting anti-Glypican-1 antibodies with esophageal cancer cells. Further, it is a suppressant for growth of esophageal cancer cells, comprising a Glypican-1 antagonist. Further, it is a method of suppressing growth of esophageal cancer cells, comprising contacting a Glypican-1 antagonist with esophageal cancer cells. The therapeutic drug or suppressant for growth of esophageal cancer cells according to the embodiment of the present invention may be an agent that reduces the growth rate, amount of growth, or volume of esophageal cancer by 10, 20, 30, 40, 50, or 70% or more relative to a case where a therapeutic drug or growth suppressant is not added. The percentage may be within the range of two numerical values listed above.

One embodiment of the present invention is an agent for suppressing cell division of esophageal cancer cells, comprising an anti-Glypican-1 antibody. Further, it is a method of suppressing cell division of esophageal cancer cells, comprising contacting an anti-Glypican-1 antibody with esophageal cancer cells. Further it is an agent for suppressing cell division of an esophageal cancer cell, comprising a Glypican-1 antagonist. Further, it is a method of suppressing cell division of esophageal cancer cells, comprising contacting a Glypican-1 antagonist with esophageal cancer cells. The agent for suppressing cell division of an esophageal cancer cell according to the embodiment of the present invention may be an agent that reduces the rate of esophageal cancer cell division by 10, 20, 30, or 50% or more relative to a case where an agent for suppressing cell division is not added. The percentage may be within the range of two numerical values listed above.

One embodiment of the present invention is a therapeutic drug for Glypican-1-dependent esophageal cancer, comprising an anti-Glypican-1 antibody. Glypican-1-dependent esophageal cancer can be treated by using such a therapeutic drug.

One embodiment of the present invention is use of an anti-Glypican-1 antibody or Glypican-1 antagonist for producing a therapeutic drug for esophageal cancer. In another embodiment, it is a use of an anti-Glypican-1 antibody for manufacturing a companion diagnostic drug for esophageal cancer treatment targeting Glypican-1.

One embodiment of the present invention is a method of producing an anti-Glypican-1 antibody, comprising: introducing a polynucleotide encoding Glypican-1 into a cell; expressing the Glypican-1 in the cell; and immunizing a chicken with an antigen comprising a cell expressing the Glypican-1. According to the production method, an anti-Glypican-1 antibody that is excellent for the treatment or diagnosis of Glypican-1 positive esophageal cancer can be efficiently produced.

(General Techniques)

Molecular biological approach, biochemical approach, and microbiological approach used herein are well known and conventional approaches in the art that are described in, for example, Sambrook J. et al. (1989). Molecular Cloning: A Laboratory Manual, Cold Spring Harbor and 3rd Ed. thereof (2001); Ausubel, F. M. (1987). Current Protocols in Molecular Biology, Greene Pub. Associates and Wiley-Interscience; Ausubel, F. M. (1989). Short Protocols in Molecular Biology: A Compendium of Methods from Current Protocols in Molecular Biology, Greene Pub. Associates and Wiley-Interscience; Innis, M. A. (1990). PCR Protocols: A Guide to Methods and Applications, Academic Press; Ausubel, F. M. (1992). Short Protocols in Molecular Biology: A Compendium of Methods from Current Protocols in Molecular Biology, Greene Pub. Associates; Ausubel, F. M. (1995). Short Protocols in Molecular Biology: A Compendium of Methods from Current Protocols in Molecular Biology, Greene Pub. Associates; Innis, M. A. et al. (1995). PCR Strategies, Academic Press; Ausubel, F. M. (1999). Short Protocols in Molecular Biology: A Compendium of Methods from Current Protocols in Molecular Biology, Wiley, and annual updates; Sninsky, J. J. et al. (1999). PCR Applications: Protocols for Functional Genomics, Academic Press, Bessatsu Jikken Igaku [*Experimental Medicine, Supplemental Volume*], Idenshi Donyu Oyobi Hatsugen Kaiseki Jikken Ho [*Experimental Methods for Transgenesis & Expression Analysis*], Yodosha, 1997, and the like, the relevant portions (which can be the entire document) of which are incorporated herein by reference.

DNA synthesis techniques and nucleic acid chemistry for making an artificially synthesized gene are described in, for example, Gait, M. J. (1985). Oligonucleotide Synthesis: A Practical Approach, IRL Press; Gait, M. J. (1990). Oligonucleotide Synthesis: A Practical Approach, IRL Press; Eckstein, F. (1991). Oligonucleotides and Analogues: A Practical Approach, IRL Press; Adams, R. L. et al. (1992). The Biochemistry of the Nucleic Acids, Chapman & Hall; Shabarova, Z. et al. (1994). Advanced Organic Chemistry of Nucleic Acids, Weinheim; Blackburn, G. M. et al. (1996), Nucleic Acids in Chemistry and Biology, Oxford University Press; Hermanson, G. T. (1996). Bioconjugate Techniques, Academic Press and the like, the relevant portions of which are incorporated herein by reference.

For example, as used herein, the oligonucleotide of the present invention can also be synthesized by a standard method known in the art, such as by using an automated DNA synthesizer (a synthesizer commercially available from Biosearch, Applied Biosystems or the like). For example, a phosphorothioate-oligonucleotide can also be synthesized by the method of Stein et al. (1988, Nucl. Acids Res. 16: 3209), and a methyl phosphonate-oligonucleotide can also be prepared by using a control pore glass polymer support (Sarin et al., 1988, Proc. Natl. Acad. Sci. USA 85: 7448-7451).

As used herein, "or" is used when "at least one or more" of the matters listed in the sentence can be employed. When explicitly described herein as "within the range of two values", the range also includes the two values themselves.

Reference literatures such as scientific literatures, patents, and patent applications cited herein are incorporated herein by reference to the same extent that the entirety of each document is specifically described.

As described above, the present invention has been described while showing preferred embodiments to facilitate understanding. The present invention is described below based on Examples. The aforementioned description and the following Examples are not provided to limit the present invention, but for the sole purpose of exemplification. Thus, the scope of the present invention is not limited to the embodiments and Examples specifically described herein and is limited only by the scope of claims.

EXAMPLES

Examples are described below. If required, animals used in the Examples below were handled based on the Helsinki Declaration and, as necessary, with the criteria defined in the National Institute of Biomedical Innovation. As reagents and the like, specifically, products described in the Examples were used. However, equivalent products of other makers (Sigma-Aldrich, Wako Pure Chemical Industries, Ltd., NACALAI, R&D Systems, USCN Life Science INC, and the like) are also substitutable.

(Samples Used)

Tissues on which surgery has been performed for esophageal cancer were provided from patients whose agreements to informed consents were obtained from Osaka University Hospital.

Example 1: Expression of Glypican-1 in Various Cells by Western Blot

In the present example, the expression of Glypican-1 in various cells by Western blot was investigated.
(Western Blot Analysis)

Normal esophageal epithelial cells HEEpic and Het1A and esophageal squamous cell carcinoma cell strains TE1, TE5, TE6, TE8, TE9, TE10, TE11, TE14, and TE15 were washed with ice-cooled PBS (−), and then peeled off with a cell scraper. The cells were then recovered by centrifugation. The cells were lysed by a Lysis buffer (20 mM Tris-HCl, pH 7.5, 150 mM NaCl, 1% Triton X-100, 1× protease inhibitor cocktail (NACALAI TESQUE), 1× phosphatase inhibitor cocktail (NACALAI TESQUE)), The supernatant was recovered as a protein extract liquid by centrifugation (13, 200 rpm, 4° C., 15 min). The protein concentration was quantified with a protein quantifying kit (DC Protein Assay kit (Bio-Rad Laboratories, Inc.)) using bovine serum albumin (BSA) as a standard.

A sager chain of Glypican-1 was enzymatically cleaved with Heparinase III (Sigma). Sixty milliUnit of Heparinase III was added to 30 µg of the extracted protein and an enzymatic reaction was carried out at 37° C. for 6 hours. After the reaction, a 5×SOS-PAGE sample buffer was added such that the final concentration was 1×, and heated at 95° C. for 5 minutes.

Ten µg of a protein was applied to SDS-PAGE (5-20% gradient gel (Wako Pure Chemical Industries, Ltd.)). It was subjected to migration at 40 mA for 50 minutes and then was transferred to a PVDF membrane at 120 mA for 1 hour. After the transfer, blocking was carried out in 1% BSA/TEST (TBS+0.1% Tween 20) at room temperature for 1 hour and then incubation was carried out with an anti-GPC-1 antibody (Atlas antibodies: HPA030571) at room temperature for 1 hour. After washing with TEST 3 times for 10 minutes each time, the PVDF membrane was incubated at room temperature for 1 hour using an HRP-labeled anti-rabbit antibody (GE healthcare) that had been diluted 5,000 times with TBST. The PVDF membranes were washed with TBST 3 times for 10 minutes each time and then the reacted proteins were detected by a fluorescence reaction system (Perkin Elmer, Inc.). An anti-β-actin antibody (Sigma) was used as a loading control.
(Result)

Figure 1:
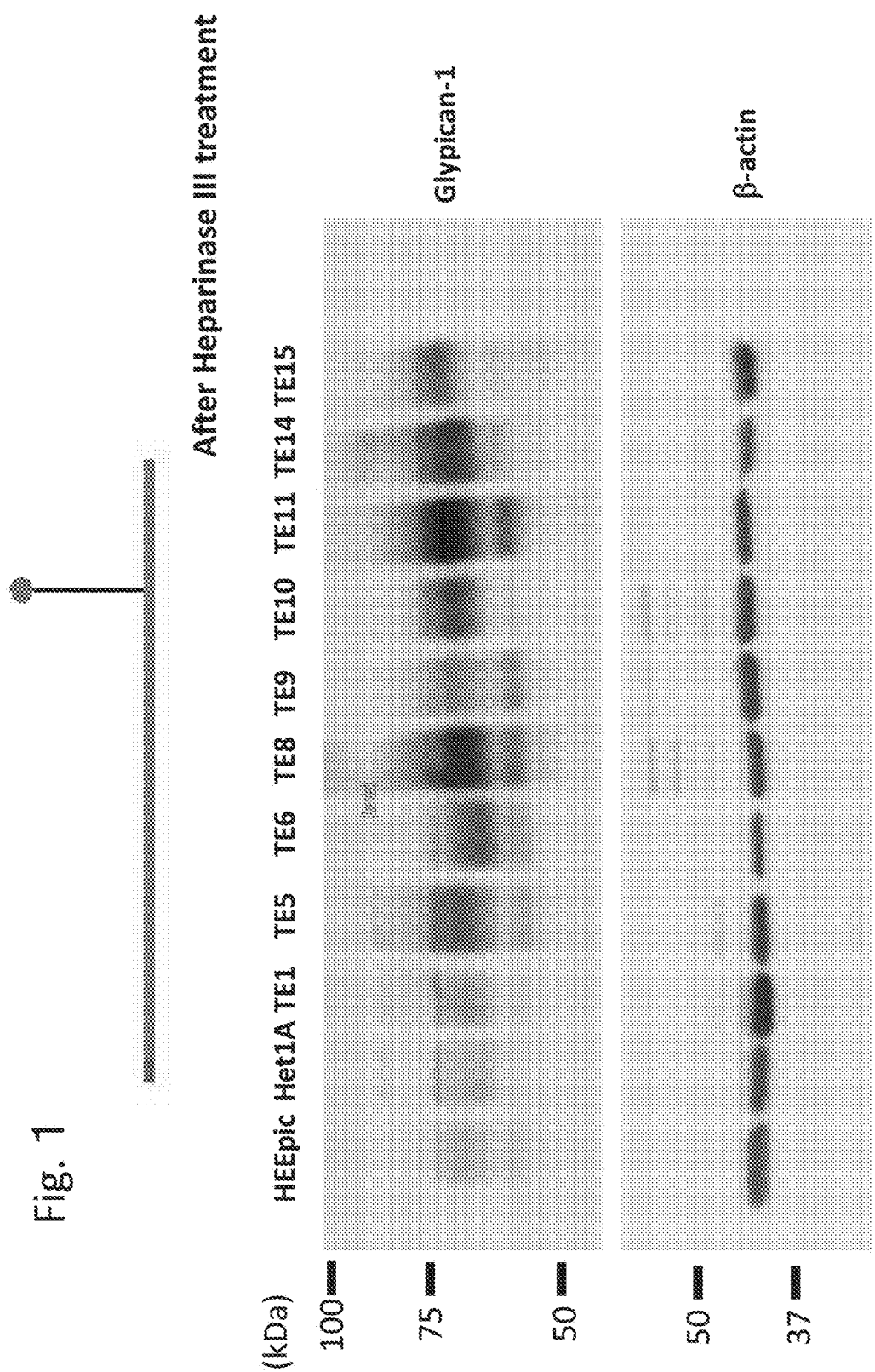
FIG. 1 is a result showing expression of Glypican-1 in various cells by Western blot. Molecular weight indication (kDa) based on molecular weight markers of protein is shown at the left edge. As samples, HEEpic, Het1A (normal cells), TE1, TE5, TE6, TE8, TE9, TE10, TE11, TE14, and TE15 (esophageal cancer cell strains) are shown from the left. For Glypican-1 shown in the upper panel, a band is seen around 70 kDa. For a control shown in the lower panel, β-actin was used.

The result is shown in FIG. 1. Analysis for Glypican-1 was carried out by a Western blot method using a specific antibody. As the result, it was confirmed that Glypican-1 was not expressed in HEEpic and Het1A and was expressed in esophageal squamous cell carcinoma cell strains.

From these results, it became clear that Glypican-1 is specifically and highly expressed in esophageal cancer cells, but not normal esophageal cells.

Example 2: Relative Expression Level of Glypican-1 (Accession No. P35052)

In the present example, the relative expression level of Glypican-1 (Accession No. P35052) was investigated in normal cells and various esophageal cancer cell strains.

(Techniques)

The expression level of Glypican-1 in esophageal squamous cell carcinoma cell strains TE1, TE6, TE8, TE9, TE10, and TE14 was evaluated relative to normal esophageal epithelial cells HEEpic and Het1A.

For 8 types of cell strains cultured in 150 mm Petri dishes, a cell surface membrane protein comprising Glypican-1 was biotinylated with sulfo-NHS—SS-biotin. The extracted protein was purified by Neurto-avidin beads. At that time, in order to correct for the error among the samples, sulfo-NHS—SS-biotin-labeled bovine serum albumin was added to each in an equal amount as an internal standard, and was used for correction of quantification results from a mass spectrometer. The purified proteins were digested by trypsin and labeled with an iTRAQ reagent. Eight samples were mixed into one and it was roughly fractionated into 24 fractions by ion exchange HPLC. Each of the fractions was desalinated and then measured by a mass spectrometer (nano LC-MS/MS) analysis. A database was searched for the obtained data using proteome discoverer ver. 1.3 and thereby cell surface membrane protein comprising Glypican-1 was identified and quantified.

(Result)

The result is shown in FIG. 2. As shown in FIG. 2, while the normal strain showed relative ratio of 1.2, the esophageal cancer cell strains, TE6, TE9, TE10, and TE14 showed a higher relative ratio of 2 times or more and TE1 and TE8 also showed higher relative ratios of 1.6 to 1.7. It was found that Glypican-1 was 2 times or more highly expressed in four of six types of esophageal squamous cell carcinoma cell strains. Therefore, it was shown that Glypican-1 is useful as a marker for esophageal cancer.

Example 3: FACS Analysis to Show that Glypican-1 is Expressed on Cell Surface of Esophageal Cancer Cells Then, in the present example, it was confirmed by FACS that Glypican-1 was expressed on cell surface of esophageal cancer cells.

(FACS Analysis)

Cells were washed with PBS (Nacalai Tesque) twice and peeled off from a dish by 0.02% EDTA solution (Nacalai Tesque). The cells were washed with a FACS staining buffer (PBS supplemented with 1% FBS and 0.1% sodium azide) twice, stained with a 5-time-diluted goat anti-human Glypican-1 antibody (R&D Systems, Minneapolis, Minn.), and subsequently stained with a 50-time-diluted PE-labeled anti-goat IgG antibody. The stained cells were measured by FACS Canto II (Becton Dickinson, Mountain View, Calif., USA) and the data was analyzed using FlowJo software (TreeStar, Stanford, Calif., USA).

(Result)

Figure 3:
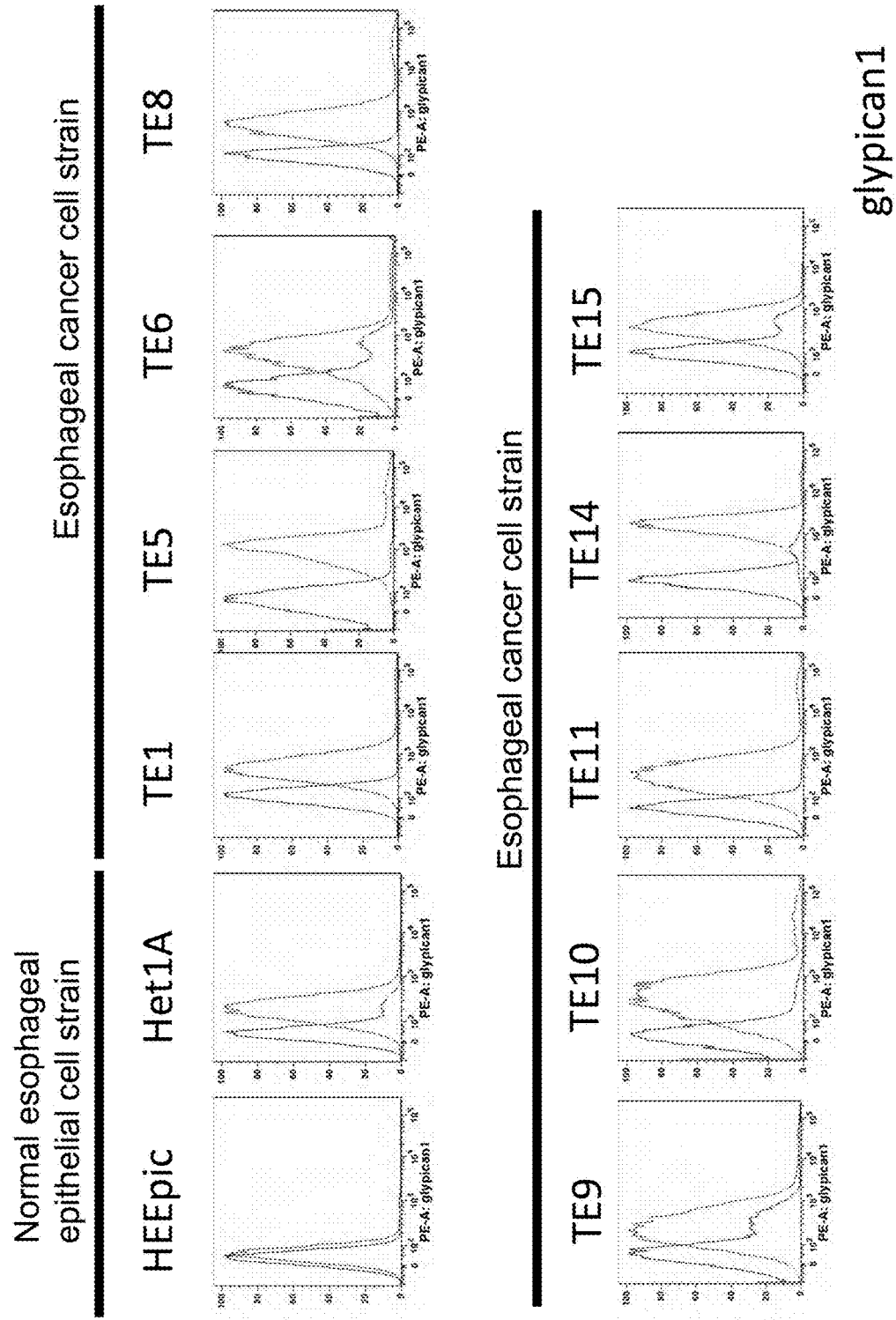
FIG. 3 is a figure showing by a FACS experiment that Glypican-1 is expressed on the cell surface of esophageal cancer cells. Ratio between PE-A and Glypican-1 is shown. With regard to cells used, HEEpic and Het1A (the 1st strain to the 2nd strain from the upper left) are used as normal esophageal epithelial cell strains, and TE1, TE5, TE6, TE8 (the 3rd strain to the 6th strain from the upper left), TE9, TE10, TE11, TE14 and TE15 (five strains in the lower row) were used as esophageal cancer cell strains.

The result is shown in FIG. 3. As shown, while the expression of Glypican-1 in the normal cells was considered the background, it was shown that in all the esophageal cancer cell strains, the expression of Glypican-1 was significantly increased.

The above FACS analysis clarified that Glypican-1 was not expressed in HEEpic and was expressed on cell surface of the esophageal cancer cell strains.

From the results of Examples 1 to 3, it became clear that Glypican-1 is specifically and highly expressed in esophageal cancer cells, but not in normal esophageal cells.

Example 4: Expression by Immunostaining of Glypican-1 in Esophageal Squamous Cell Carcinoma In the present example, Glypican-1 in tissue of an esophageal squamous cell carcinoma (primary and lymph node metastasis) was confirmed by immunohistochemical staining.

(Expression Analysis of Cancer Antigen by Immunohistochemical Staining Method)

A slice of paraffin-embedded tissue was deparaffinization-treated and dehydrated with alcohol. Immunohistochemical staining of Glypican-1 was carried out according to an ABC method using an anti-GPC-1 antibody (Atlas antibodies: HPA030571).

(Result)

Figure 4A:
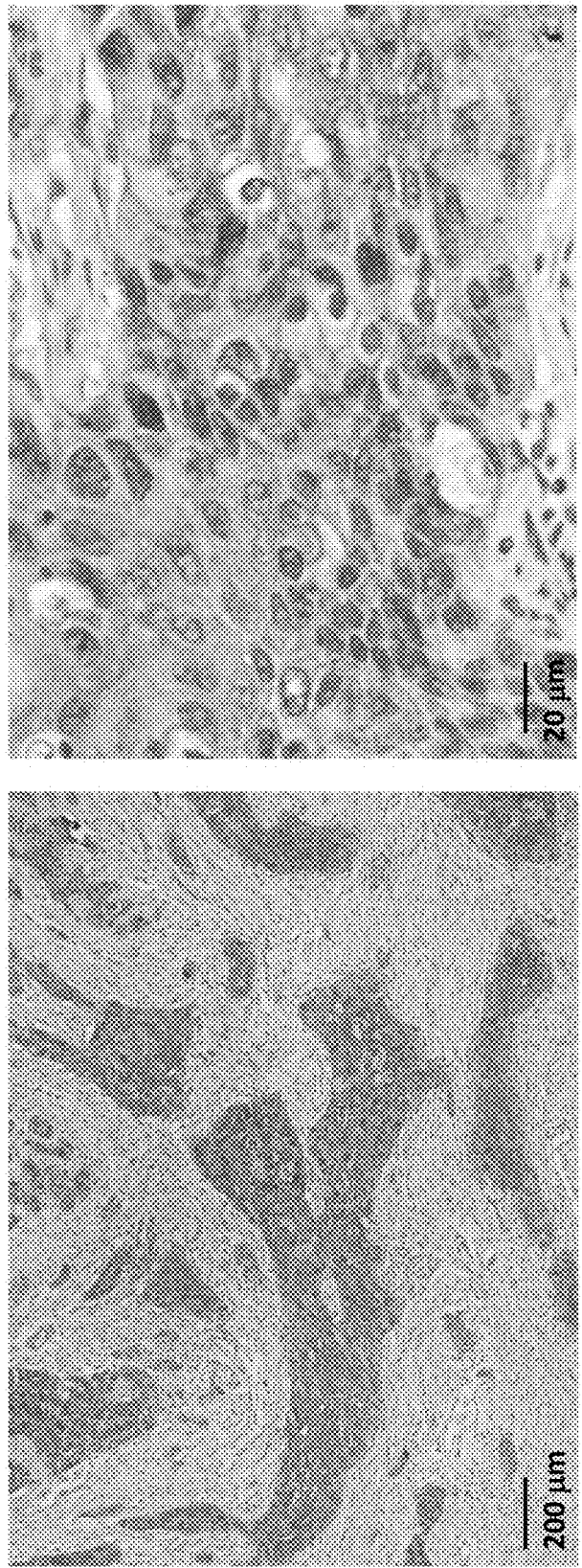
FIG. 4A is a photograph showing the expression of Glypican-1 in esophageal squamous cell carcinoma. An antibody used is HPA030571 from Atlas Antibodies. The left bar is 200 μm and the right bar is 20 μm.

The result is shown in FIG. 4A. In addition, a result of further carrying out another series is shown in FIG. 4B. In all the series, by carrying out immunohistochemical staining of Glypican-1 on surgery tissue, the expression of a cancer antigen candidate molecule in cancer tissue, rather than a cell strain, was evaluated. As shown, by immunohistochemical staining, significant expression enhancement of Glypican-1 was observed in an esophageal cancer cell strain. From the result of this experiment, it became clear that Glypican-1 is highly expressed at cell membrane of esophageal squamous cell carcinoma tissue.

Moreover, it was confirmed that Glypican-1 was also expressed in lymph node metastasis sites of esophageal cancer (FIG. 4C)). Specifically, for an anti-Glypican-1 antibody, a therapeutic effect is expected not only at primary sites but also at metastatic foci. Then, for tissues of esophageal squamous cell carcinoma (88), the expression of Glypican-1 was analyzed by immunohistochemical staining. A primary antibody from Atlas antibodies (HPA030571) was used and the Dako ChemMate ENVISION Kit/HRP (DAB)-universal kit (K5007) was used to carry out staining. The stain intensity was rated using three grades from 0 to 2, the area was rated using four grades from 0 to 3, and the product of them was obtained as a stain score. The stain scores were classified in two groups: scores of 0 to 3 were classified as a GPC1 low expression group and scores of 4 to 6 were classified as a GPC1 high expression group. A survival curve was created using the Kaplan-Meier method and a log-rank test was carried out. Consequently, 35 of 88 cases were classified into the GPC1 low expression group, 53 cases were classified into the Glypican-1 high expression group, and it became clear that the prognosis in the Glypican-1 high expression cases were significantly worse than that in the low expression cases (Log-rank test, p=0.0001) (FIG. 4D).

Example 5: Analysis for Glypican-1 Expression in Various Normal Tissues and Esophageal Cancer Cell Strain TE11 by Real-Time PCR As RNA derived from various human normal tissues, Human Total RNA Master Panel II (Clontech, Palo Alto, Calif., USA) was used. For esophageal squamous cell carcinoma cell strain TE11, RNA was purified by a RNeasy mini kit (QIAGEN). QuantiTect Reverse Transcription Kit (Qiagen) was used to reverse-transfer the total RNA to cDNA.

The real-time PCR was carried out using SYBR Premix Ex taq (Takara Bio, Shiga, Japan). ABI7900HT (Applied Biosystems) was used as the apparatus. The following primer sequences were used.

GPC-1, forward primer
(SEQ ID NO: 27; NM_002046.3)
5'-GCCAGATCTACGGAGCCAAG-3'

GPC-1, reverse primer
(SEQ ID NO: 28; NM_002046.3)
5'-AGGTTCTCCTCCATCTCGCT-3'

GAPDH, forward primer
(SEQ ID NO: 29; NM_002081.2)
'-AGCAATGCCTCCTGCACCACCAAC-3'

GAPDH, reverse primer
(SEQ ID NO: 30; NM_002081.2)
5'-CCGGAGGGGCCATCCACAGTCT-3'

β-actin, forward primer
(SEQ ID NO: 31; NM_001101.3)
'-AGCCTCGCCTTTGCCGA-3'

β-actin, reverse primer
(SEQ ID NO: 32; NM_001101.3)
5'-CTGGTGCCTGGGGCG-3'.

(Result)

Figure 5A:
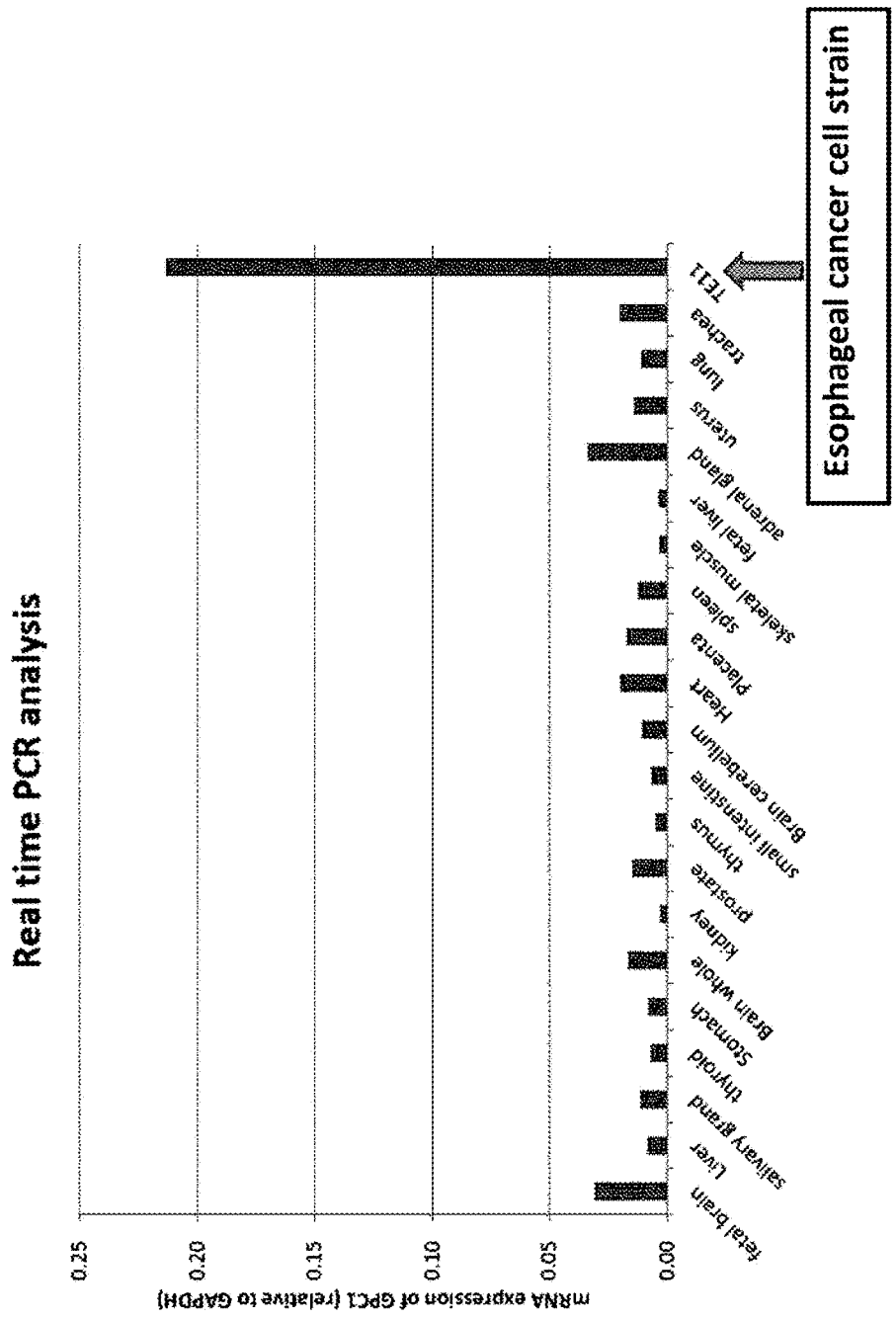
FIG. 5A is a result of comparing the expression level of mRNA level of Glypican-1 (GPC1) in various normal tissues with an esophageal cancer cell strain (TE11) by real-time PCR analysis. The vertical axis represents relative GPC1 mRNA expression (GADPH or β-actin was used as control). On the horizontal axis, data on various tissues were lined up. From the left, there are fetal brain, liver, salivary grand, thyroid, stomach, brain whole, kidney, prostate, thymus, small intestine, cerebellum, heart, placenta, spleen, skeletal muscle, fetal liver, adrenal gland, uterus, lung, trachea, and TE11 (esophageal cancer cell strain). It was shown that the expression of Glypican-1 in normal tissues is low.
Figure 5B:
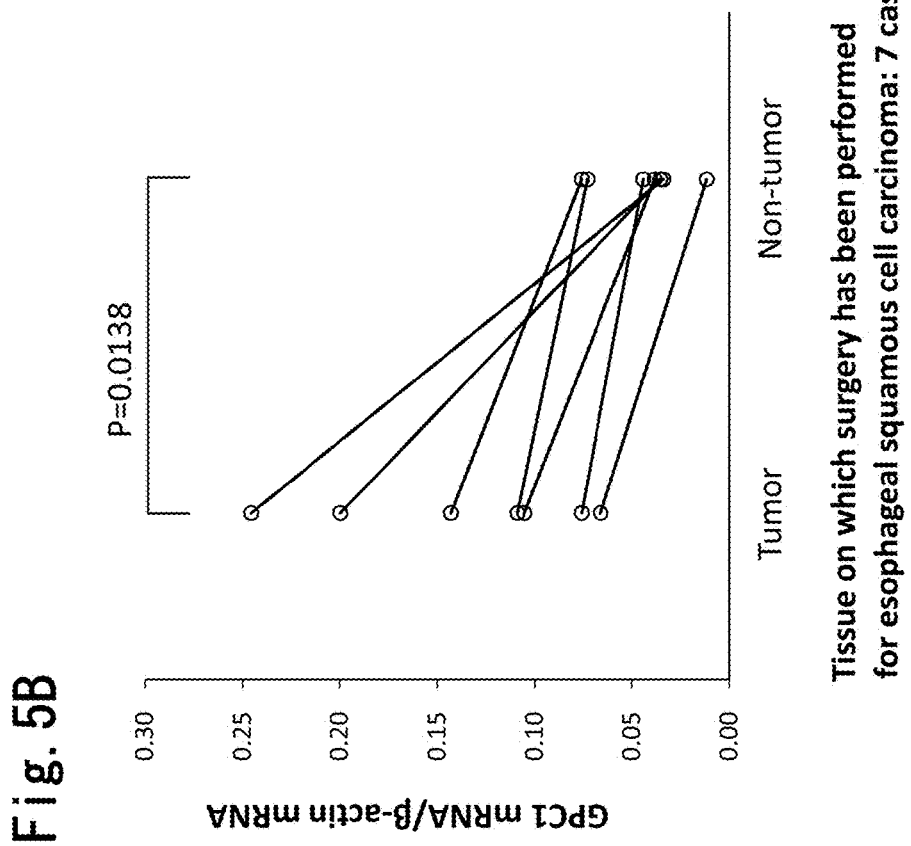
FIG. 5B shows that in esophageal cancer tissue, higher mRNA expression of GPC-1 is observed than that in non-cancer sites. The left is tumor and the right is non-tumor. The vertical axis indicates GPC1 mRNA level relative to β-actin mRNA expression. Seven cases of tissue on which surgery has been performed for esophageal squamous cell carcinoma were used.

The result is shown in FIG. 5A. As shown in the figure, RNAs derived from various commercially available normal human tissues were used to analyze the expression of glypican-1 in various normal tissues by real-time PCR analysis, and it was confirmed that when the expression level of glypican-1 was investigated as a relative value to GAPDH expression, the expression in the normal tissue was low. While significant expression of Glypican-1 is not observed in all the tissues, a remarkable increase in expression was observed in the esophageal cancer cell strain (FIG. 5A) Even in the case that an esophageal cancer tissue, a non-cancer site, and TE14 were added, a similar tendency was observed. FIG. 5B shows a result of analyzing the expression of Glypican-1 in an esophageal cancer tissue and a non-cancer site of the same patient by real-time PCR analysis. When the expression level of Glypican-1 was investigated as a relative value to β-actin expression, a significant increase in expression level was recognized in the esophageal cancer tissue in comparison with the non-cancer site. Accordingly, it is understood from these results that glypican-1 of the present invention is useful as a marker for esophageal cancer.

Figure 6:
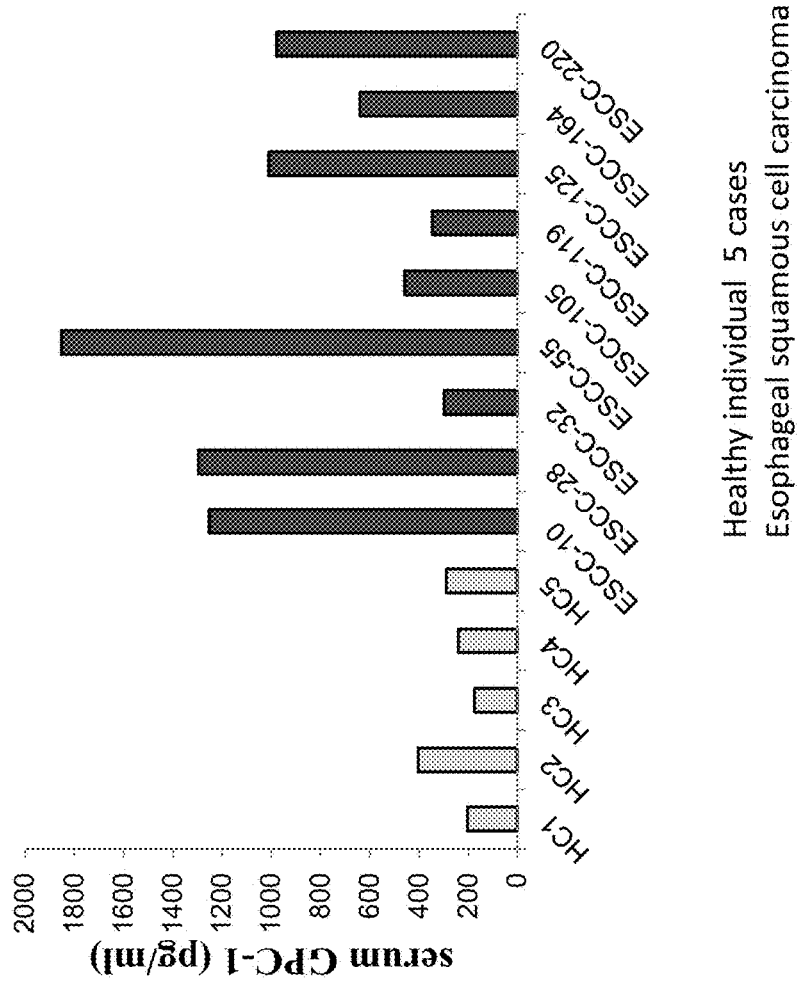
FIG. 6 shows the Glypican-1 concentration in serum in healthy individuals and esophageal squamous cell carcinoma patients. It is a result of measuring the concentration of GPC-1 in serum obtained from a blood sample of each subject. The unit of the vertical axis is pg/ml. The samples are derived from blood of HC1, HC2, HC3, HC4, HC5 (healthy individual samples), ESCC-10, ESCC-28, ESCC-32, ESCC-55, ESCC-105, ESCC-119, ESCC-125, ESCC-164, and ESCC-220 (esophageal squamous cell carcinoma patient samples) from the left. For the esophageal squamous cell carcinoma patients, they exhibit a higher Glypican-1 concentration in serum than the healthy individuals. Based on this, screening for patients to undergo treatment with an anti-Glypican-1 antibody by quantifying the Glypican-1 concentration in serum, that is, application as a companion diagnostic drug is expected.
Figure 7:
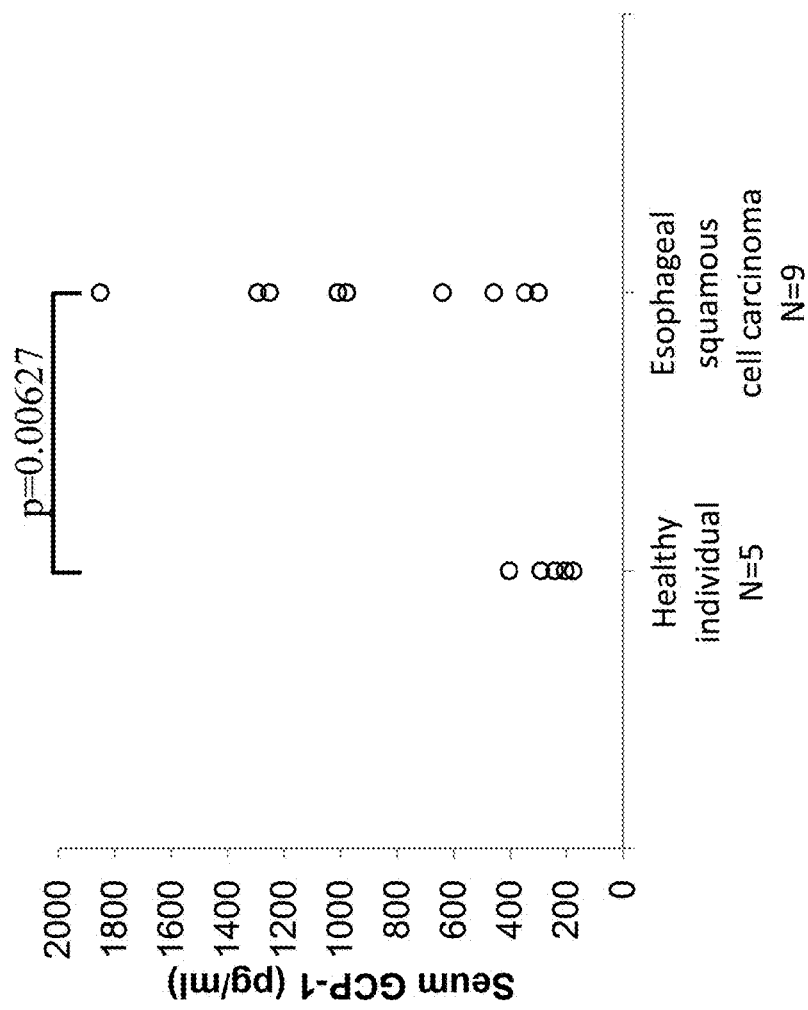
FIG. 7 measures the Glypican-1 concentration in serum in healthy individuals and compares to concentration of esophageal squamous cell carcinoma patients by Mann-Whitney U-test. The concentration of GPC-1 in serum was measured in the serum obtained from blood samples of each subject and the Mann-Whitney U-test was performed. The unit of the vertical axis is pg/ml. Based on the same samples as FIG. 6, the test was carried out with N=5 for the healthy individuals and with N=9 for esophageal squamous cell carcinoma patients. Subsequently, it was determined as significant at p=0.00627. Accordingly, screening for patients to undergo treatment with an anti-Glypican-1 antibody by quantifying the Glypican-1 concentration in serum, that is, application as a companion diagnostic drug is expected.
Figure 8:
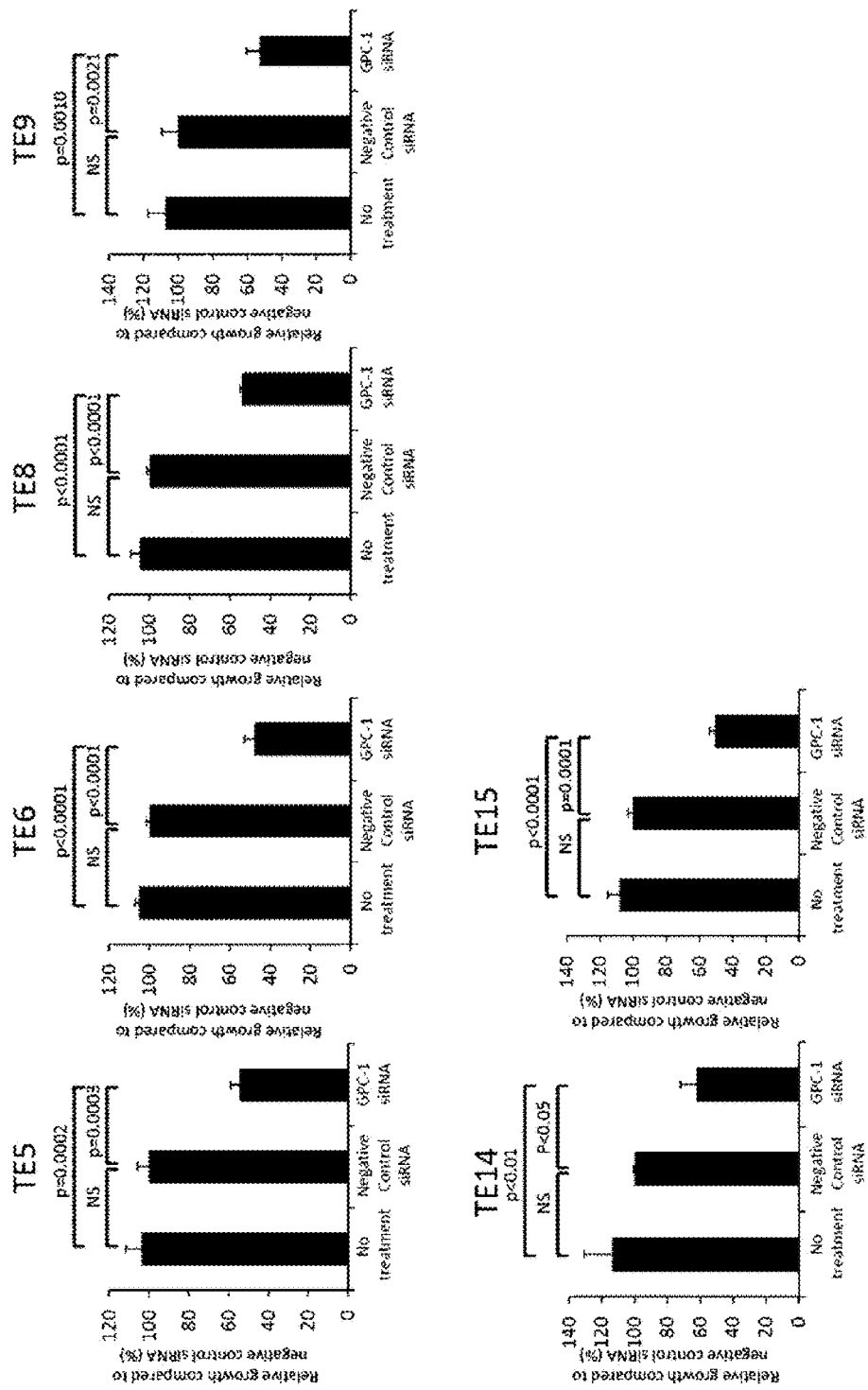
FIG. 8 is a result showing expression suppression using siRNA against Glypican-1. Targeted cell strains are TE5, TE6, TE8, and TE9 shown from the left in the upper row, and TE14 and TE15 shown from the left in the lower row. The vertical axis of each graph shows relative growth in % to negative control siRNA. In each experiment, three types of experiments were carried out: an experiment without siRNA (No treatment), an experiment using negative control siRNA (Negative Control siRNA), and an experiment using siRNA against Glypican-1 (GPC-1 siRNA). In the graphs, NS denotes no significant difference and the numerical value following p indicates statistical significance with a critical rate in the case of a numerical value shown. The expression suppression using siRNA against GPC-1 suppressed growth of esophageal cancer cell strain. It should be noted that in normal cells (HEEpic), as Glypican-1 negative cells, there is no targeted sequence even if siRNA against Glypican-1 is transfected, and accordingly it is presumed that any change in the cells is not found.
Figure 10C:
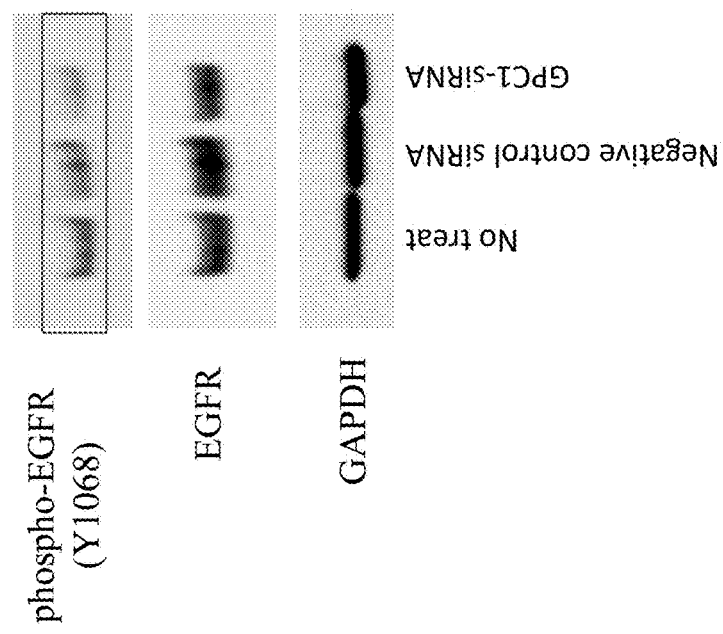
FIG. 10C shows that in an esophageal cancer cell strain, the inhibition of phosphorylation of EGFR is seen by expression suppression of GPC-1. It shows phosphorylated EGFR (Y1068), EGFR, and GAPDH from the top. It shows No treatment, Negative control siRNA, GPC-1 siRNA from the left column.

Example 6: Comparison of Glypican-1 Concentration in Serum in Healthy Individuals and Esophageal Squamous Cell Carcinoma Patients Healthy individual serum (N=5) and esophageal cancer patient serum (N=9) were diluted two times with PBS and quantified by a human ELISA kit of USCN Life Science, INC. From the result, it became clear that in six of nine esophageal cancer patient cases, higher concentrations of Glypican-1 in serum was exhibited than the healthy individual serum (FIG. 6 to FIG. 7).

In order to clinically apply an antibody pharmaceutical product with an anti-Glypican-1 antibody, it is believed that Glypican-1-expressing esophageal cancer patient-selective treatment should lead to personalized medicine. Accordingly, a method of screening a Glypican-1 positive patient is required. Although a technique of inspecting Glypican-1 in biopsy tissue of esophageal cancer in accordance with an immunohistochemical staining method is also possible, since it is high invasive, a less-invasive method is preferable. Glypican-1 or an extracellular domain thereof that is expressed in esophageal cancer tissue can be liberated into blood and be present therein. Thus, if Glypican-1 in blood of an esophageal cancer patient can be quantified, when the Glypican-1 concentration in blood is high, the possibility that the expression level of Glypican-1 is high in esophageal cancer tissue is suggested. A blood sample has the advantage of being less invasive than a biopsy. In the present invention, as a result of quantifying the Glypican-1 concentration in blood in accordance with an ELISA method, we first succeeded in detecting an esophageal cancer patient having an increased Glypican-1 concentration in blood in comparison with a healthy individual. It is highly probable that Glypican-1 is highly expressed in these patient tissues, and the measurement of the Glypican-1 concentration in blood is believed to be highly useful as a companion diagnostic drug.

Example 7: Expression Suppression, Apoptosis, and Suppression of AKT Using siRNA Against Glypican-1

In the present example, in order to clarify whether Glypican-1 relates to the growth of an esophageal squamous cell carcinoma cell strain, the expression suppression of Glypican-1 using siRNA against Glypican-1 was used to examine an anti-tumor effect in vitro.

(Growth Inhibition Assay with siRNA, and a Monoclonal Antibody)

Esophageal cancer cells were seeded into a 96-well plate at 2,000 cells/well. Seventy two hours after siRNA transfection using lipofectamine 2000, cell growth assay was carried out according to the WST-8 assay method. siRNA against Glypican-1 and negative control siRNA was obtained from QIAGEN.

(Apoptosis Assay)

siRNA was transfected into TE6, TE8, and TE14 cells using lipofectamine 2000, 72 hours after which, the cells were washed with PBS, and then measured with a caspase-3 fluorometric assay kit (R&D systems).

(Western Blot Analysis of AKT)

TE6, TE8, and TE14 were washed with ice-cooled PBS (−) and then were peeled off with a cell scraper, and the cells were recovered by centrifugation. The cells were lysed in a RIPA buffer (10 mM Tris-HCl, pH 7.5, 150 mM NaCl, 1% Nonidet P-40, 0.1% sodium deoxycholate, 0.1% SDS, phosphatase, lx protease inhibitor (NACALAI TESQUE) cocktail (NACALAI TESQUE)), and then the supernatant by centrifugation (13,200 rpm, 4° C., 15 min) was recovered as a protein extract liquid. The protein concentration was quantified using a protein quantification kit (DC Protein Assay kit (Bio-Rad Laboratories, Inc.)) and using bovine serum albumin (BSA) as a standard.

SDS-PAGE and the transfer to a PVDF membrane, and blocking were carried out according to the method described in Example 1.

An anti-phospho-AKT (Thr308) antibody, an anti-phospho-AKT (Sre473) antibody, an anti-AKT antibody, and an anti-cleaved caspase-3 antibody were purchased from Cell Signaling Technology. The membranes were incubated with various primary antibodies for 1 hour at room temperature. After washing with TBST 3 times for 10 minutes each time, the PVDF membranes were incubated at room temperature for 1 hour using an HRP-labeled anti-rabbit antibody (GE healthcare) that had been diluted 5,000 times with TBST. The PVDF membranes were washed with TBST 3 times for 10 minutes each time and then a reacted protein was detected by a fluorescence reaction system (Perkin Elmer, Inc.). An anti-GAPDH antibody (Santa Cruz Biotechnology) was used as a loading control.

(Result)

The results are shown in FIGS. 8, 9, 10A, 10B, and 10C. siRNA against Glypican-1 exhibited an antitumor effect on Glypican-1 positive esophageal squamous cell carcinoma cells (TE5, TE6, TE8, TE14, and TE15). At that time, from the fact that an increase in caspase-3 activity due to expression suppression of Glypican-1 by siRNA of Glypican-1 was recognized in TE6, TE8, and TE14, it became clear that apoptosis was induced. In addition, it became clear that the expression suppression of Glypican-1 in TE6, TE8, and TE14 causes a decrease in the phosphorylation level of AKT. In the TE8 cell, an increase in the expression of pro-apoptotic proteins Puma, Bik, and Bim and a decrease in the expression of an anti-apoptotic protein Bcl-w due to expression suppression of Glypican-1 by siRNA of Glypican-1 were recognized; and additionally recognized was a decrease in the phosphorylation level of EGFR.

From the above, it was shown that the present invention may function as a therapeutic agent or a prophylactic agent for esophageal cancer, particularly esophageal squamous cell carcinoma.

Example 8: Antibody Production and Characterization

In the present example, a GPC-1 chicken antibody was prepared and characterized. A protocol is shown below.
(Preparation of Human Glypican-1 Expressing Chicken Cell Strain and Immunization of Chicken)

cDNA of human Glypican-1 was ligated to a mammalian expression vector (pcDNA 3.1-V5/His-TOPO) and cloned such that a V5/His-tag fused protein is at the C-terminal. Then, an expression vector was transfected into a chicken lymphoblast-like cell strain according to an electroporation method and then 2 mg/ml of G418 was added to select an expression cell. Chicken was hyperimmunized with the obtained Glypican-1-expressing cell strain. An antibody titer was measured by cell-ELISA. As a cell strain, a Glypican-1 expressing chicken lymphoblast-like cell strain was used at $4 \times 10^5$ cells/well.
(Preparation of scFv Phage Antibody Library from Immunized Chicken Spleen)

The spleen was extracted from an immunized chicken and then the lymphocytes were separated. The RNA was extracted from the obtained lymphocytes, a cDNA was synthesized, and a scFv phage antibody library was prepared. For the preparation of a phage antibody library, a general method described in [nakamura et al., J Vet Med Sci. 2004 July; 66 (7):807-14] was followed.
(Selection of Panning and Evaluation of Reactivity of scFv Clone)

Cell panning was carried out using the scFv phage library and the Glypican-1-specific phage was concentrated. It was added to a non-Glypican-1-expressing cell strain to carry out the absorption operation of a nonspecific phage, and then was reacted with a human Glypican-1-expressing cell strain. As the cell strain, a lymphoblast-like cell strain was used. After washing with organic solvent, phages specifically binding to the Glypican-1-expressing cell strain were recovered and then *Escherichia coli* were infected with it. Panning was carried out four times and then the reactivity of the library was confirmed by cell-ELISA and FACS analysis using the Glypican-1-expressing cell strain. A phage was cloned from a library of which the reactivity had begun to increase and the reactivity was confirmed by cell-ELISA and FACS analysis. A positive clone was selected and then the sequence was determined. For cell panning, a method described in [Giordano et al., Nat Med. 2001 November; 7 (11):1249-53.] was followed.
(Analysis)

In carrying out FACS analysis using an antibody, a chicken T-lymphoblast-like cell strain (CT01 cell) was used as a Glypican-1 negative cell and a CT01 cell (CT01-GPC-1#42) forcibly expressing human Glypican-1 was used as a Glypican-1 positive cell. Various clones of the developed antibodies were used as primary antibodies, a FITC-labeled Goat anti-Mouse IgG (H+L chain specific) (Southern Biotech) was used as a secondary antibody, measurement was carried out using FACS Cantoll (BD), and the measurement data was analyzed using Flow Jo (Tree Star). As a result, twenty types of clones were successfully developed as antibodies that can stain Glypican-1 with FACS.
(Result)

Figure 11:
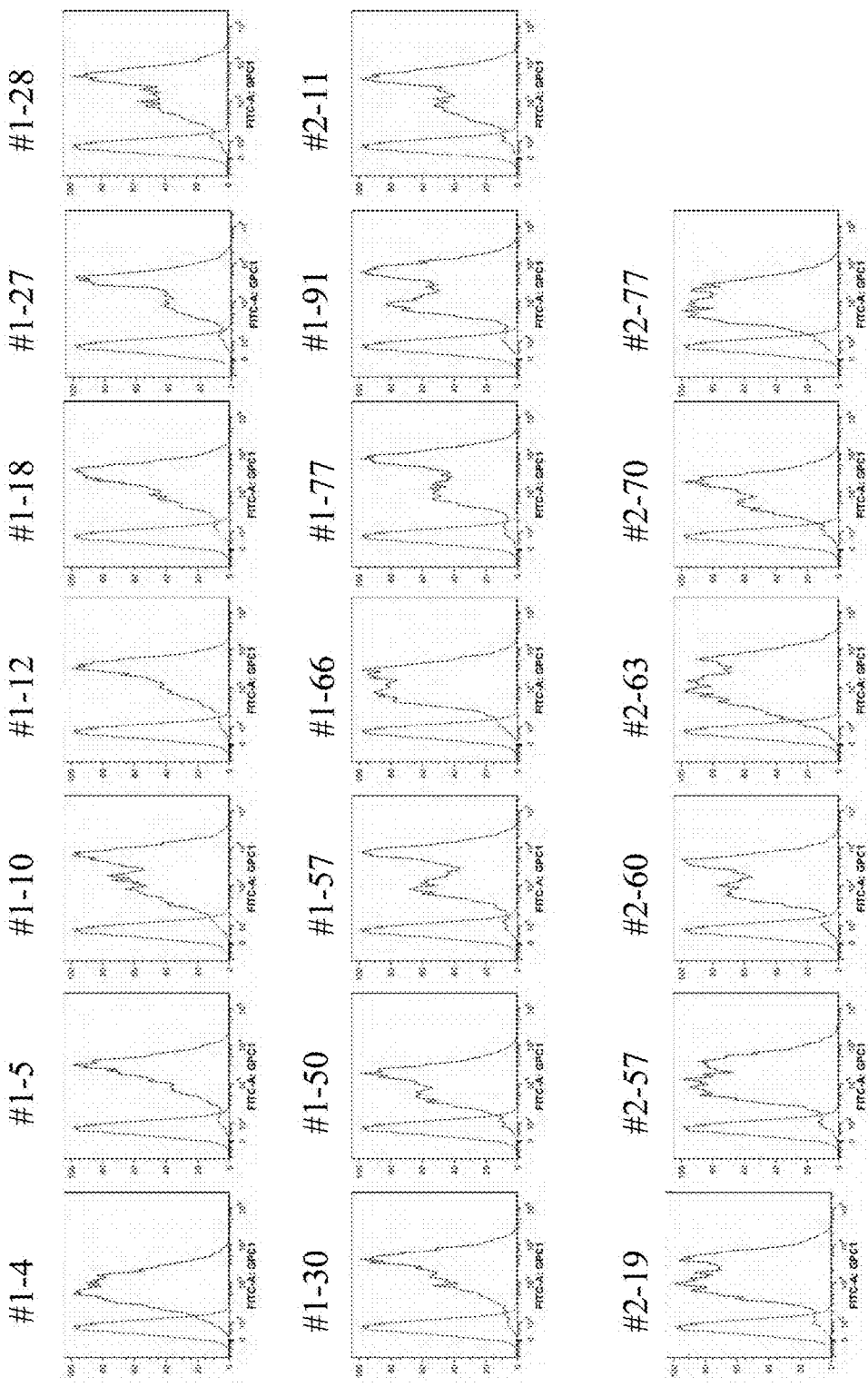
FIG. 11 is a result of confirming the reactivity of an obtained antibody to Glypican-1 by FACS (FITC-A:GPC1). From the result of the reactivity, it is understood that these antibodies may be used as a diagnostic drug or a therapeutic drug.

The result is shown in FIG. 11. As shown, with regard to all the antibodies, it is understood from the result of reactivity that these antibodies can be used as diagnostic drugs/ therapeutic drugs.

Example 9: Analysis of Antitumor Effect on Mouse with Anti-Glypican-1 Monoclonal Antibody An esophageal cancer cell strain TE-8 is subcutaneously implanted to Scid mice (6-week old, female) at $2 \times 10^6$ cells/100 μl (PBS:Matrigel=1:1). On day 14 after the implantation, the mice were divided into two groups and an anti-Glypican-1 antibody or an isotype control antibody (Mouse IgG2a, M7769, Sigma) was intraperitoneally administered at 10 mg/kg at a frequency of twice a week and a total of 6 times. The TE-8-implanted mice are dissected on day 25 after the start of the antibody administration, and the tumor weight is also measured. It was calculated according to the following: tumor volume=major axis×minor axis× height. By this, an antitumor effect can be confirmed.

In order to investigate whether an antitumor effect via an anti-Glypican-1 antibody is dependent or independent from ADCC, an esophageal cancer cell strain TE-8 is subcutaneously implanted to NOD/Scid mice (6-week old, female) at $1 \times 10^6$ cells/100 μl (PBS:Matrigel=1:1). On day 14 after the implantation, the mice are divided into two groups and an anti-Glypican-1 antibody or an isotype control antibody (Mouse IgG2a, M7769, Sigma) is intraperitoneally administered at 10 mg/kg at a frequency of twice a week and a total of 6 times. The TE-8-implanted mice are dissected on day 25 after the start of the antibody administration, and the tumor weight is also measured. It was calculated according to the following formula: tumor volume=major axis×minor axis× height. Since the activity of NK cells in NOD/Scid mice is low, if an antitumor effect is not recognized, it can be said that the antitumor effect by an anti-Glypican-1 antibody that was exhibited in Scid mice is mainly ADCC activity. When an antitumor effect is also observed at some level in NOD/ Scid mice, it means that the anti-Glypican-1 antibody exhibits an antitumor effect by inhibiting Glypican-1 s function itself instead of ADCC activity.
(Affinity Analysis of Anti-Glypican-1 Antibody by Biacore Analysis)

Affinity analysis of an anti-Glypican-1 antibody was measured using Biacore 3000. A rabbit anti-mouse IgG polyclonal antibody of the Mouse Antibody Capture Kit was solid-phased to a CM5 sensor tip, various anti-Glypican1 antibody clones were captured, recombinant Glypican-1 (R&D systems 4519-GP-050) was added at various concentrations as a ligand, and binding and dissociation were monitored. The obtained sensorgram was analyzed using BIAevaluation 4.1 software and a $K_D$ value was calculated (FIG. 12). Consequently, it became clear that the anti-GPC1 antibody (#1-12) exhibits high affinity as the $K_D$ value is 2.61 nM.

(Cross Reaction Assay of Anti-Glypican-1 Monoclonal Antibody with Mouse Glypican-1)

Figure 13:
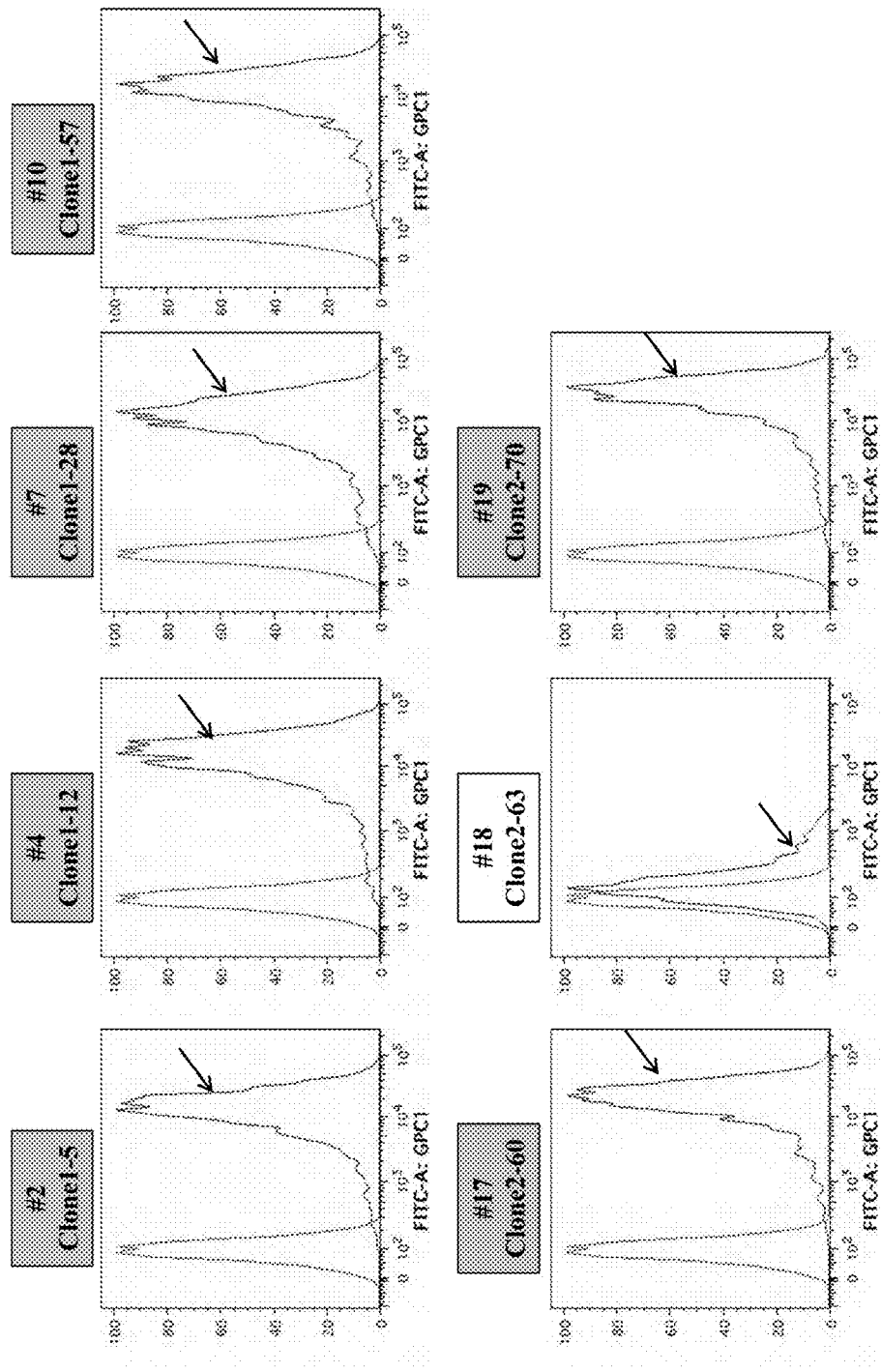
FIG. 13 shows that a GPC-1 monoclonal antibody exhibits cross reaction with a mouse GPC-1. The upper section shows, from the left, clones 1-5, 1-12, 1-28, and 1-57 (#2, #4, #7, and #10, respectively) and the lower section shows, from the left, clones 2-60, 2-63, and 2-70 (#17, #18, and #19, respectively). Since the original figure is drawn by red and blue colors, the blue color is indicated by an arrow. Curves indicated by an arrow are curves of investigating the reactivity with various clones in the 293 cell forcibly expressing mouse GPC1. Clones 1-5, 1-12, 1-28, 1-57, 2-60, and 2-70 (#2, #4, #7, #10, #17, and #19, respectively) exhibited the reactivity with mouse GPC1, however clone 2-63 (#18) did not exhibit the reactivity with mouse GPC1.

A mouse Glypican-1 expression vector or an empty vector was transfected to the 293 cell using lipofectamine 2000 and the reactivity with various clones of an anti-Glypican-1 antibody was analyzed by FACS. Consequently, it became clear that clones other than #18(2-63) exhibit cross reaction with a mouse Glypican-1 (FIG. 13).

(Cell Growth Inhibition Assay with Anti-Glypican-1 Monoclonal Antibody)

Figure 14:
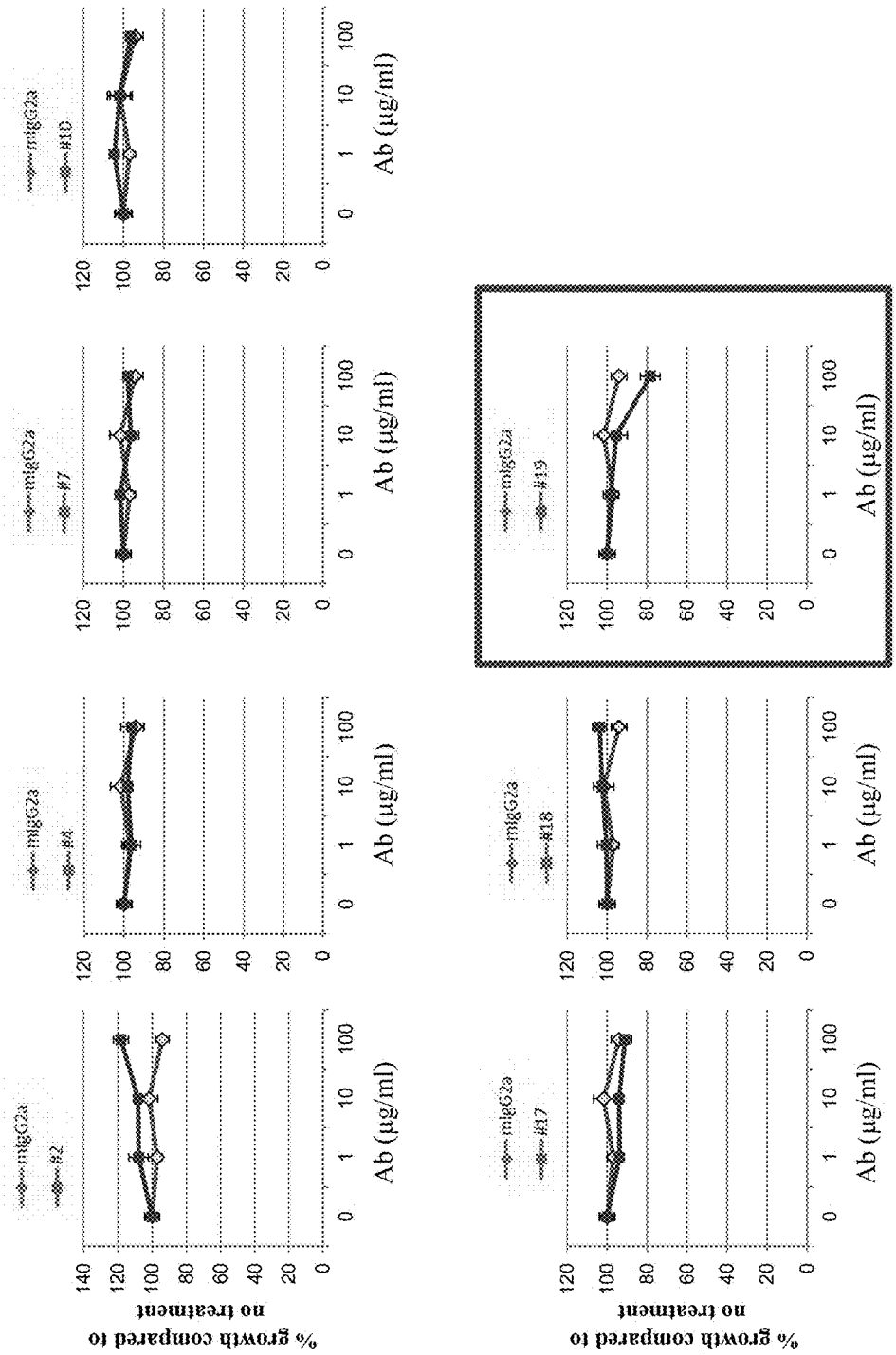
FIG. 14 is a figure showing that anti-GPC-1 antibody #19 exhibits the growth suppression activity towards TE14 cells. The upper section shows, from the left, clones 1-5, 1-12, 1-28, and 1-57 (#2, #4, #7, and #10, respectively) and the lower section shows, from the left, clones 2-60, 2-63, and 2-70 (#17, #18, and #19, respectively). The black circles indicate the relevant antibody and the white circles indicate mIgG2a. The horizontal axis shows antibody concentration (µg/ml).

The TE14 cell was seeded into a 96-well plate at 2000 cells/well and incubated in a $CO_2$ incubator at 37° C. overnight. The cell supernatant on the 96-well plate was discarded and diluted solutions of an anti-Glypican-1 antibody (0 µg/ml, 1 µg/ml, 10 µg/ml, and 100 µg/ml) were each added at 100 µL/well. After 72 hours, cell growth assay was carried out according to the WST-8 assay method. In addition, mouse IgG2 (Biolegend, Inc., 400224, MOPC-173), which is non-anti-GPC-1 antibody, was used as a control. The result is shown in FIG. 14. By contacting anti-Glypican-1 antibody #19(2-70), growth of the esophageal cancer cell (TE14) was suppressed.

(Epitope Analysis)

Figure 16B:
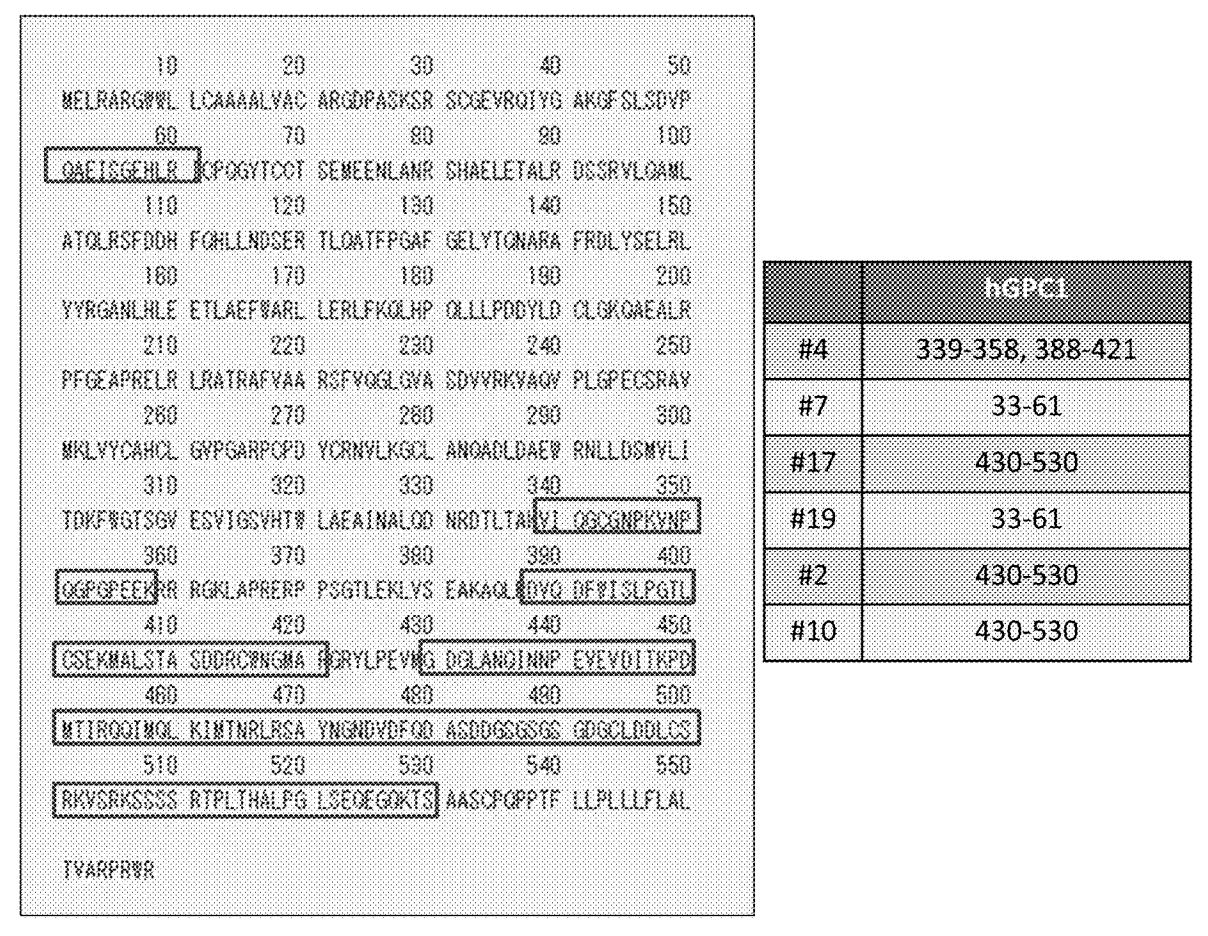

Epitope analysis was carried out for various anti-Glypican-1 antibodies. From an expression vector of the full length of human Glypican-1, a truncated mutant having the 33rd to the 61st amino acids deleted was prepared. This expression vector was transfected into the 293 cell and the reactivity with various anti-Glypican-1 antibodies was analyzed by FACS. Consequently, since the reactivity in FACS disappeared in two clones #7(1-28) and #19(2-70), it was believed that epitopes for #7 (1-28) and #19 (2-70) are present in the region of the 33rd to the 61st (FIGS. 16A and 16B).

Figure 18:
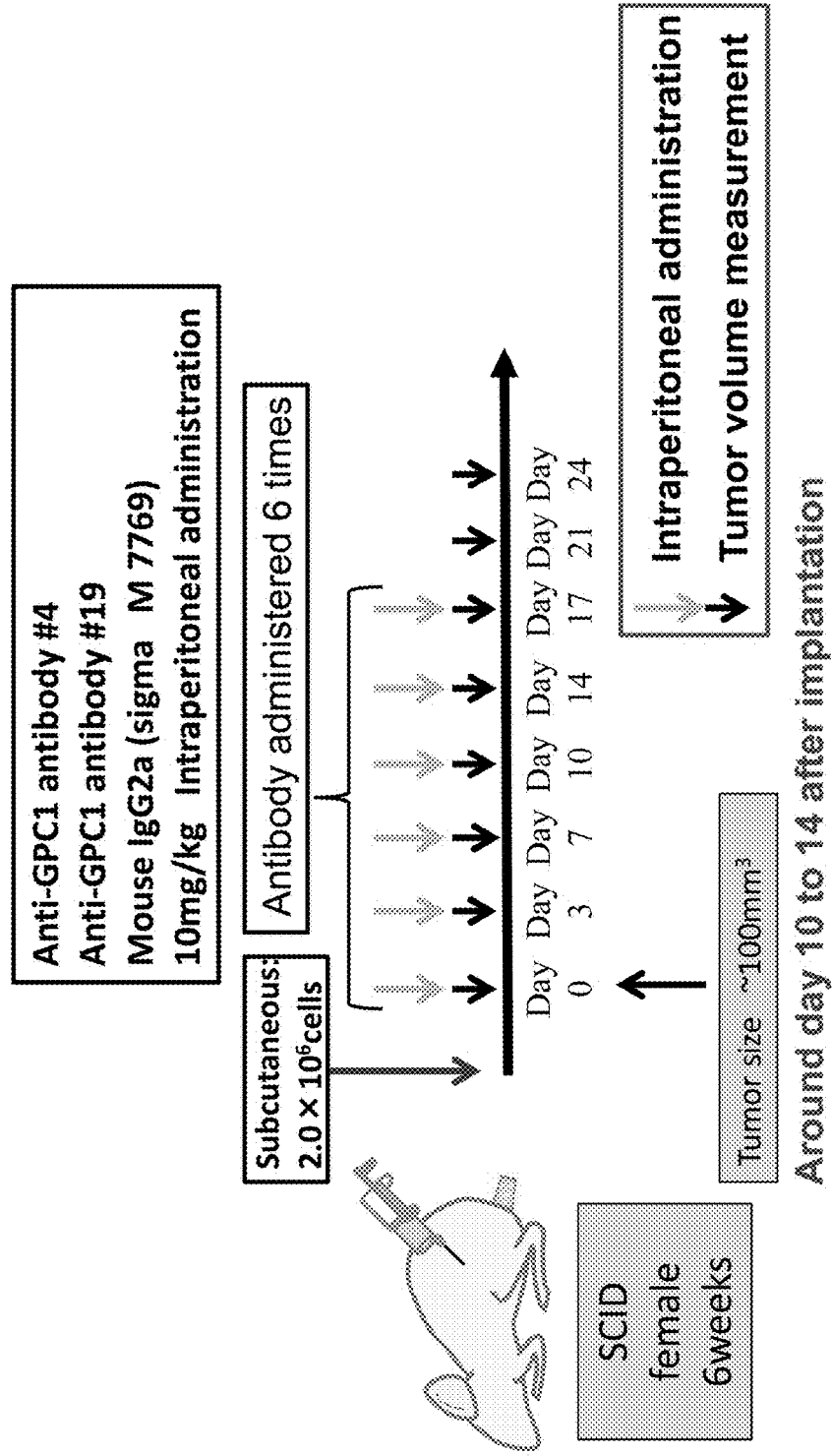
FIG. 18 shows an examination of antitumor effect of an anti-GPC1 antibody against esophageal cancer. As shown, anti-GPC1 antibodies #4 and #19 were used and mouse IgG2a (Sigma M7769) was used. Intraperitoneal administration of 10 mg/kg was carried out. As a model, SCID female 6-week-old mice were used. First, $2 \times 10^6$ cells were subcutaneously implanted. The tumor size reached about 100 mm$^3$ (10 to 14 days after the implantation). Each of the antibodies was administered 6 times. In addition, the tumor volume was measured two times after the administration (Day 21 and Day 24).

Subsequently, a characteristic of various anti-Glypican-1 antibodies that reacted with Glypican-1, but not with Glypican-3 was determined to prepare a chimeric protein expression vector having an amino acid sequence of the 430th or more position of Glypican-1 substituted with that of Glypican-3 (FIG. 17). Various expression vectors were transfected into the 293 cell and the reactivity with various anti-Glypican-1 antibodies was analyzed by FACS. Consequently, since the reactivity in FACS is not recognized in three clones #17(2-60), #2(1-5), and #10(1-57), it is believed that the epitope region in these clones is present in the 430th to the 530th corresponding to an extracellular region of Glypican-1 (FIG. 18).

In addition, an antigen-antibody complex of anti-Glypican-1 antibody #4(1-12) that had been immunoprecipitated with an epitope region was digested by trypsin, and the peptide region bound to the antibody was identified with a mass spectrometer.

Anti-Glypican-1 antibody #4(1-12) or mouse IgG2 (Biolegend, Inc., 400224, MOPC-173) and recombinant Glypican-1 (R&D systems 4519-GP-050) were mixed and immunoprecipitated using protein G sepharose. Then, enzymatic digestion was carried out using trypsin in the form of beads, the beads were further washed, and then a peptide bound to the antibody was eluted with 0.1% formic acid, and the peptide was analyzed by LC-MS/MS analysis and database search by MASCOT search program (version 2.4.1; Matrix Science). Consequently, 339-358, 388-404, and 405-421( ) were detected as peptide sequences that were specifically detected for samples of anti-Glypican-1 antibody #4(1-12) in comparison with a control antibody. Accordingly, it was confirmed that the epitope for anti-Glypican-1 antibody #4 (1-12) is present in an amino acid region of the 339th to the 358th and an amino acid region of the 388th to the 421st.

Example 10: Analysis of Antitumor Effect in Mouse by Anti-GPC1 Monoclonal Antibody An esophageal squamous cell carcinoma cell strain E14 was subcutaneously implanted to SCID mice (6-week old, female) at $2 \times 10^6$ cells/100 µl (PBS:Matrigel=1:1). On day 14 after the implantation, the mice were divided into two groups and anti-GPC1 antibody #4(1-12), anti-GPC1 antibody #19(2-70), or an isotype control antibody (Mouse IgG2a, M7769, Sigma) was intraperitoneally administered at 10 mg/kg at a frequency of twice a week and a total of 6 times (FIG. 18). The TE14-implanted mice were dissected on day 24 after the start of the antibody administration, and the tumor weight was also measured. It was calculated according to the following: tumor volume=major axis× minor axis×minor axis×0.5.

Figure 19:
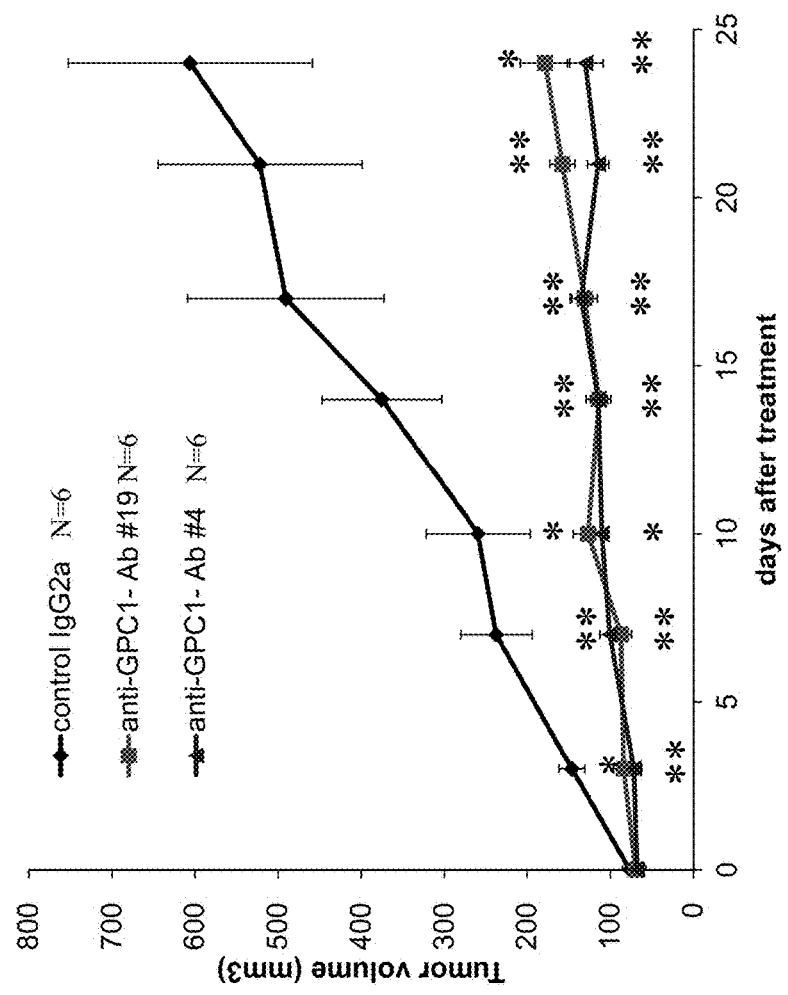
FIG. 19 is a figure showing that anti-GPC-1 antibodies exhibit an antitumor effect on an esophageal cancer xenograft model of SCID mice. The horizontal axis indicates the number of day after treatment and the vertical axis indicates tumor volume (mm$^3$). The rhombuses indicate control IgG2a (N=6), the squares indicate anti-GPC-1 antibody #19 (N=6), and the triangles indicate anti-GPC-1 antibody #4 (N=6). The statistical significance was confirmed by one way ANOVA and Dunnett's test. * denotes p<0.05,  denotes p<0.01, and * denotes p<0.001.
Figure 20:
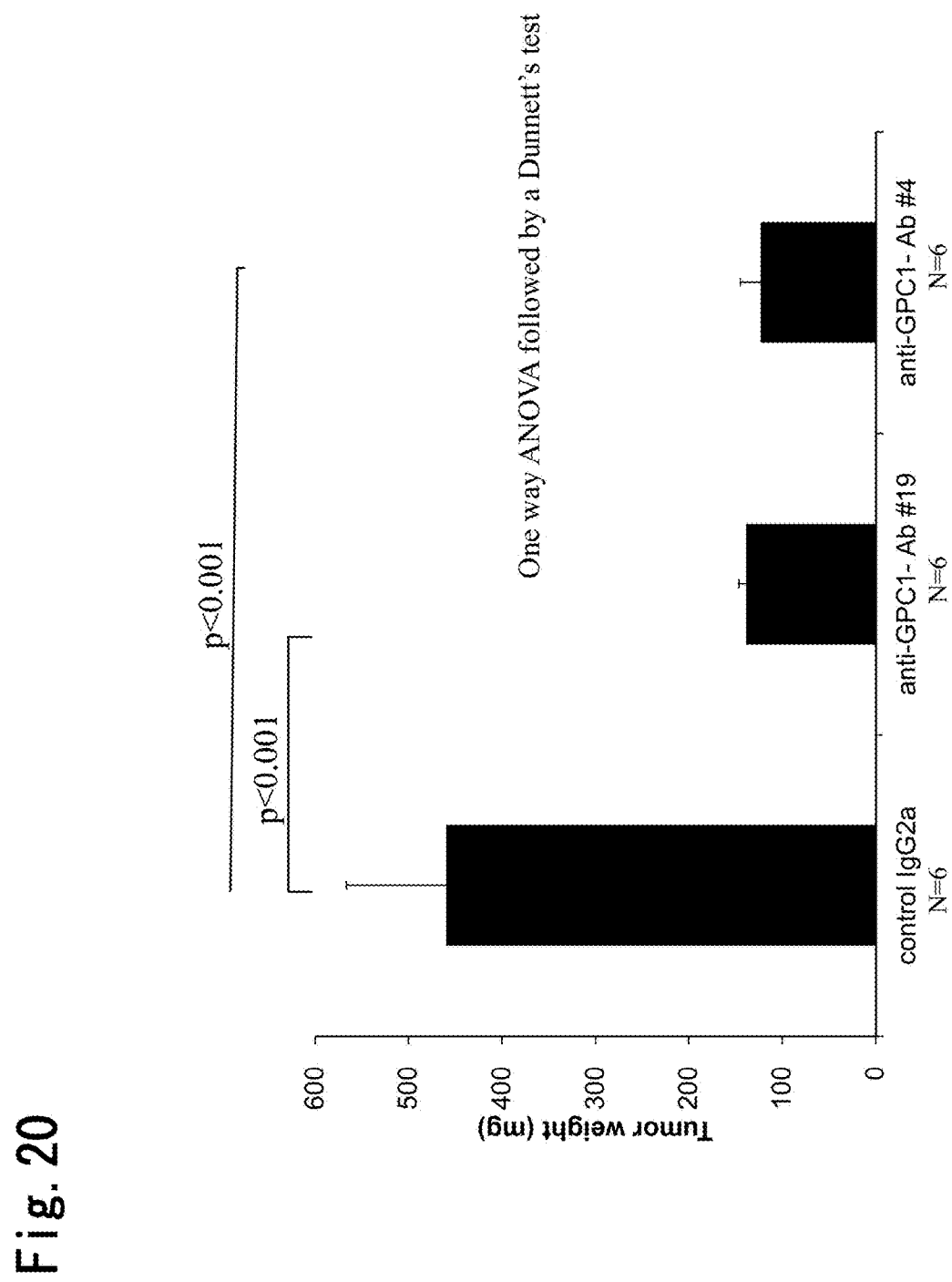
FIG. 20 is a graph showing that anti-GPC-1 antibodies exhibit an antitumor effect on an esophageal cancer xenograft model of SCID mice. From the left, control IgG2a, anti-GPC-1 antibody #19, and anti-GPC-1 antibody #4 are shown. All of them were at N=6. The vertical axis indicates tumor weight (mg). The statistical significance was confirmed by one way ANOVA and Dunnett s test. All the antibodies were statistically significant at p<0.001.

As a result of measuring a tumor volume, in the anti-GPC1 antibody administered group, a significant inhibitory effect on tumor growth in vivo was also recognized in the TE14-implanted mice relative to the control IgG administered group (FIGS. 19 to 20). A significant difference in tumor weight was also recognized.

Example 11: Analysis of Antitumor Effect in Mouse by Anti-GPC1 Monoclonal Antibody An esophageal squamous cell carcinoma cell strain TE14 was subcutaneously implanted to NOD/SCID mice (6-week old, female) at $2 \times 10^6$ cells/100 µl (PBS:Matrigel=1:1). On day 14 after the implantation, the mice were divided into two groups and anti-GPC1 antibody #4(1-12), anti-GPC1 antibody #19(2-70), or the isotype control antibody (Mouse IgG2a, M7769, Sigma) was intraperitoneally administered at 10 mg/kg at a frequency of twice a week and a total of 6 times. The TE14-implanted mice were dissected on day 24 after the start of the antibody administration, and the tumor weight is also measured. It was calculated according to the following formula: tumor volume=major axis×minor axis× minor axis×0.5.

Figure 21:
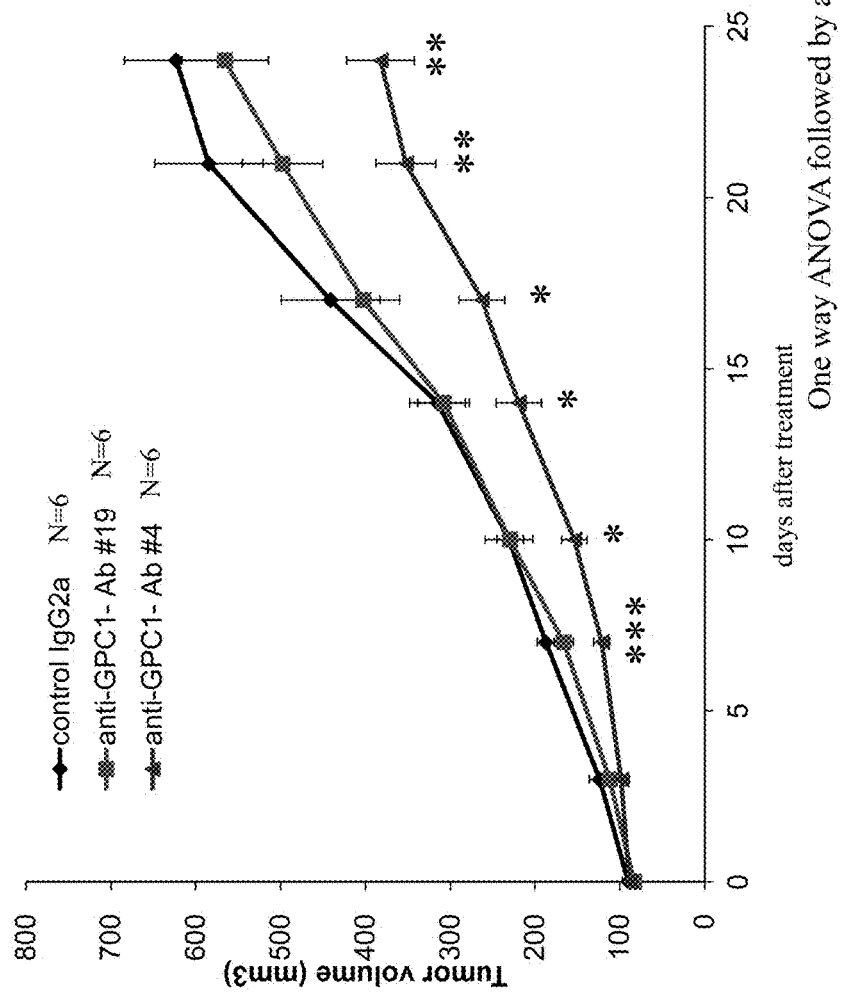
FIG. 21 is a figure showing that anti-GPC-1 antibody #4 exhibits an ADCC non-dependent antitumor effect on an esophageal cancer xenograft model of NOD/SOLD mice. The horizontal axis indicates the number of day after treatment and the vertical axis indicates tumor volume (mm$^3$). The rhombuses indicate control IgG2a (N=6), the squares indicate anti-GPC-1 antibody #19 (N=6), and the triangles indicate anti-GPC-1 antibody #4 (N=6). The statistical significance was confirmed by one way ANOVA and Dunnett's test * denotes p<0.05,  denotes p<0.01, and * denotes p<0.001.
Figure 22:
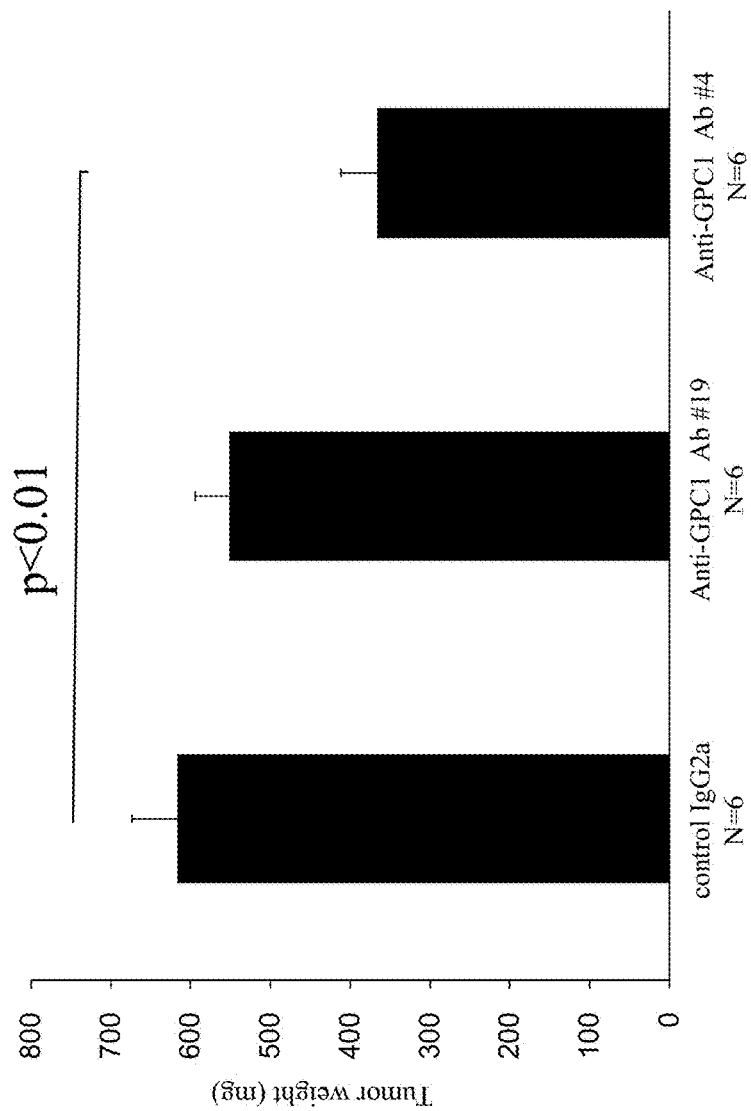
FIG. 22 is a figure showing that anti-GPC antibody #4 exhibits an ADCC non-dependent antitumor effect on an esophageal cancer xenograft model of NOD/SCID mice. From the left, control IgG2a, anti-GPC-1 antibody #19, and anti-GPC-1 antibody #4 are shown. All of them are at N=6.

As a result of measuring a tumor volume, a significantly, but partially, inhibitory effect on in vivo growth of tumor in the NOD/SCID mice was recognized in anti-GPC1 antibody #4 (1-12) administered group relative to the control IgG administered group (FIG. 21). A significant difference in tumor weight was also recognized. A similar result was also recognized in tumor weight (FIG. 22).

Example 12: Analysis of Antitumor Effect in Mouse by Anti-GPC1 Monoclonal Antibody A lung squamous cell carcinoma cell strain LK2, which is GPC1 negative, was subcutaneously implanted to SCID mice (6-week old, female) at $2 \times 10^6$ cells/100 µl (PBS: Matrigel=1:1). On day 14 after the implantation, the mice were divided into two groups and the anti-GPC1 antibody (#1-12) or an isotype control antibody (Mouse IgG2a, M7769, Sigma) was intraperitoneally administered at a frequency of twice a week and a total of 6 times (FIG. 23). The mice were dissected on day 24 after the start of the antibody administration, and the tumor weight was also measured. It was calculated according to the following: tumor volume=major axis×minor axis×minor axis×0.5.

As a result of measuring a tumor volume, in the GPC1 negative LK2-implanted SCID mice, a significantly inhibitory effect on tumor growth in vivo was not recognized in the anti-GPC1 antibody administered group relative to the control IgG administered group (FIG. 24). A similar result was also obtained in tumor weight (FIG. 25). From this, it was suggested that in order for an anti-GPC1 antibody to exhibit an antitumor effect, it is necessary that GPC1 is expressed at a tumor cell.

Example 13: Safety Test

Since anti-Glypican-1 antibody #4(1-12) also exhibits cross reaction with mouse Glypican-1, an acute toxicity test in the case of administration to a mouse was carried out. One mg of Mouse IgG2a (Sigma, M7769) or anti-Glypican-1 antibody #4(1-12) was intraperitoneally administered to each of male and female C57BL/6J (8w) mice, the mice were dissected on day 7, the brain, heart, kidney, liver, lung, and spleen were extracted, and pathological analysis by HE staining was carried out. In addition, the blood was collected and analyzed using an automated blood cell counter (VetScan HMII) and a biochemical blood analyzer for animal (VetScan VS2) (FIG. 26). Consequently, in the data of blood cell number, any significant change was not recognized in the both (FIGS. 27 and 28). Similarly, in the blood biochemical data, any significant change was not recognized in the both (FIGS. 29 and 30). From this, it was suggested that anti-Glypican-1 antibody #1-25 has low toxicity and high safety.

As described above, the present invention is illustrated by preferable embodiments of the present invention. However, it will be understood that the scope of the present invention should be interpreted only by the claims. It will be understood that the contents of patents, patent applications, and literatures cited herein should be incorporated herein by reference as if their contents per se are specifically described herein. The present application claims priority to Japanese Patent Application No. 2013-272085 (filed on Dec. 27, 2013) and it is understood that the contents of the specification of the Patent application should be incorporated by reference to the present specification.

INDUSTRIAL APPLICABILITY

Esophageal cancer markers and esophageal cancer control technologies are provided and technologies applicable in industries (reagents, medicine manufacture, and the like) involved in technologies related to diagnosis, treatment, and prevention of esophageal cancer are provided.

SEQUENCE LISTING FREE TEXT

SEQ ID NO: 1: the human Glypican-1 nucleic acid sequence (NM 002081.2)
SEQ ID NO: 2: the human Glypican-1 protein sequence (P35052)
SEQ ID NO: 3: the anti-GPC-1 antibody 1-4 sequence
SEQ ID NO: 4: the anti-GPC-1 antibody 1-5 sequence
SEQ ID NO: 5: the anti-GPC-1 antibody 1-10 sequence
SEQ ID NO: 6: the anti-GPC-1 antibody 1-12 sequence
SEQ ID NO: 7: the anti-GPC-1 antibody 1-18 sequence
SEQ ID NO: 8: the anti-GPC-1 antibody 1-27 sequence
SEQ ID NO: 9: the anti-GPC-1 antibody 1-28 sequence
SEQ ID NO: 10: the anti-GPC-1 antibody 1-30 sequence
SEQ ID NO: 11: the anti-GPC-1 antibody 1-50 sequence
SEQ ID NO: 12: the anti-GPC-1 antibody 1-57 sequence
SEQ ID NO: 13: the anti-GPC-1 antibody 1-66 sequence
SEQ ID NO: 14: the anti-GPC-1 antibody 1-77 sequence
SEQ ID NO: 15: the anti-GPC-1 antibody 1-91 sequence
SEQ ID NO: 16: the anti-GPC-1 antibody 2-11 sequence
SEQ ID NO: 17: the anti-GPC-1 antibody 2-14 sequence
SEQ ID NO: 18: the anti-GPC-1 antibody 2-57 sequence
SEQ ID NO: 19: the anti-GPC-1 antibody 2-60 sequence
SEQ ID NO: 20: the anti-GPC-1 antibody 2-63 sequence
SEQ ID NO: 21: the anti-GPC-1 antibody 2-70 sequence
SEQ ID NO: 22: the anti-GPC-1 antibody 2-77 sequence
SEQ ID NO: 23: the sense chain sequence of the Glypican-1 siRNA core sequence (guide sequence)
SEQ ID NO: 24: the antisense chain sequence of the Glypican-1 siRNA core sequence (guide sequence)
SEQ ID NO: 25: the Glypican-1 siRNA sense chain full length sequence
SEQ ID NO: 26: the Glypican-1 siRNA antisense chain full length sequence
SEQ ID NO: 27: the GPC-1 forward primer sequence
SEQ ID NO: 28: the GPC-1 reverse primer sequence
SEQ TD NO: 29: the GAPDH forward primer sequence
SEQ ID NO: 30: the GAPDH reverse primer sequence
SEQ ID NO: 31: the β-actin forward primer sequence
SEQ ID NO: 32: the β-actin reverse primer sequence

The invention claimed is:

1. A therapeutic drug for esophageal cancer, comprising an effective amount of a Glypican-1 suppressant, wherein the Glypican-1 suppressant is an antibody or an antigen-binding fragment thereof, which antibody is an antibody of which heavy chain CDRs 1, 2, and 3 and light chain CDRs 1, 2, and 3 comprise the amino acid sequences set forth in positions 31 to 35, positions 51 to 66, positions 99 to 112, positions 160 to 170, positions 187 to 193, and positions 226 to 236 of SEQ ID NO: 6, respectively.

2. The therapeutic drug according to claim 1, wherein the esophageal cancer is Glypican-1 positive.

3. The therapeutic drug according to claim 1, wherein the esophageal cancer comprises those in lymph node metastasis sites, squamous cell carcinoma, and/or adenocarcinoma.

4. The therapeutic drug according to claim 1, wherein the esophageal cancer comprises squamous cell carcinoma.

5. The therapeutic drug according to claim 1 or 2, which is for administration to a patient who has been judged as developing Glypican-1 positive esophageal cancer.

6. The therapeutic drug according to claim 1, wherein the Glypican-1 suppressant is an antibody or an antigen-binding fragment thereof the antibody having positions 339 to 358 of SEQ ID NO: 2 as an epitope for binding by the antibody or antigen-binding fragment thereof.

7. The therapeutic drug according to claim 6, wherein the antibody is an antibody selected from monoclonal antibody, chimeric antibody, humanized antibody, multifunctional antibody, bispecific or oligospecific antibody, single chain antibody, scFV, diabody, sc(Fv)$_2$ (single chain (Fv)$_2$), and scFv-Fc.

8. A therapeutic drug for esophageal cancer, comprising a Glypican-1 binding agent and a cell-killing agent, wherein the Glypican-1 binding agent is an antibody or an antigen-binding fragment thereof, which antibody is an antibody of which heavy chain CDRs 1, 2, and 3 and light chain CDRs 1, 2, and 3 comprise the amino acid sequences set forth in positions 31 to 35, positions 51 to 66, positions 99 to 112, positions 160 to 170, positions 187 to 193, and positions 226 to 236 of SEQ ID NO: 6, respectively.

9. The therapeutic drug according to claim 8, wherein the esophageal cancer comprises those in lymph node metastasis sites, squamous cell carcinoma, and/or adenocarcinoma.

10. The therapeutic drug according to claim 8, wherein the Glypican-1 binding agent is an antibody or an antigen-binding fragment thereof and wherein the cell-killing agent is further bound to the Glypican-1 binding agent.

11. The therapeutic drug according to claim 8, wherein the esophageal cancer is Glypican-1 positive.

12. The therapeutic drug according to claim 8, wherein the esophageal cancer comprises squamous cell carcinoma.

13. The therapeutic drug according to claim 8, wherein the Glypican-1 binding agent is an antibody or an antigen-binding fragment thereof, the antibody having positions 339 to 358 of SEQ ID NO: 2 as an epitope for binding by the antibody or antigen-binding fragment thereof.

14. The therapeutic drug according to claim 13, wherein the antibody is an antibody selected from monoclonal antibody, chimeric antibody, humanized antibody, multifunctional antibody, bispecific or oligospecific antibody, single chain antibody, scFV, diabody, sc(Fv)$_2$ (single chain (Fv)$_2$), and scFv-Fc.

15. The therapeutic drug according to claim 7 or 14, further comprising a pharmacologically acceptable carrier.

16. An isolated antibody or an antigen-binding fragment thereof which isolated antibody is an antibody of which heavy chain CDRs 1, 2, and 3 and light chain CDRs 1, 2, and 3 comprise the amino acid sequences set forth in positions 31 to 35, positions 51 to 66, positions 99 to 112, positions 160 to 170, positions 187 to 193, and positions 226 to 236 of SEQ ID NO: 6, respectively.

17. An isolated antibody, or an antigen-binding fragment thereof, having: positions 339 to 358 of SEQ ID NO: 2 as an epitope for binding by the antibody or antigen-binding fragment thereof; wherein heavy chain CDRs 1, 2, and 3 and light chain CDRs 1, 2, and 3 comprise the amino acid sequences set forth in positions 31 to 35, positions 51 to 66, positions 99 to 112, positions 160 to 170, positions 187 to 193, and positions 226 to 236 of SEQ ID NO: 6, respectively.

18. The isolated antibody or an antigen-binding fragment thereof according to claim 16 or 17, wherein the antibody is an antibody selected from monoclonal antibody, chimeric antibody, humanized antibody, multifunctional antibody, bispecific or oligospecific antibody, single chain antibody, scFV, diabody, sc(Fv)$_2$ (single chain (Fv)$_2$), and scFv-Fc.

* * * * *

SEQUENCE LISTING

<160> NUMBER OF SEQ ID NOS: 32

<210> SEQ ID NO 1
<211> LENGTH: 3686
<212> TYPE: DNA
<213> ORGANISM: Homo sapiens

<400> SEQUENCE: 1

```
ggctgcccga gcgagcgttc ggacctcgca ccccgcgcgc cccgcgccgc cgccgccgcc      60
ggcttttgtt gtctccgcct cctcggccgc cgccgcctct ggaccgcgag ccgcgcgcgc     120
cgggaccttg gctctgccct tcgcgggcgg gaactgcgca ggacccggcc aggatccgag     180
agaggcgcgg gcgggtggcc gggggcgccg ccggccccgc catggagctc cgggcccgag     240
gctggtggct gctatgtgcg gccgcagcgc tggtcgcctg cgcccgcggg gacccggcca     300
```

```
gcaagagccg gagctgcggc gaggtccgcc agatctacgg agccaagggc ttcagcctga      360
gcgacgtgcc ccaggcggag atctcgggtg agcacctgcg gatctgtccc cagggctaca      420
cctgctgcac cagcgagatg gaggagaacc tggccaaccg cagccatgcc gagctggaga      480
ccgcgctccg ggacagcagc cgcgtcctgc aggccatgct tgccacccag ctgcgcagct      540
tcgatgacca cttccagcac ctgctgaacg actcggagcg gacgctgcag gccaccttcc      600
ccggcgcctt cggagagctg tacacgcaga acgcgagggc cttccgggac ctgtactcag      660
agctgcgcct gtactaccgc ggtgccaacc tgcacctgga ggagacgctg gccgagttct      720
gggcccgcct gctcgagcgc ctcttcaagc agctgcaccc cagctgctg ctgcctgatg       780 actacctgga ctgcctgggc aagcaggccg aggcgctgcg gcccttcggg gaggccccga      840
gagagctgcg cctgcgggcc acccgtgcct tcgtggctgc tcgctccttt gtgcagggcc      900
tgggcgtggc cagcgacgtg gtccggaaag tggctcaggt cccccctgggc ccggagtgct     960 cgagagctgt catgaagctg gtctactgtg ctcactgcct gggagtcccc ggcgccaggc     1020
cctgccctga ctattgccga aatgtgctca agggctgcct tgccaaccag gccgacctgg     1080
acgccgagtg gaggaacctc ctggactcca tggtgctcat caccgacaag ttctggggta     1140
catcgggtgt ggagagtgtc atcggcagcg tgcacacgtg gctggcggag gccatcaacg     1200
ccctccagga caacagggac acgctcacgg ccaaggtcat ccagggctgc gggaaccca     1260 aggtcaaccc ccagggcccc gggcctgagg agaagcggcg ccggggcaag ctggcccgc      1320 gggagaggcc accttcaggc acgctggaga agctggtctc cgaagccaag gcccagctcc     1380
gcgacgtcca ggacttctgg atcagcctcc cagggacact gtgcagtgag aagatggccc     1440
tgagcactgc cagtgatgac cgctgctgga acgggatggc cagaggccgg tacctccccg     1500
aggtcatggg tgacggcctg gccaaccaga tcaacaaccc cgaggtggag gtggacatca     1560
ccaagccgga catgaccatc cggcagcaga tcatgcagct gaagatcatg accaaccggc     1620
tgcgcagcgc ctacaacggc aacgacgtgg acttccagga cgccagtgac acggcagcg      1680 gctcgggcag cggtgatggc tgtctggatg acctctgcag ccggaaggtc agcaggaaga     1740
gctccagctc ccggacgccc ttgacccatg ccctcccagg cctgtcagag caggaaggac     1800
agaagacctc ggctgccagc tgccccagc ccccgacctt cctcctgccc ctcctcctct      1860
tcctggccct tacagtagcc aggccccggt ggcggtaact gccccaaggc cccagggaca     1920
gaggccaagg actgactttg ccaaaaatac aacacagacg atatttaatt caccctcagcc    1980 tggagaggcc tggggtggga cagggagggc cggcggctct gagcaggggc aggcgcagag     2040
gtcccagccc caggcctggc ctcgcctgcc tttctgcctt ttaattttgt atgaggtcct     2100
caggtcagct gggagccagt gtgcccaaaa gccatgtatt tcaggaccct caggggcacc     2160
tccggctgcc tagccctccc cccagctccc tgcaccgccg cagaagcagc ccctcgaggc     2220
ctacagagga ggcctcaaag caacccgctg gagcccacag cgagcctgtg ccttcctccc     2280
cgcctcctcc cactgggact cccagcagag cccaccagcc agccctggcc cacccccag      2340 cctccagaga agccccgcac gggctgtctg ggtgtccgcc atccagggtc tggcagagcc     2400
tctgagatga tgcatgatgc cctccctca gcgcaggctg cagagccgg ccccacctcc       2460 ctgcgccctt gagggccc agcgtctgca gggtgacgcc tgagacagca ccactgctga      2520
ggagtctgag gactgtcctc ccacagacct gcagtgaggg gccctccatg cgcagatgag     2580
gggccactga cccacctgcg cttctgctgg aggaggggaa gctgggccca aaggcccagg     2640
gaggcagcgt gggctctgcc aatgtgggct gcccctcgca cacagggctc acagggcagg    2700
```

```
ccttgctggg gtccagggct gttggaggac cccgagggct gaggagcagc caggacccgc    2760
ctgctcccat cctcacccag atcaggaacc agggcctccc tgttcacggt gacacaggtc    2820
agggctcaga gtgaccctca gctgtcacct gctcacaggg atgctggtgg ctggtgagac    2880
cccgcactgc agacgggaat gcctaggtcc cttcccgacc cagccagctg cagggcacgg    2940
ggacctggat agttaagggc ttttccaaac atgcatccat ttactgacac ttcctgtcct    3000
tgttcatgga gagctgttcg ctcctcccag atggcttcgg agggccgcag ggcccacctt    3060
ggaccctggt gacctcctgt cactcactga ggccatcagg gccctgcccc aggcctggac    3120
gggccctcct tccctcctgt gccccagctg ccaggcggcc ctggggaggg gtggtgtggt    3180
gttgggaagg ggtcctgcag ggggaggagg acttggaggg tctgggggca gctgtcctga    3240
accgactgac cctgaggagg ccgcttagtg ctgctttgct tttcatcacc gtcccgcaca    3300
gtggacggag gtccccggtt gctggtcagg tccccatggc ttgttctctg gaacctgact    3360
ttagatgttt tgggatcagg agcccccaac acaggcaagt ccaccccata ataaccctgc    3420
cagtgccagg gtgggctggg gactctggca cagtgatgcc gggcgccagg acagcagcac    3480
tcccgctgca cacagacggc ctaggggtgg cgctcagacc ccaccctacg ctcatctctg    3540 gaagggcag ccctgagtgg tcactggtca gggcagtggc caagcctgct gtgtccttcc    3600
tccacaaggt ccccccaccg ctcagtgtca gcgggtgacg tgtgttcttt tgagtccttg    3660
tatgaataaa aggctggaaa cctaca                                         3686
```

<210> SEQ ID NO 2
<211> LENGTH: 558
<212> TYPE: PRT
<213> ORGANISM: Homo sapiens

<400> SEQUENCE: 2

```
Met Glu Leu Arg Ala Arg Gly Trp Trp Leu Leu Cys Ala Ala Ala
1               5                   10                  15

Leu Val Ala Cys Ala Arg Gly Asp Pro Ala Ser Lys Ser Arg Ser Cys
            20                  25                  30

Gly Glu Val Arg Gln Ile Tyr Gly Ala Lys Gly Phe Ser Leu Ser Asp
        35                  40                  45

Val Pro Gln Ala Glu Ile Ser Gly Glu His Leu Arg Ile Cys Pro Gln
    50                  55                  60

Gly Tyr Thr Cys Cys Thr Ser Glu Met Glu Glu Asn Leu Ala Asn Arg
65                  70                  75                  80

Ser His Ala Glu Leu Glu Thr Ala Leu Arg Asp Ser Ser Arg Val Leu
                85                  90                  95

Gln Ala Met Leu Ala Thr Gln Leu Arg Ser Phe Asp Asp His Phe Gln
            100                 105                 110

His Leu Leu Asn Asp Ser Glu Arg Thr Leu Gln Ala Thr Phe Pro Gly
        115                 120                 125

Ala Phe Gly Glu Leu Tyr Thr Gln Asn Ala Arg Ala Phe Arg Asp Leu
    130                 135                 140

Tyr Ser Glu Leu Arg Leu Tyr Tyr Arg Gly Ala Asn Leu His Leu Glu
145                 150                 155                 160

Glu Thr Leu Ala Glu Phe Trp Ala Arg Leu Leu Glu Arg Leu Phe Lys
                165                 170                 175

Gln Leu His Pro Gln Leu Leu Leu Pro Asp Asp Tyr Leu Asp Cys Leu
            180                 185                 190
```

Gly Lys Gln Ala Glu Ala Leu Arg Pro Phe Gly Ala Pro Arg Glu
            195                 200                 205

Leu Arg Leu Arg Ala Thr Arg Ala Phe Val Ala Ala Arg Ser Phe Val
    210                 215                 220

Gln Gly Leu Gly Val Ala Ser Asp Val Val Arg Lys Val Ala Gln Val
225                 230                 235                 240

Pro Leu Gly Pro Glu Cys Ser Arg Ala Val Met Lys Leu Val Tyr Cys
            245                 250                 255

Ala His Cys Leu Gly Val Pro Gly Ala Arg Pro Cys Pro Asp Tyr Cys
            260                 265                 270

Arg Asn Val Leu Lys Gly Cys Leu Ala Asn Gln Ala Asp Leu Asp Ala
            275                 280                 285

Glu Trp Arg Asn Leu Leu Asp Ser Met Val Leu Ile Thr Asp Lys Phe
            290                 295                 300

Trp Gly Thr Ser Gly Val Glu Ser Val Ile Gly Ser Val His Thr Trp
305                 310                 315                 320

Leu Ala Glu Ala Ile Asn Ala Leu Gln Asp Asn Arg Asp Thr Leu Thr
            325                 330                 335

Ala Lys Val Ile Gln Gly Cys Gly Asn Pro Lys Val Asn Pro Gln Gly
            340                 345                 350

Pro Gly Pro Glu Glu Lys Arg Arg Arg Gly Lys Leu Ala Pro Arg Glu
            355                 360                 365

Arg Pro Pro Ser Gly Thr Leu Glu Lys Leu Val Ser Glu Ala Lys Ala
            370                 375                 380

Gln Leu Arg Asp Val Gln Asp Phe Trp Ile Ser Leu Pro Gly Thr Leu
385                 390                 395                 400

Cys Ser Glu Lys Met Ala Leu Ser Thr Ala Ser Asp Asp Arg Cys Trp
            405                 410                 415

Asn Gly Met Ala Arg Gly Arg Tyr Leu Pro Glu Val Met Gly Asp Gly
            420                 425                 430

Leu Ala Asn Gln Ile Asn Asn Pro Glu Val Glu Val Asp Ile Thr Lys
            435                 440                 445

Pro Asp Met Thr Ile Arg Gln Gln Ile Met Gln Leu Lys Ile Met Thr
450                 455                 460

Asn Arg Leu Arg Ser Ala Tyr Asn Gly Asn Asp Val Asp Phe Gln Asp
465                 470                 475                 480

Ala Ser Asp Asp Gly Ser Gly Ser Gly Asp Gly Cys Leu Asp
            485                 490                 495

Asp Leu Cys Ser Arg Lys Val Ser Arg Lys Ser Ser Ser Arg Thr
            500                 505                 510

Pro Leu Thr His Ala Leu Pro Gly Leu Ser Glu Gln Glu Gly Gln Lys
            515                 520                 525

Thr Ser Ala Ala Ser Cys Pro Gln Pro Pro Thr Phe Leu Leu Pro Leu
530                 535                 540

Leu Leu Phe Leu Ala Leu Thr Val Ala Arg Pro Arg Trp Arg
545                 550                 555

<210> SEQ ID NO 3
<211> LENGTH: 244
<212> TYPE: PRT
<213> ORGANISM: Gallus gallus

<400> SEQUENCE: 3

Ala Val Thr Leu Glu Glu Ser Gly Gly Gly Leu Gln Thr Pro Gly Gly
1               5                   10                  15

```
Gly Leu Ser Leu Val Cys Lys Ala Ser Gly Phe Asp Phe Arg Asn Asn
            20                  25                  30

Gly Met Ala Trp Val Arg Gln Ala Pro Gly Lys Gly Leu Glu Trp Val
        35                  40                  45

Ala Gly Ile Ser Gly Thr Ala Tyr Ala Val Tyr Gly Ala Ala Val Lys
50                  55                  60

Gly Arg Ala Thr Ile Ser Arg Asp Asn Gly Gln Ser Thr Val Arg Leu
65                  70                  75                  80

Gln Leu Asn Asn Leu Arg Ala Glu Asp Thr Ala Thr Tyr Tyr Cys Ala
                85                  90                  95

Lys Thr Val Gly Ser Cys Gly Ile Asp Cys His Thr Thr Gly Phe Ile
            100                 105                 110

Asp Gly Trp Gly His Gly Thr Glu Val Ile Val Ser Thr Gly Gly Gly
        115                 120                 125

Gly Ser Gly Gly Gly Gly Ser Gly Gly Gly Gly Ser Asp Val Ala Leu
    130                 135                 140

Thr Gln Pro Ser Ser Val Ser Ala Asn Pro Gly Glu Thr Val Lys Ile
145                 150                 155                 160

Thr Cys Ser Gly Gly Ser Tyr Ser Tyr Gly Trp Phe Gln Gln Lys Ser
                165                 170                 175

Pro Gly Ser Ala Pro Val Thr Val Ile Tyr Trp Asp Asp Glu Arg Pro
            180                 185                 190

Ser Gly Ile Pro Ser Arg Phe Ser Gly Ser Lys Ser Gly Ser Thr Gly
        195                 200                 205

Thr Leu Thr Ile Thr Gly Val Gln Ala Glu Asp Glu Ala Val Tyr Phe
210                 215                 220

Cys Gly Ser Arg Asp Ser Ser Tyr Val Gly Ile Phe Gly Ala Gly Thr
225                 230                 235                 240

Thr Leu Thr Val

<210> SEQ ID NO 4
<211> LENGTH: 240
<212> TYPE: PRT
<213> ORGANISM: Gallus gallus

<400> SEQUENCE: 4

Ala Val Thr Leu Asp Glu Ser Gly Gly Leu Gln Thr Pro Gly Gly
1               5                   10                  15

Ala Leu Ser Leu Val Cys Lys Ala Ser Gly Phe Lys Phe Arg Ser Tyr
            20                  25                  30

Asp Met Tyr Trp Val Arg Gln Ala Pro Gly Lys Gly Leu Glu Tyr Val
        35                  40                  45

Ala Gly Ile Ile Asn Thr Gly Arg Glu Thr Tyr Tyr Gly Ala Ala Val
50                  55                  60

Lys Gly Arg Ala Thr Ile Ser Arg Asp Asn Gly Arg Ser Thr Val Arg
65                  70                  75                  80

Leu Gln Leu Asn Asn Leu Arg Ala Glu Asp Thr Gly Thr Tyr Phe Cys
                85                  90                  95

Ala Lys Gly Ala Ala Trp Asn Tyr Ala Gly Ser Ile Asp Ala Trp Gly
            100                 105                 110

His Gly Thr Glu Val Ile Val Ser Thr Gly Gly Gly Ser Gly Gly
        115                 120                 125

Gly Gly Ser Gly Gly Gly Gly Ser Asp Val Ala Leu Thr Gln Pro Ala
    130                 135                 140
```

Ser Val Ser Ala Asn Pro Gly Glu Thr Val Lys Ile Thr Cys Ser Gly
145                 150                 155                 160

Gly Ser Gly Ser Tyr Gly Trp Tyr Gln Gln Lys Ser Pro Gly Ser Ala
                165                 170                 175

Pro Val Thr Val Ile Tyr Gly Asp Asn Lys Arg Pro Thr Asp Ile Ser
            180                 185                 190

Ser Arg Phe Ser Gly Ser Thr Ser Gly Ser Thr Asn Thr Leu Thr Ile
        195                 200                 205

Thr Gly Val Gln Ala Glu Asp Glu Ala Val Tyr Phe Cys Gly Ser Arg
    210                 215                 220

Asp Asn Thr Tyr Ala Gly Ile Phe Gly Ala Gly Thr Thr Leu Thr Val
225                 230                 235                 240

<210> SEQ ID NO 5
<211> LENGTH: 246
<212> TYPE: PRT
<213> ORGANISM: Gallus gallus

<400> SEQUENCE: 5

Ala Val Thr Leu Asp Glu Ser Gly Gly Leu Gln Thr Pro Gly Gly Gly
1               5                   10                  15

Gly Leu Ser Leu Val Cys Lys Ala Ser Gly Phe Thr Phe Ser Gly Tyr
            20                  25                  30

Asp Met Met Trp Val Arg Gln Ala Pro Gly Lys Gly Leu Glu Trp Val
        35                  40                  45

Gly Gln Ile Ser Ser Thr Gly Ser Ile Gln Lys Tyr Gly Ala Ala Val
    50                  55                  60

Lys Gly Arg Ala Thr Ile Ser Arg Asp Asn Gly Gln Ser Thr Met Arg
65                  70                  75                  80

Leu Gln Leu Asn Asp Leu Arg Ala Glu Asp Thr Gly Thr Tyr Phe Cys
                85                  90                  95

Ala Lys Ser Ala Tyr Gly Tyr Ser Ser Gly Pro Glu Asp Ile Asp
            100                 105                 110

Ala Trp Gly His Gly Thr Glu Val Ile Val Ser Thr Gly Gly Gly Gly
        115                 120                 125

Ser Gly Gly Gly Gly Ser Gly Gly Gly Ser Asp Val Ala Leu Thr
    130                 135                 140

Gln Pro Ala Ser Val Ser Ala Asn Leu Gly Gly Thr Val Lys Ile Thr
145                 150                 155                 160

Cys Ser Gly Gly Ser Ser Asp Ala Tyr Gly Trp Tyr Gln Gln Lys Ser
                165                 170                 175

Pro Asp Ser Ala Pro Val Thr Val Ile Tyr Gly Asn Asn Asn Arg Pro
            180                 185                 190

Ser Asp Ile Pro Ser Arg Phe Ser Gly Ser Thr Ser Gly Ser Thr Asn
        195                 200                 205

Thr Leu Thr Ile Thr Gly Val Gln Ala Asp Asp Glu Ala Val Tyr Phe
    210                 215                 220

Cys Gly Ser Tyr Asp Gly Ser Thr Asp Ser Asp Gly Ile Phe Gly Ala
225                 230                 235                 240

Gly Thr Thr Leu Thr Val
                245

<210> SEQ ID NO 6
<211> LENGTH: 245
<212> TYPE: PRT

<213> ORGANISM: Gallus gallus

<400> SEQUENCE: 6

Ala Val Thr Leu Asp Glu Ser Gly Gly Gly Leu Gln Thr Pro Gly Arg
1               5                   10                  15

Ala Leu Ser Leu Val Cys Lys Ala Ser Gly Phe Thr Phe Ser Arg Tyr
            20                  25                  30

Ala Met Tyr Trp Val Arg Gln Ala Pro Gly Lys Gly Leu Glu Phe Val
        35                  40                  45

Ala Gly Ile Gly Asn Thr Gly Arg Tyr Thr Gly Tyr Gly Ser Ala Val
    50                  55                  60

Lys Gly Arg Ala Thr Ile Ser Arg Asp Ser Gly Gln Ser Thr Val Arg
65                  70                  75                  80

Leu Gln Leu Asn Asn Leu Arg Ala Glu Asp Thr Gly Asn Tyr Tyr Cys
                85                  90                  95

Ala Lys Ser Val Ser Pro Tyr Cys Cys Asp Ala Ala Asp Ile Asp Ala
            100                 105                 110

Trp Gly His Gly Thr Glu Val Ile Val Ser Thr Gly Gly Gly Gly Ser
        115                 120                 125

Gly Gly Gly Gly Ser Gly Gly Gly Ser Asp Val Ala Leu Thr Gln
130                 135                 140

Pro Ala Ser Val Ser Ala Asn Pro Gly Glu Thr Val Lys Ile Thr Cys
145                 150                 155                 160

Ser Gly Gly Ser Ser Gly Tyr Ala Tyr Gly Trp Tyr Gln Gln Lys Ser
                165                 170                 175

Pro Gly Ser Ala Pro Val Thr Leu Leu Tyr Ser Asn Asn Asn Arg Pro
            180                 185                 190

Ser Asp Ile Pro Ser Arg Phe Ser Gly Ser Lys Ser Gly Ser Thr Ala
        195                 200                 205

Thr Leu Thr Ile Thr Gly Val Gln Ala Glu Asp Glu Ala Val Tyr Phe
    210                 215                 220

Cys Gly Ser Val Asp Ser Ser Tyr Ala Gly Ile Phe Gly Ala Gly
225                 230                 235                 240

Thr Thr Leu Thr Val
                245

<210> SEQ ID NO 7
<211> LENGTH: 251
<212> TYPE: PRT
<213> ORGANISM: Gallus gallus

<400> SEQUENCE: 7

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser Tyr
            20                  25                  30

Thr Met Phe Trp Val Arg Gln Ala Pro Gly Lys Gly Leu Glu Phe Val
        35                  40                  45

Ala Gly Ile Asp Asn Thr Gly Ile Tyr Thr Pro Tyr Gly Ser Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Tyr Cys
                85                  90                  95

Ala Lys Tyr Ala Asp Ala Cys Thr Gly Pro Trp Cys Gly Ser Ser Ala

```
            100                 105                 110
Tyr Thr Gly Ser Thr Ile Asp Ala Trp Gly His Gly Thr Glu Val Thr
            115                 120                 125

Val Ser Thr Gly Gly Gly Ser Gly Gly Gly Ser Gly Gly Gly
    130                 135                 140

Gly Ser Asp Val Ala Leu Thr Gln Pro Ser Val Ser Ala Asn Pro
145                 150                 155                 160

Gly Glu Thr Val Lys Leu Thr Cys Ser Gly Gly Ser Tyr Tyr Gly
                165                 170                 175

Trp Tyr Gln Gln Lys Ser Pro Gly Ser Ala Pro Val Thr Val Ile Tyr
            180                 185                 190

Glu Asn Thr Glu Arg Pro Ser Asn Ile Pro Ser Arg Phe Ser Gly Ser
            195                 200                 205

Thr Ser Gly Ser Thr Ser Thr Leu Thr Ile Ile Gly Val Gln Ala Asp
            210                 215                 220

Asp Glu Ala Val Tyr Phe Cys Gly Gly Tyr Asp Ser Ser Thr Asp Ala
225                 230                 235                 240

Gly Ile Phe Gly Ala Gly Thr Thr Leu Thr Val
                245                 250

<210> SEQ ID NO 8
<211> LENGTH: 244
<212> TYPE: PRT
<213> ORGANISM: Gallus gallus

<400> SEQUENCE: 8

Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Asp Phe Ser Asn Asn
            20                  25                  30

Gly Met Gly Trp Val Arg Gln Ala Pro Gly Lys Gly Leu Glu Trp Val
        35                  40                  45

Ala Gly Ile Ser Gly Ser Gly Thr Thr Ala Tyr Gly Ala Ala Val Lys
    50                  55                  60

Gly Arg Val Thr Ile Ser Arg Asp Asn Gly Gln Ser Thr Val Arg Leu
65                  70                  75                  80

Gln Leu Asn Asn Leu Arg Ala Glu Asp Thr Gly Thr Tyr Tyr Cys Ala
                85                  90                  95

Lys Ala Ala Gly Ser Cys Gly Ser Asp Cys Tyr Thr Thr Gly Phe Ile
            100                 105                 110

Asp Ala Trp Gly His Gly Thr Glu Val Thr Val Ser Thr Gly Gly Gly
        115                 120                 125

Gly Ser Gly Gly Gly Gly Ser Gly Gly Gly Gly Ser Asp Val Ala Leu
    130                 135                 140

Thr Gln Pro Ala Ser Val Ser Ala Asn Pro Gly Glu Thr Val Glu Ile
145                 150                 155                 160

Thr Cys Ser Gly Gly Ser Gly Asn Tyr Gly Trp Phe Gln Gln Lys Ser
                165                 170                 175

Pro Gly Ser Ala Pro Val Thr Leu Ile Tyr Trp Asp Asp Glu Arg Pro
            180                 185                 190

Ser Asn Ile Pro Ser Arg Phe Ser Gly Ser Thr Ser Gly Ser Thr Ala
            195                 200                 205

Thr Leu Thr Ile Thr Gly Val Gln Ala Asp Asp Glu Ala Val Tyr Phe
            210                 215                 220
```

```
Cys Gly Ser Arg Asp Thr Asn Tyr Val Gly Met Phe Gly Ala Gly Thr
225                 230                 235                 240

Thr Leu Thr Val
```

<210> SEQ ID NO 9
<211> LENGTH: 250
<212> TYPE: PRT
<213> ORGANISM: Gallus gallus

<400> SEQUENCE: 9

```
Ala Val Thr Leu Asp Glu Ser Gly Gly Gly Leu Gln Thr Pro Gly Arg
1               5                   10                  15

Ala Leu Ser Leu Val Cys Lys Ala Ser Gly Phe Thr Phe Ser Ser Tyr
            20                  25                  30

Thr Met Phe Trp Val Arg Gln Ala Pro Gly Lys Gly Leu Glu Phe Val
        35                  40                  45

Ala Gly Ile Asp Asn Thr Gly Ile Tyr Thr Pro Tyr Gly Ser Ala Val
50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Tyr Cys
                85                  90                  95

Ala Lys Tyr Ala Asp Ala Cys Thr Gly Pro Trp Cys Gly Ser Ser Ala
            100                 105                 110

Tyr Thr Ala Ser Thr Ile Asp Ala Trp Gly His Gly Thr Glu Val Ile
        115                 120                 125

Val Ser Thr Gly Gly Gly Ser Ala Gly Gly Gly Ser Gly Gly Gly
130                 135                 140

Gly Ser Asp Val Ala Leu Thr Gln Pro Ala Ser Val Ser Ala Asn Leu
145                 150                 155                 160

Gly Gly Thr Val Glu Ile Thr Cys Ser Gly Gly Asn Asp Tyr Gly
                165                 170                 175

Trp Tyr Gln Gln Lys Ser Pro Gly Ser Ala Pro Val Thr Val Ile Tyr
            180                 185                 190

Asp Ser Ile Asn Arg Pro Ser Asn Ile Pro Ser Arg Phe Ser Gly Ser
        195                 200                 205

Thr Ser Gly Ser Thr Ala Thr Leu Thr Ile Thr Gly Val Gln Ala Asp
210                 215                 220

Asp Glu Ala Val Tyr Phe Cys Gly Ser Tyr Asp Ser Ser Tyr Val Gly
225                 230                 235                 240

Ile Phe Gly Ala Gly Thr Thr Leu Thr Val
                245                 250
```

<210> SEQ ID NO 10
<211> LENGTH: 246
<212> TYPE: PRT
<213> ORGANISM: Gallus gallus

<400> SEQUENCE: 10

```
Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Thr Leu Asn Ser Tyr
            20                  25                  30

Asp Met Leu Trp Val Arg Gln Ala Pro Gly Lys Gly Leu Glu Phe Val
        35                  40                  45

Ala Ala Ile Ser Ile Ala Ser Gly Ser Ser Tyr Ala Pro Ala Val Lys
```

```
Gly Arg Ala Thr Ile Ser Arg Asp Asn Gly Gln Ser Thr Val Arg Leu
 65                  70                  75                  80

Gln Leu Asn Asn Leu Arg Ala Glu Asp Thr Gly Thr Tyr Tyr Cys Ala
                 85                  90                  95

Arg Gly Gly Thr Gly Tyr Tyr Ser Asp Ala Thr Gly Gln Ile Asp
            100                 105                 110

Ala Trp Gly His Gly Thr Glu Val Ile Val Ser Thr Gly Gly Gly
            115                 120                 125

Ser Gly Gly Gly Gly Ser Gly Gly Gly Ser Asp Val Ala Leu Thr
    130                 135                 140

Gln Pro Ser Ser Val Ser Ala Asn Pro Gly Glu Thr Val Lys Ile Thr
145                 150                 155                 160

Cys Ser Gly Gly Ser Gly Tyr Gly Tyr Gly Trp Tyr Gln Gln Lys
                165                 170                 175

Ala Pro Gly Ser Ala Pro Val Thr Val Ile Tyr Ser Asn Asn Gln Arg
                180                 185                 190

Pro Ser Asn Ile Pro Ser Arg Phe Ser Gly Ser Thr Ser Gly Ser Thr
                195                 200                 205

Ser Thr Leu Thr Ile Thr Gly Val Gln Ala Asp Asp Glu Ala Val Tyr
210                 215                 220

Tyr Cys Gly Ser Thr Asp Ser Ser Thr Tyr Asp Gly Ile Phe Gly Ala
225                 230                 235                 240

Gly Thr Thr Leu Thr Val
                245

<210> SEQ ID NO 11
<211> LENGTH: 244
<212> TYPE: PRT
<213> ORGANISM: Gallus gallus

<400> SEQUENCE: 11

Ala Val Thr Leu Asp Glu Ser Gly Gly Gly Leu Gln Thr Pro Gly Gly
 1               5                  10                  15

Ala Leu Ser Leu Val Cys Lys Ala Ser Gly Phe Thr Phe Asn Asn Asn
                 20                  25                  30

Gly Met Ser Trp Val Arg Gln Ala Pro Gly Lys Gly Leu Glu Trp Val
             35                  40                  45

Ala Gly Ile Ser Gly Ala Gly Tyr Ser Asn Tyr Ala Pro Ala Val Lys
 50                  55                  60

Gly Arg Ala Thr Ile Ser Arg Asp Asn Gly Gln Ser Thr Val Arg Leu
 65                  70                  75                  80

Gln Leu Asn Ser Leu Arg Ala Glu Asp Thr Gly Thr Tyr Phe Cys Ala
                 85                  90                  95

Lys Val Ala Ser Ser Cys Gly Asn Glu Cys Tyr Thr Ser Gly Phe Ile
            100                 105                 110

Asp Ala Trp Gly His Gly Thr Glu Val Ile Val Ser Thr Gly Gly Gly
            115                 120                 125

Gly Ser Gly Gly Gly Gly Ser Gly Gly Gly Ser Asp Val Ala Leu
    130                 135                 140

Thr Gln Pro Ala Ser Val Ser Ala Asn Leu Gly Gly Thr Val Lys Ile
145                 150                 155                 160

Thr Cys Ser Gly Gly Ser Gly Ser Tyr Gly Trp Tyr Gln Gln Lys Ser
                165                 170                 175
```

Pro Gly Ser Ala Pro Val Thr Val Ile Phe Trp Asp Asn Glu Arg Pro
            180                 185                 190

Ser Asp Ile Pro Ser Arg Phe Ser Gly Ser Lys Ser Gly Ser Thr His
            195                 200                 205

Thr Leu Thr Ile Thr Gly Val Gln Ala Glu Asp Glu Ala Val Tyr Phe
            210                 215                 220

Cys Gly Ser Arg Asp Arg Met Tyr Asp Gly Ile Phe Gly Ala Gly Thr
225                 230                 235                 240

Thr Leu Thr Val

<210> SEQ ID NO 12
<211> LENGTH: 243
<212> TYPE: PRT
<213> ORGANISM: Gallus gallus

<400> SEQUENCE: 12

Ala Val Thr Leu Asp Glu Ser Gly Gly Gly Leu Gln Thr Pro Gly Gly
1               5                   10                  15

Gly Leu Ser Leu Val Cys Lys Gly Ser Gly Phe Thr Leu Thr Asp Arg
            20                  25                  30

Gly Met His Trp Val Arg Gln Ala Pro Gly Lys Gly Leu Glu Trp Val
            35                  40                  45

Ala Ala Ile Ser Ser Ser Gly Arg Phe Thr Leu Tyr Ala Pro Ala Val
        50                  55                  60

Thr Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Tyr Cys
                85                  90                  95

Ala Arg Gly Asn Ala Gly Gly Trp Trp Ala Asp Gly Gly Glu Ile Asp
            100                 105                 110

Ala Trp Gly His Gly Thr Glu Val Ile Val Ser Thr Gly Gly Gly Gly
            115                 120                 125

Ser Gly Gly Gly Gly Ser Gly Gly Gly Ser Asp Val Ala Leu Thr
130                 135                 140

Gln Pro Ser Ser Val Ser Ala Asn Pro Gly Glu Thr Val Lys Ile Thr
145                 150                 155                 160

Cys Ser Gly Gly Ser Gly Ser Tyr Gly Trp Phe Gln Gln Lys Ser Pro
            165                 170                 175

Gly Ser Ala Pro Val Thr Val Ile Tyr Ser Asn Asn Lys Arg Pro Thr
            180                 185                 190

Asp Ile Pro Ser Arg Phe Ser Gly Ser Lys Ser Gly Ser Thr Asn Thr
            195                 200                 205

Leu Thr Ile Thr Gly Val Gln Ala Asp Glu Ala Val Tyr Phe Cys
            210                 215                 220

Gly Ser Ala Asp Ser Ser Tyr Ile Gly Ile Phe Gly Ala Gly Thr Thr
225                 230                 235                 240

Leu Thr Val

<210> SEQ ID NO 13
<211> LENGTH: 249
<212> TYPE: PRT
<213> ORGANISM: Gallus gallus

<400> SEQUENCE: 13

Ala Val Thr Leu Asp Glu Ser Gly Gly Gly Leu Gln Thr Pro Gly Gly
1               5                   10                  15

-continued

Ala Leu Ser Leu Val Cys Lys Ala Ser Gly Phe Thr Phe Ser Ser Tyr
               20                  25                  30

Ala Met Gly Trp Val Arg Gln Ala Pro Gly Lys Gly Leu Glu Phe Val
            35                  40                  45

Ala Gly Ile Asp Arg Thr Gly Thr Tyr Ala Gly Tyr Gly Ala Ala Val
 50                  55                  60

Lys Gly Arg Ala Thr Ile Ser Arg Asp Asn Gly Gln Ser Thr Val Arg
 65                  70                  75                  80

Leu Gln Leu Asn Asn Leu Arg Ala Glu Asp Thr Gly Thr Tyr Tyr Cys
                 85                  90                  95

Ala Lys Glu Ser Thr Ser Gly Cys Ala Ser Gly Ile Cys Thr Ala Ala
            100                 105                 110

Trp Ile Asp Ala Trp Gly His Gly Thr Glu Val Ile Val Ser Thr Gly
            115                 120                 125

Gly Gly Gly Ser Gly Gly Gly Ser Gly Gly Gly Ser Asp Val
        130                 135                 140

Ala Leu Thr Gln Pro Ser Ser Val Ser Ala Asn Pro Gly Glu Thr Val
145                 150                 155                 160

Lys Ile Thr Cys Ser Gly Gly Ser Asp Tyr Gly Tyr Gly Trp His
                165                 170                 175

Gln Gln Lys Ser Pro Gly Ser Ala Pro Val Thr Val Ile Tyr Ser Asn
            180                 185                 190

Asn Lys Arg Pro Thr Asp Ile Pro Ser Arg Phe Ser Gly Ser Thr Ser
            195                 200                 205

Gly Ser Thr Ala Thr Leu Thr Ile Thr Gly Val Arg Ala Glu Asp Glu
210                 215                 220

Ala Val Tyr Tyr Cys Gly Ser Ala Asp Ser Ser Thr Phe His Gly Ile
225                 230                 235                 240

Phe Gly Ala Gly Thr Thr Leu Thr Val
                245

<210> SEQ ID NO 14
<211> LENGTH: 243
<212> TYPE: PRT
<213> ORGANISM: Gallus gallus

<400> SEQUENCE: 14

Ala Val Thr Leu Asp Glu Ser Gly Gly Gly Leu Gln Thr Pro Gly Gly
 1               5                  10                  15

Gly Leu Ser Leu Val Cys Lys Gly Ser Gly Phe Thr Leu Thr Asp Arg
                20                  25                  30

Gly Met His Trp Val Arg Gln Ala Pro Gly Lys Gly Leu Glu Trp Val
            35                  40                  45

Ala Ala Ile Ser Ser Ser Gly Arg Phe Thr Leu Tyr Ala Pro Ala Val
 50                  55                  60

Thr Gly Arg Ala Thr Ile Ser Arg Asp Asn Gly Gln Ser Thr Val Arg
 65                  70                  75                  80

Leu Gln Leu Asn Asn Leu Arg Ala Glu Asp Thr Gly Thr Tyr Tyr Cys
                 85                  90                  95

Ala Arg Gly Asn Ala Gly Gly Trp Trp Ala Asp Gly Gly Glu Ile Asp
            100                 105                 110

Ala Trp Gly His Gly Thr Glu Val Ile Val Ser Thr Gly Gly Gly Gly
            115                 120                 125

Ser Gly Gly Gly Gly Ser Gly Gly Gly Ser Asp Val Ala Leu Thr

```
            130                 135                 140
Gln Pro Ser Ser Val Ser Ala Asn Pro Gly Glu Thr Val Lys Ile Thr
145                 150                 155                 160

Cys Ser Gly Gly Ser Gly Ser Tyr Gly Trp Phe Gln Gln Lys Ser Pro
                165                 170                 175

Gly Ser Ala Pro Val Thr Val Ile Tyr Ser Asn Asn Lys Arg Pro Ser
            180                 185                 190

Asp Ile Pro Ser Arg Phe Ser Gly Ser Lys Ser Gly Ser Thr Asn Thr
        195                 200                 205

Leu Thr Ile Thr Gly Val Gln Ala Asp Asp Glu Ala Val Tyr Phe Cys
        210                 215                 220

Gly Ser Ala Asp Ser Ser Tyr Ile Gly Ile Phe Gly Ala Gly Thr Thr
225                 230                 235                 240

Leu Thr Val

<210> SEQ ID NO 15
<211> LENGTH: 245
<212> TYPE: PRT
<213> ORGANISM: Gallus gallus

<400> SEQUENCE: 15

Ala Val Thr Leu Asp Glu Ser Gly Gly Gly Leu Gln Thr Pro Gly Arg
1               5                   10                  15

Ala Leu Ser Leu Val Cys Lys Ala Ser Gly Phe Thr Phe Ser Asn Tyr
            20                  25                  30

Asp Met Leu Trp Val Arg Gln Ala Pro Gly Lys Gly Leu Glu Trp Val
        35                  40                  45

Gly Val Ile Ser Ser Ser Gly Ser Ser Thr Asn Tyr Gly Ala Ala Val
    50                  55                  60

Lys Gly Arg Ala Thr Ile Ser Arg Asp Asn Gly Gln Asn Thr Val Arg
65                  70                  75                  80

Leu Gln Leu Asn Asn Leu Arg Ala Glu Asp Thr Ala Thr Tyr Tyr Cys
                85                  90                  95

Ala Lys Ser Ala Tyr Gly Tyr Tyr Gly Ser Gly Val Ser Asp Ile Asp
            100                 105                 110

Ala Trp Gly Leu Gly Thr Glu Val Ile Val Ser Thr Gly Gly Gly Gly
        115                 120                 125

Ser Gly Gly Gly Gly Ser Gly Gly Gly Gly Ser Asp Val Ala Leu Thr
    130                 135                 140

Gln Pro Ser Ser Val Ser Ala Asn Pro Gly Glu Thr Val Lys Ile Thr
145                 150                 155                 160

Cys Ser Gly Gly Ser Gly Asn Asn Tyr Gly Trp Tyr Gln Gln Lys Ser
                165                 170                 175

Pro Gly Ser Ala Leu Val Thr Val Ile Tyr Asp Asn Asn Lys Arg Pro
            180                 185                 190

Thr Asp Ile Pro Ser Arg Phe Ser Gly Ser Thr Ser Gly Ser Thr Gly
        195                 200                 205

Thr Leu Thr Ile Thr Gly Val Gln Ala Glu Asp Glu Ala Val Tyr Phe
        210                 215                 220

Cys Gly Gly Tyr Asp Ser Ser Thr Tyr Ala Asp Ile Phe Gly Ala Gly
225                 230                 235                 240

Thr Thr Leu Thr Val
                245
```

-continued

```
<210> SEQ ID NO 16
<211> LENGTH: 241
<212> TYPE: PRT
<213> ORGANISM: Gallus gallus

<400> SEQUENCE: 16
```

Ala Val Thr Leu Asp Glu Ser Gly Gly Leu His Thr Pro Gly Gly
1               5                   10                  15

Thr Leu Ser Leu Val Cys Lys Ala Ser Gly Phe Thr Phe Ser Ser Tyr
            20                  25                  30

Asp Met Ile Trp Val Arg Gln Ala Pro Gly Lys Gly Leu Glu Tyr Val
        35                  40                  45

Ala Glu Ile Ile Asn Thr Gly Arg Glu Thr Tyr Tyr Gly Ala Ala Val
    50                  55                  60

Lys Gly Arg Ala Thr Ile Ser Arg Asp Asn Arg Gln Ser Thr Leu Arg
65                  70                  75                  80

Leu Gln Leu Asn Asn Leu Arg Ala Glu Asp Thr Gly Thr Tyr Phe Cys
                85                  90                  95

Ala Lys Ala Ala Pro Trp Asn Tyr Ala Gly Ser Ile Asp Ala Trp Gly
            100                 105                 110

His Gly Thr Glu Val Ile Val Ser Thr Gly Gly Gly Ser Gly Gly
        115                 120                 125

Gly Gly Ser Gly Gly Gly Gly Ser Asp Val Ala Leu Thr Gln Pro Ala
    130                 135                 140

Ser Val Ser Ala Asn Pro Gly Glu Thr Val Lys Ile Thr Cys Ser Gly
145                 150                 155                 160

Asp Asp Ser Asp Tyr Gly Trp Tyr Gln Gln Lys Ser Pro Gly Ser Ala
                165                 170                 175

Pro Val Thr Val Ile Tyr Ser Asn Asp Glu Arg Pro Ser Asp Ile Pro
            180                 185                 190

Ser Arg Phe Ser Gly Ser Lys Ser Gly Ser Thr Ala Thr Leu Thr Ile
        195                 200                 205

Thr Gly Val Gln Ala Asp Asp Glu Ala Val Tyr Tyr Cys Gly Ser Ala
    210                 215                 220

Asp Thr Ser Ser Gly Thr Asn Ile Phe Gly Ala Gly Thr Thr Leu Thr
225                 230                 235                 240

Val

```
<210> SEQ ID NO 17
<211> LENGTH: 246
<212> TYPE: PRT
<213> ORGANISM: Gallus gallus

<400> SEQUENCE: 17
```

Ala Val Thr Leu Asp Glu Ser Gly Gly Leu Gln Thr Pro Gly Gly
1               5                   10                  15

Ala Leu Ser Leu Ile Cys Lys Ala Ser Gly Phe Ser Phe Ser Asn Tyr
            20                  25                  30

Asp Ile Leu Trp Val Arg Gln Ala Pro Gly Lys Gly Leu Glu Phe Val
        35                  40                  45

Ala Ala Val Ser Ser Val Ser Val Pro Ser Tyr Ala Pro Ala Val Lys
    50                  55                  60

Gly Arg Ala Thr Ile Ser Arg Asp Asn Gly Gln Ser Thr Val Arg Met
65                  70                  75                  80

Gln Leu Asn Asn Leu Arg Ala Glu Asp Ser Ala Thr Tyr Tyr Cys Ala
                85                  90                  95

Arg Gly Gly Ala Gly His Tyr Ser Thr Ala Thr Gly Asn Ile Asp
            100                 105                 110

Val Trp Gly His Gly Thr Glu Val Thr Val Ser Thr Gly Gly Gly
            115                 120                 125

Ser Gly Gly Gly Ser Gly Gly Gly Ser Asp Val Ala Leu Thr
130                 135                 140

Gln Pro Ser Ser Val Ser Ala Asn Pro Gly Glu Thr Val Lys Ile Thr
145                 150                 155                 160

Cys Ser Gly Gly Tyr Ser Gly Tyr Gly Trp Tyr Gln Gln Lys
                165                 170                 175

Ser Pro Gly Ser Ala Pro Val Thr Val Ile Tyr Asp Asn Thr Asn Arg
            180                 185                 190

Pro Ser Asn Ile Pro Ser Arg Phe Ser Gly Ser Leu Ser Gly Ser Thr
            195                 200                 205

Asn Thr Leu Thr Ile Thr Gly Val Gln Ala Asp Asp Glu Ala Val Tyr
            210                 215                 220

Tyr Cys Gly Ser Thr Asp Gly Ser Thr Tyr Ile Gly Ile Phe Gly Ala
225                 230                 235                 240

Gly Thr Thr Leu Thr Val
                245

<210> SEQ ID NO 18
<211> LENGTH: 249
<212> TYPE: PRT
<213> ORGANISM: Gallus gallus

<400> SEQUENCE: 18

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Asp Phe Ser Ser Phe
            20                  25                  30

Asn Met Phe Trp Val Arg Gln Ala Pro Gly Lys Gly Leu Glu Tyr Val
            35                  40                  45

Ala Gln Ile Ser Ser Asp Gly Ser Phe Thr Ala Tyr Gly Ala Ala Val
    50                  55                  60

Lys Gly Arg Ala Thr Ile Ser Lys Asp Asn Gly Gln Ser Thr Val Arg
65                  70                  75                  80

Leu Gln Leu Ser Asn Leu Arg Ala Glu Asp Thr Gly Thr Tyr Tyr Cys
                85                  90                  95

Thr Lys Ser Ala Ser Gly Ser Val Trp Thr Ala Ala Phe Ser Ala Gly
            100                 105                 110

Ser Ile Asp Ala Trp Gly His Gly Thr Glu Val Ile Val Ser Thr Gly
            115                 120                 125

Gly Gly Gly Ser Gly Gly Gly Gly Ser Gly Gly Gly Ser Asp Val
130                 135                 140

Ala Leu Thr Gln Pro Ala Ser Val Ser Ala Lys Pro Gly Glu Thr Val
145                 150                 155                 160

Lys Ile Thr Cys Ser Gly Gly Ser Ile Gly Tyr Ser Tyr Gly Trp Phe
            165                 170                 175

Gln Gln Lys Ser Pro Gly Ser Ala Pro Val Thr Val Ile Tyr Asn Asn
            180                 185                 190

Asn Asn Arg Pro Trp Asp Ile Pro Ser Arg Phe Ser Gly Ser Lys Ser
            195                 200                 205

Gly Ser Thr Ala Thr Leu Thr Ile Thr Gly Val Gln Val Ala Asp Glu

Ala Val Tyr Tyr Cys Gly Ser Ala Asp Ser Ala Gly Tyr Ser Gly Met
225                 230                 235                 240

Phe Gly Ala Gly Thr Thr Leu Thr Val
                245

<210> SEQ ID NO 19
<211> LENGTH: 251
<212> TYPE: PRT
<213> ORGANISM: Gallus gallus

<400> SEQUENCE: 19

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Tyr Ser Ser Tyr
                20                  25                  30

Ala Met Gly Trp Val Arg Gln Ala Pro Gly Lys Gly Leu Glu Phe Val
            35                  40                  45

Ala Ser Ile Ser Ser Asp Gly Ser Asp Thr Ala Tyr Gly Ser Ala Val
        50                  55                  60

Lys Gly Arg Ala Thr Ile Ser Arg Asp Asn Arg Gln Ser Thr Leu Arg
65                  70                  75                  80

Leu Gln Leu Asn Asn Leu Arg Ala Glu Asp Thr Gly Thr Tyr Tyr Cys
                85                  90                  95

Ala Lys Ser Tyr Arg Cys Ser Trp Asn Cys Trp Asp Tyr Ala Ala Lys
                100                 105                 110

Ile Asp Ala Trp Gly His Gly Thr Glu Val Thr Val Ser Thr Gly Gly
            115                 120                 125

Gly Gly Ser Gly Gly Gly Gly Ser Gly Gly Gly Gly Ser Asp Val Ala
        130                 135                 140

Leu Thr Gln Pro Ala Ser Val Ser Ala Asn Pro Gly Glu Thr Val Lys
145                 150                 155                 160

Ile Thr Cys Ser Gly Ser Gly Ser Tyr Thr Gly Ser Tyr Tyr Tyr Gly
                165                 170                 175

Trp Tyr Gln Gln Lys Ser Pro Gly Ser Ala Pro Val Thr Val Ile Tyr
            180                 185                 190

Asn Asn Asn Lys Arg Pro Ser Asp Ile Pro Ser Arg Phe Ser Gly Ser
        195                 200                 205

Thr Ser Gly Ser Thr Ala Thr Leu Thr Ile Thr Gly Val Gln Ala Glu
210                 215                 220

Asp Glu Ala Val Tyr Phe Cys Gly Ser Tyr Asp Arg Ser Ser Asp Ser
225                 230                 235                 240

Gly Ile Phe Gly Ala Gly Thr Thr Leu Thr Val
                245                 250

<210> SEQ ID NO 20
<211> LENGTH: 251
<212> TYPE: PRT
<213> ORGANISM: Gallus gallus

<400> SEQUENCE: 20

Ala Val Thr Leu Asp Glu Ser Gly Gly Gly Leu Gln Thr Pro Gly Gly
1               5                   10                  15

Thr Leu Ser Leu Val Cys Lys Ala Ser Gly Phe Asp Phe Ser Ser Val
                20                  25                  30

Asn Met Phe Trp Val Arg Gln Ala Pro Gly Lys Gly Leu Glu Phe Val

```
                35                  40                  45
Ala Gly Ile Asp Asn Asp Ala Thr Phe Thr Leu Tyr Gly Ser Ala Val
 50                  55                  60

Lys Gly Arg Ala Ser Ile Ser Arg Asp Asn Gly Gln Ser Thr Val Arg
 65                  70                  75                  80

Leu Gln Leu Asn Asn Leu Arg Ala Glu Asp Thr Gly Thr Tyr Tyr Cys
                 85                  90                  95

Ala Lys Thr Leu Cys Ser Thr Thr Trp Gly Cys Gly Ala Tyr Ser Ala
                100                 105                 110

Gly Asp Ile Asp Ala Trp Gly His Gly Thr Glu Val Thr Val Ser Thr
                115                 120                 125

Gly Gly Gly Gly Ser Gly Gly Gly Ser Gly Gly Gly Ser Asp
                130                 135                 140

Val Ala Leu Thr Gln Pro Ser Ser Val Ser Ala Asn Pro Gly Glu Thr
145                 150                 155                 160

Val Lys Ile Thr Cys Ser Gly Gly Ser Ser Gly Tyr Gly Tyr Tyr
                165                 170                 175

Gly Trp Tyr Gln Gln Lys Ser Pro Gly Ser Ala Pro Val Thr Val Ile
                180                 185                 190

Tyr Asn Asn Asn Lys Arg Pro Thr Asp Ile Pro Ser Arg Phe Ser Gly
                195                 200                 205

Ala Leu Ser Gly Ser Thr Ala Thr Leu Thr Ile Thr Gly Val Gln Val
                210                 215                 220

Glu Asp Glu Ala Val Tyr Tyr Cys Gly Ser Arg Asp Asn Thr Tyr Val
225                 230                 235                 240

Gly Ile Phe Gly Ala Gly Thr Thr Leu Thr Val
                245                 250

<210> SEQ ID NO 21
<211> LENGTH: 245
<212> TYPE: PRT
<213> ORGANISM: Gallus gallus

<400> SEQUENCE: 21

Ala Val Thr Leu Asp Glu Ser Gly Gly Gly Leu Gln Thr Pro Gly Gly
  1               5                  10                  15

Ala Leu Ser Leu Val Cys Lys Ala Ser Gly Leu Ser Thr Phe Ser Asp
                 20                  25                  30

Arg Gly Met His Trp Val Arg Gln Ala Pro Gly Lys Gly Leu Glu Phe
                 35                  40                  45

Val Ala Ala Ile Ser Ser Ser Gly Arg Phe Thr Leu Tyr Gly Ala Ala
 50                  55                  60

Val Lys Gly Arg Ala Thr Ile Ser Arg Asp Asn Gly Gln Ser Thr Val
 65                  70                  75                  80

Arg Leu Gln Leu Asn Asp Leu Arg Ala Glu Asp Thr Ala Ile Tyr Tyr
                 85                  90                  95

Cys Ala Arg Gly Thr Thr Thr Gly Trp Trp Ala Asp Ala Gly Glu Ile
                100                 105                 110

Asp Ala Trp Gly His Gly Thr Glu Val Ile Val Ser Thr Gly Gly Gly
                115                 120                 125

Gly Ser Gly Gly Gly Gly Ser Gly Gly Gly Ser Asp Val Ala Leu
                130                 135                 140

Thr Gln Pro Ala Phe Met Ser Ala Asn Pro Gly Glu Thr Val Lys Ile
145                 150                 155                 160
```

Thr Cys Ser Gly Gly Ser Tyr Ser Ala Tyr Gly Trp Phe Gln Gln Lys
                165                 170                 175

Ser Pro Gly Ser Ala Pro Val Thr Leu Ile Tyr Asn Asp Asn Ile Arg
            180                 185                 190

Pro Ser Asp Ile Ser Ser Arg Phe Ser Gly Ser Lys Ser Gly Ser Thr
        195                 200                 205

Ala Thr Leu Thr Ile Thr Gly Val Gln Ala Asp Asp Glu Ala Val Tyr
    210                 215                 220

Phe Cys Gly Asn Glu Asp Arg Asn Asn Thr Ala Thr Phe Gly Ala Gly
225                 230                 235                 240

Thr Thr Leu Thr Val
                245

<210> SEQ ID NO 22
<211> LENGTH: 244
<212> TYPE: PRT
<213> ORGANISM: Gallus gallus

<400> SEQUENCE: 22

Ala Val Thr Leu Asp Glu Ser Gly Gly Leu Gln Thr Pro Gly Gly
1               5                   10                  15

Gly Leu Ser Leu Val Cys Lys Ala Ser Gly Phe Asp Phe Ser Asn Asn
            20                  25                  30

Gly Met Gly Trp Val Arg Gln Ala Pro Gly Lys Gly Leu Glu Trp Val
        35                  40                  45

Ala Gly Ile Ser Gly Ser Gly Thr Thr Ala Tyr Gly Ala Ala Val Lys
    50                  55                  60

Gly Arg Val Thr Ile Ser Arg Asp Asn Gly Gln Ser Thr Val Arg Leu
65                  70                  75                  80

Gln Leu Asn Asn Leu Arg Ala Glu Asp Thr Gly Thr Tyr Tyr Cys Ala
                85                  90                  95

Lys Ala Ala Gly Ser Cys Gly Ser Asp Cys Tyr Thr Thr Gly Phe Ile
            100                 105                 110

Asp Ala Trp Gly His Gly Thr Glu Val Thr Val Ser Thr Gly Gly Gly
        115                 120                 125

Gly Ser Gly Gly Gly Gly Ser Gly Gly Gly Gly Ser Asp Val Ala Leu
    130                 135                 140

Thr Gln Pro Ala Ser Val Ser Ala Asn Pro Gly Glu Thr Val Glu Ile
145                 150                 155                 160

Thr Cys Ser Gly Gly Ser Gly Asn Tyr Gly Trp Phe Gln Gln Lys Ser
                165                 170                 175

Pro Gly Ser Ala Pro Val Thr Leu Ile Tyr Trp Asp Asp Glu Arg Pro
            180                 185                 190

Ser Asn Ile Pro Ser Arg Phe Ser Gly Ser Thr Ser Gly Ser Thr Ala
        195                 200                 205

Thr Leu Thr Ile Thr Gly Val Gln Ala Asp Asp Glu Ala Val Tyr Phe
    210                 215                 220

Cys Gly Ser Arg Asp Thr Asn Tyr Val Gly Met Phe Gly Ala Gly Thr
225                 230                 235                 240

Thr Leu Thr Val

<210> SEQ ID NO 23
<211> LENGTH: 19
<212> TYPE: DNA
<213> ORGANISM: Artificial Sequence
<220> FEATURE:

```
<223> OTHER INFORMATION: Sense Strand of Glypican-1 siRNA Target
      Sequence

<400> SEQUENCE: 23
gggacacgcu cacggccaa                                           19

<210> SEQ ID NO 24
<211> LENGTH: 19
<212> TYPE: DNA
<213> ORGANISM: Artificial Sequence
<220> FEATURE:
<223> OTHER INFORMATION: Antisense Strand of Glypican-1 siRNA Target
      Sequence

<400> SEQUENCE: 24
ggccgugagc guguccctg                                           19

<210> SEQ ID NO 25
<211> LENGTH: 21
<212> TYPE: DNA
<213> ORGANISM: Artificial Sequence
<220> FEATURE:
<223> OTHER INFORMATION: Glypican-1 siRNA Sense Sequence

<400> SEQUENCE: 25
gggacacgcu cacggccaat t                                        21

<210> SEQ ID NO 26
<211> LENGTH: 21
<212> TYPE: DNA
<213> ORGANISM: Artificial sequence
<220> FEATURE:
<223> OTHER INFORMATION: Glypican-1 siRNA Antisense Sequence

<400> SEQUENCE: 26
uuggccguga gcguguccct g                                        21

<210> SEQ ID NO 27
<211> LENGTH: 20
<212> TYPE: DNA
<213> ORGANISM: Artificial Sequence
<220> FEATURE:
<223> OTHER INFORMATION: Glypican-1(GPC-1) Forward Primer

<400> SEQUENCE: 27
gccagatcta cggagccaag                                          20

<210> SEQ ID NO 28
<211> LENGTH: 20
<212> TYPE: DNA
<213> ORGANISM: Artificial Sequence
<220> FEATURE:
<223> OTHER INFORMATION: Glypican-1(GPC-1) Reverse Primer

<400> SEQUENCE: 28
aggttctcct ccatctcgct                                          20

<210> SEQ ID NO 29
<211> LENGTH: 24
<212> TYPE: DNA
<213> ORGANISM: Artificial Sequence
<220> FEATURE:
<223> OTHER INFORMATION: GAPDH Forward Primer

<400> SEQUENCE: 29
agcaatgcct cctgcaccac caac                                     24
```

```
<210> SEQ ID NO 30
<211> LENGTH: 22
<212> TYPE: DNA
<213> ORGANISM: Artificial Sequence
<220> FEATURE:
<223> OTHER INFORMATION: GAPDH Reverse Primer

<400> SEQUENCE: 30
ccggaggggc catccacagt ct                                              22

<210> SEQ ID NO 31
<211> LENGTH: 17
<212> TYPE: DNA
<213> ORGANISM: artificial sequence
<220> FEATURE:
<223> OTHER INFORMATION: Beta Actin Forward Primer

<400> SEQUENCE: 31
agcctcgcct ttgccga                                                    17

<210> SEQ ID NO 32
<211> LENGTH: 15
<212> TYPE: DNA
<213> ORGANISM: artificial sequence
<220> FEATURE:
<223> OTHER INFORMATION: Beta Actin Reverse Primer

<400> SEQUENCE: 32
ctggtgcctg gggcg                                                      15
```